United States Patent [19]
Norbeck et al.

[11] Patent Number: 5,990,135
[45] Date of Patent: *Nov. 23, 1999

[54] RETROVIRAL PROTEASE INHIBITING COMPOUNDS

[75] Inventors: Daniel W. Norbeck, Crystal Lake; Hing Leung Sham, Mundelein; Dale J. Kempf, Libertyville; Chen Zhao, Gurnee, all of Ill.

[73] Assignee: Abbott Laboratories, Abbott Park, Ill.

[ * ] Notice: This patent is subject to a terminal disclaimer.

[21] Appl. No.: 08/455,052

[22] Filed: May 31, 1995

Related U.S. Application Data

[60] Division of application No. 08/185,666, Feb. 1, 1994, Pat. No. 5,461,067, which is a continuation-in-part of application No. 08/023,226, Feb. 25, 1993, abandoned.

[51] Int. Cl.$^6$ .......................... A61K 31/44; C07D 413/14
[52] U.S. Cl. .......................... 514/340; 514/342; 514/369; 514/370; 514/372; 514/374; 514/376; 514/377; 514/378; 514/380; 546/269.7; 546/271.1; 546/272.1; 546/272.4; 546/280.4; 546/283.4; 546/275.4; 548/182; 548/183; 548/184; 548/186; 548/187; 548/189; 548/190; 548/191
[58] Field of Search .................................... 514/333, 340, 514/342, 365, 369, 370, 372, 374, 376, 377, 378, 380; 546/256, 275, 280; 548/182, 183, 184, 186, 187, 189, 190, 191, 194, 213, 214, 204, 225, 226, 227, 228, 229, 233, 234, 235, 236, 243, 245, 246, 247, 248

[56] References Cited

FOREIGN PATENT DOCUMENTS

| 0486948 | 5/1992 | European Pat. Off. . |
| 0521827 | 1/1993 | European Pat. Off. . |
| 9208699 | 5/1992 | WIPO . |
| 9318006 | 9/1993 | WIPO . |

OTHER PUBLICATIONS

Sham, H. L., et al., "Facile Synthesis of Potent HIV–1 Protease Inhibitors containing a Novel Pseudo–symmetric Dipeptide Isotere", *Journal of the Chemical Society*, 13:1052–1053 (1993).

*Primary Examiner*—Zinna Northington Davis
*Attorney, Agent, or Firm*—Steven R. Crowley; Michael J. Ward

[57] ABSTRACT

A retroviral protease inhibiting compound of the formula:

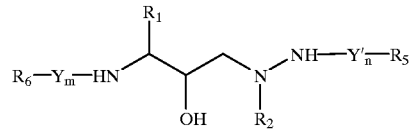

is disclosed.

12 Claims, No Drawings

RETROVIRAL PROTEASE INHIBITING COMPOUNDS

This is a division of U.S. patent application Ser. No. 08/185,666, filed Feb. 1, 1994, now U.S. Pat. No. 5,461,067 which is a continuation-in-part of U.S. patent application Ser. No. 023,226, filed Feb. 25, 1993, now abandoned.

This invention was made with Government support under contract number AI27220 awarded by the National Institute of Allergy and Infectious Diseases. The Government has certain rights in this invention.

TECHNICAL FIELD

The present invention relates to novel compounds and a composition and method for inhibiting retroviral proteases and in particular for inhibiting human immunodeficiency virus (HIV) protease, a composition and method for treating a retroviral infection and in particular an HIV infection, processes for making such compounds and synthetic intermediates employed in these processes.

BACKGROUND ART

Retroviruses are those viruses which utilize a ribonucleic acid (RNA) intermediate and a RNA-dependent deoxyribonucleic acid (DNA) polymerase, reverse transcriptase, during their life cycle. Retroviruses include, but are not limited to, the RNA viruses of the Retroviridae family, and also the DNA viruses of the Hepadnavirus and Caulimovirus families. Retroviruses cause a variety of disease states in man, animals and plants. Some of the more important retroviruses from a pathological standpoint include human immunodeficiency viruses (HIV-1 and HIV-2), which cause acquired immune deficiency syndrome (AIDS) in man, hepatitis B virus, which causes hepatitis and hepatic carcinomas in man, human T-cell lymphotrophic viruses I, II, IV and V, which cause human acute cell leukemia, and bovine and feline leukemia viruses which cause leukemia in domestic animals.

Proteases are enzymes which cleave proteins at specific peptide bonds. Many biological functions are controlled or mediated by proteases and their complementary protease inhibitors. For example, the protease renin cleaves the peptide angiotensinogen to produce the peptide angiotensin I. Angiotensin I is further cleaved by the protease angiotensin converting enzyme (ACE) to form the hypotensive peptide angiotensin II. Inhibitors of renin and ACE are known to reduce high blood pressure in vivo. An inhibitor of a retroviral protease will provide a therapeutic agent for diseases caused by the retrovirus.

The genomes of retroviruses encode a protease that is responsible for the proteolytic processing of one or more polyprotein precursors such as the pol and gag gene products. See Wellink, Arch. Virol. 98 1 (1988). Retroviral proteases most commonly process the gag precursor into core proteins, and also process the pol precursor into reverse transciptase and retroviral protease. In addition, retroviral proteases are sequence specific. See Pearl, Nature 328 482 (1987).

The correct processing of the precursor polyproteins by the retroviral protease is necessary for the assembly of infectious virions. It has been shown that in vitro mutagenesis that produces protease-defective virus leads to the production of immature core forms which lack infectivity. See Crawford, J. Virol. 53 899 (1985); Katoh, et al., Virology 145 280 (1985). Therefore, retroviral protease inhibition provides an attractive target for antiviral therapy. See Mitsuya, Nature 325 775 (1987).

Current treatments for viral diseases usually involve administration of compounds that inhibit viral DNA synthesis. Current treatments for AIDS involve administration of compounds such as 3'-azido-3'-deoxythymidine (AZT), 2',3'-dideoxycytidine (DDC) and 2',3'-dideoxyinosine (DDI) and compounds which treat the opportunistic infections caused by the immunosuppression resulting from HIV infection. None of the current AIDS treatments have proven to be totally effective in treating and/or reversing the disease. In addition, many of the compounds currently used to treat AIDS cause adverse side effects including low platelet count, renal toxicity and bone marrow cytopenia.

DISCLOSURE OF THE INVENTION

In accordance with the present invention, there are retroviral protease inhibiting compounds of the formula A:

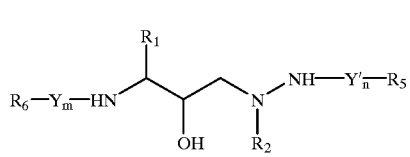

wherein $R_1$ and $R_2$ are independently selected from:
 (i) hydrogen,
 (ii) loweralkyl,
 (iii) aryl,
 (iv) thioalkoxyalkyl,
 (v) (aryl)alkyl,
 (vi) cycloalkyl,
 (vii) cycloalkylalkyl,
 (viii) hydroxyalkyl,
 (ix) alkoxyalkyl,
 (x) aryloxyalkyl,
 (xi) haloalkyl,
 (xii) carboxyalkyl,
 (xiii) alkoxycarbonylalkyl,
 (xiv) aminoalkyl,
 (xv) (N-protected)aminoalkyl,
 (xvi) alkylaminoalkyl,
 (xvii) ((N-protected)(alkyl)amino)alkyl,
 (xviii) dialkylaminoalkyl,
 (xix) guanidinoalkyl,
 (xx) loweralkenyl,
 (xxi) heterocyclic,
 (xxii) (heterocyclic)alkyl,
 (xxiii) arylthioalkyl,
 (xxiv) arylsulfonylalkyl,
 (xxv) (heterocyclic)thioalkyl,
 (xxvi) (heterocyclic)sulfonylalkyl,
 (xxvii) (heterocyclic)oxyalkyl,
 (xxviii) arylalkoxyalkyl,
 (xxix) arylthioalkoxyalkyl,
 (xxx) arylalkylsulfonylalkyl,
 (xxxi) (heterocyclic)alkoxyalkyl,
 (xxxii) (heterocyclic)thioalkoxyalkyl,
 (xxxiii) (heterocyclic)alkylsulfonylalkyl,
 (xxxiv) cycloalkyloxyalkyl,
 (xxxv) cycloalkylthioalkyl,
 (xxxvi) cycloalkylsulfonylalkyl,
 (xxxvii) cycloalkylalkoxyalkyl,
 (xxxviii) cycloalkylthioalkoxyalkyl,
 (xxxix) cycloalkylalkylsulfonylalkyl,
 (xl) aminocarbonyl,
 (xli) alkylaminocarbonyl, (xlii) dialkylaminocarbonyl,
(xliii) aroylalkyl,
(xliv) (heterocyclic)carbonylalkyl,
(xlv) polyhydroxyalkyl,
(xlvi) aminocarbonylalkyl,
(xlvii) alkylaminocarbonylalkyl,
(xlviii) dialkylaminocarbonylalkyl,
(xlix) aryloxyalkyl and
(l) alkylsulfonylalkyl;

Y is

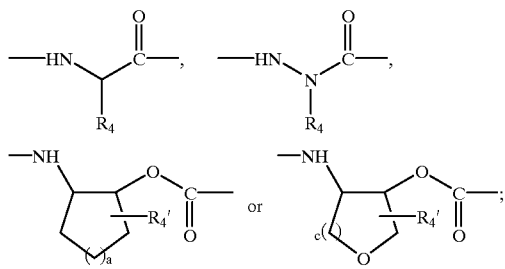

Y' is

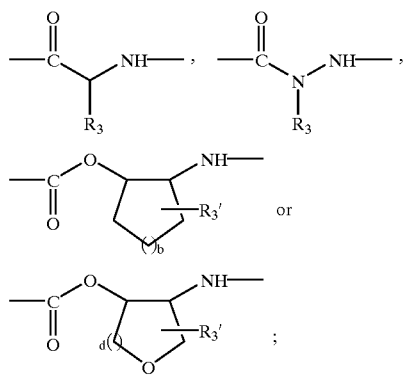

a is 0–3;
b is 0–3;
c is 1–2;
d is 1–2
$R_3'$ and $R_4'$ are independently selected from hydrogen and loweralkyl;
m is 0 or 1;
n is 0 or 1;
$R_3$ and $R_4$ are independently selected from:
(i) hydrogen,
(ii) loweralkyl,
(iii) aryl,
(iv) thioalkoxyalkyl,
(v) (aryl)alkyl,
(vi) cycloalkyl,
(vii) cycloalkylalkyl,
(viii) hydroxyalkyl,
(ix) alkoxyalkyl,
(x) aryloxyalkyl,
(xi) haloalkyl,
(xii) carboxyalkyl,
(xiii) alkoxycarbonylalkyl,
(xiv) aminoalkyl,
(xv) (N-protected)aminoalkyl,
(xvi) alkylaminoalkyl,
(xvii) ((N-protected)(alkyl)amino)alkyl,
(xviii) dialkylaminoalkyl,
(xix) guanidinoalkyl,
(xx) loweralkenyl,
(xxi) heterocyclic,
(xxii) (heterocyclic)alkyl,
(xxiii) arylthioalkyl,
(xxiv) arylsulfonylalkyl,
(xxv) (heterocyclic)thioalkyl,
(xxvi) (heterocyclic)sulfonylalkyl,
(xxvii) (heterocyclic)oxyalkyl,
(xxviii) arylalkoxyalkyl,
(xxix) arylthioalkoxyalkyl,
(xxx) arylalkylsulfonylalkyl,
(xxxi) (heterocyclic)alkoxyalkyl,
(xxxii) (heterocyclic)thioalkoxyalkyl,
(xxxiii) (heterocyclic)alkylsulfonylalkyl,
(xxxiv) cycloalkyloxyalkyl,
(xxxv) cycloalkylthioalkyl,
(xxxvi) cycloalkylsulfonylalkyl,
(xxxvii) cycloalkylalkoxyalkyl,
(xxxviii) cycloalkylthioalkoxyalkyl,
(xxxix) cycloalkylalkylsulfonylalkyl,
(xl) aminocarbonyl,
(xli) alkylaminocarbonyl,
(xlii) dialkylaminocarbonyl,
(xliii) aroylalkyl,
(xliv) (heterocyclic)carbonylalkyl,
(xlv) polyhydroxyalkyl,
(xlvi) aminocarbonylalkyl,
(xlvii) alkylaminocarbonylalkyl,
(xlviii) dialkylaminocarbonylalkyl,
(xlix) aryloxyalkyl and
(l) alkylsulfonylalkyl;

$R_5$ and $R_6$ are —C(T)—G—$R_7$ wherein at each occurrence T is independently selected from O and S; at each occurrence G is independently selected from —$CH_2$—, —O—, —S— and —N($R_8$)— wherein at each occurrence $R_8$ is independently selected from hydrogen, loweralkyl and cycloalkyl; and at each occurrence $R_7$ is independently selected from:
(i) loweralkyl,
(ii) cycloalkyl,
(iii) aryl,
(iv) arylalkyl
(v) (aryl)alkoxyalkyl,
(vi) aminoalkyl,
(vii) N-protected-aminoalkyl,
(viii) alkylaminoalkyl,
(ix) (N-protected)(alkyl)aminoalkyl,
(x) dialkylaminoalkyl,
(xi) carboxyalkoxyalkyl,
(xii) (alkoxycarbonyl)alkoxyalkyl,
(xiii) carboxyalkyl
(xiv) alkoxycarbonylalkyl,
(xv) (amino)carboxyalkyl,
(xvi) ((N-protected)amino)carboxyalkyl,
(xvii) (alkylamino)carboxyalkyl,
(xviii) ((N-protected)alkylamino)carboxyalkyl,
(xix) (dialkylamino)carboxyalkyl,
(xx) (amino)alkoxycarbonylalkyl,
(xxi) ((N-protected)amino)alkoxycarbonylalkyl,
(xxii) (alkylamino)alkoxycarbonylalkyl,
(xxiii) ((N-protected)alkylamino)alkoxycarbonylalkyl,
(xxiv) (dialkylamino)alkoxycarbonylalkyl,
(xxv) aminocycloalkyl,
(xxvi) alkoxyalkyl,
(xxvii) (polyalkoxy)alkyl, (xxviii) heterocyclic,
(xxix) (heterocyclic)alkyl,
(xxx) N-protecting group,
(xxxi) (hydroxyamino)alkyl,
(xxxii) (alkoxyamino)alkyl,
(xxxiii) cycloalkylalkyl,
(xxxiv) loweralkenyl,
(xxxv) hydroxyalkyl,
(xxxvi) dihydroxyalkyl,
(xxxvii) (alkoxy)(alkyl)aminoalkyl,
(xxxviii) alkylaminocycloalkyl,
(xxxix) dialkylaminocycloalkyl and
(Xl) polyhydroxyalkyl; or
a pharmaceutically acceptable salt, ester or prodrug thereof.

Preferred compounds of the formula A are those wherein m is 0 and n is 1 or m is 1 and n is 0.

Preferred compounds of the formula A are those wherein Y is

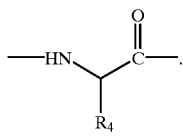

Preferred compounds of the formula A are those wherein Y' is

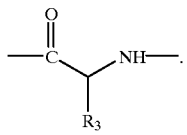

Preferred compounds of the formula A are those wherein $R_1$ and $R_2$ are independently selected from loweralkyl, cycloalkylalkyl, aryl, arylalkyl, heterocyclic and (heterocyclic)alkyl.

Preferred compounds of the formula A are those wherein $R_3$ and $R_4$ are independently selected from loweralkyl.

Preferred compounds of the formula A are those wherein $R_5$ and $R_6$ are —C(O)—G—$R_7$ wherein at each occurrence G is independently selected from —O—, —S— and —N($R_8$)— wherein at each occurrence $R_8$ is independently selected from hydrogen, loweralkyl and cycloalkyl; and at each occurrence $R_7$ is independently selected from arylalkyl and (heterocyclic)alkyl.

More preferred compounds of the invention are compounds of the formula B:

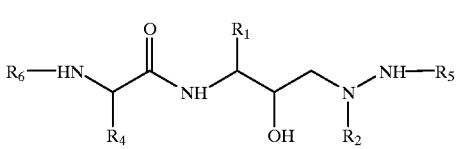

wherein $R_1$ and $R_2$ are independently selected from:
(i) hydrogen,
(ii) loweralkyl,
(iii) aryl,
(iv) thioalkoxyalkyl,
(v) (aryl)alkyl,
(vi) cycloalkyl,
(vii) cycloalkylalkyl,
(viii) hydroxyalkyl,
(ix) alkoxyalkyl,
(x) aryloxyalkyl,
(xi) haloalkyl,
(xii) carboxyalkyl,
(xiii) alkoxycarbonylalkyl,
(xiv) aminoalkyl,
(xv) (N-protected)aminoalkyl,
(xvi) alkylaminoalkyl,
(xvii) ((N-protected)(alkyl)amino)alkyl,
(xviii) dialkylaminoalkyl,
(xix) guanidinoalkyl,
(xx) loweralkenyl,
(xxi) heterocyclic,
(xxii) (heterocyclic)alkyl,
(xxiii) arylthioalkyl,
(xxiv) arylsulfonylalkyl,
(xxv) (heterocyclic)thioalkyl,
(xxvi) (heterocyclic)sulfonylalkyl,
(xxvii) (heterocyclic)oxyalkyl,
(xxviii) arylalkoxyalkyl,
(xxix) arylthioalkoxyalkyl,
(xxx) arylalkylsulfonylalkyl,
(xxxi) (heterocyclic)alkoxyalkyl,
(xxxii) (heterocyclic)thioalkoxyalkyl,
(xxxiii) (heterocyclic)alkylsulfonylalkyl,
(xxxiv) cycloalkyloxyalkyl,
(xxxv) cycloalkylthioalkyl,
(xxxvi) cycloalkylsulfonylalkyl,
(xxxvii) cycloalkylalkoxyalkyl,
(xxxviii) cycloalkylthioalkoxyalkyl,
(xxxix) cycloalkylalkylsulfonylalkyl,
(xl) aminocarbonyl,
(xli) alkylaminocarbonyl,
(xlii) dialkylaminocarbonyl,
(xliii) aroylalkyl,
(xliv) (heterocyclic)carbonylalkyl,
(xlv) polyhydroxyalkyl,
(xlvi) aminocarbonylalkyl,
(xlvii) alkylaminocarbonylalkyl,
(xlviii) dialkylaminocarbonylalkyl,
(xlix) aryloxyalkyl and
(l) alkylsulfonylalkyl;

$R_4$ is selected from:
(i) hydrogen,
(ii) loweralkyl,
(iii) aryl,
(iv) thioalkoxyalkyl,
(v) (aryl)alkyl,
(vi) cycloalkyl,
(vii) cycloalkylalkyl,
(viii) hydroxyalkyl,
(ix) alkoxyalkyl,
(x) aryloxyalkyl,
(xi) haloalkyl,
(xii) carboxyalkyl,
(xiii) alkoxycarbonylalkyl,
(xiv) aminoalkyl,
(xv) (N-protected)aminoaikyl,
(xvi) alkylaminoalkyl,
(xvii) ((N-protected)(alkyl)amino)alkyl,
(xviii) dialkylaminoalkyl,
(xix) guanidinoalkyl,
(xx) loweralkenyl,
(xxi) heterocyclic,
(xxii) (heterocyclic)alkyl,
(xxiii) arylthioalkyl, (xxiv) arylsulfonylalkyl,
(xxv) (heterocyclic)thioalkyl,
(xxvi) (heterocyclic)sulfonylalkyl,
(xxvii) (heterocyclic)oxyalkyl,
(xxviii) arylalkoxyalkyl,
(xxix) arylthioalkoxyalkyl,
(xxx) arylalkylsulfonylalkyl,
(xxxi) (heterocyclic)alkoxyalkyl,
(xxxii) (heterocyclic)thioalkoxyalkyl,
(xxxiii) (heterocyclic)alkylsulfonylalkyl,
(xxxiv) cycloalkyloxyalkyl,
(xxxv) cycloalkylthioalkyl,
(xxxvi) cycloalkylsulfonylalkyl,
(xxxvii) cycloalkylalkoxyalkyl,
(xxxviii) cycloalkylthioalkoxyalkyl,
(xxxix) cycloalkylalkylsulfonylalkyl,
(xl) aminocarbonyl,
(xli) alkylaminocarbonyl,
(xlii) dialkylaminocarbonyl,
(xliii) aroylalkyl,
(xliv) (heterocyclic)carbonylalkyl,
(xlv) polyhydroxyalkyl,
(xlvi) aminocarbonylalkyl,
(xlvii) alkylaminocarbonylalkyl,
(xlviii) dialkylaminocarbonylalkyl,
(xlix) aryloxyalkyl and
(l) alkylsulfonylalkyl;

$R_5$ and $R_6$ are —C(T)—G—$R_7$ wherein at each occurrence T is independently selected from O and S; at each occurrence G is independently selected from —$CH_2$—, —O—, —S— and —N($R_8$)— wherein at each occurrence $R_8$ is independently selected from hydrogen, loweralkyl and cycloalkyl; and at each occurrence $R_7$ is independently selected from:
(i) loweralkyl,
(ii) cycloalkyl,
(iii) aryl,
(iv) arylalkyl
(v) (aryl)alkoxyalkyl,
(vi) aminoalkyl,
(vii) N-protected-aminoalkyl,
(viii) alkylaminoalkyl,
(ix) (N-protected)(alkyl)aminoalkyl,
(x) dialkylaminoalkyl,
(xi) carboxyalkoxyalkyl,
(xii) (alkoxycarbonyl)alkoxyalkyl,
(xiii) carboxyalkyl
(xiv) alkoxycarbonylalkyl,
(xv) (amino)carboxyalkyl,
(xvi) ((N-protected)amino)carboxyalkyl,
(xvii) (alkylamino)carboxyalkyl,
(xviii) ((N-protected)alkylamino)carboxyalkyl,
(xix) (dialkylamino)carboxyalkyl,
(xx) (amino)alkoxycarbonylalkyl,
(xxi) ((N-protected)amino)alkoxycarbonylalkyl,
(xxii) (alkylamino)alkoxycarbonylalkyl,
(xxiii) ((N-protected)alkylamino)alkoxycarbonylalkyl,
(xxiv) (dialkylamino)alkoxycarbonylalkyl,
(xxv) aminocycloalkyl,
(xxvi) alkoxyalkyl,
(xxvii) (polyalkoxy)alkyl,
(xxviii) heterocyclic,
(xxix) (heterocyclic)alkyl,
(xxx) N-protecting group,
(xxxi) (hydroxyamino)alkyl,
(xxxii) (alkoxyamino)alkyl,
(xxxiii) cycloalkylalkyl,
(xxxiv) loweralkenyl,
(xxxv) hydroxyalkyl,
(xxxvi) dihydroxyalkyl,
(xxxvii) (alkoxy)(alkyl)aminoalkyl,
(xxxviii) alkylaminocycloalkyl,
(xxxix) dialkylaminocycloalkyl and
(xl) polyhydroxyalkyl; or
a pharmaceutically acceptable salt, ester or prodrug thereof.

Preferred compounds of the formula B are those wherein $R_1$ and $R_2$ are independently selected from loweralkyl, cycloalkylalkyl, aryl, arylalkyl, heterocyclic and (heterocyclic)alkyl.

Preferred compounds of the formula B are those wherein $R_4$ is loweralkyl.

Preferred compounds of the formula B are those wherein $R_5$ and $R_6$ are —C(O)—G—$R_7$ where at each occurrence G is independently selected from —O—, —S— and —N($R_8$)— wherein at each occurrence $R_8$ is independently selected from hydrogen, loweralkyl and cycloalkyl; and at each occurrence $R_7$ is independently selected from arylalkyl and (heterocyclic)alkyl.

More preferred compounds of the invention are compounds of the formula C:

$$R_6-NH-\underset{R_1}{CH}-\underset{OH}{CH}-\underset{R_2}{CH}-NH-NH-\underset{O}{C}-\underset{R_3}{CH}-NH-R_5 \qquad C$$

wherein $R_1$ and $R_2$ are independently selected from:
(i) hydrogen,
(ii) loweralkyl,
(iii) aryl,
(iv) thioalkoxyalkyl,
(v) (aryl)alkyl,
(vi) cycloalkyl,
(vii) cycloalkylalkyl,
(viii) hydroxyalkyl,
(ix) alkoxyalkyl,
(x) aryloxyalkyl,
(xi) haloalkyl,
(xii) carboxyalkyl,
(xiii) alkoxycarbonylalkyl,
(xiv) aminoalkyl,
(xv) (N-protected)aminoalkyl,
(xvi) alkylaminoalkyl,
(xvii) ((N-protected)(alkyl)amino)alkyl,
(xviii) dialkylaminoalkyl,
(xix) guanidinoalkyl,
(xx) loweralkenyl,
(xxi) heterocyclic,
(xxii) (heterocyclic)alkyl,
(xxiii) arylthioalkyl,
(xxiv) arylsulfonylalkyl,
(xxv) (heterocyclic)thioalkyl,
(xxvi) (heterocyclic)sulfonylalkyl,
(xxvii) (heterocyclic)oxyalkyl,
(xxviii) arylalkoxyalkyl,
(xxix) arylthioalkoxyalkyl,
(xxx) arylalkylsulfonylalkyl,
(xxxi) (heterocyclic)alkoxyalkyl,
(xxxii) (heterocyclic)thioalkoxyalkyl,
(xxxiii) (heterocyclic)alkylsulfonylalkyl,
(xxxiv) cycloalkyloxyalkyl,
(xxxv) cycloalkylthioalkyl, (xxxvi) cycloalkylsulfonylalkyl,
(xxxvii) cycloalkylalkoxyalkyl,
(xxxviii) cycloalkylthioalkoxyalkyl,
(xxxix) cycloalkylalkylsulfonylalkyl,
(xl) aminocarbonyl,
(xli) alkylaminocarbonyl,
(xlii) dialkylaminocarbonyl,
(xliii) aroylalkyl,
(xliv) (heterocyclic)carbonylalkyl,
(xlv) polyhydroxyalkyl,
(xlvi) aminocarbonylalkyl,
(xlvii) alkylaminocarbonylalkyl,
(xlviii) dialkylaminocarbonylalkyl,
(xlix) aryloxyalkyl and
(l) alkylsulfonylalkyl;

$R_3$ is selected from:
(i) hydrogen,
(ii) loweralkyl,
(iii) aryl,
(iv) thioalkoxyalkyl,
(v) (aryl)alkyl,
(vi) cycloalkyl,
(vii) cycloalkylalkyl,
(viii) hydroxyalkyl,
(ix) alkoxyalkyl,
(x) aryloxyalkyl,
(xi) haloalkyl,
(xii) carboxyalkyl,
(xiii) alkoxycarbonylalkyl,
(xiv) aminoalkyl,
(xv) (N-protected)aminoalkyl,
(xvi) alkylaminoalkyl,
(xvii) ((N-protected)(alkyl)amino)alkyl,
(xviii) dialkylaminoalkyl,
(xix) guanidinoalkyl,
(xx) loweralkenyl,
(xxi) heterocyclic,
(xxii) (heterocyclic)alkyl,
(xxiii) arylthioalkyl,
(xxiv) arylsulfonylalkyl,
(xxv) (heterocyclic)thioalkyl,
(xxvi) (heterocyclic)sulfonylalkyl,
(xxvii) (heterocyclic)oxyalkyl,
(xxviii) arylalkoxyalkyl,
(xxix) arylthioalkoxyalkyl,
(xxx) arylalkylsulfonylalkyl,
(xxxi) (heterocyclic)alkoxyalkyl,
(xxxii) (heterocyclic)thioalkoxyalkyl,
(xxxiii) (heterocyclic)alkylsulfonylalkyl,
(xxxiv) cycloalkyloxyalkyl,
(xxxv) cycloalkylthioalkyl,
(xxxvi) cycloalkylsulfonylalkyl,
(xxxvii) cycloalkylalkoxyalkyl,
(xxxviii) cycloalkylthioalkoxyalkyl,
(xxxix) cycloalkylalkylsulfonylalkyl,
(xl) aminocarbonyl,
(xli) alkylaminocarbonyl,
(xlii) dialkylaminocarbonyl,
(xliii) aroylalkyl,
(xliv) (heterocyclic)carbonylalkyl,
(xlv) polyhydroxyalkyl,
(xlvi) aminocarbonylalkyl,
(xlvii) alkylaminocarbonylalkyl,
(xlviii) dialkylaminocarbonylalkyl,
(xlix) aryloxyalkyl and
(l) alkylsulfonylalkyl;

$R_5$ and $R_6$ are —C(T)—G—$R_7$ wherein at each occurrence T is independently selected from O and S; at each occurrence G is independently selected from —CH$_2$—, —O—, —S— and —N($R_8$)— wherein at each occurrence $R_8$ is independently selected from hydrogen, loweralkyl and cycloalkyl; and at each occurrence $R_7$ is independently selected from:
(i) loweralkyl,
(ii) cycloalkyl,
(iii) aryl,
(iv) arylalkyl
(v) (aryl)alkoxyalkyl,
(vi) aminoalkyl,
(vii) N-protected-aminoalkyl,
(viii) alkylaminoalkyl,
(ix) (N-protected)(alkyl)aminoalkyl,
(x) dialkylaminoalkyl,
(xi) carboxyalkoxyalkyl,
(xii) (alkoxycarbonyl)alkoxyalkyl,
(xiii) carboxyalkyl,
(xiv) alkoxycarbonylalkyl,
(xv) (amino)carboxyalkyl,
(xvi) ((N-protected)amino)carboxyalkyl,
(xvii) (alkylamino)carboxyalkyl,
(xviii) ((N-protected)alkylamino)carboxyalkyl,
(xix) (dialkylamino)carboxyalkyl,
(xx) (amino)alkoxycarbonylalkyl,
(xxi) ((N-protected)amino)alkoxycarbonylalkyl,
(xxii) (alkylamino)alkoxycarbonylalkyl,
(xxiii) ((N-protected)alkylamino)alkoxycarbonylalkyl,
(xxiv) (dialkylamino)alkoxycarbonylalkyl,
(xxv) aminocycloalkyl,
(xxvi) alkoxyalkyl,
(xxvii) (polyalkoxy)alkyl,
(xxviii) heterocyclic,
(xxix) (heterocyclic)alkyl,
(xxx) N-protecting group,
(xxxi) (hydroxyamino)alkyl,
(xxxii) (alkoxyamino)alkyl,
(xxxiii) cycloalkylalkyl,
(xxxiv) loweralkenyl,
(xxxv) hydroxyalkyl,
(xxxvi) dihydroxyalkyl,
(xxxvii) (alkoxy)(alkyl)aminoalkyl,
(xxxviii) alkylaminocycloalkyl,
(xxxix) dialkylaminocycloalkyl and
(xl) polyhydroxyalkyl; or
a pharmaceutically acceptable salt, ester or prodrug thereof.

Preferred compounds of the formula C are those wherein $R_1$ and $R_2$ are independently selected from loweralkyl, cycloalkylalkyl, aryl, arylalkyl, heterocyclic and (heterocyclic)alkyl.

Preferred compounds of the formula C are those wherein $R_3$ is loweralkyl.

Preferred compounds of the formula C are those wherein $R_5$ and $R_6$ are —C(O)—G—$R_7$ where at each occurrence G is independently selected from —O—, —S— and —N($R_8$)— wherein at each occurrence $R_8$ is independently selected from hydrogen, loweralkyl and cycloalkyl; and at each occurrence $R_7$ is independently selected from arylalkyl and (heterocyclic)alkyl.

More preferred compounds of the invention are compounds of the formula B wherein $R_1$ and $R_2$ are independently selected from cyclohexylmethyl, arylalkyl, substituted arylalkyl wherein the aryl ring of the arylalkyl group is substituted with loweralkyl, halo, alkoxy, amino or alkylamino, dialkylamino, (heterocyclic)methyl wherein the heterocycle is independently selected from pyridyl, thiazolyl, isothiazolyl, furanyl, thienyl, oxazolyl, isoxazolyl, tetrahydofuranyl and tetrahydropyranyl and (substituted-heterocyclic)methyl wherein the heterocycle is substituted with loweralkyl, halo, alkoxy, amino, alkylamino or dialkylamino.

More preferred compounds of the invention are compounds of the formula B wherein $R_5$ is —C(O)—G—$R_7$ wherein G is —O— and $R_7$ is selected from benzyl, pyridylmethyl, oxazolylmethyl, isoxazolylmethyl, thiazolylmethyl and isothiazolylmethyl.

More preferred compounds of the invention are compounds of the formula B wherein $R_6$ is —C(O)—G—$R_7$ wherein G is selected from —O— and —N(CH$_3$)— and $R_7$ is selected from pyridylmethyl, substituted pyridylmethyl wherein the pyridine ring is substituted with loweralkyl, oxazolylmethyl, substituted oxazolylmethyl wherein the oxazole ring is substituted with loweralkyl, isoxazolylmethyl, substituted isoxazolylmethyl wherein the isoxazole ring is substituted with loweralkyl, thiazolylmethyl, substituted thiazolylmethyl wherein the thiazole ring is substituted with loweralkyl, isothiazolylmethyl and substituted isothiazolylmethyl wherein the isothiazole ring is substituted with loweralkyl.

More preferred compounds of the invention are compounds of the formula C wherein $R_1$ and $R_2$ are independently selected from cyclohexylmethyl, arylalkyl, substituted arylalkyl wherein the aryl ring of the arylalkyl group is substituted with loweralkyl, halo, alkoxy, amino or alkylamino, dialkylamino, (heterocyclic)methyl wherein the heterocycle is independently selected from pyridyl, thiazolyl, isothiazolyl, furanyl, thienyl, oxazolyl, isoxazolyl, tetrahydofuranyl and tetrahydropyranyl and (substituted-heterocyclic)methyl wherein the heterocycle is substituted with loweralkyl, halo, alkoxy, amino, alkylamino or dialkylamino.

More preferred compounds of the invention are compounds of the formula C wherein $R_6$ is —C(O)—G—$R_7$ wherein G is —O— and $R_7$ is selected from benzyl, pyridylmethyl, oxazolylmethyl, isoxazolylmethyl, thiazolylmethyl and isothiazolylmethyl.

More preferred compounds of the invention are compounds of the formula C wherein $R_5$ is —C(O)—G—$R_7$ wherein G is selected from —O— and —N(CH$_3$)— and $R_7$ is selected from pyridylmethyl, substituted pyridylmethyl wherein the pyridine ring is substituted with loweralkyl, oxazolylmethyl, substituted oxazolylmethyl wherein the oxazole ring is substituted with loweralkyl, isoxazolylmethyl, substituted isoxazolylmethyl wherein the isoxazole ring is substituted with loweralkyl, thiazolylmethyl, substituted thiazolylmethyl wherein the thiazole ring is substituted with loweralkyl, isothiazolylmethyl and substituted isothiazolylmethyl wherein the isothiazole ring is substituted with loweralkyl.

Even more preferred compounds of the invention are compounds of the formula B wherein $R_1$ and $R_2$ are benzyl, phenethyl, 1-phenylprop-1-yl or 2-phenylprop-2-yl.

Even more preferred compounds of the invention are compounds of the formula B wherein $R_4$ is methyl, sec-butyl or isopropyl.

Even more preferred compounds of the invention are compounds of the formula B wherein $R_5$ is —C(O)—G—$R_7$ wherein G is —O— and $R_7$ is selected from benzyl, 3-pyridylmethyl, 5-oxazolylmethyl, 5-isoxazolylmethyl, 4-isoxazolylmethyl, 5-thiazolylmethyl and 5-isothiazolylmethyl.

Even more preferred compounds of the invention are compounds of the formula B wherein $R_6$ is —C(O)—G—$R_7$ wherein G is —O— or —N(CH$_3$)— and $R_7$ is 2-substituted-4-oxazolylmethyl wherein the oxazole ring is substituted with loweralkyl or 2-substituted-4-thiazolylmethyl wherein the thiazole ring is substituted with loweralkyl.

Even more preferred compounds of the invention are compounds of the formula C wherein $R_1$ and $R_2$ are benzyl, phenethyl, 1-phenylprop-1-yl or 2-phenylprop-2-yl.

Even more preferred compounds of the invention are compounds of the formula C wherein $R_3$ is methyl, sec-butyl or isopropyl.

Even more preferred compounds of the invention are compounds of the formula C wherein $R_6$ is —C(O)—G—$R_7$ wherein G is —O— and $R_7$ is selected from benzyl, 3-pyridylmethyl, 5-oxazolylmethyl, 5-isoxazolylmethyl, 4-isoxazolylmethyl, 5-thiazolylmethyl and 5-isothiazolylmethyl.

Even more preferred compounds of the invention are compounds of the formula C wherein $R_5$ is —C(O)—G—$R_7$ wherein G is —O— or —N(CH$_3$)— and $R_7$ is 2-substituted-4-oxazolylmethyl wherein the oxazole ring is substituted with loweralkyl or 2-substituted-4-thiazolylmethyl wherein the thiazole ring is substituted with loweralkyl.

Most preferred compounds of the invention are compounds of the formula B wherein $R_1$ and $R_2$ are benzyl, $R_4$ is methyl, sec-butyl or isopropyl, $R_5$ is —C(O)—G—$R_7$ wherein G is —O— and $R_7$ is selected from benzyl, 3-pyridylmethyl, 5-oxazolylmethyl, 5-isoxazolyl methyl, 4-isoxazolylmethyl, 5-thiazolylmethyl and 5-isothiazolylmethyl and $R_6$ is —C(O)—G—$R_7$ wherein G is —O— or —N(CH$_3$)— and $R_7$ is 2-substituted-4-oxazolylmethyl wherein the oxazole ring is substituted with ethyl or isopropyl or 2-substituted-4-thiazolylmethyl wherein the thiazole ring is substituted with ethyl or isopropyl.

Most preferred compounds of the invention are compounds of the formula C wherein $R_1$ and $R_2$ are benzyl, $R_3$ is methyl, sec-butyl or isopropyl, $R_6$ is —C(O)—G—$R_7$ wherein G is —O— and $R_7$ is selected from benzyl, 3-pyridylmethyl, 5-oxazolylmethyl, 5-isoxazolylmethyl, 4-isoxazolylmethyl, 5-thiazolylmethyl and 5-isothiazolylmethyl and $R_5$ is —C(O)—G—$R_7$ wherein G is —O— or —N(CH$_3$)— and $R_7$ is 2-substituted-4-oxazolylmethyl wherein the oxazole ring is substituted with ethyl or isopropyl or 2-substituted-4-thiazolylmethyl wherein the thiazole ring is substituted with ethyl or isopropyl.

Preferred compounds of the formula A, B and C are also those wherein the configuration of the carbon atom bearing $R_1$ is S, the configuration of the carbon atom bearing —OH is S, the configuration of the carbon atom bearing $R_3$ is S and the configuration of the carbon atom bearing $R_4$ is S.

The compounds of the invention comprise asymmetrically substituted carbon atoms. The present invention is intended to include all stereoisomeric forms of the compounds, including racemic mixtures, mixtures of diastereomers, as well as single diastereomers of the compounds of the invention. The terms "S" and "R" configuration are as defined by the IUPAC 1974 Recommendations for Section E, Fundamental Stereochemistry, Pure Appl. Chem. (1976) 45, 13–30.

The terms "Val" and "Ala" as used herein refer to valine and alanine, respectively. Unless otherwise noted, when "Val" and "Ala" are used herein they refer to the L-isomer. In general, the amino acid abbreviations used herein follow the IUPAC-IUB Joint Commission on Biochemical Nomenclature for amino acids and peptides (Eur. J. Biochem. 1984, 158, 9–31).

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "O-protecting group" as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)). O-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The term "loweralkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "alkylene" as used herein refers to a straight or branched chain carbon diradical containing from 1 to 6 carbon atoms including, but not limited to, —$CH_2$—, —$CH_2CH_2$—, —$CH(CH_3)CH_2$—, —$CH_2CH_2CH_2$— and the like.

The term "loweralkenyl" as used herein refers to a loweralkyl radical which contains at least one carbon-carbon double bond including, but not limited to, propenyl, butenyl and the like.

The term "aryl" as used herein refers to a $C_6$ monocyclic aromatic ring system or a $C_9$ or $C_{10}$ bicyclic carbocyclic ring system having one or two aromatic rings including, but not limited to, phenyl, naphthyl, tetrahydronaphthyl, indanyl, indenyl and the like. Aryl groups can be unsubstituted or substituted with one or two substituents independently selected from loweralkyl, haloalkyl, alkoxy, thioalkoxy, alkoxycarbonyl, alkanoyl, hydroxy, halo, mercapto, nitro, amino, alkylamino, dialkylamino, carboxaldehyde, carboxy, carboxamide, aryl, arylalkyl, arylalkoxy, heterocyclic, (heterocyclic)alkyl, (heterocyclic)alkoxy, aminoalkyl, aminoalkoxy, alkylaminoalkyl, alkylaminoalkoxy, dialkylaminoalkyl, dialkylaminoalkoxy, (alkoxyalkyl) aminoalkyl, (alkoxyalkyl)aminoalkoxy, di-(alkoxyalkyl) aminoalkyl, di-(alkoxyalkyl)aminoalkoxy, (alkoxyalkyl) (alkyl)aminoalkyl, (alkoxyalkyl)(alkyl)aminoalkoxy, hydroxyalkyl, hydroxyalkoxy, carboxyalkyl, carboxyalkoxy, alkoxyalkyl, thioalkoxyalkyl, polyalkoxyalkyl and dialkoxyalkyl. In addition, substituted aryl groups include tetrafluorophenyl and pentafluorophenyl.

The term "arylalkyl" as used herein refers to an aryl group appended to a loweralkyl radical including, but not limited to, benzyl, 4-hydroxybenzyl, 1-naphthylmethyl and the like.

The term "aminoalkyl" as used herein refers to —$NH_2$ appended to a loweralkyl radical.

The term "hydroxyalkyl" as used herein refers to —OH appended to a loweralkyl radical.

The term "dihydroxyalkyl" as used herein refers to a loweralkyl radical disubstituted with —OH groups.

The term "polyhydroxyalkyl" as used herein refers to a loweralkyl radical substituted with more than two —OH groups.

The term "mercaptoalkyl" as used herein refers to a loweralkyl radical to which is appended a mercapto (—SH) group.

The term "hydroxyaminoalkyl" as used herein refers to a hydroxyamino group (—NHOH) appended to a loweralkyl radical.

The term "alkoxyaminoalkyl" as used herein refers to —$NHR_{20}$ (wherein $R_{20}$ is an alkoxy group) appended to a loweralkyl radical.

The term "(alkoxy)(alkyl)aminoalkyl" as used herein refers to $(R_{21})(R_{22})N$— wherein $R_{21}$ is alkoxy and $R_{22}$ is loweralkyl appended to a loweralkyl radical.

The term "alkylamino" as used herein refers to a loweralkyl radical appended to an NH radical.

The term "cycloalkyl" as used herein refers to an aliphatic ring having 3 to 7 carbon atoms including, but not limited to, cyclopropyl, cyclopentyl, cyclohexyl and the like. Cycloalkyl groups can be unsubstituted or substituted with one or two substituents independently selected from loweralkyl, haloalkyl, alkoxy, thioalkoxy, amino, alkylamino, dialkylamino, hydroxy, halo, mercapto, nitro, carboxaldehyde, carboxy, carboalkoxy and carboxamide.

The term "cycloalkylalkyl" as used herein refers to a cycloalkyl group appended to a loweralkyl radical, including but not limited to cyclohexylmethyl.

The term "alkylaminocycloalkyl" as used herein refers to an alkylamino group appended to a cycloalkyl radical.

The term "dialkylaminocycloalkyl" as used herein refers to a dialkylamino group appended to a cycloalkyl radical.

The terms "alkoxy" and "thioalkoxy" as used herein refer to $R_{29}O$— and $R_{29}S$—, respectively, wherein $R_{29}$ is a loweralkyl group or benzyl.

The term "alkoxyalkyl" as used herein refers to an alkoxy group appended to a loweralkyl radical.

The term "thioalkoxyalkyl" as used herein refers to a thioalkoxy group appended to a loweralkyl radical.

The term "guanidinoalkyl" as used herein refers to a guanidino group (—NHC(=NH)$NH_2$) appended to a loweralkyl radical.

The term "alkenyloxy" as used herein refers to $R_{32}O$— wherein $R_{32}$ is a loweralkenyl group.

The term "hydroxyalkoxy" as used herein refers to —OH appended to an alkoxy radical.

The term "dihydroxyalkoxy" as used herein refers to an alkoxy radical which is disubstituted with —OH groups.

The term "arylaikoxy" as used herein refers $R_{33}O$— wherein $R_{33}$ is a arylalkyl group as defined above.

The term "(heterocyclic)alkoxy" as used herein refers to $R_{34}O$— wherein $R_{34}$ is a (heterocyclic)alkyl group.

The term "aryloxyalkyl" as used herein refers to a $R_{35}O$— group appended to a loweralkyl radical, wherein $R_{35}$ is an aryl group.

The term "dialkylamino" as used herein refers to —$NR_{36}R_{37}$ wherein $R_{36}$ and $R_{37}$ are independently selected from loweralkyl groups.

The term "N-protected aminoalkyl" as used herein refers to —$NHR_{40}$ appended to a loweralkyl group, wherein $R_{40}$ is an N-protecting group.

The term "alkylaminoalkyl" as used herein refers to —$NHR_{41}$ appended to a loweralkyl radical, wherein $R_{41}$ is a loweralkyl group.

The term "(N-protected)(alkyl)aminoalkyl" as used herein refers to —$NR_{42}R_{43}$, which is appended to a loweralkyl radical, wherein $R_{42}$ is an N-protecting group and $R_{43}$ is loweralkyl.

The term "dialkylaminoalkyl" as used herein refers to —$NR_{44}R_{45}$ which is appended to a loweralkyl radical wherein $R_{44}$ and $R_{45}$ are independently selected from loweralkyl.

The term "carboxyalkyl" as used herein refers to a carboxylic acid group (—COOH) appended to a loweralkyl radical.

The term "alkoxycarbonylalkyl" as used herein refers to a $R_{46}C(O)$— group appended to a loweralkyl radical, wherein $R_{46}$ is an alkoxy group.

The term "carboxyalkoxyalkyl" as used herein refers to a carboxylic acid group (—COOH) appended to an alkoxy group which is appended to a loweralkyl radical.

The term "alkoxycarbonylalkoxyalkyl" as used herein refers to an alkoxycarbonyl group ($R_{47}C(O)$— wherein $R_{47}$ is an alkoxy group) appended to an alkoxy group which is appended to a loweralkyl radical.

The term "(amino)carboxyalkyl" as used herein refers to a loweralkyl radical to which is appended a carboxylic acid group (—COOH) and an amino group (—$NH_2$).

The term "((N-protected)amino)carboxyalkyl" as used herein refers to a loweralkyl radical to which is appended a carboxylic acid group (—COOH) and —$NHR_{48}$ wherein $R_{48}$ is an N-protecting group.

The term "(alkylamino)carboxyalkyl" as used herein refers to a loweralkyl radical to which is appended a carboxylic acid group (—COOH) and an alkylamino group.

The term "((N-protected)alkylamino)carboxyalkyl" as used herein refers to a loweralkyl radical to which is appended a carboxylic acid group (—COOH) and an —$NR_{48}R_{49}$ wherein $R_{48}$. is as defined above and $R_{49}$ is a loweralkyl group.

The term "(dialkylamino)carboxyalkyl" as used herein refers to a loweralkyl radical to which is appended a carboxylic acid group (—COOH) and —$NR_{49}R_{49}$ wherein $R_{49}$ is as defined above.

The term "(amino)alkoxycarbonylalkyl" as used herein refers to a loweralkyl radical to which is appended an alkoxycarbonyl group as defined above and an amino group (—$NH_2$).

The term "((N-protected)amino)alkoxy-carbonylalkyl" as used herein refers to a loweralkyl radical to which is appended an alkoxycarbonyl group as defined above and —$NHR_{50}$ wherein $R_{50}$ is an N-protecting group.

The term "(alkylamino)alkoxycarbonylalkyl" as used herein refers to a loweralkyl radical to which is appended an alkoxycarbonyl group as defined above and an alkylamino group as defined above.

The term "((N-protected)alkylamino)alkoxycarbonylalkyl" as used herein refers to a loweralkyl radical to which is appended an alkoxycarbonyl group as defined above and —$NR_{51}R_{52}$ wherein $R_{51}$ is an N-protecting group and $R_{52}$ is a loweralkyl group.

The term "(dialkylamino)alkoxycarbonylalkyl" as used herein refers to a loweralkyl radical to which is appended an alkoxycarbonyl group as defined above and —$NR_{53}R_{54}$ wherein $R_{53}$ and $R_{54}$ are independently selected from loweralkyl.

The term "aminocycloalkyl" as used herein refers to an $NH_2$ appended to a cycloalkyl radical.

The term "((alkoxy)alkoxy)alkyl" as used herein refers to an alkoxy group appended to an alkoxy group which is appended to a loweralkyl radical.

The term "polyalkoxyalkyl" as used herein refers to a polyalkoxy residue appended to a loweralkyl radical.

The term "polyalkoxy" as used herein refers to —$OR_{67}$ wherein $R_{67}$ is a straight or branched chain containing 1–5, $C_{n'}$—O—$C_{n''}$ linkages wherein n' and n" are independently selected from 1 to 3, including but not limited to methoxyethoxymethoxy, methoxymethoxy and the like.

The term "halo" or "halogen" as used herein refers to —Cl, —Br, —I or —F.

The term "haloalkyl" as used herein refers to a loweralkyl radical in which one or more of the hydrogen atoms are replaced by halogen including, but not limited to, chloromethyl, trifluoromethyl, 1-chloro-2-fluoroethyl and the like.

The term "thioalkoxyalkyl" as used herein refers to a thioalkoxy group appended to a loweralkyl radical.

The term "alkylsulfonyl" as used herein refers to $R_{93}SO_2$— wherein $R_{93}$ is loweralkyl group.

The term "alkylsulfonylalkyl" as used herein refers to an alkylsufonyl group appended to a loweralkyl radical.

The term "arylthioalkyl" as used herein refers to $R_{94}$—S—$R_{95}$— wherein $R_{94}$ is an aryl group and $R_{95}$ is an alkylene group.

The term "aryloxyoalkyl" as used herein refers to $R_{94}$—O—$R_{95}$— wherein $R_{94}$ is an aryl group and $R_{95}$ is an alkylene group.

The term "arylsulfonylalkyl" as used herein refers to $R_{96}$—$S(O)_2$—$R_{97}$— wherein $R_{96}$ is any aryl group and $R_{97}$ is an alkylene group.

The term "(heterocyclic)oxyalkyl" as used herein refers to $R_{98}$—O—$R_{99}$— wherein $R_{98}$ is a heterocyclic group and $R_{99}$ is an alkylene group.

The term "(heterocyclic)thioalkyl" as used herein refers to $R_{100}$—S—$R_{101}$— wherein $R_{100}$ is a heterocyclic group and $R_{101}$ is an alkylene group.

The term "(heterocyclic)sulfonylalkyl" as used herein refers to $R_{102}$—$S(O)_2$—$R_{103}$— wherein $R_{102}$ is a heterocyclic group and $R_{103}$ is an alkylene group.

The "arylalkoxyalkyl" as used herein refers to $R_{104}$—O—$R_{105}$— wherein $R_{104}$ is an arylalkyl group and $R_{105}$ is an alkylene group.

The "arylthioalkoxyalkyl" as used herein refers to $R_{106}$—S—$R_{107}$— wherein $R_{106}$ is an arylalkyl group and $R_{107}$ is an alkylene group.

The "arylalkylsulfonylalkyl" as used herein refers to $R_{108}$—$S(O)_2$—$R_{109}$— wherein $R_{108}$ is an arylalkyl group and $R_{109}$ is an alkylene group.

The term "(heterocyclic)alkoxyalkyl" as used herein refers to $R_{110}$—O—$R_{111}$— wherein $R_{110}$ is a (heterocyclic) alkyl group and $R_{111}$ is an alkylene group.

The term "(heterocyclic)thioalkoxyalkyl" as used herein refers to $R_{112}$—S—$R_{113}$— wherein $R_{112}$ is a (heterocyclic) alkyl group and $R_{113}$ is an alkylene group.

The term "(heterocyclic)alkylsulfonylalkyl" as used herein refers to $R_{114}$—S(O)$_2$—$R_{115}$— wherein $R_{114}$ is a (heterocyclic)alkyl group and $R_{115}$ is an alkylene group.

The term "cycloalkyloxyalkyl" as used herein refers to $R_{116}$—O—$R_{117}$— wherein $R_{116}$ is a cycloalkyl group and $R_{117}$ is an alkylene group.

The term "cycloalkylthioalkyl" as used herein refers to $R_{118}$—S—$R_{119}$— wherein $R_{118}$ is a cycloalkyl group and $R_{119}$ is an alkylene group.

The term "cycloalkylsulfonylalkyl" as used herein refers to $R_{120}$—S(G)$_2$—$R_{121}$— wherein $R_{120}$ is a cycloalkyl group and $R_{121}$ is an alkylene group.

The term "cycloalkylalkoxyalkyl" as used herein refers to $R_{122}$—O—$R_{123}$— wherein $R_{122}$ is a cycloalkylalkyl group and $R_{123}$ is an alkylene group.

The term "cycloalkylthioalkoxyalkyl" as used herein refers to $R_{124}$—S—$R_{125}$— wherein $R_{124}$ is a cycloalkylalkyl group and $R_{125}$ is an alkylene group.

The term "cycloalkylalkylsulfonylalkyl" as used herein refers to $R_{126}$—S(O)$_2$—$R_{127}$— wherein $R_{126}$ is a cycloalkylalkyl group and $R_{127}$ is an alkylene group.

The term "alkanoyl" as used herein refers to $R_k$—C(O)— wherein $R_k$ is a loweralkyl group.

The term "aminocarbonyl" as used herein refers to —C(O)NH$_2$.

The term "aminocarbonylalkyl" as used herein refers to an aminocarbonyl group appended to a loweralkyl radical.

The term "alkylaminocarbonyl" as used herein refers to —C(O)NHR$_{128}$ wherein $R_{128}$ is loweralkyl.

The term "alkylaminocarbonylalkyl" as used herein refers to an alkylaminocarbonyl group appended to a loweralkyl radical.

The term "dialkylaminocarbonyl" as used herein refers to —C(O)NR$_{129}$R$_{130}$ wherein $R_{129}$ and $R_{130}$ are independently selected from loweralkyl.

The term "dialkylaminocarbonylalkyl" as used herein refers to a dialkylaminocarbonyl group appended to a loweralkyl group.

The term "aroylalkyl" as used herein refers to $R_{131}$—C(O)—$R_{132}$— wherein $R_{131}$ is an aryl group and $R_{132}$ is an alkylene group.

The term "(heterocyclic)carbonylalkyl" as used herein refers to $R_{133}$—C(O)—$R_{134}$— wherein $R_{133}$ is a heterocyclic group and $R_{134}$ is an alkylene group.

The term "aminoalkoxy" as used herein refers to an alkoxy radical to which is appended an amino (—NH$_2$) group.

The term "alkylaminoalkoxy" as used herein refers to an alkoxy radical to which is appended an alkylamino group.

The term "dialkylaminoalkoxy" as used herein refers to an alkoxy radical to which is appended a dialkylamino group.

The term "(alkoxyalkyl)aminoalkyl" refers to a loweralkyl radical to which is appended an (alkoxyalkyl)amino group.

The term "(alkoxyalkyl)aminoalkoxy" as used herein refers to an alkoxy radical to which is appended an (alkoxyalkyl)amino group.

The term "(alkoxyalkyl)(alkyl)aminoalkyl" refers to a loweralkyl radical to which is appended an (alkoxyalkyl)(alkyl)amino group.

The term "(alkoxyalkyl)(alkyl)aminoalkoxy" as used herein refers to an alkoxy radical to which is appended an (alkoxyalkyl)(alkyl)amino group.

The term "di-(alkoxyalkyl)aminoalkyl" refers to a loweralkyl radical to which is appended an di-(alkoxyalkyl)amino group.

The term "di-(alkoxyalkyl)aminoalkoxy" as used herein refers to an alkoxy radical to which is appended an di-(alkoxyalkyl)amino group.

The term "carboxyalkoxy" as used herein refers to an alkoxy radical to which is appended a carboxy (—COOH) group.

The term "aminocarbonylalkyl" as used herein refers to a loweralkyl radical to which is appended an aminocarbonyl (H$_2$NC(O)—) group.

The term "alkylaminocarbonylalkyl" as used herein refers to a loweralkyl radical to which is appended an alkylaminocarbonyl group.

The term "dialkylaminocarbonylalkyl" as used herein refers to a loweralkyl radical to which is appended an dialkylaminocarbonyl group.

At each occurrence, the term "heterocyclic ring" or "heterocyclic" as used herein independently refers to a 3- or 4-membered ring containing a heteroatom selected from oxygen, nitrogen and sulfur; or a 5- or 6-membered ring containing one, two or three heteroatoms independently selected from N, O and S. The 5-membered ring has 0–2 double bonds and the 6-membered ring has 0–3 double bonds. The nitrogen heteroatoms can be optionally quaternized or N-oxidized. The sulfur heteroatoms can be optionally S-oxidized. The term "heterocyclic also includes bicyclic groups in which any of the above heterocyclic rings is fused to a benzene ring or a cyclohexane ring or another heterocyclic ring. Heterocyclics include: pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolinyl, oxazolidinyl, isoxazolyl, isoxazolinyl, isoxazolidinyl, morpholinyl, thiazolyl, thiazolidinyl, isothiazolyl, isothiazolidinyl, indolyl, quinolinyl, tetrahydroquinolyl, isoquinolinyl, benzimidazolyl, benzothiazolyl, benzoxazolyl, benzofuranyl, furyl, dihydrofuranyl, tetrahydrofuranyl, pyranyl, dihydropyranyl, tetrahydropyranyl, dioxanyl, dioxolanyl, thienyl and benzothienyl.

Heterocyclics also include:

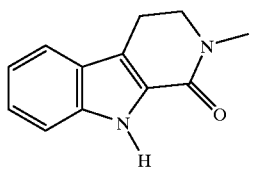

Preferred heterocyclics are pyridyl, thiazolyl, isothiazolyl, oxazolyl, isoxazolyl, furanyl, thienyl, tetrahydrofuranyl, tetrahydrothienyl and tetrahydro[2H]pyranyl.

Heterocyclics can be unsubstituted or monosubstituted or disubstituted with substituents independently selected from hydroxy, halo, oxo (=O), alkylimino (R*N= wherein R* is a loweralkyl group), amino, (N-protected)amino, alkylamino, (N-protected)alkylamino, dialkylamino, alkoxy, polyalkoxy, haloalkyl, cycloalkyl, cycloalkylalkyl, aryl, arylalkyl, —COOH, —SO$_3$H, loweralkenyl and loweralkyl. Heterocyclics can also be substituted with a heterocycle selected from aziridinyl, azetidinyl, pyrrolidinyl, piperidinyl, piperazinyl, morpholinyl, thiomorpholinyl, thiazolyl, oxazolyl, isoxazolyl, isothiazolyl, pyridinyl, pyrimidinyl, pyridazinyl and pyrazinyl, each of which can be unsubstituted or substituted with a substituent selected from halo, loweralkyl, hydroxy, alkoxy and thioalkoxy.

In addition, nitrogen containing heterocycles can be N-protected.

The term "(heterocyclic)alkyl" as used herein refers to a heterocyclic group appended to a loweralkyl radical, including but not limited to imidazolylmethyl and thiazolylmethyl.

In the compounds of the invention, combinations of substituents and/or variables are permissible only if such combinations result in stable compounds.

Preferred compounds of the invention are selected from the group consisting of:
5S-N-((2-Pyridinyl)methoxycarbonyl)valinylamino-2-((N-3-pyridinyl)methoxycarbonyl)amino-4S-hydroxy-1,6-diphenyl-2-azahexane;
5S-(((5-Thiazolyl)methoxy)carbonyl)amino-2-N-((N-methyl-N-((2-isopropyl-4-thiazolyl)methyl)amino)carbonyl)-L-valinylamino-4S-hydroxy-1,6-diphenyl-2-azahexane;
5S-((5-Thiazolyl)methoxy)carbonylamino-2-N-((N-methyl-N-((2-isopropyl-4-oxazolyl)methyl)amino)carbonyl)-L-valinylamino-4S-hydroxy-1,6-diphenyl-2-azahexane;
5S-N-((5-isoxazolyl)methoxy)carbonylamino-2-N-((N-methyl-N-((2-isopropyl-4-oxazolyl)methyl)amino)carbonyl)-L-valinylamino-4S-hydroxy-1,6-diphenyl-2-azahexane;
5S-(((5-Thiazolyi)methoxy)carbonyl)amino-2-N-(((N-methyl-N-((2-isopropyl-4-thiazolyl)methyl)amino)carbonyl)-L-valinyl)amino-4S-hydroxy-1-(3-furanyl)-6-phenyl-2-azahexane;
5S-(((5-Thiazolyl)methoxy)carbonyl)amino-2-((N-2-isopropyl-4-oxazolyl)methoxycarbonyl)amino-4S-hydroxy-1-(3-furanyl)-6-phenyl-2-azahexane;
5S-(((5-Thiazolyl)methoxy)carbonyl)amino-2-((N-2-isopropyl-4-oxazolyl)methoxycarbonyl)amino-4S-hydroxy-1,6-diphenyl-2-azahexane;
5S-(((2-Isopropyl-4-oxazolyl)methoxycarbonyl)-valinyl)amino-2-(t-butyloxycarbonyl)amino-4S-hydroxy-1-(4-hydroxyphenyl)-6-phenyl-2-azahexane; and
5S-(((5-Thiazolyl)methoxy)carbonyl)amino-2-N-((N-methyl-N-2-isopropyl-4-thiazolyl)methyl)amino) carbonyl)-L-valinyl-amino-4S-hydroxy-1-(4-hydroxyphenyl)-6-phenyl-2-azahexane.

Compounds useful as intermediates for the preparation of the compounds of formula A, B or C include the compound of the formula D:

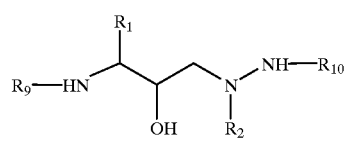

wherein R$_1$ and R$_2$ are independently selected from:
(i) hydrogen,
(ii) loweralkyl,
(iii) aryl,
(iv) thioalkoxyalkyl,
(v) (aryl)alkyl,
(vi) cycloalkyl,
(vii) cycloalkylalkyl,
(viii) hydroxyalkyl,
(ix) alkoxyalkyl,
(x) aryloxyalkyl,
(xi) haloalkyl,
(xii) carboxyalkyl,
(xiii) alkoxycarbonylalkyl,
(xiv) aminoalkyl,
(xv) (N-protected)aminoalkyl,
(xvi) alkylaminoalkyl,
(xvii) ((N-protected)(alkyl)amino)alkyl,
(xviii) dialkylaminoalkyl,
(xix) guanidinoalkyl,
(xx) loweralkenyl,
(xxi) heterocyclic,
(xxii) (heterocyclic)alkyl),
(xxiii) arylthioalkyl,
(xxiv) arylsulfonylalkyl,
(xxv) (heterocyclic)thioalkyl,
(xxvi) (heterocyclic)sulfonylalkyl,
(xxvii) (heterocyclic)oxyalkyl,
(xxviii) arylalkoxyalkyl,
(xxix) arylthioalkoxyalkyl,
(xxx) arylalkylsulfonylalkyl,
(xxxi) (heterocyclic))alkoxyalkyl,
(xxxii) (heterocyclic)thioalkoxyalkyl,
(xxxiii) (heterocyclic)alkylsulfonylalkyl,
(xxxiv) cycloalkyloxyalkyl,
(xxxv) cycloalkylthioalkyl,
(xxxvi) cycloalkylsulfonylalkyl,
(xxxvii) cycloalkylalkoxyalkyl,
(xxxviii) cycloalkylthioalkoxyalkyl,
(xxxix) cycloalkylalkylsulfonylalkyl,
(xl) aminocarbonyl,
(xli) alkylaminocarbonyl,
(xlii) dialkylaminocarbonyl,
(xliii) aroylalkyl,
(xliv) (heterocyclic)carbonylalkyl,
(xlv) polyhydroxyalkyl,
(xlvi) aminocarbonylalkyl,
(xlvii) alkylaminocarbonylalkyl,
(xlviii) dialkylaminocarbonylalkyl,
(xlix) aryloxyalkyl and
(l) alkylsulfonylalkyl;

R$_9$ and R$_{10}$ are independently selected from hydrogen and an N-protecting group; or an acid addition salt thereof.

Preferred compounds of the formula D are those wherein R$_1$ and R$_2$ are independently selected from loweralkyl, cycloalkylalkyl, aryl, arylalkyl, heterocyclic and (heterocyclic)alkyl.

Preferred compounds of the formula D are those wherein when both $R_9$ and $R_{10}$ are N-protecting groups, $R_9$ and $R_{10}$ are different.

Preferred compounds of the formula D are those wherein when both $R_9$ and $R_{10}$ are N-protecting groups, $R_9$ and $R_{10}$ can be selectively removed.

A preferred N-protecting group $R_9$ is t-butyloxycarbonyl or benzyloxycarbonyl.

A preferred N-protecting group $R_9$ is t-butyloxycarbonyl or benzyloxycarbonyl.

More preferred compounds of the formula D are those wherein $R_1$ and $R_2$ are independently selected from cyclohexylmethyl, arylalkyl, substituted arylalkyl wherein the aryl ring of the arylalkyl group is substituted with loweralkyl, halo, alkoxy, amino, alkylamino or dialkylamino, (heterocyclic)methyl wherein the heterocycle is independently seleted from pyridyl, thiazolyl, isothiazolyl, furanyl, thienyl, oxazolyl, isoxazolyl, tetrahydrofuranyl and tetrahydropyranyl and (substituted-heterocyclic)methyl wherein the heterocycle is substituted with loweralkyl, halo, alkoxy, amino, alkylamino or dialkylamino.

Even more preferred compounds of the formula D are those wherein $R_1$ and $R_2$ are benzyl, phenethyl, 1-phenylprop-1-yl or 2-phenylprop-2-yl.

The compounds of the invention can be prepared as shown in Schemes 1–6. As outlined in Scheme 1, olefination (for example, by Wittig reaction) of N-protected aldehyde 1 provides olefin 2. Epoxidation of olefin 2 (for example, with m-chloroperbenzoic acid (MCPBA)) provides a mixture of epoxides 3 and 4. Separation of the epoxides (for example, by chromatography) provides the desired epoxide isomer 4.

As outlined in Scheme 2, reaction of N-protected hydrazine 5 with an aldehyde or ketone derivative of substituent $R_2$ provides hydrazone 6. Reduction of hydrazone 6 (for example, by hydrogenation) provides hydrazine 7.

As outlined in Scheme 3, reaction of epoxide 4 with hydrazine 7 provides hydroxy hydrazine 8. Removal of N-protecting group $R_{10}$, followed by coupling with $R_5NHCH(R_3)C(O)OH$ or an activated derivative thereof, provides 10. Removal of N-protecting group $R_9$ provides 11. Reaction of 11 with $R_7$—G—C(T)—OH or an activated derivative thereof provides 12.

Alternatively, as outlined in Scheme 5, substitutent $R_6$ can be introduced before substituent —C(O)CH($R_3$)NH—$R_5$.

As outlined in Scheme 4, removal of N-protecting group $R_9$, followed by coupling with $R_6NHCH(R_4)C(O)OH$ or an activated derivative thereof, provides 14. Removal of N-protecting group $R_{10}$ provides 15. Reaction of 15 with $R_7$—G—C(T)—OH or an activated derivative thereof provides 16.

Alternatively, as outlined in Scheme 6, substitutent $R_5$ can be introduced before substituent —C(O)CH($R_4$)NH—$R_6$.

Scheme 7 outlines an alternative method for preparing 10. N-protected amino acid 21 or an activated derivative thereof is reacted with hydrazine to give 22. N-alkylation of 22 provides 23. Reaction of 23 with epoxide 4 gives 10.

Scheme 8 outlines an alternative method for preparing 14. N-protected amino acid 24 or an activated derivative thereof is reacted with 25 to provide 26. Epoxidation of 26 and separation of the epoxide isomers gives 27. Reaction of 27 with hydrazine 7 provides 14.

In the schemes, only one of the alternative definitions of substituent Y and Y' has been illustrated. However, one of ordinary skill in the art would know that the corresponding methods can be applied with the alternative definitions of substituents Y and Y'.

Activated derivates of carboxylic acids as used herein refers to acid halides and activated esters. Acid halide derivatives include the acid chloride. Activated ester derivatives include activated esters commonly used by those skilled in the art for activating carboxylic acid groups for coupling with an amine to form an amide bond or for coupling with an alcohol for forming an ester bond including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters, p-nitrophenol derived esters and the like.

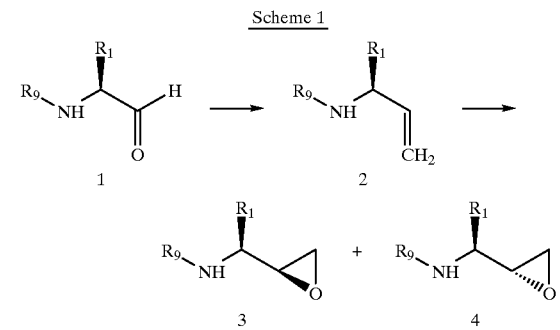

Scheme 1

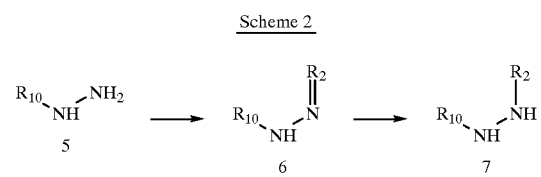

Scheme 2

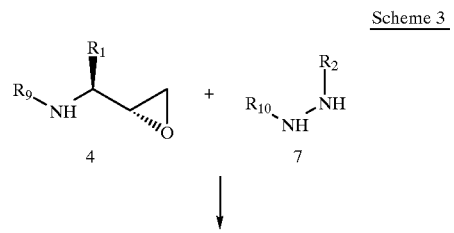

Scheme 3

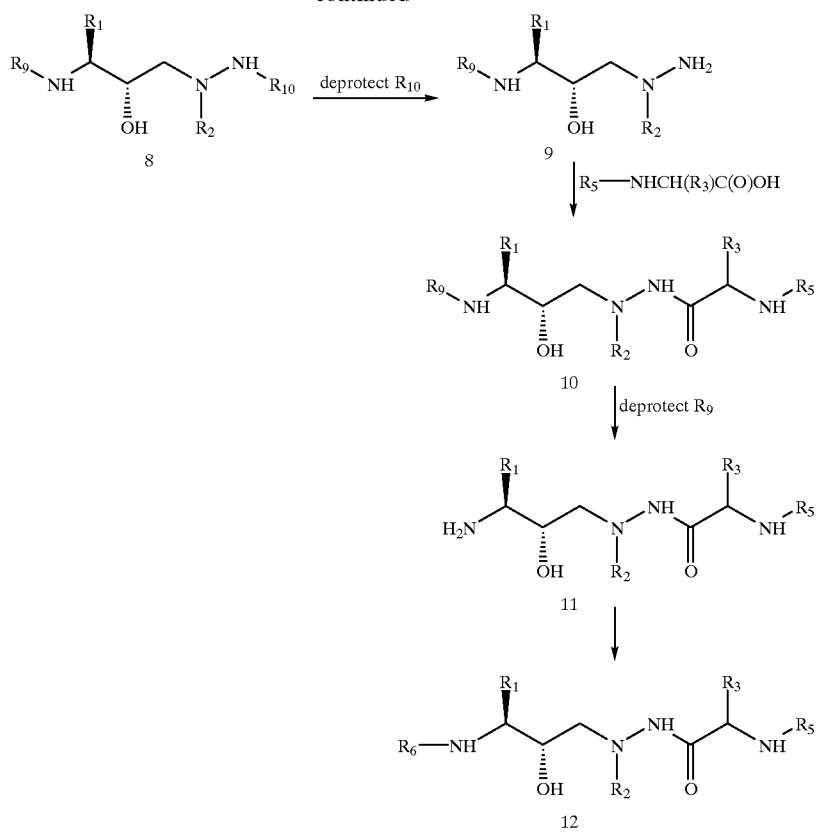
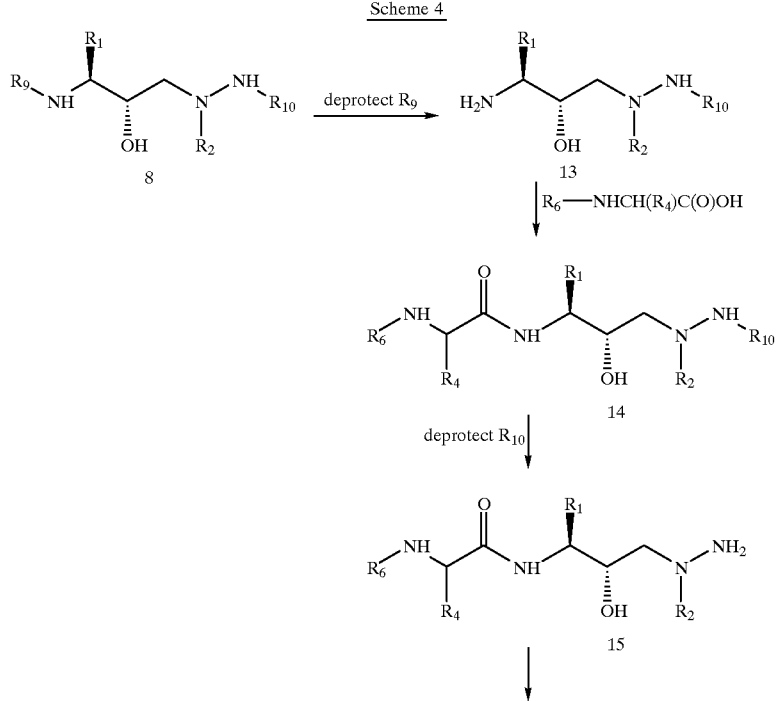
Scheme 4

-continued
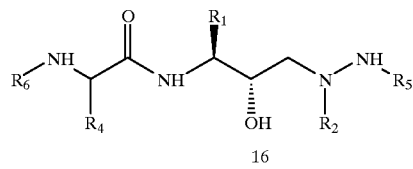
Scheme 5
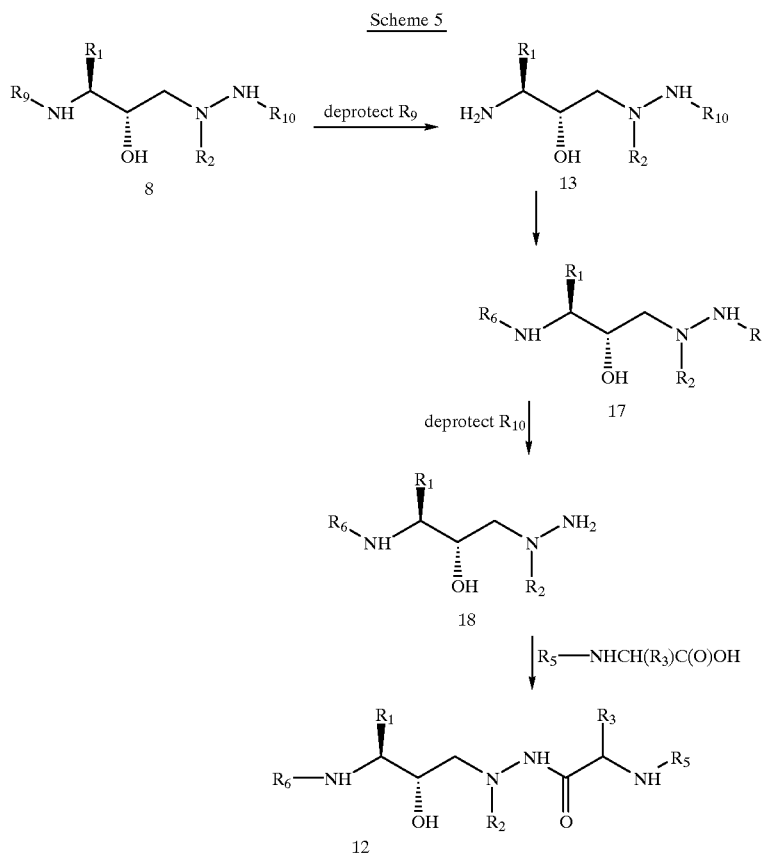
Scheme 6
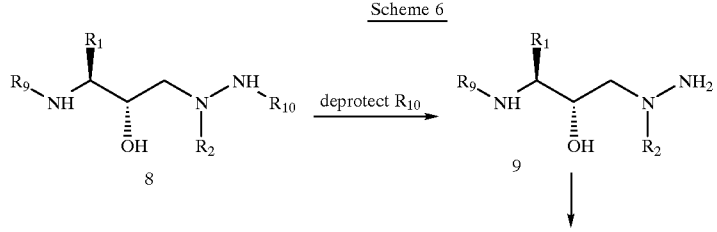

-continued
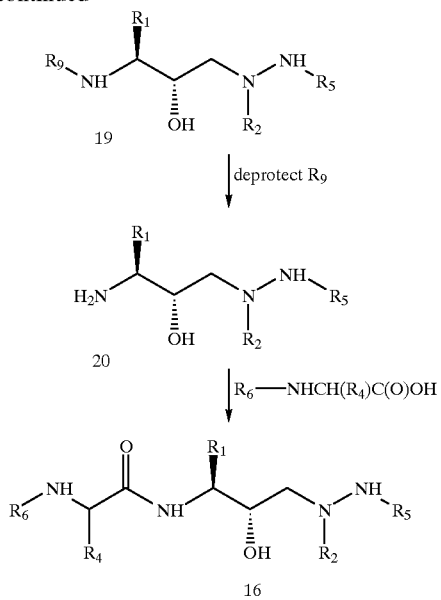
Scheme 7
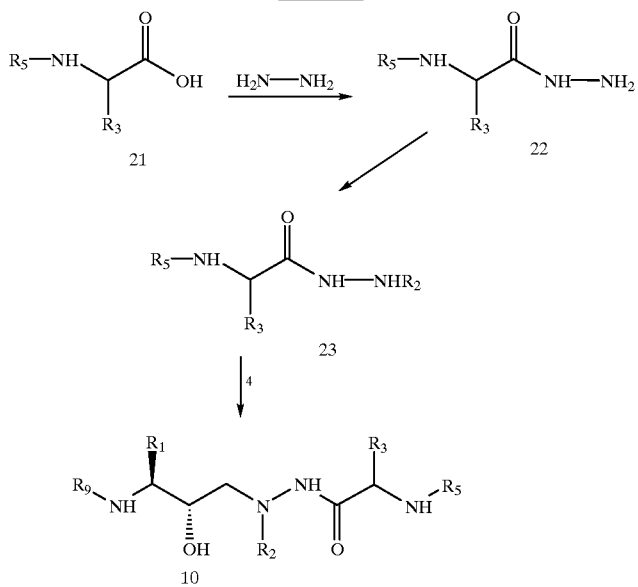

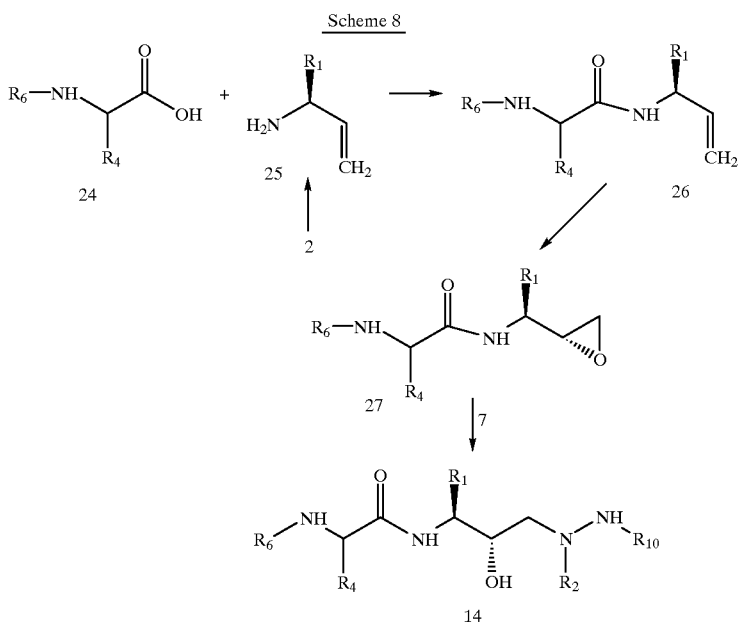

Scheme 8

The following examples will serve to further illustrate the preparation of the novel compounds of the invention.

EXAMPLE 1

A. N-((Benzyloxy)carbonyl)-L-phenylalaninal

To a solution of 1.8 ml of dimethyl sulfoxide in 20 ml of dichloromethane cooled to −78° C. was added slowly 1.65 ml of oxalyl chloride. The solution was stirred for 10 min at −78° C. and a solution of 3.6 g (0.012 mol) of N-((benzyloxy)carbonyl)-L-phenylalaninol in 45 ml of dichloromethane was added slowly. The resulting solution was stirred at −78° C. for 15 min, then 1 min at 0° C., recooling to −78° C. and 7.6 ml of triethylamine was added over 10 min. After stirring at −78° C. for 25 min, 20 ml of cold 10% aq. citric acid solution was added. After warming to 0° C., 200 ml of ether and 55 ml of cold 10% citric acid added. The organic layer was separated by separatory funnel and washed repeatedly (5×60 ml) with water and finally with satd. NaCl solution. The organic layer was dried over anhydrous sodium sulfate, filtered and concentrated in vacuo at RT to give 3.51 g of the desired compound as an off-white solid.

B. N-((Benzyloxy)carbonyl)-2S-amino-1-phenyl-but-3-ene

To a dry 3-neck flask was added 14.34 g of triphenylmethylphosphonium bromide. To this was added 70 ml of THF, cooled to 0° C., and 4.42 g of 35% potassium hydride dispersion in oil was added. The mixture was stirred at RT for 24 h. To this mixture was added 30 ml of toluene and let stand for 30 min. The supernatant was cannulated over into a solution of 3.37 g of N-((benzyloxy)carbonyl)-L-phenylalaninal in 50 ml of toluene at −78° C. The reaction mixture was stirred at −78° C. for 2 h, followed by 0.5 h at RT. Satd. ammonium chloride (50 ml) was added. The layers were separated; the aqueous layer was extracted with ethyl acetate (3×100 ml). The combined organic layer was washed with satd. aq. NaCl solution and dried over anhydrous sodium sulfate, filtered and concentrated to a yellow oil which was purified by silica gel column chromatography (30% ether/hexane) to provide 2.23 g (67%) of desired compound as a white solid.

C. N-((Benzyloxy)carbonyl)-2S-amino-1-phenyl-3R-3,4-epoxybutane

According to the procedure of Luly, et al. (J. Org. Chem. 52 1487 (1987)), to a solution of 1 g of the N-((benzyloxy)carbonyl)-2S-amino-1-phenyl-but-3-ene in 10 ml of dichloromethane at 0° C. was added 1.4 g of MCPBA. The solution was stirred at 0° C. for 1 h and then at RT overnight. It was added to 150 ml of ether and washed successively with cold 10% sodium thiosulfate, 10% sodium carbonate and then satd. aq. NaCl solution. The organic layer was dried and concentrate d to a colorless oil which was purified by silica gel column chromatography (20% EtOAc/hexane) to provide 0.9 g of the desired product containing small amount of the 3S diastereomer. $^1$H NMR (CDCl$_3$): δ 2.57 (m, 1 H), 2.70 (t, J=4.5 Hz, 1 H), 2.90–3.05 (m, 3 H), 4.20 (m, 1 H), 4.70 (br d, 1 H) 5.05 (s, 2 H), 7.20–7.38 (m, 10 H).

D. Hydrazone of benzaldehyde and t-butylcarbazate

To a solution of 10 g of t-butylcarbazate in 100 ml of THF was added slowly 8.03 g of benzaldehyde (1 eq.). The reaction mixture was stirred at RT overnight and the solvent was completely removed in vacuo. The solid residue was recrystallized from methanol to provide 11.6 g of desired product. $^1$H NMR (CDCl$_3$): δ 1.55 (s, 9 H), 7.37 (m, 3 H), 7.68 (m, 2 H), 7.84 (s, 1 H), 7.98 (s, 1 H).

E. N(1)-t-Butyloxycarbonyl-N(2)-benzyl-hydrazine

A solution of 5 g of the resultant compound of Example 1 D in 100 ml of ethyl acetate was hydrogenated using 10% palladium charcoal (1 g) as catalyst and under a hydrogen pressure of approx. 50 psi for 1 h. The catalyst was filtered off and the filtrate was concentrated in vacuo and purified by silica gel column chromatography (10% EtOAc/CH$_2$Cl$_2$) to provide 4.86 g of desired product. $^1$H NMR (CDCl$_3$): δ 1.47 (s, 9 H), 4.00 (s, 2 H), 4.20 (br s, 1 H), 6.03 (br s, 1 H), 7.37 (m, 5 H).

F. 2-(t-Butyloxycarbonyl)amino-4S-hydroxy-5S-(benzyloxycarbonyl)amino-1,6-diphenyl-2-azahexane To a solution of 150 mg of N-((benzyloxy)carbonyl)-2S-amino-3R-3,4-epoxybutane in 6 ml of ether an d 3 ml of THF was added 5 g of W-200 neutral alumina. The suspension was stirred vigorously at RT for 30 mn and a solution of N(1)-t-butyloxycarbonyl-N(2)-benzyl-hydrazine (330 mg) in 4 ml of ether was added. The reaction mixture was stirred vigorously for 72 h at RT. The alumina was filtered and washed with 100 ml of methanol. The filtrate was concentrated in vacuo and the residue was purified by silica gel column chromatography (20% EtOAc/hexane) to provide 138 mg (53%) of the desired compound. $^1$H NMR (CDCl$_3$): δ 1.33 (s, 9 H), 2.45 (m, 1H), 2.80 (m, 1 H), 2.96 (m, 2 H), 3.55–400 (m, 5 H), 5.08 (s, 2 H), 5.20 (s, 1 H), 5.37 (br d, 1 H), 7.18–7.36 (m, 15 H). Anal. Calcd. for C$_{30}$H$_{37}$N$_3$O$_5$: C, 69.34; H, 7.18; N, 8.09. Found: C, 69.52; H, 7.20; N, 8.00.

EXAMPLE 2

A. α-Isocyanato-valine Methyl Ester

A suspension of L-valine methyl ester hydrochloride (49 g, 0.29 mol) in toluene (700 ml) was heated to 100° C. and phosgene gas was bubbled into the reaction mixture. After approximately 6 h, the mixture became homogeneous. The bubbling of phosgene was continued for 10 more min, then the solution was cooled with the bubbling of N$_2$ gas . The solvent was then evaporated and the residue chased with toluene two times. Evaporation of solvent gave 40.8 g (89%) of the crude desired compound.

B. N-((2-Pyridinyl)methoxycarbonyl)valine Methyl Ester

A solution of 0.78 g (5.0 mmol) of α-isocyanato-valine methyl ester and 0.55 ml (5.7 mmol) of pyridine-2-methanol in 30 mL of toluene was heated at reflux under N$_2$ atmosphere for 4 h. The solvent was removed in vacuo, and the residue was purified by silica gel chromatography using 2% methanol in chloroform to give 0.72 g (54%) of the desired compound as an oil. $^1$H NMR (CDCl$_3$) δ 0.91 (d, J=7 Hz, 3 H), 0.98 (d, J=7 Hz, 3 H), 2.19 (m, 1 H), 3.75 (s, 3 H), 4.32 (dd, J=9, 5 Hz, 1 H), 5.24 (s, 2 H), 5.39 (br d, 1 H), 7.23 (ddd, J=8, 4, 1 Hz, 1 H), 7.37 (d, J=8 Hz, 1 H), 7.70 (td, J=8, 2 Hz, 1 H), 8.60 (br d, 1 H). Mass spectrum: (M+H)$^+$=267.

C. N-((2-Pyridinyl)methoxycarbonyl)valine

Using the procedure of Example 3E but replacing N-((N-methyl-N-((2-pyridinyl)methyl)amino)carbonyl)valine methyl ester with N-((2-pyridinyl)-methoxycarbonyl)valine methyl ester provided the desired compound.

D. 2-t-(Butyloxycarbonyl)amino-4S-hydroxy-5S-amino-1,6-diphenyl-2-azahexane

A solution of 50 mg of 2-(t-butyloxycarbonyl)amino-4S-hydroxy-5S-(benzyloxycarbonyl)amino-2-azahexane in 5 ml of methanol was stirred vigorously under a hydrogen atmosphere with catalytic amount of 10% Pd/C. After 1 h, the catalyst was filtered, washed with methanol and the filtrate conc. in vacuo to give 36 mg of the desired compound, which was used without further purification.

E. 5S-N-((2-Pyridinyl)methoxycarbonyl) valinylamino-2-t-butyloxycarbonyl-amino-4S-hydroxy-1,6-diphenyl-2-azahexane To 1.5 ml of dry DMF was added successively at 0° C. the following: N-((2-pyridinyl)methoxycarbonyl)valine (30 mg); 2-t-(butyloxycarbonyl)amino-4S-hydroxy-5S-amino-1,6-diphenyl-2-azahexane (36 mg); ethyl-dimethylamino-propyl-carbodiimide hydrochloride (48 mg); N-hydroxybenzotriazole (47 mg); triethylamine (0.017 ml). The reaction mixture was stirred at 0° C., for 2 h, then at RT overnight. The solvent was removed in vacuo and the residue was dissolved in 100 ml ethyl acetate and washed with satd. NaHCO$_3$ solution and then satd. brine. The organic layer was dried with anhydrous sodium sulfate, filtered and the filtrate conc. in vacuo. The crude product obtained was purified by silica gel column chromatography (2% MeOH in CH$_2$Cl$_2$) to provide 43 mg of desired compound as a white solid. $^1$H NMR (CDCl$_3$): δ 0.71 (m, 6 H), 1.25 (s, 9 H), 1.80 (m, 1 H), 2.55–2.90 (m, 2 H), 3.80 (m, 2 H), 4.00 (m, 1 H), 4.70 (br s, 1 H), 5.08 (s, 2 H), 7.20–7.28 (m, 11 H), 7.36 (br d, 1 H), 7.60 (br d, 1 H), 7.70 (t, 1 H), 7.90 (br s, 1 H), 8.50 (br d, 1 H). Mass spectrum: (M+H)$^+$= 620.

EXAMPLE 3

A. 2-(N-(t-Butyloxycarbonyl)aminomethyl)pyridine

A solution of 21.2 g (97 mmol) of di-t-butyldicarbonate in 200 ml of dichloromethane was cooled to 0° C. and treated in portions with 10 ml (97 mmol) of 2-(aminomethyl) pyridine. After being allowed to warm to ambient temperature and stirred overnight, the resulting solution was diluted with 100 ml of dichloromethane, washed with three 100 ml portions of water, dried over Na$_2$SO$_4$, and concentrated in vacuo to provide 19.8 g (98%) of the desired compound (R$_f$ 0.28, 5% methanol in chloroform). $^1$H NMR (CDCl$_3$) δ 1.47 (s, 9 H), 4.45 (d, J=6 Hz, 2 H), 5.56 (br, 1 H), 7.18 (m, 1 H), 7.28 (d, J=8 Hz, 1 H), 7.66 (td, J=7, 2 Hz, 1 H), 8.53 (m, 1 H). Mass spectrum: (M+H)$^+$=209.

B. 2-((N-(t-Butyloxycarbonyl)-N-methylamino) methyl)pyridine

A solution of 19.8 g (95 mmol) of 2-(N-(t-butyloxycarbonyl)aminomethyl)-pyridine in anhydrous tetrahydrofuran was cooled under N$_2$ atmosphere to 0° C. and treated with 4.95 g (124 mmol) of sodium hydride (60% dispersion in oil). The solution was stirred for 15 min, treated dropwise with 7.1 ml (114 mmol) of methyl iodide, stirred at ambient temperature for 2 h, and quenched cautiously with water. The resulting mixture was partitioned between ether and water, dried over Na$_2$SO$_4$, and concentrated in vacuo. Chromatography on silica gel provided 14.9 g (70%) of the desired compound as a colorless oil. $^1$H NMR (CDCl$_3$) δ 1.43, 1.49 (two s, 9 H), 2.89, 2.94 (two s, 3 H), 4.54, 4.57 (two s, 2 H), 7.2 (m, 2 H), 7.67 (td, J=8, 2 Hz, 1 H), 8.55 (d, J=4 Hz, 1 H). Mass spectrum: (M+H)$^+$=223.

C. 2-(N-Methylamino)methyl)pyridine Dihydrochloride 2-((N-(t-Butyloxycarbonyl)-N-methylamino)methyl) pyridine (10 g) was treated with 200 ml of 6 M aqueous HCl and heated at reflux for 10 min. After being allowed to cool, the solution was concentrated in vacuo. The residue was treated twice with 50 ml of dioxane and concentrated in vacuo to provide the crude desired compound as a light brown solid.

D. N-((N-Methyl-N-((2-pyridinyl)methyl)amino) carbonyl)valine Methyl Ester

A mixture of 1.61 g (7.2 mmol) of 2-(N-methylamino) methyl)pyridine dihydrochloride and 1.14 g (7.2 mmol) of α-isocyanato-valine methyl ester in 40 ml of dichloromethane was treated with 2 ml (18 mmol) of 4-methylmorpholine. After being stirred for 2 h, the solution was partitioned between dichloromethane and water, dried over $Na_2SO_4$, and concentrated. Chromatography on silica gel using 2% methanol in chloroform provided 1.94 g (96%) of the desired compound ($R_f$ 0.32, 5% methanol in chloroform) as a colorless oil. $^1$H NMR (CDCl$_3$) δ 0.93 (d, J=7 Hz, 3 H), 0.97 (d, J=7 Hz, 3 H), 2.16 (m, 1 H), 3.03 (s, 3 H), 3.72 (s, 3 H), 4.43 (dd, J=8, 5 Hz, 1 H), 4.55 (s, 2 H), 6.15 (br, 1 H), 7.22 (dd, J=8, 6 Hz, 1 H), 7.28 (d, J=6 Hz, 1 H), 7.69 (br t, 1 H), 8.55 (d, J=5 Hz, 1 H). Mass spectrum: (M+H)$^+$=280.

E. N-((N-Methyl-N-((2-pyridinyl)methyl)amino)carbonyl)valine

A solution of 4.47 g (16 mmol) of N-((N-methyl-N-((2-pyridinyl)methyl)-amino)carbonyl)valine methyl ester in 65 ml of dioxane was treated with 65 ml of 0.5 M aqueous lithium hydroxide. After being stirred at ambient temperature for 1 h, the resulting solution was concentrated in vacuo to a small volume (ca. 5 ml), neutralized to pH 5 with 1 M aqueous HCl, and extracted with three 100 ml portions of ethyl acetate. The combined organic layers were dried over $Na_2SO_4$ and concentrated in vacuo to provide 3.61 g (85%) of the desired compound as an oil.

F. 5S-N-((N-Methyl)-N-((2-pyridinyl)methyl)amino)carbonyl)valinylamino-2-t-butyloxycarbonylamino-4S-hydroxy-1,6-diphenyl-2-azahexane Using the coupling procedure of Example 2E but replacing N-((2-pyridinyl)methoxycarbonyl)valine with N-((N-methyl-N-((2-pyridinyl)methyl)-amino)carbonyl)valine provided the desired compound.

EXAMPLE 4

A. ((3-Pyridinyl)methyl)-(4-nitrophenyl)carbonate

A solution 20 g (0.1 mol) of (4-nitrophenyl)-chloroformate in 150 ml of dichloromethane was cooled to 0° C. and treated sequentially with 8.0 ml (0.083 mol) of pyridine-3-methanol and 11 ml (0.1 mol) of 4-methylmorpholine. After addition, the solution was allowed to come to ambient temperature, stirred for 0.5 h, diluted with dichloromethane, washed sequentially with aqueous NaHCO$_3$ and water, dried over Na$_2$SO$_4$, and concentrated in vacuo. The residue was broken up, triturated with 3:1 hexane:ethyl acetate, and filtered. The resulting solid was dissolved in a minimum amount of boiling ethyl acetate/hexane, filtered hot to remove an insoluble dark oil, and allowed to cool. The desired crystalline product (18.65 g, 82%) was collected by filtration.

B. 5S-((3-Pyridinyl)methoxycarbonyl)amino-2-t-butyloxycarbonylamino-4S-hydroxy-1,6-diphenyl-2-azahexane To a solution of 32 mg of the compound from Example 4A in 0.5 ml of DMF was added 30 mg of the compound from Example 2D. The reaction mixture was stirred at RT overnight and the solvent was removed in vacuo. The crude product was purified by silica gel column chromatography (20% acetone in CH$_2$Cl$_2$) to provide 22 mg of the desired compound. $^1$H NMR (CDCl$_3$): δ 1.34 (s, 9 H), 2.45 (m, 1 H), 2.77 (m, 1 H), 2.95 (m, 2 H), 3.60–4.00 (m, 4 H), 5.10 (m, 2 H), 5.40 (br d, 1 H), 7.20–7.38 (m, 11 H), 7.70 (br d, 1 H), 8.60 (m, 2 H).

EXAMPLE 5

A. 5S-N-((2-Pyridinyl)methoxycarbonyl)valinylamino-2-amino-4S-hydroxy-1,6-diphenyl-2-azahexane To 200 mg of the compound from Example 2E was added 6 ml of 4N HCl in dioxane. After 1 h at RT, the solvent was removed in vacuo and the residue was neutralized with satd. NaHCO$_3$ and extracted with EtOAc (3×100 ml), dried with anhydrous Na$_2$SO$_4$; filtered and conc. in vacuo. The crude product was purified by silica gel column chromatography (5% methanol in CH$_2$Cl$_2$) to provide 126 mg of desired compound. $^1$H NMR (CDCl$_3$): δ 0.80 (d, 2 H), 0.90 (d, 2 H), 2.12 (m, 1 H), 2.60 (m, 2 H), 2.90 (m, 2 H), 3.55 (d, 1 H), 3.85 (d, 1 H), 4.00 (m, 2 H), 4.12 (m, 1 H), 5.20 (q, 2 H), 5.32 (d, 1 H), 6.55 (br d, 1 H), 7.10–7,40 (m, 12 H), 7.70 (m, 1 H), 8.60 (d, 1 H).

B. 5S-N-((2-Pyridinyl)methoxycarbonyl)valinylamino-2-((N-3-pyridinyl)methoxycarbonyl)amino-4S-hydroxy-1,6-diphenyl-2-azahexane To a solution of 120 mg of the compound from Example 5A in 3 ml of DMF was added 126 mg of ((3-pyridinyl)methyl)-(4-nitrophenyl)carbonate and the reaction mixture was heated to 55° C. for 16 h; cooled and the solvent removed in vacuo. The crude product was purified by silica gel column chromatography (3% to 5% methanol in CH$_2$Cl$_2$) to provide 100 mg of desired compound. $^1$H NMR (CDCl$_3$): δ 0.68 (d, 3 H), 0.72 (d, 3 H), 1.82 (m, 1 H), 2.62–2.80 (m, 2 H), 3.60 (m, 1 H), 3.80 (m, 2 H), 4.15 (m, 1 H), 4.70 (m, 1 H), 4.98 (s, 2 H), 5.10 (s, 2 H), 7.15–7.38 (m, 10 H), 7.50 (m, 2 H), 7.80 (m, 1 H), 8.50 (m, 4 H). Mass spectrum: (M+H)$^+$=655.

EXAMPLE 6

A. 2-Methylpropane-thioamide

A suspension of 100 g (1.15 mol) of isobutyramide in 4 L of diethyl ether was stirred vigorously and treated in portions with 51 g (0. 115 mol) of P$_4$S$_{10}$. The resulting mixture was stirred at ambient temperature for 2 h, filtered, and concentrated in vacuo to provide 94.2 g (80%) of the crude desired compound. $^1$H NMR (DMSO-d$_6$) δ 1.08 (d, J=7 Hz, 6 H), 2.78 (heptet, J=7 Hz, 1 H), 9.06 (br, 1 H), 9.30 (br, 1 H). Mass spectrum: (M+H)$^+$=104.

B. 4-(Chloromethyl)-2-ispronylthiazole hydrochloride

A mixture of 94.0 g (0.91 mol) of 2-methylpropane-thioamide, 115.7 g (0.91 mol) of 1,3-dichloroacetone, and 109.7 g (0.91 mol) of MgSO$_4$ in 1.6 liters of acetone was heated at reflux for 3.5 h. The resulting mixture was allowed to cool, filtered, and the solvent was removed in vacuo to provide the crude desired compound as a yellow oil. $^1$H NMR (DMSO-d$_6$) δ 1.32 (d, J=7 Hz, 6 H), 3.27 (heptet, J=7 Hz, 1 H), 4.78 (s, 2 H), 7.61 (s, 1 H). Mass spectrum: (M+H)$^+$=176.

C. 2-Isopropyl-4-(((N-methyl)amino)methyl)thiazole

A solution of 40 g of 4-(chloromethyl)-2-isopropylthiazole hydrochloride in 100 ml of water was added dropwise with stirring to 400 ml of 40% aqueous methylamine. The resulting solution was stirred for 1 h, then concentrated in vacuo. The residue was taken up in chloroform, dried over Na$_2$SO$_4$, and concentrated in vacuo. Purification of the residue by silica gel chromatography using 10% methanol in chloroform provided 21.35 g (55%) of the desired compound. $^1$H NMR (DMSO-d$_6$) δ 1.34 (d, J=7 Hz, 6 H), 2.56 (s, 3 H), 3.30 (heptet, J=7 Hz, 1 H), 4.16 (s, 2 H), 7.63 (s, 1 H). Mass spectrum: (M+H)$^+$=171.

D. N-(((4-Nitrophenyl)oxy)carbonyl)-L-valine Methyl Ester

A solution of 66.1 g (0.328 mol) of 4-nitrophenyl chloroformate in 1.2 liters of CH$_2$Cl$_2$ was cooled to 0° C. and treated with L-valine methyl ester hydrochloride. The resulting mixture was treated slowly, with stirring, with 68.9 ml (0.626 mol) of 4-methylmorpholine. The resulting solution was allowed to slowly warm to ambient temperature and was stirred overnight. After washing with 3 portions of 10% aqueous NaHCO$_3$, the solution was dried over Na$_2$SO$_4$ and concentrated in vacuo. The residue was purified by silica gel chromatography by eluting with chloroform to provide the desired compound. $^1$H NMR (DMSO-d$_6$) δ 0.94 (d, J=7Hz, 3 H), 0.95 (d, J=7 Hz, 3 H), 2.12 (octet, J=7 Hz, 1 H), 3.69 (s, 3 H), 4.01 (dd, J=8, 6 Hz, 1 H), 7.41 (dt, J=9, 3 Hz, 2 H), 8.27 (dt, J=9, 3 Hz, 2 H), 8.53 (d, J=8 Hz, 1 H). Mass spectrum: (M+NH$_4$)$^+$=314.

E. N-((N-Methyl-N-((2-isopropyl-4-thiazolyl)methyl)amino)carbonyl)-L-valine Methyl Ester A solution of 15.7 g (92 mmol) of 2-isopropyl-4-(((N-methyl)amino)-methyl)thiazole in 200 ml of THF was combined with a solution of 20.5 g (69 mmol) of N-(((4-nitrophenyl)oxy)carbonyl)-L-valine methyl ester. The resulting solution was treated with 1.6 g of 4-dimethylaminopyridine and 12.9 ml (92 mmol) of triethylamine, heated at reflux for 2 h, allowed to cool, and concentrated in vacuo. The residue was taken up in CH$_2$Cl$_2$, washed extensively with 5% aqueous K$_2$CO$_3$, dried over Na$_2$SO$_4$, and concentrated in vacuo. The resulting product mixture was purified by silica gel chromatography using chloroform as an eluent to provide 16.3 g (54%) of the desired compound. $^1$H NMR (DMSO-d$_6$) δ 0.88 (d, J=7 Hz, 3 H), 0.92 (d, J=7 Hz, 3 H), 1.32 (d, J=7 Hz, 3 H), 2.05 (octet, J=7 Hz, 1 H), 2.86 (s, 3 H), 3.25 (heptet, J=7 Hz, 1 H), 3.61 (s, 3 H), 3.96 (dd, J=8, 7 Hz, 1 H), 4.44 (AA', 2 H), 6.58 (d, J=8 Hz, 1 H), 7.24 (s, 1 H). Mass spectrum: (M+H)$^+$=328.

F. N-((N-Methyl-N-((2-isopropyl-4-thiazolyl)methyl)amino)carbonyl)-L-valine

A solution of 1.42 g (4.3 mmol) N-((N-methyl-N-((2-isopropyl-4-thiazolyl)methyl)amino)carbonyl)-L-valine methyl ester in 17 ml of dioxane was treated with 17.3 ml of 0.50 M aqueous LiOH. The resulting solution was stirred at ambient temperature for 30 m in, treated with 8.7 ml of 1 M HCl, and concentrated in vacuo. The residue was taken up in dichloromethane, washed with water, dried over Na$_2$SO$_4$, and concentrated in vacuo to provide 1.1 g (81%) of the desired compound. Mass spectrum: (M+H)$^+$=314.

G. 5-S (Benzyloxycarbonyl-amino-2-amino-4S-hydroxy-1,6-diphenyl-2-azahexane

A solution of 300 mg of the compound from Example 1F in 10 ml of 4N HCl in dioxane was stirred at RT for 1 h. The solvent was removed in vacuo and the residue was neutralized with satd. NaHCO$_3$ and extracted with EtOAc (3×50 ml), dried and conc. in vacuo. Purification by silica gel column chromatography (30% EtOAc in CH$_2$Cl$_2$) provided 140 mg of the desired compound

H. 5S-(Benzyloxycarbonyl)amino-2-N-(((N-methyl-N-((2-isopropyl-4-thiazolyl)methyl)amino)carbonyl)-L-valinyl)amino-4S-hydroxy-1,6-diphenyl-2-azahexane Coupling of 130 mg of the compound from Example 6G with 115 mg of the compound from Example 6F, using the procedure described in Example 2E provided the desired compound (175 mg). $^1$H NMR (CDCl$_3$): δ 0.50 (d, 3 H), 0.58 (d, 3 H), 1.27 (d, 6 H), 1.65 (m, 1 H), 2.70 (m, 3 H), 2.85 (s, 3 H), 3.62 (m, 1 H), 3.70–3.98 (m, 3 H), 4.95 (m, 3 H), 6.10 (br d, 1 H), 7.15–7.30 (m, 15 H), 9.01 (s, 1 H).

EXAMPLE 7

A. Thioformamide

To a cooled (0° C.) 2 L three neck round bottom flask equipped with an overhead stirrer charged with a solution of formamide (30.5 mL, 0.76 mol) in 1 L of diethyl ether was added 89 g (0.19 mol) of phosphorous pentasulfide in small portions. The reaction mixture was allowed to warm to ambient temperature, stirred for 2 h, filtered, and concentrated in vacuo to afford thioformamide as a yellow offensive smelling oil which was used without purification.

B. Ethyl 2-Chloro-2-formylacetate

To a three neck 2 L round bottom flask charged with potassium t-butoxide (0.5 mol, 500 mL of a 1 M solution in THF) and 500 mL of dry THF cooled to 0° C. was added dropwise from an addition funnel a solution of ethyl chloroacetate (0.5 mol, 53.5 mL) and ethyl formate (0.5 mol, 40.4 mL), in 200 mL of THF over 3 hours. After completion of addition, the reaction mixture was stirred for 1 hour and allowed to stand overnight. The resulting solid was diluted with diethyl ether and cooled in an ice bath. Then, the pH was lowered to approximately 3 using 6N HCl. The organic phase was separated, and the aqueous layer was washed 3 times with diethyl ether. The combined ethereal portions were dried over NaSO$_4$, and concentrated in vacuo. The crude desired compound was stored at −30° C. and used without further purification.

C. Ethyl Thiazole-5-carboxylate

To a round bottom flask was added 250 mL of dry acetone, 7.5 g (0.123 mol) of thioformamide, and 18.54 g (0.123 mol) of ethyl 2-chloro-2-formylacetate. The reaction was heated at reflux for 2 hours. The solvent was removed in vacuo, and the residue was purified by chromatography (SiO$_2$, 6 cm o.d. column, 100% CHCl$_3$, R$_f$=0.25) to provide 11.6 g (60%) of the desired compound as a light yellow oil. NMR (CDCl$_3$) δ 1.39 (t, J=7 Hz, 3 H), 4.38 (q, J=7 Hz, 2 H), 8.50 (s, 1 H), 8.95 (s, 1 H).

D. 5-(Hydroxymethyl)thiazole

To a precooled (ice bath) three neck 500 mL flask containing lithium aluminum hydride (76 mmol) in 250 mL of THF was added ethyl thiazole-5-carboxylate (11.82 g, 75.68 mmol) in 100 mL of THF dropwise over 1.5 hours to avoid excess foaming. The reaction was stirred for an additional hour, and treated cautiously with 2.9 mL of water, 2.9 mL of 15% NaOH, and 8.7 mL of water. The solid salts were filtered, and the filtrate set aside. The crude salts were heated at reflux in 100 mL of ethyl acetate for 30 min. The resulting mixture was filtered, and the two filtrates were combined, dried over Na$_2$SO$_4$, and concentrated in vacuo. The product was purified by silica gel chromatography eluting sequentially with 0%–2%–4% methanol in chloroform, to provide the desired compound, Rf=0.3 (4% methanol in chloroform), which solidified upon standing in 75% yield. NMR (CDCl$_3$) δ 4.92 (s, 2 H), 7.78 (s, 1 H), 8.77 (s, 1 H). Mass spectrum: (M+H)$^+$=116.

E. ((5-Thiazolyl)methyl)-(4-nitrophenyl)carbonate

A solution of 3.11 g (27 mmol) of 5-(hydroxymethyl)thiazole and excess N-methyl morpholine in 100 ml of methylene chloride was cooled to 0° C. and treated with 8.2 g (41 mmol) of 4-nitrophenyl chloroformate. After being stirred for 1 h, the reaction mixture was diluted with CHCl$_3$, washed successively with 1N HCl, saturated aqueous NaHCO$_3$, and saturated brine, dried over NaSO$_4$, and concentrated in vacuo. The residue was purified by silica gel chromatography (SiO2, 1–2% MeOH/CHCl$_3$, Rf=0.5 in 4% MeOH/CHCl$_3$) to yield 5.9 g (78%) of the desired compound as a yellow solid. NMR (CDCl$_3$) δ 5.53 (s, 2 H), 7.39 (dt, J=9, 3 Hz, 2 H), 8.01 (s, 1 H), 8.29 (dt, J=9, 3 Hz, 2 H), 8.90 (s, 1 H). Mass spectrum: (M+H)$^+$=281.

F. 5S-(((5-Thiazolyl)methoxy)carbonyl)amino-2-(t-butyloxycarbonyl)amino-4S-hydroxy-1,6-diphenyl-2-azahexane To a solution of 270 mg of the compound from Example 2D in 3 ml of DMF was added 216 mg of the resultant compound of Example 7E. The solution was stirred at RT overnight and the solvent was removed in vacuo. The crude product was purified by silica gel column chromatography (10% to 20% acetone in CH$_2$Cl$_2$) to provide 310 mg of the desired compound. $^1$H NMR (CDCl$_3$): δ 1.25 (s, 9 H), 2.55–2.86 (m, 4 H), 3.60 (m, 1 H), 3.82 (m, 2 H), 4.60 (m, 1 H), 5.14 (s, 2 H), 7.15–7.30 (m, 10 H), 7.84 (s, 1 H), 8.00 (s, 1 H), 9.03 (s, 1 H).

EXAMPLE 8

5S-(((5-Thiazoly)methoxy)carbonyl)amnio-2-N-((N-methyl-N-((2-isopropyl-4-thiazoly)methyl)amino)carbonyl)-L-valinylamino-4S-hydroxy-1,6-diphenyl-2-azahexane Deprotecion of the t-butyloxycarbonyl protecting group of the compound from Example 7F according to the procedure of Example 6G and coupling of the resulting compound with the compound from Example 6F, using the procedure described in Example 2E provided the desired compound. $^1$H NMR (CDCl$_3$): δ 0.48 (d, 3 H), 0.57 (d, 3 H), 1.28 (d, 6 H), 1.65 (m, 1 H), 2.70 (m, 3 H), 2.83 (s, 3 H), 3.60 (m, 1 H), 3.70–3.95 (m, 4 H), 4.43 (s, 2 H), 4.88 (d, 1 H), 5.13 (s, 2 H), 6.14 (br d, 1 H), 7.12–7.30 (m, 10 H), 7.82 (s, 1 H), 9.01 (s, 1 H), 9.03 (s, 1 H). Mass spectrum: (M+H)$^+$=722.

EXAMPLE 9

A. 4-Chlomromethyl-4-hydroxy-2-isopropyloxazoline

To a solution of isobutyramide (9.876 g, 0.1122 mol) in acetone (130 mL) was added 1,3-dichloroacetone (10.0 g, 0.0748 mol), NaHCO$_3$ (9.429 g, 0.122 mol), and MgSO$_4$ (18.01 g, 0.1496 mol). The mixture was heated at reflux under argon for 63 hrs, then cooled to room temperature, vacuum filtered, and concentrated in vacuo to a dark brown semi-solid. The residue was purified by SiO$_2$ flash chromatography using a gradient of EtOAc/CH$_2$Cl$_2$ (5%, 10%, 20%, 40%) to obtain the desired product as an orange liquid (6.06 g, 0.0341 mol, 46%): $^1$H NMR (CDCl$_3$) δ 1.20–1.28 (m, 6H), 2.56–2.72 (m, 1H), 3.70 (s, 2H), 4.18 (d, J=9.6 Hz, 1H), 4.38 (d, J=9.6 Hz, 1H). Mass spectrum: (M+H)$^+$=178, 180.

B. 4-Chloromethyl-2-isopropyloxazole

A solution of 4-chloromethyl-4-hydroxy-2-isopropyloxazoline (4.88 g, 0.0275 mol) in 1,2-dichloroethane (20 mL) was added to a solution of SOCl$_2$ (2.40 mL, 0.0329 mol) in 1,2-dichloroethane (80 mL) at 0° C., under argon, and the solution was heated to 70° C. After 15 min at 70° C., the reaction was cooled to room temperature and the solvent removed by rotary evaporation in vacuo. Drying the residue on high vacuum gave the desired compound as a brown semi-solid (4.20 g, 0.0263 mol, 96%): $^1$H NMR (CDCl$_3$) δ 1.36 (d, J=7.5 Hz, 6H), 3.03–3.18 (m, 1H), 4.50 (s, 2H), 7.56 (s, 1H). Mass spectrum: (M+H)$^+$=160, 162.

C. 2-Isopropyl-4-(((N-methyl)amino)methyl)oxazole

To 40% aqueous methylamine (100 mL) was added dropwise a suspension of 4-chloromethyl-2-isopropyloxazole (4.20 g, 0.0263 mol) in p-dioxane/H$_2$O (1:1 (v/v), 20 mL) over a 25 min period. After stirring for 45 min at ambient temperature, the volume was reduced to ca. 50 mL by rotary evaporation in vacuo, and NaCl was added. The aqueous was extracted with CHCl$_3$ (4×100 mL), and the combined extract was dried over Na$_2$SO$_4$ and concentrated in vacuo. The resulting brown liquid was chromatographed on a 200 g SiO$_2$ flash column with 2% iPrNH$_2$/CH$_2$Cl$_2$ followed by a gradient of iPrNH$_2$/MeOH/CH$_2$Cl$_2$ (0.5:2:97.5, 0.5:4:95.5). Concentration in vacuo of the product-containing fractions afforded the desired compound as a golden oil (2.89 g, 0.0187 mol, 71%): $^1$H NMR (CDCl$_3$) δ 1.33 (d, J=6.9 Hz, 6H), 2.46 (s, 3H), 2.99–3.14 (m, 1H), 3.64 (s, 2H), 7.42 (s, 1H). Mass spectrum: (M+H)$^+$=155, (M+NH$_4$)$^+$=172.

D. N-((N-Methyl-N-((2-isopropyl-4-oxazolyl)methyl)amino)carbonyl)-L-valine Methyl Ester A solution of N-(((4-nitrophenyl)oxy)carbonyl)-L-valine methyl ester (0.903 g, 0.00305 mol) in anhydrous DMF (6 mL) was added to a solution of 2-isopropyl-4-(((N-methyl)amino)methyl)oxazole (9, 0.470 g, 0.00305 mol) in anhydrous DMF (6 mL) under argon, and the yellow solution was stirred at room temperature for 30 min. Solvent was removed by rotary evaporation in vacuo and the resulting oil dried on high vacuum for 1 hr. The residue was applied to a 150 g SiO$_2$ flash column and eluted with 20% EtOAc/CH$_2$Cl$_2$ and 3% MeOH/CH$_2$Cl$_2$. The material obtained after concentration of the product fractions was repurified on a 100 g SiO$_2$ flash column with a gradient of MeOH/CH$_2$Cl$_2$ (1%, 2%, 3%) to obtain the desired compound as an oil (0.515 g, 0.00165 mol, 54%): $^1$H NMR (CDCl$_3$) δ 0.97 (dd, J$_1$=9 Hz, J$_2$=6.9 Hz, 6H), 1.33 (d, J=6.9 Hz, 6H), 2.11–2.23 (m, 1H), 2.98 (s, 3H), 3.00–3.13 (m, 1H), 3.77 (s, 3H), 4.23–4.36 (m, 2H), 4.36–4.42 (m, 1H), 5.79–5.86 (br d, 1H), 7.46 (s, 1 H). Mass spectrum: (M+H)$^+$=312.

E. N-((N-Methyl-N-((2-isopropyl-4-oxazolyl)methyl)amino)carbonyl)-L-valine

To a solution of N-((N-methyl-N-((2-isopropyl-4-oxazolyl)methyl)amino)-carbonyl)-L-valine methyl ester 10

(0.511 g, 0.00164 mol) in p-dioxane (10 mL) and H$_2$O (5 mL) was added LiOH monohydrate (0.103 g, 0.00246 mol). After stirring at room temperature for 1 hr, the p-dioxane was removed by rotary evaporation in vacuo, and the remaining aqueous solution was treated with 1N aq HCl (2.46 mL) and extracted with ethyl acetate (4×100 mL). The combined organic extract was washed with saturated brine and dried for 15 mins over Na$_2$SO$_4$. Concentration in vacuo followed by CH$_2$Cl$_2$ chases (2×) afforded the desired compound as a white solid (0.480 g, 0.00161 mol, 98%): $^1$H NMR (DMSO-d$_6$) δ 0.90 (dd, J$_1$=6.9 Hz, J$_2$=2.4 Hz, 6H), 1.24 (d, J=6.9 Hz, 6H), 1.99–2.12 (m, 1H), 2.83 (s, 3H), 2.96–3.10 (m, 1H), 3.96 (dd, J$_1$=8.4 Hz, J$_2$=6 Hz, 1H), 4.19–4.32 (m, 2H), 6.26 (d, J=8.4 Hz, 1H), 7.80 (s, 1H). Mass spectrum: (M+H)$^+$=298

F. 5S-N-((N-Methyl-N-((2-isopropyl-4-oxazolyl)methyl)amino)carbonyl)-L-valinylamino-2-N-(-butyloxycarbonyl)amino-4S-hydroxy-1,6-diphenyl-2-azahexane Coupling of the compound from Example 2D with the compound from Example 9E using the procedure described in Example 2E provided the desired compound. $^1$H NMR (CDCl$_3$): δ 0.70 (m, 6 H), 1.24 (d, 9 H), 2.80 (s, 3 H), 3.30 (s, 1 H), 3.90 (m, 1 H), 4.00 (m, 1 H), 4.20 (m, 2 H), 4.62 (d, 1 H), 6.02 (br d, 1 H), 7.20–7.30 (m, 10 H), 7.50 (br d, 1 H), 7.76 (s, 1 H), 7.90 (s, 1 H). Mass spectrum: (M+H)$^+$=665.

EXAMPLE 10

A. 3-Carboethoxy-5-(3-hydroxybutyl)-isoxazoline

To a solution of 6 g of 3-hydroxy-5-hexene in 150 ml of diethyl ether was added 18.1 g of ethyl chlorooximidoacetate. The solution was cooled to 0° C., and a solution of 21 ml of triethylamine in 210 ml of diethyl ether was added over 2.5 h. The amine hydrochloride salt was filtered and the residue was purified by silica gel column chromatography (5% to 10% EtOAc in CH$_2$Cl$_2$) to provide 5.5 g of desired product. $^1$H NMR (CDCl$_3$): δ 0.96 (t, 3 H), 1.47 (t, 3 H), 1.50–1.95 (m, 4 H), 2.90 (m, 1 H), 3.35 (m, 1 H), 3.80 (m, 1 H), 4.35 (q, 2 H), 5.02 (m, 1 H).

B. 3-Carboethoxy-5-(3-oxobutyl)-isoxazoline

Oxidation of 5.5 g of the resultant compound of Example 10A by the Swern procedure provided 5.05 g of the desired compound. $^1$H NMR (CDCl$_3$): δ 1.08 (t, 3 H), 1.35 (t, 3 H), 2.50 (m, 2 H), 2.70 (m, 1 H), 2.85 (m, 1 H), 3.02 (m, 1 H), 3.45 (m, 1 H), 4.35 (q, 2 H), 5.15 (m, 1 H).

C. 2-Carboethoxy-6-ethyl-pyridine

To a solution of 1.8 g of the resultant compound of Example 10B in 180 ml of absolute ethanol was added 6 ml of a suspension of Raney nickel in ethanol and 1.2 ml of 40% fluoroboric acid. The reaction mixture was stirred vigorously under a hydrogen atmosphere for 4.5 h. The catalyst was filtered, the solvent was concentrated in vacuo, and the residue was purified by silica gel column chromatography (10% EtOAc in CH$_2$Cl$_2$) to provide 0.77 g of the desired compound. $^1$H NMR (CDCl$_3$): δ 1.34 (t, 3 H), 1.45 (t, 3 H), 2.95 (q, 2 H), 4.50 (q, 2 H), 7.25 (d, 1 H), 7.75 (t, 1 H), 7.95 (d, 1 H).

D. 6-Ethyl-2-pyridine methanol

To a solution of 1.2 g of the resultant compound of Example 10C in 30 ml of dry THF at 0° C. was added slowly 6.7 ml of a 1 M lithium aluminum hydride solution. After 30 min, 0.5 ml of water was added carefully, followed by 0.5 ml of 15% sodium hydroxide and 1 ml of water. The mixture was stirred vigorously for 30 min and the solid formed was filtered and washed thoroughly with 100 ml of ethyl acetate, the combined filtrate was conc. in vacuo and the residue purified by silica gel column chromatography (10% MeOH in CH$_2$Cl$_2$) to provide 0.87 g of desired compound. $^1$H NMR (CDCl$_3$): δ 1.33 (t, 3 H), 2.86 (q, 2 H), 4.20 (br s, 1 H), 4.75 (s, 2 H), 7.10 (m, 2 H), 7.65 (t, 1 H).

E. 2-((N-Methylamino)methyl)-6-ethylpyridine

Oxidation of the resultant compound of Example 10D by the Swern procedure and reductive amination of the resulting aldehyde with methylamine under 50 psi hydrogen pressure and Pd/C as catalyst provided the desired compound. $^1$H NMR (CDCl$_3$): δ 1.30 (t, 3 H), 2.54 (s, 3 H), 2.80 (q, 2 H), 3.00 (br s, 1 H), 3.90 (s, 2 H), 7.05 (d, 1 H), 7.10 (d, 1 H), 7.58 (t, 1 H).

F. N-((N-Methyl-N-((6-ethyl-2-pyridinyl)methyl)amino)carbonyl)valine

Using the procedures of Examples 3D and 3E, but replacing 2-(N-methylamino)methyl)pyridine with the resultant compound of Example 10E provided the desired compound as an oil.

G. 5S-(Benzyloxycarbonyl)amino-2-N-((N-methyl-N-((6-ethyl-2-pyridinyl)methyl)amino)carbonyl)-L-valinylamino-4S-hydroxy-1,6-diphenyl-2-azahexane Coupling of the compound from Example 6G with N-((N-methyl-N-((6-ethyl-2-pyridinyl)methyl)amino)carbonyl)-L-valine using the procedure of Example 2E provided the desired compound. $^1$H NMR (CDCl$_3$): δ 0.48 (d, 3 H), 0.57 (d, 3 H), 0.90 (m, 1 H), 1.20 (t, 3 H), 1.66 (m, 1 H), 2.70 (m, 4 H), 2.86 (s, 3 H), 3.65 (m, 1 H), 3.72–3.98 (m, 4 H), 4.42 (m, 2 H), 4.90 (m, 2 H), 6.35 (br d, 1 H), 7.00 (d, 1 H), 7.15–7.30 (m, 15 H), 7.65 (t, 1 H), 9.02 (s, 1 H). Mass spectrum: (M+H)$^+$=695.

EXAMPLE 11

5S-(Benzyloxycarbonyl)amino-2-N-((N-methyl-N-((2-isopropyl-4-oxazolyl)methyl)amino)carbonyl)-L-valinylamino-4S-hydroxy-1,6-diphenyl-2-azahexane Coupling of the compound from Example 6G with the compound from Example 9E using the procedure of Example 2E provided the desired compound. $^1$H NMR (CDCl$_3$): δ 0.50 (d, 3 H), 0.59 (d, 3 H), 1.18 (d, 3 H), 1.20 (d, 3 H), 1.65 (m, 1 H), 2.70 (m, 3 H), 2.82 (s, 3 H), 2.95 (m, 1 H), 3.62 (m, 1 H), 3.72–3.98 (m, 4 H), 4.23 (s, 2 H), 4.90 (m, 2 H), 6.05 (br d, 1 H), 7.15–7.30 (m, 15 H), 7.70 (s, 1 H), 9.00 (s, 1 H).

EXAMPLE 12

5S-((5-Thiazolyl)methoxy)carbonylamino-2-N-((N-methyl-N-((2-isopropyl-4-oxazolyl)methyl)amino)carbonyl)-L-valinylamino-4S-hydroxy-1,6-diphenyl-2-azahexane Removal of the benzyloxycarbonyl protecting group from the compound from Example 11 by hydrogenolysis and coupling of the resulting amine with the compound from Example 7E provided the desired compound. $_1$H NMR (CDCl$_3$): δ 0.48 (d, 3 H), 0.57 (d, 3 H), 1.18 (d, 3 H), 1.20

(d, 3 H), 1.65 (m, 1 H), 2.62 (m, 3 H), 2.80 (s, 3 H), 2.98 (m, 1 H), 3.62 (m, 1 H), 3.70–3.95 (m, 4 H), 4.24 (s, 2 H), 4.88 (d, 1 H), 5.12 (s, 2 H), 6.05 (br d, 1 H), 7.15–7.30 (m, 10 H), 7.72 (s, 1 H), 7.82 (s, 1 H), 9.02 (s, 1 H), 9.05 (s, 1 H). Mass spectrum: $(M+H)^+=706$.

EXAMPLE 13

A. 1,1-Diethoxy-4-((3,4,5,6-tetrahydro-2H-pyran-2-yl)oxy)-2-butyne

A 1 M solution of ethylmagnesium bromide in THF (200 ml, 0.2 mol) was treated with 29 ml (0.2 mol) of a solution of 3,4,5,6-tetrahydro-2-(2-propynyloxy)-2H-pyran in toluene, while maintaining ambient temperature through use of a cool water bath. The resulting solution was stirred for 4 h and treated with 47 ml (0.28 mol) of a solution of triethylorthoformate in toluene, while maintaining ambient temperature with a cool water bath. The resulting solution was heated to 85° C. for 8 h, allowing the removal of THF by distillation. After being allowed to cool, the resulting solution was poured into 500 ml of ice-water containing 29 g of $NH_4OAc$, extracted with two portions of ether, dried over $K_2CO_3$, and concentrated in vacuo. The residue was distilled at ca. 0.5 mm Hg pressure (b.p. 103–108° C.) to provide 39.5 g (79%) of the desired compound. $^1$H NMR ($CDCl_3$) δ 1.24 (t, J=7 Hz, 6 H), 1.5–1.9 (m, 6 H), 3.5–3.65 (m, 3 H), 3.7–3.9 (m, 3 H), 4.32 (AA', 2 H), 4.81 (m, 1 H), 5.31 (m, 1 H). Mass spectrum: $(M+NH_4)^+=260$.

B. 5-(Hydroxymethyl)isoxazole

A solution of 39.28 g (161 mmol) of 1,1-diethoxy-4-((3,4,5,6-tetrahydro-2H-pyran-2-yl)oxy)-2-butyne and 26 g (376 mmol) of hydroxylamine hydrochloride in 168 ml of ethanol and 34 ml of water was heated at reflux under $N_2$ atmosphere for 1 h. After being allowed to cool, the resulting solution was concentrated in vacuo to ⅓ the original volume, diluted with 50 ml of water, and extracted with 2 portions, of ether. The combined extracts were concentrated to an oil. The crude product (7.04 g, 44%) was obtained after distillation (79–84° C., 0.5 mm Hg). Silica gel chromatography using 0–3% methanol in dichloromethane provided 4.9 g of the desired compound contaminated with 5-hydroxypentanal oxime. $^1$ H NMR ($CDCl_3$) δ 1.95 (br, 1 H), 4.81 (s, 2 H), 6.27 (d, J=1 Hz, 1 H), 8.23 (d, J=1 Hz, 1 H). Mass spectrum: $(M+NH_4)^+=117$.

C. ((5-Isoxazolyl)methyl)-(4-nitrophenyl)carbonate

Using the procedure of Example 7E, but replacing 5-(hydroxymethyl)-thiazole with 5-(hydroxymethyl) isoxazole provided, after silica gel chromatography using 8:2 dichloromethane:hexane, the desired compound. $^1$H NMR ($CDCl_3$) δ 5.41 (s, 2 H), 6.46 (d, J=1 Hz, 1 H), 7.40 (m, 2 H), 8.30 (m, 3 H). Mass spectrum: $(M+NH_4)^+=282$.

D. 5S-N-((5-Isoxazolyl)methoxy)carbonylamino-2-N-((N-methyl-N-((2-isopropyl-4-oxazolyl)methyl)amino)carbonyl)-L-valinylamino-4S-hydroxy-1,6-diphenyl-2-azahexane Removal of the benzyloxycarbonyl protecting group of the compound from Example 11 by hydrogenolysis and coupling of the resulting amino compound with the compound from Example 13C provided the desired compound. $^1$H NMR ($CDCl_3$): δ 0.48 (d, 3 H), 0.58 (d, 3 H), 1.18 (d, 3 H), 1.21 (d, 3 H), 2.70 (m, 3 H), 2.80 (s, 3 H), 2.98 (m, 1 H), 3.60 (m, 1 H), 3.70–3.96 (m, 4 H), 4.22 (s, 2 H), 4.90 (d, 1 H), 5.12 (s, 2 H), 6.05 (br s, 1 H), 6.26 (s, 1 H), 7.15–7.30 (m, 11 H), 7.70 (s, 1 H), 8.50 (d, 1 H), 9.03 (s, 1 H). Mass spectrum: $(M+H)^+=690$.

EXAMPLE 14

A. N-1-t-Butyloxycarbonyl-N-2-p-methoxybenzyl-hydrazine

To a solution of 5.0 g of p-anisaldehyde in 50 ml of dry THF was added 5 g of t-butyl carbazate. The reaction mixture was left at RT overnight and the solvent was removed in vacuo. The resulting solid was recrystallized from cyclohexane/THF to provide 7 g of pure hydrazone which was subjected to hydrogenation at 60 psi hydrogen pressure with 10% Pd/C as catalyst. After 2 h at RT, the catalyst was filtered off and the filtrate conc. and the residue purified by silica gel column chromatography to provide 6.2 g of the desired compound. $^1$H NMR ($CDCl_3$): δ 1.46 (s, 9 H), 3.80 (s, 3 H), 3.94 (s, 2 H), 6.10 (br s, 1 H), 6.87 (d, 2 H), 7.27 (d, 2 H).

B. 5S-N-(Benzyloxycarbonyl)amino-2-N-(t-butyloxycarbonyl)amino-4S-hydroxy-1-p-methoxyphenyl-6-phenyl-2-azahexane Using the procedure of Example 1F, but replacing the hydrazine with the hydrazine from Example 14A provided the desired compound. $^1$H NMR ($CDCl_3$): δ 1.35 (s, 9 H), 2.45 (m, 2 H), 2.80–3.00 (m, 3 H), 3.60–4.00 (m, 3 H), 3.80 (s, 3 H), 5.08 (s, 2 H), 5.40 (br d, 1 H), 6.83 (d, 2 H), 7.25–7.40 (m, 12 H). Anal. Calcd. for $C_{31}H_{39}N_3O_6$: C, 67.74; H, 7.15; N, 7.64. Found: C, 67.39; H, 7.05; N, 7.57.

EXAMPLE 15

5S-N-((2-Pyridinyl)methoxycarbonyl)-L-valinylamino-2-N-(t-butyloxycarbonyl)amino-4S-hydroxy-1-p-methoxypohenyl-6-phenyl-2-azahexane Removal of the benzyloxycarbonyl group of the compound from Example 14B and coupling of the resulting amine with N-((2-pyridinyl)methoxycarbonyl)-L-valine using the procedure of Example 2E provided the desired compound. $^1$H NMR ($CDCl_3$): δ 0.72 (m, 6 H), 1.25 (s, 9 H), 1.80 (m, 1 H), 2.60–2.85 (m, 4 H), 3.60 (m, 1 H), 3.80 (s, 3 H), 3.85 (m, 1 H), 4.00 (m, 1 H), 4.68 (br s, 1 H), 5.10 (s, 2 H), 6.80 (d, 2 H), 7.15–7.40 (m, 7 H), 7.60 (br d, 1 H), 7.80 (t, 1 H), 7.90 (s, 1 H), 8.52 (d, 1 H). Mass spectrum: $(M+H)^+=650$.

EXAMPLE 16

5S-N-((2-Pyridinyl)methoxycarbonyl)-L-valinylamino-2-N-((3-pyridinyl)methoxycarbonyl)amino-4S-hydroxy-1-p-methoxyphenyl-6-phenyl-2-azahexane Removal of the t-butyloxycarbonyl protecting group of the compound from Example 15 by 4N HCl and coupling of the resulting compound with ((3-pyridinyl)methyl)-(4-nitrophenyl)carbonate using the procedure of Example 5B provided the desired compound. $^1$H NMR ($CDCl_3$): δ 0.70 (d, 3 H), 0.74 (d, 3 H), 1.80 (m, 1 H), 2.60–2.80 (m, 4 H), 3.60 (m, 1 H), 3.70 (s, 3 H), 3.68–3.80 (m, 3 H), 4.10 (m, 1 H), 4.67 (m, 1 H), 4.97 (s, 2 H), 5.10 (s, 2 H), 6.80 (d, 2 H), 7.15–7.40 (m, 7 H), 7.52 (m, 2 H), 7.80 (m, 2 H), 8.38 (s, 1 H), 8.47 (s, 1 H), 8.52 (m, 2 H). Mass spectrum: $(M+H)^+=685$.

EXAMPLE 17

A. N-1-t-Butyloxycarbonyl-N-2-m-methoxybenzyl-hydrazine

Using the procedure of Example 14A, but replacing p-anisaldehyde with m-anisaldehyde provided the desired compound. ¹H NMR (CDCl₃): δ 1.50 (s, 9 H), 3.80 (s, 3 H), 4.00 (s, 2 H), 6.10 (br s, 1 H), 6.82 (m, 1 H), 6.93 (m, 2 H), 7.25 (m, 1 H).

B. 5S-N-(Benzyloxycarbonyl)amino-2-N-(t-butyloxycarbonyl)amino-4S-hydroxy-1-ortho-methoxyphenyl-6-phenyl-2-azahexane Using the procedure of Example 1F, but replacing the hydrazine with the hydrazine from Example 17A provided the desired compound. ¹H NMR (CDCl₃): δ 1.35 (s, 9 H), 2.50 (m, 1 H), 2.80 (m, 1 H), 2.97 (m, 2 H), 3.60–4.00 (m, 4 H), 3.80 (s, 3 H), 5.05 (s, 2 H), 5.35 (br d, 1 H), 6.80–6.90 (m, 3 H), 7.16–7.40 (m, 12 H).

EXAMPLE 18

5S-N-((2-Pyridinyl)methoxycarbonyl)-L-valinylamino-2-N-(t-butyloxycarbonyl)amino-4S-hydroxy-1-ortho-methoxyphenyl-6-phenyl-2-azahexane Removal of the benzyloxycarbonyl protecting group of the compound from Example 17 by hydrogenolysis and coupling of the resulting amine with N-((2-pyridinyl)methoxycarbonyl)-L-valine using the procedure of Example 2E provided the desired compound. ¹H NMR (CDCl₃): δ 0.72 (m, 6 H), 1.27 (s, 9 H), 2.60–2.90 (m, 4 H), 3.60 (m, 1 H), 3.70 (s, 3 H), 3.72–4.05 (m, 4 H), 4.70 (br s, 1 H), 5.07 (s, 2 H), 6.75 (m, 1 H), 6.83 (br d, 1 H), 7.15–7.40 (m, 9 H), 7.60 (br d, 1 H), 7.80 (t, 1 H), 7.96 (s, 1 H), 8.50 (d, 1 H). Mass spectrum: (M+H)⁺=650.

EXAMPLE 19

A. N-1-t-Butyloxycarbonyl-N-2-((2-furanyl)methyl)-hydrazine

Using the procedure of Example 14A, but replacing p-anisaldehyde with 2-furaldehyde provided the desired compound. ¹H NMR (CDCl₃): δ 1.48 (s, 9 H), 3.85 (br s, 1 H), 4.02 (s, 2 H), 6.15 (br s, 1 H), 6.25 (m, 1 H), 6.32 (m, 1 H), 6.90 (m, 1 H).

B. 5S-(Benzyloxycarbonyl)amino-2-N-(t-butyloxycarbonyl)amino-4S-hydroxy-1-(2-furanyl)-6-phenyl-2-azahexane Using the procedure of Example 1 F, but replacing the hydrazine with the hydrazine from Example 19A provided the desired compound. ¹H NMR (CDCl₃): δ 1.40 (s, 9 H), 2.40 (m, 1 H), 2.70 (m, 1 H), 2.95 (d, 2 H), 3.50–4.05 (m, 4 H), 5.10 (s, 2 H), 5.40 (br d, 1 H), 5.80 (br s, 1 H), 6.20 (m, 1 H), 6.30 (m, 1 H), 7.15–7.40 (m, 11 H).

EXAMPLE 20

5S-N-((2-Pyridinyl)methoxycarbonyl)-L-valinylamino-2-N-(t-butyloxycarbonyl)amino-4S-hydroxy-1-(2-furanyl)-6-phenyl-2-azahexane Removal of the benzyloxycarbonyl protecting group of the compound from Example 19B by hydrogenolysis and coupling of the resulting amine with N-((2-pyridinyl)methoxycarbonyl)-L-valine using the procedure of Example 2E provided the desired compound. ¹H NMR (CDCl₃): δ 0.75 (m, 6 H), 1.30 (s, 9 H), 1.86 (m, 1 H), 2.55–2.80 (m, 4 H), 3.50–4.00 (m, 4 H), 4.60 (br s, 1 H), 5.08 (s, 2 H), 6.20 (m, 1 H), 6.35 (m, 1 H), 7.15–7.40 (5H), 7.50 (s, 1 H), 7.60 (br d, 1 H), 7.80 (m, 1 H), 7.95 (br s, 1 H), 8.52 (d, 1 H). Mass spectrum: (M+H)⁺=610.

EXAMPLE 21

A. N-1-Benzyloxycarbonyl-N-2-(3-furanylmethyl)-hydrazine

Using the procedure of Example 14A, but replacing p-anisaldehyde with 3-furaldehyde provided the desired compound. ¹H NMR (CDCl₃): δ 1.48 (s, 9 H), 4.10 (br s, 1 H), 6.02 (br s, 1 H), 6.40 (m, 1 H), 7.40 (m, 2 H).

B. 5S-N-(Benzyloxycarbonyl)amino-2-N-(t-butyloxycarbonyl)amino-4S-hydroxy-1-(3-furanyl)-6-phenyl-2-azahexane Using the procedure of Example 1F, but replacing the hydrazine with the hydrazine from Example 21A provided the desired compound. ¹H NMR (CDCl₃): δ 1.40 (s, 9 H), 2.40 (m, 1 H), 2.70 (m, 1 H), 2.95 (m, 1 H), 3.52–3.85 (m, 4 H), 4.45 (br s, 1 H), 5.08 (s, 2 H), 5.22 (br s, 1 H), 5.40 (br d, 1 H), 6.32 (s, 1 H), 7.15–7.40 (m, 12 H). Mass spectrum: (M+H)⁺=510.

EXAMPLE 22

A. 4-(Chloromethyl)-2-(dimethylamino)thiazole

A mixture of 15 g (144 mmol) of N,N-dimethylthiourea and excess MgSO₄ in 350 ml of acetone was heated to reflux and treated dropwise with a solution of 18.3 g (144 mmol) of 1,3-dichloroacetone in 35 ml of acetone. The resulting mixture was heated at reflux for 1.5 h, allowed to cool, filtered, and concentrated in vacuo. The residue was purified by silica gel chromatography using 20% ethyl acetate in hexane to provide 14.0 g (70%) of the desired compound.

B. 2-(N,N-Dimethylamino)-4-(hydroxymethyl)thiazole

A solution of 5.186 g (29 mmol) of 4-(chloromethyl)-2-(dimethylamino)thiazole in 100 ml of 1:1 THF/H₂O was cooled to 0° C. and treated dropwise with a solution of 5.73 g (29 mmol) of silver tetrafluoroborate in 50 ml of 1:1 THF/H₂O. After being stirred for 1 h, the mixture was filtered, the solid mass was washed with ethyl acetate, and the combined filtrates were concentrated in vacuo. The black residue was purified by silica gel chromatography to provide 0.80 g (17%) of the desired compound (R_f 0.24, 6% methanol in chloroform) as an oil. ¹H NMR (CDCl₃) δ 2.67 (br, 1 H), 3.09 (s, 6 H), 4.54 (s, 2 H), 6.35 (s, 1 H). Mass spectrum: (M+H)⁺=159.

C. N-((2-(N,N-Dimethylamino)-4-thiazolyl)methoxycarbonyl)valine Methyl Ester A solution of 505 mg (3.19 mmol) of 2-(N,N-dimethylamino)-4-(hydroxymethyl)thiazole, 3.19 mmol of α-isocyanato-L-valine methyl ester, and 100 mg of 4-dimethylaminopyridine in 30 ml of dichloromethane was heated at reflux for 3 h. The resulting solution was allowed to cool, diluted with dichloromethane, washed sequentially with 10% citric acid, aqueous Na₂CO₃, and brine, dried over Na₂SO₄, and concentrated in vacuo. The residue was purified by silica gel chromatography using 2% methanol in chloroform to provide 0.95 g (95%) of the desired compound, R_f 0.42 (4% methanol in chloroform). ¹H NMR (CDCl₃) δ 0.84 (d, J=7 Hz, 3 H), 0.93 (d, J=7 Hz, 3 H), 2.12 (m, 1 H), 3.11 (s, 6 H), 3.73 (s, 3 H), 4.24 (dd, J=8,4 Hz, 1 H), 4.99 (s, 2 H), 5.26 (br d, 1 H), 6.49 (s, 1 H). Mass spectrum: (M+H)⁺=316.

D. N-((2-(N,N-Dimethylamino)-4-thiazolyl)methoxycarbonyl)valine

Using the procedure of Example 3E but replacing N-((N-methyl-N-((2-pyridinyl)methyl)amino)carbonyl)valine methyl ester with N-((2-(N,N-dimethylamino)-4-thiazolyl) methoxycarbonyl)valine methyl ester provided the desired compound.

E. 5S-(((5-Thiazolyl)methoxy)carbonyl)amino-2-N-((2-(N,N-dimethylamino)-4-thiazolyl) methoxycarbonyl)valinylamino-4S-hydroxy-1,6-diphenyl-2-azahexane Deprotection of the t-butyloxycarbonyl protecting group of the compound from Example 7F according to the procedure of Example 6G and coupling of the resulting compound with the compound from Example 22D, using the procedure described in Example 2E provided the desired compound.

EXAMPLE 23

A. 4-((Amino)thiocarbonyl)morpholine

A solution of 3.35 g (18.8 mmol) of thiocarbonyl diimidazole in 100 ml of THF was treated with 0.82 ml (9.4 mmol) of morpholine. After being stirred at ambient temperature for 3.5 h, an additional 0.82 ml portion of morpholine was added, and stirring was continued. After 6 h, the solution was treated with excess concentrated aqueous ammonia, and stirred overnight. The resulting solution was concentrated in vacuo, taken up in chloroform, separated from the aqueous phase, dried over $Na_2SO_4$, and concentrated. Purification of the residue by silica gel chromatography using ethyl acetate provided 1.85 g (76%) of the desired compound, $R_f$ 0.17 (10% methanol in chloroform), as a white solid. $^1$H NMR ($CDCl_3$) δ 3.76 (m, 4 H), 3.83 (m, 4 H), 5.75 (br, 2 H). Mass spectrum: $(M+H)^+=147$.

B. Ethyl 2-(4-Morpholinyl)thiazole-4-carboxylate

A mixture of 1.85 g (12.7 mmol) of 4-((amino) thiocarbonyl)morpholine, 1.59 ml (12.7 mmol) of ethyl bromopyruvate, and excess $MgSO_4$ in 50 ml of acetone was heated at reflux for 2 h. The resulting mixture was allowed to cool, filtered, and concentrated in vacuo. The residue was taken up in chloroform, washed with aqueous $NaHCO_3$, dried over $Na_2SO_4$, and concentrated. Silica gel chromatography using 1% methanol in chloroform provided 1.7 g (55%) of the desired compound, $R_f$ 0.70 (ethyl acetate). Mass spectrum: $(M+H)^+=243$.

C. 2-(4-Morpholinyl)-4-(hydroxymethyl)thiazole

A solution of 7.0 ml (7.0 mmol) of lithium aluminum hydride in toluene was diluted with 10 ml of THF, cooled to 0° C., and treated with a solution of 1.7 g (7.0 mmol) of ethyl 2-(4-morpholinyl)thiazole-4-carboxylate in 25 ml of THF. The resulting solution was stirred for 1 h, quenched cautiously with aqueous Rochelle's salts, diluted with chloroform, filtered, dired over $Na_2SO_4$, and concentrated in vacuo. Silica gel chromatography using 2–4% methanol in chloroform provided 856 mg (61%) of the desired compound, $R_f$ 0.16 (4% methanol in chloroform). $^1$H NMR ($CDCl_3$) δ 2.44 (br, 1 H), 3.46 (t, J=5 Hz, 4 H), 3.81 (t, J=5 Hz, 1 H), 4.55 (br s, 2 H), 6.45 (s, 1 H). Mass spectrum: $(M+H)^+=200$.

D. N-((2-(4-Morpholinyl)-4-thiazolyl) methoxycarbonyl)valine Methyl Ester

Using the procedure of Example 22C but replacing 2-(N,N-dimethylamino)-4-(hydroxymethyl)thiazole with 2-(4-morpholinyl)-4-(hydroxymethyl)thiazole provided, after silica gel chromatography using 1% methanol in chloroform, the desired compound, $R_f$ 0.54 (4% methanol in chloroform), in 65% yield. $^1$H NMR ($CDCl_3$) δ 0.97 (d, J=7 Hz, 3 H), 1.00 (d, J=7 Hz, 3 H), 2.25 (m, 1 H), 3.50 (dd, J=5, 4 Hz, 2 H), 3.76 (s, 3 H), 3.84 (dd, J=5, 4 Hz, 2 H), 4.67 (dd, J=9, 5 Hz, 1 H), 7.63 (br d, 1 H), 8.02 (s, 1 H).

E. N-((2-(4-Morpholinyl)-4-thiazolyl) methoxycarbonyl)valine

Using the procedure of Example 3E but replacing N-((N-methyl-N-((2-pyridinyl)methyl)amino)carbonyl)valine methyl ester with N-((2-(4-morpholinyl)-4-thiazolyl) methoxycarbonyl)valine methyl ester provided the desired compound.

F. 5S-(((5-Thiazolyl)methoxy)carbonyl)amino-2-N-((2-(4-morpholinyl)-4-thiazolyl)methoxycarbonyl) valinylamino-4S-hydroxy-1,6-diphenyl-2-azahexane Deprotection of the t-butyloxycarbonyl protecting group of the compound from Example 7F according to the procedure of Example 6G and coupling of the resulting compound with the compound from Example 23E, using the procedure described in Example 2E provided the desired compound.

EXAMPLE 24

A. 1-((Amino)thiocarbonyl)pyrrolidine

Using the procedure of Example 23A but replacing morpholine with pyrrolidine, and stirring the solution for six days after addition of aqueous ammonia provided the desired compound. $^1$H NMR ($CDCl_3$) δ 1.97 (m, 2 H), 2.11 (m, 2 H), 3.38 (br t, 2 H), 3.85 (br t, 2 H), 5.56 (br, 2 H). Mass spectrum: $(M+H)^+=131$.

B. Ethyl 2-(1-Pyrrolidinyl)thiazole-4-carboxylate

Using the procedure of Example 23B but replacing 4-((amino)thiocarbonyl)morpholine with 1-((amino) thiocarbonyl)pyrrolidine provided the desired compound. $^1$H NMR ($CDCl_3$) δ 1.37 (t, J=7 Hz, 3 H), 2.04 (m, 4 H), 3.51 (m, 4 H), 4.35 (q, J=7 Hz, 2 H), 7.37 (s, 1 H). Mass spectrum: $(M+H)^+=227$.

C. 2-(1-Pyrrolidinyl)-4-(hydroxymethyl)thiazole

Using the procedure of Example 23C but replacing ethyl 2-(4-morpholinyl)thiazole-4-carboxylate with ethyl 2-(1-pyrrolidinyl)thiazole-4-carboxylate provided, after silica gel chromatography using 2–4% methanol in chloroform, the desired compound ($R_f$ 0.26, 4% methanol in chloroform) in 53% yield. $^1$H NMR ($CDCl_3$) δ 2.04 (m, 4 H), 2.75 (br, 1 H), 3.45 (m, 4 H), 4.56 (s, 2 H), 6.32 (s, 1 H). Mass spectrum: $(M+H)^+=185$.

D. N-((2-(1-Pyrrolidinyl)-4-thiazolyl) methoxycarbonyl)valine Methyl Ester

Using the procedure of Example 22C but replacing 2-(N,N-dimethylamino)-4-(hydroxymethyl)thiazole with 2-(1-pyrrolidinyl)-4-(hydroxymethyl)thiazole provided, after silica gel chromatography using 1.5% methanol in chloroform, the desired compound ($R_f$ 0.34). $^1$H NMR ($CDCl_3$) δ 0.89 (d, J=7 Hz, 6 H), 2.04 (m, 4 H), 2.14 (m, 1 H), 3.46 (m, 4 H), 3.74 (s, 3 H), 4.30 (dd, J=9, 4 Hz, 1 H), 5.01 (s, 2 H), 5.33 (br d, 1 H), 6.44 (s, 1 H). Mass spectrum: $(M+H)^+=342$.

E. N-((2-(1-Pyrrolidinyl)-4-thiazolyl) methoxycarbonyl)valine

Using the procedure of Example 3E but replacing N-((N-methyl-N-((2-pyridinyl)methyl)amino)carbonyl)valine methyl ester with N-((2-(1-pyrrolidinyl)-4-thiazolyl) methoxycarbonyl)valine methyl ester provided the desired compound.

F. 5S-(((5-Thiazolyl)methoxy)carbonyl)amino-2-N-((2-(1-pyrrolidinyl)-4-thiazolyl)methoxycarbonyl) valinylamino-4S-hydroxy-1,6-diphenyl-2-azahexane Deprotection of the t-butyloxycarbonyl protecting group of the compound from Example 7F according to the procedure of Example 6G and coupling of the resulting compound with the compound from Example 24E, using the procedure described in Example 2E provided the desired compound.

EXAMPLE 25

A. 2-(N,N-Dimethylamino)-4-(((N-methyl)amino) methyl)thiazole

Using the procedure of Example 6C but replacing 4-(chloromethyl)-2-isopropylthiazole hydrochloride with 4-(chloromethyl)-2-(dimethylamino)-thiazole dihydrochloride provided, after silica gel chromatography using first 10% methanol in chloroform followed by 4% methanol/2% isopropylamine in chloroform, the desired compound, $R_f$ 0.05 (10% methanol in chloroform). $^1$H NMR (CDCl$_3$) δ 2.46 (s, 3 H), 3.08 (s, 6 H), 3.66 (s, 2 H), 6.30 (s, 1 H). Mass spectrum: (M+H)$^+$=172.

B. N-((N-Methyl-N-(((N,N-dimethylamino)-4-thiazolyl)methyl)amino)carbonyl)-L-valine Methyl Ester A solution of 741 mg (4.42 mmol) of α-isocyanato-L-valine in in 5 ml of dichloromethane was added to a solution of 720 mg (4.21 mmol) of 2-(N,N-dimethylamino)-4-(((N-methyl)amino)methyl)thiazole in 25 ml of dichloromethane. The resulting solution was stirred at ambient temperature for 16 h, partitioned between chloroform and aqueous NaHCO$_3$, dried over Na$_2$SO$_4$, and concentrated in vacuo. The residue was purified by silica gel chromatography using 2% methanol in chloroform to provide 463 mg (34%) of the desired compound, $R_f$ 0.25 (2% methanol in chloroform). NMR (CDCl$_3$) δ 0.96 (d, J=7 Hz, 3 H), 0.98 (d, J=7 Hz, 3 H), 2.13 (m, 1 H), 2.97 (s, 3 H), 3.11 (s, 6 H), 3.71 (s, 3 H), 4.07 (br d, J=16 Hz, 1 H), 4.34 (dd, J=9, 5 Hz, 1 H), 4.42 (d, J=16 Hz, 1 H), 6.29 (s, 1 H), 6.37 (br, 1 H). Mass spectrum: (M+H)$^+$=329.

C. N-((N-Methyl-N-(((N,N-dimethylamino -4-thiazolyl)methyl)amino)carbonyl)-L-valine Using the procedure of Example 3E but replacing N-((N-methyl-N-((2-pyridinyl)methyl)amino)carbonyl)valine methyl ester with N-((N-methyl-N-(((N,N-dimethylamino)-4-thiazolyl)methyl)amino)carbonyl)-L-valine methyl ester provided the desired compound.

D. 5S-(((5-Thiazolyl)methoxy)carbonyl)amino-2-N-((N-Methyl-N-(((N,N-dimethylamino)-4-thiazolyl) methyl)amino)carbonyl)-L-valinylamino-4S-hydroxy-1,6-diphenyl-2-azahexane Deprotection of the t-butyloxycarbonyl protecting group of the compound from Example 7F according to the procedure of Example 6G and coupling of the resulting compound with the compound from Example 25C, using the procedure described in Example 2E provided the desired compound.

EXAMPLE 26

A. 2-Methoxythioacetamide

Using the procedure of Example 6A but replacing isobutyramide with 2-methoxyacetamide provided the desired compound in 52% yield.

B. 4-(Chloromethyl)-2-(methoxymethyl)thiazole hydrochloride

Using the procedure of Example 6B but replacing 2-methylpropanethioamide with 2-methoxythioacetamide provided the crude desired compound in 41% yield.

C. 2-(Methoxymethyl)-4-(((N-methyl)amino) methyl)thiazole

Using the procedure of Example 6C but replacing 4-(chloromethyl)-2-isopropylthiazole hydrochloride with 4-(chloromethyl)-2-(methoxymethyl)-thiazole hydrochloride provided, after silica gel chromatography using 3% methanol in chloroform, the desired compound, $R_f$ 0.1, (5% methanol in chloroform) in 73% yield.

D. N-((N-Methyl-N-((2-(methoxymethyl)-4-thiazolyl)methyl)amino)carbonyl)-L-valine Methyl Ester Using the procedure of Example 6E but replacing 2-isopropyl-4-(((N-methyl)amino)-methyl)thiazole with 2-(methoxymethyl)-4-(((N-methyl)amino)-methyl)thiazole provided, after silica gel chromatography using 3% methanol in chloroform, the desired compound, Rf 0.5, (5% methanol in chloroform) in 23% yield.

E. N-((N-Methyl-N-((2-(methoxymethyl)-4-thiazolyl)methyl)amino)carbonyl)-L-valine Using the procedure of Example 3E but replacing N-((N-methyl-N-((2-pyridinyl)methyl)amino)carbonyl)valine methyl ester with N-((N-methyl-N-((2-(methoxymethyl)-4-thiazolyl)methyl)amino)carbonyl)-L-valine methyl ester provided the desired compound.

F. 5S-(((5-Thiazolyl)methoxy)carbonyl)amino-2-N-((N-Methyl-N-((2-(methoxymethyl)-4-thiazolyl) methyl)amino)carbonyl)-L-valinylamino-4S-hydroxy-1,6-diphenyl-2-azahexane Deprotection of the t-butyloxycarbonyl protecting group of the compound from Example 7F according to the procedure of Example 6G and coupling of the resulting compound with the compound from Example 26E, using the procedure described in Example 2E provided the desired compound.

EXAMPLE 27

A. 5-Methyl-1-((3,4,5,6-tetrahydro-2H-pyran-2-yl) oxy)-2-hexyn-4-one

The desired compound was prepared from isobutyryl chloride and 3,4,5,6-tetrahydro-2-(2-propynyloxy)-2H-pyran by analogy to the procedure of Tohda, et. al. (Synthesis, 777 (1977)).

B. 5-(Hydroxymethyl)-3-isopropylisoxazole

Using the procedure of Example 13B but replacing 1,1-diethoxy-4-((3,4,5,6-tetrahydro-2H-pyran-2-yl)oxy)-2-butyne with 5-methyl-1-((3,4,5,6-tetrahydro-2H-pyran-2-yl) oxy)-2-hexyn-4-one provided the desired compound.

C. N-((3-Isopropyl-5-isoxazolyl)methoxycarbonyl) valine Methyl Ester

Using the procedure of Example 22C but replacing 2-(N, N-dimethylamino)-4-(hydroxymethyl)thiazole with 5-(hydroxymethyl)-3-isopropylisoxazole provided the desired compound.

49

D. N-((3-Isopropyl-5-isoxazolyl)methoxycarbonyl) valine

Using the procedure of Example 3E but replacing N-((N-methyl-N-((2-pyridinyl)methyl)amino)carbonyl)valine methyl ester with N-((3-isopropyl-5-isoxazolyl) methoxycarbonyl)valine methyl ester provided the desired compound.

E. 5S-(((5-Thiazolyl)methoxy)carbonyl)amino-2-N-((3- Isopropyl-5-isoxazolyl)methoxycarbonyl) valinylamino-4S-hydroxy-1,6-dighenyl-2-azahexane Deprotection of the t-butyloxycarbonyl protecting group of the compound from Example 7F according to the procedure of Example 6G and coupling of the resulting compound with the compound from Example 27D, using the procedure described in Example 2E provided the desired compound.

EXAMPLE 28

A. 5-(Hydroxymethyl)-3-isopropylisothiazole

The desired compound was prepared from the resultant compound of Example 29A using the procedure of Lucchesini, et. al. (Heterocycles, 29, 97 (1989).

B. N-((3-lsopropyl-5-isothiazolyl)methoxycarbonyl) valine Methyl Ester

Using the procedure of Example 22C but replacing 2-(N,N-dimethylamino)-4-(hydroxymethyl)thiazole with 5-(hydroxymethyl)-3-isopropylisothiazole provided the desired compound.

C. N-((3-Isopropyl-5-isothiazolyl)methoxycarbonyl) valine

Using the procedure of Example 3E but replacing N-((N-methyl-N-((2-pyridinyl)methyl)amino)carbonyl)valine methyl ester with N-((3-isopropyl-5-isothiazolyl) methoxycarbonyl)valine methyl ester provided the desired compound.

D. 5S-(((5-Thiazolyl)methoxy)carbonyl)amino-2-N-((3-Isopropyl-5-isothiazolyl)methoxycarbonyl) valinylamino-4S-hydroxy-1,6-diphenyl-2-azahexane Deprotection of the t-butyloxycarbonyl protecting group of the compound from Example 7F according to the procedure of Example 6G and coupling of the resulting compound with the compound from Example 28C, using the procedure described in Example 2E provided the desired compound.

EXAMPLE 29

A. ((5-Isothiazolyl)methyl)-(4-nitrophenyl)carbonate

Using the procedure of Example 7E but replacing 5-(hydroxymethyl)-thiazole with 5-(hydroxymethyl) isothiazole (Bennett, et. al., *J. Chem. Soc.*, 3834 (1965)) provided the desired compound.

B. 5S-(((5-Isothiazolyl)methoxy)carbonyl)amino-2-(t-butyloxycarbonyl)amino-4S-hydroxy-1,6-diphenyl-2-azahexane Using the procedure of Example 7F but replacing the resultant compound of Example 7E with ((5-isothiazolyl) methyl)-(4-nitrophenyl)carbonate provided the desired compound.

EXAMPLE 30

5S-(((5-Isothiazolyl)methoxy)carbonyl)amino-2-N-((N-Methyl-N-((2-isopropyl-4-thiazolyl)methyl) amino)carbonyl)-L-valinylamino-4S-hydroxy-1,6-diphenyl-2-azahexane Deprotection of the t-butyloxycarbonyl protecting group of the compound from Example 29B according to the procedure of Example 6G and coupling of the resulting compound with the compound from Example 6F, using the procedure described in Example 2E provided the desired compound.

EXAMPLE 31

A. N-1-t-Butyloxycarbonyl-N-(cyclohexyl)methyl-hydrazine

Using the procedure of Example 14A, but replacing p-anisaldehyde with cyclohexanecarboxaldehyde, provided the desired compound. $_1$H NMR (CDCl$_3$) δ 0.88–1.00 (m, 2H), 1.13–1.30 (m, 3H), 1.46 (s, 9H), 1.63–1.77 (m, 6H), 2.68 (d, 2H), 3.90 (br s, 1H), 6.03 (br s, 1H). Mass spectrum: $(M+H)^+=229$.

B. 5S-N-(Benzyloxycarbonyl)amino-2-N-(t-butyloxycarbonyl)amino-4S-hydroxy-1-cyclohexyl-6-phenyl-2-azahexane Using the procedure of Example 1F, but replacing N(1)-t-butyloxycarbonyl-N(2)-benzyl-hydrazine with the resultant compound of Example 31A provided the desired compound. Mass spectrum: $(M+H)^+=526$.

EXAMPLE 32

A. N-1-t-Butyloxycarbonyl-N-(4-pyridinyl)methyl-hydrazine

Using the procedure of Example 14A, but replacing p-anisaldehyde with pyridine-4-carboxaldehyde, provided the desired compound. $_1$H NMR (CDCl$_3$) δ 1.46 (s, 9H), 4.02 (d, 2H), 4.33 (br s, 1H), 6.23 (br s, 1H),7.28 (dd, 2H), 8.56 (dd, 2H).

B. 5S-N-(Benzyloxycarbonyl)amino-2-N-(t-butyloxycarbonyl)amino-4S-hydroxy-1-(4-pyridinyl)-6-phenyl-2-azahexane Using the procedure of Example 1F, but replacing N(1)-t-butyloxycarbonyl-N(2)-benzyl-hydrazine with the resultant compound of Example 32A provided the desired compound. $_1$H NMR (CDCl$_3$) δ 1.47 (s, 9H), 2.51 (m, 1H), 2.81 (m, 1H), 2.97 (m, 2H), 3 61 (m, 1H), 3.77 (m, 2H), 3.98 (m, 1H), 4.40 (br s, 1H), 5.05 (s, 2H), 5.20 (s, 1H), 5.35 (br d, 1H), 7.19–7.37 (m, 12H), 8.53 (d, 2H). Mass spectrum: $(M+H)^+=521$.

EXAMPLE 33

A. N-1-t-Butyloxycarbonyl-N-(3-pyridinyl)methyl-hydrazine

Using the procedure of Example 14A, but replacing p-anisaldehyde with pyridine-3-carboxaldehyde, provided the desired compound.

B. 5S-N-(Benzyloxycarbonyl)amino-2-N-(t-butyloxycarbonyl)amino-4S-hydroxy-1-(3-gyridinyl)-6-phenyl-2-azahexane Using the procedure of Example 1F, but replacing N(1)-t-butyloxycarbonyl-N(2)-benzyl-hydrazine with the resultant compound of Example 33A provided the desired compound.

EXAMPLE 34

A. N-1-t-Butyloxycarbonyl-N-(2-pyridinyl)methyl-hydrazine

Using the procedure of Example 14A, but replacing p-anisaldehyde with pyridine-2-carboxaldehyde, provided the desired compound. $_1$H NMR (CDCl$_3$) δ 1.46 (s, 9H), 4.16 (s, 2H), 5.78 (br s, 1H), 6.36 (br s, 1H), 7.18 (ddd, 1H), 7.29 (d, 1H), 7.65 (td, 1H), 8.58 (d, 1H).

B. 5S-N-(Benzyloxycarbonyl)amino-2-N-(t-butyloxycarbonyl)amino-4S-hydroxy-1-(2-pyridinyl)-6-phenyl-2-azahexane Using the procedure of Example 1F, but replacing N(1)-t-butyloxycarbonyl-N(2)-benzyl-hydrazine with the resultant compound of Example 34A provided the desired compound.

EXAMPLE 35

A. N-1-t-Butyloxycarbonyl-N-(6-methyl-2-pyridinyl)methyl-hydrazine

Using the procedure of Example 14A, but replacing p-anisaldehyde with 6-methylpyridine-2-carboxaldehyde, provided the desired compound.

B. 5S-N-(Benzyloxycarbonyl)amino-2-N-(t-butyloxycarbonyl)amino-4S-hydroxy-1-(6-methyl-2-pyridinyl)-6-phenyl-2-azahexane Using the procedure of Example 1F, but replacing N(1)-t-butyloxycarbonyl-N(2)-benzyl-hydrazine with the resultant compound of Example 35A provided the desired compound.

EXAMPLE 36

A. N-1-t-Butyloxycarbonyl-N-(5-oxazolyl)methyl-hydrazine

Using the procedure of Example 14A, but replacing p-anisaldehyde with oxazole-5-carboxaldehyde (Kende, et.al., *J. Am. Chem. Soc.*, 112, 4070 (1990)), provided the desired compound.

B. 5S-N-(Benzyloxycarbonyl)amino-2-N-(t-butyloxycarbonyl)amino-4S-hydroxy-1-(5-oxazolyl)-6-phenyl-2-azahexane Using the procedure of Example 1F, but replacing N(1)-t-butyloxycarbonyl-N(2)-benzyl-hydrazine with the resultant compound of Example 36A provided the desired compound.

EXAMPLE 37

A. N-1-t-Butyloxycarbonyl-N-(4-isoxazolyl)methyl-hydrazine

Using the procedure of Example 14A, but replacing p-anisaldehyde with isoxazole-4-carboxaldehyde (Taylor, et.al., *J. Heterocycl. Chem.*, 27, 1 (1990)), provided the desired compound.

B. 5S-N-(Benzyloxycarbonyl)amino-2-N-(t-butyloxycarbonyl)amino-4S-hydroxy-1-(4-isoxazolyl)-6-phenyl-2-azahexane Using the procedure of Example 1F, but replacing N(1)-t-butyloxycarbonyl-N(2)-benzyl-hydrazine with the resultant compound of Example 37A provided the desired compound.

EXAMPLE 38

A. N-1-t-Butyloxycarbonyl-N-(3,4,5,6-tetrahydro[2H]pyran-4-yl)methyl-hydrazine

Using the procedure of Example 14A, but replacing p-anisaldehyde with 3,4,5,6-tetrahydro[2H]pyran-4-carboxaldehyde (Klein, et.al., *Angew. Chem. Internat. Edit.*, 13, 672(1974)), provided the desired compound.

B. 5S-N-(Benzyloxycarbonyl)amino-2-N-(t-butyloxycarbonyl)amino-4S-hydroxy-1-(3,4,5,6-tetrahydro[2H]pyran-4-yl)-6-phenyl-2-azahexane Using the procedure of Example 1F, but replacing N(1)-t-butyloxycarbonyl-N(2)-benzyl-hydrazine with the resultant compound of Example 38A provided the desired compound.

EXAMPLE 39

A. Hydrazone of 5-thiazolecarboxaldehyde and t-butylcarbazate

Using the procedure of Example 1D, but replacing benzaldehyde with 5-thiazolecarboxaldehyde (Dondoni, et. al., *Synthesis*, 998(1987)), provided the desired compound.

B. N-1-t-Butyloxycarbonyl-N-(5-thiazolyl)methyl-hydrazine

BH$_3$.THF (1M solution, 1.0 eq) was added to the solid resultant compound of Example 39A, which was allowed to stir for 30 min at RT. HCl (1N) was then added dropwise to the reaction mixture at 0° C. After being stirred for 5 min, the reaction mixture was basified with conc. ammonium hydroxide and extracted with EtOAc. The extract was dried over NaSO$_4$ and concentrated to provide the desired compound.

C. 5S-N-(Benzyloxycarbonyl)amino-2-N-(t-butyloxycarbonyl)amino-4S-hydroxy-1-(5-thiazolyl)-6-phenyl-2-azahexane Using the procedure of Example 1F, but replacing N(1)-t-butyloxycarbonyl-N(2)-benzyl-hydrazine with the resultant compound of Example 39B provided the desired compound.

EXAMPLE 40

A. N-1-t-Butyloxycarbonyl-N-2-isopropyl hydrazine

Hydrogenation of the hydrazone resulting from acetone and t-butyl carbazate using the procedure described in Example 1D and 1E provided the desired compound. $^1$H NMR (CDCl$_3$): δ 1.03 (d, 6 H), 1.46 (s, 9 H), 3.12 (m, 1 H), 6.00 (br s, 1 H). Mass spectrum: (M+H)$^+$=175.

B. N-t-Butyloxycarbonyl-azavaline-p-nitrophenyl ester

To a solution of the compound from Example 40 A in dichloromethane was added 1.2 equivalents of triethylamine and 1.0 equivalent of p-nitrophenyl chloroformate. After 1 h at 0° C., and 1 h at RT, the solvent was removed under vacuum and the crude product was purified by silica gel column chromatography to provide the desired compound. $^1$H NMR (CDCl$_3$): δ 1.25 (d, 6 H), 1.48 (s, 9 H), 4.50 (m, 1 H), 6.32 (br s, 1 H), 7.30 (d, 2 H), 8.25 (d, 2 H). Mass spectrum: (M+NH$_4$)$^+$=357.

C. 2-(t-Butyloxycarbonyl)amino-4S-hydroxy-5S-(t-butyloxycarbonyl)-azavalinylamino-1,6-diphenyl-2-azahexane To a solution of the compound from Example 2D in dry dimethylformamide was added 1 equivalent of the compound from Example 40B. The reaction mixture was heated to 50° C. for 18 h. Evaporation of the solvent in vacuo and purification by silica gel column chromatography provided the desired compound.

EXAMPLE 41

5S-N-Benzyloxycarbonyl-(2S, 3'R)-tetrahydrofuranylolycinyl-amino-4S-hydroxy-1,6-diphenyl-2-azahexane Using the procedure of Example 2E, but replacing N-((2-pyridinyl)methoxycarbonyl)valine with (N-benzyloxycarbonyl)-(2S, 3'R)-tetrahydrofuranylglycine [J. Am. Chem. Soc. 115, 801–803 (1993)], and coupling with 2-t-(butyloxycarbonyl)amino-4S-hydroxy-5S-amino-1,6-diphenyl-2-azahexane provided the desired compound.

EXAMPLE 42

A. ((3-Pyridinyl)methyl)-(4-nitroghenyl)carbonate

A solution 20 g (0.1 mol) of (4-nitrophenyl)-chloroformate in 150 ml of dichloromethane was cooled to 0° C. and treated sequentially with 8.0 ml (0.083 mol) of pyridine-3-methanol and 11 ml (0.1 mol) of 4-methylmorpholine. After addition, the solution was allowed to come to ambient temperature, stirred for 0.5 h, diluted with dichloromethane, washed sequentially with aqueous $NaHCO_3$ and water, dried over $Na_2SO_4$, and concentrated in vacuo. The residue was broken up, triturated with 3:1 hexane:ethyl acetate, and filtered. The resulting solid was dissolved in a minimum amount of boiling ethyl acetate/hexane, filtered hot to remove an insoluble dark oil, and allowed to cool. The desired crystalline product (18.65 g, 82%) was collected by filtration.

B. (1S,2S)-2-((3-Pyridinyl)methoxycarbonyl)amino-1-cyclohexanol

A mixture of 21 mg (0.18 mmol) of (S,S)-2-aminocyclohexanol (Overman and Sugai, et. al., J. Org. Chem. 1985, 50, 4154), 60 mg (0.22 mmol) of ((3-pyridinyl)methyl)-(4-nitrophenyl)carbonate in 4 ml of tetrahydrofuran was heated at reflux for 1 h. The resulting mixture was concentrated in vacuo and purified by silica gel chromatography using 4% methanol in chloroform to provide 36 mg (79%) of the desired compound. $^1$H NMR ($CDCl_3$) δ 1.1–1.4 (m, 4 H), 1.7 (m, 2 H), 1.82 (br s, 1 H), 2.02 (m, 2 H), 3.25–3.45 (m, 2 H), 4.98 (br, 1 H), 5.12 (s, 2 H), 7.29 (dd, J=7, 5 Hz, 1 H), 7.70 (m, 1 H), 8.55 (dd, J=5, 2 Hz, 1 H), 8.60 (d, J=2 Hz, 1 H). Mass spectrum: $(M+H)^+=251$.

C. (1'S,2'S)-(2-((3-Pyridinyl)methoxycarbonyl)amino-1-cyclohexyl)-4-nitrophenylcarbonate A solution of 31 mg (0.12 mmol) of (1S,2S)-2-((3-pyridinyl)methoxycarbonyl)amino-1-cyclohexanol in 5 ml of dichloromethane was treated with 35 mg (0.18 mmol) of 4-nitrophenyl chloroformate, stirred for 10 min, quenched with methanol and concentrated in vacuo. Silica gel chromatography using first 20% ethyl acetate in chloroform then 4% methanol in chloroform provided 48 mg (95%) of the desired compound. Mass spectrum: $(M+H)^+=416$.

D. (4S,5S,1'S,2'S)-2-(N-(2-(N-((3-Pyridinyl)methoxy)carbonyl)amino-1-cyclohexyl)oxycarbonyl)amino-5-((5-thiazolyl)methoxy)carbonyl)amino-4-hydroxy-1,6-diphenyl-2-azahexane Deprotection of the t-butyloxycarbonyl protecting group of the compound from Example 7F according to the procedure of Example 6G and reaction of the resulting compound with (1'S,2'S)-(2-((3-pyridinyl)methoxycarbonyl)amino-1-cyclohexyl)-4-nitrophenylcarbonate according to the procedure of Example 4B provided the desired compound.

EXAMPLE 43

A. (1S,2S)-2-((3-Pyridinyl)methoxycarbonyl)amino-1-cyclopentanol

Using the procedure of Example 42B but replacing (S,S)-2-aminocyclohexanol with (S,S)-2-aminocyclopentanol (Overman and Sugai, et. al., J. Org. Chem. 1985, 50, 4154), provided, after silica gel chromatography using first 20% ethyl acetate in chloroform then 5% methanol in chloroform, 324 mg (66%) of the desired compound ($R_f$ 0.33, 10% methanol in chloroform). $^1$H NMR ($CDCl_3$) δ 1.40 (dq, J=12, 8 Hz, 1 H), 1.6–1.9 (m, 3 H), 2.02 (m, 1 H), 2.15 (m, 1 H), 3.70 (m, 1 H), 4.01 (br q, 1 H), 4.91 (br, 1 H), 5.13 (s, 2 H), 7.30 (dd, J=7, 5 Hz, 1 H), 7.71 (d, J=8 Hz, 1 H), 8.59 (dd, J=5, 1 Hz, 1 H), 8.62 (br s, 1 H). Mass spectrum: $(M+1)^+=237$.

B. (1'S,2'S)-(2-((3-Pyridinyl)methoxycarbonyl)amino-1-cyclopentyl)-4-nitrophenylcarbonate Using the procedure of Example 42C but replacing the resultant compound of Example 42B with the resultant compound of Example 43A, provided, after silica gel chromatography using first 20% ethyl acetate in chloroform then 4% methanol in chloroform, 495 mg (90%) of the desired compound ($R_f$ 0.63, 10% methanol in chloroform). $^1$H NMR ($CDCl_3$) δ 1.5–1.6 (m, 1 H), 1.75–1.95 (m, 3 H), 2.1–2.3 (m, 2 H), 4.13 (m, 1 H), 4.98 (br, 1 H), 5.04 (m, 1 H), 5.14 (s, 2 H), 7.29 (dd, J=7, 5 Hz, 1 H), 7.38 (d, J=10 Hz, 2 H), 7.70 (d, J=8 Hz, 1 H), 8.27 (d, J=10 Hz, 2 H), 8.58 (br d, 1 H), 8.63 (br s, 1 H). Mass spectrum: $(M+H)^+=402$.

C. (4S,5S,1'S,2'S)-2-(N-(2-(N-((3-Pyridinyl)methoxy)carbonyl)amino-1-cyclolpentyl)oxycarbonyl)amino-5-((5-thiazolyl)methoxy)carbonyl)amino-4-hydroxy-1,6-diphenyl-2-azahexane Deprotection of the t-butyloxycarbonyl protecting group of the compound from Example 7F according to the procedure of Example 6G and reaction of the resulting compound with (1'S,2'S)-(2-((3-pyridinyl)methoxycarbonyl)amino-1-cyclopentyl)-4-nitrophenylcarbonate according to the procedure of Example 4B provided the desired compound.

EXAMPLE 44

A. N-((2-Isopropyl-4-thiazolyl)methyl)-N-methyl-(4-nitrophenyl)carbamate

Using the procedure of Example 42A, but replacing pyridine-3-methanol with 2-isopropyl-4-(((N-methyl)amino)-methyl)thiazole provided the desired compound.

B. (1'S,2'S)-2-N-((N-Methyl-N-((2-isopropyl-4-thiazolyl)methyl)amino)carbonyl)amino-1-cyclohexanol Using the procedure of Example 42B, but replacing ((3-pyridinyl)-methyl)-(4-nitrophenyl)carbonate with N-((2-isopropyl-4-thiazolyl)methyl)-N-methyl-(4-nitrophenyl)carbamate provided the desired compound.

C. (1'S,2'S)-(2-(N-(N-Methyl-N-((2-isopropyl-4-thiazolyl)methyl)amino)-carbonyl)amino-1-cyclohexyl)-4-nitrophenylcarbonate Using the procedure of Example 42C, but replacing (1S,2S)-2-((3-pyridinyl)methoxy-carbonyl)amino-1- cyclohexanol with (1'S,2'S)-2-N-((N-methyl-N-((2-isopropyl-4-thiazolyl)methyl)amino)carbonyl)amino-1-cyclohexanol D. (4S,5S,1'S,2'S)-2-(N-(2-(N-(N-Methyl-N-((2-isopropyl-4-thiazolyl)methyl)amino)-carbonyl)amino-1-cyclohexyl)oxycarbonyl)amino-5-((5-thiazolyl)methoxy)carbonyl)amino-4-hydroxy-1,6-diphenyl-2-azahexane Deprotection of the t-butyloxycarbonyl protecting group of the compound from Example 7F according to the procedure of Example 6G and reaction of the resulting compound with (1'S,2'S)-(2-(N-(N-methyl-N-((2-isopropyl-4-thiazolyl)methyl)amino)carbonyl)amino-1-cyclohexyl)-4-nitrophenylcarbonate according to the procedure of Example 4B provided the desired compound.

EXAMPLE 45

A. (1'S,2'S)-2-N-((N-Methyl-N-((2-isoprogyl-4-thiazolyl)methyl)amino)carbonyl)amino-1-cyclopentanol Using the procedure of Example 42B, but replacing ((3-pyridinyl)-methyl)-(4-nitrophenyl)carbonate with N-((2-isopropyl-4-thiazolyl)methyl)-N-methyl-(4-nitrophenyl) carbamate and replacing (S,S)-2-aminocyclohexanol with (S,S)-2-aminocyclopentanol provided the desired compound.

B. (1'S,2S)-(2-(N-(N-Methyl-N-((2-isopropyl-4-thiazolyl)methyl)amino)-carbonyl)amino-1-cyclopentyl)-4-nitrophenylcarbonate Using the procedure of Example 42C, but replacing (1S,2S)-2-((3-pyridinyl)methoxy-carbonyl)amino-1-cyclohexanol with (1'S,2'S)-2-N-((N-methyl-N-((2-isopropyl-4-thiazolyl)methyl)amino)carbonyl)amino-1-cyclopentanol C. (4S,5S,1'S,2'S)-2-(N-(2-(N-(N-Methyl-N-((2-isopropyl-4-thiazolyl)methyl)amino)carbonyl)amino-1-cyclopentyl)oxycarbonyl)amino-5((5-thiazolyl)methoxy)carbonyl)amino-4-hydroxy-1,6-diphenyl-2-azahexane Deprotection of the t-butyloxycarbonyl protecting group of the compound from Example 7F according to the procedure of Example 6G and reaction of the resulting compound with (1'S,2'S)-(2-(N-(N-methyl-N-((2-isopropyl-4-thiazolyl)methyl)amino)carbonyl)amino-1-cyclopentyl)-4-nitrophenylcarbonate according to the procedure of Example 4B provided the desired compound.

EXAMPLE 46

A. (3R,4S,1'R)-4-(N-(1-Phenylethyl)amino)-3-hydroxy-2,3,4,5-tetrahydrofuran

According to the procedure of Overman, et al. (J. Org. Chem. 1985, 50, 4154), 3,4-epoxy-2,5-dihydrofuran was treated with (R)-1-phenylethylamine and trimethylaluminum to give a 1:1 mixture of diastereomers. The mixture was purified by silica gel chromatography to provide the desired compound.

B. (3R,4S)-4-(N-((Benzyloxy)carbonyl)amino)-3-hydroxy-2,3,4,5-tetrahydrofuran

A solution of the resultant compound of Example 46A in methanol was treated with an equivalent weight with 20% palladium on carbon. After being shaken for 16 h under $H_2$ atmosphere, the solution was filtered and concentrated in vacuo. The residue was taken up in tetrahydrofuran and treated with 1 molar equivalent of N-(benzyloxycarbonyloxy)succinimide and stirred at ambient temperature for 16 h. The solvent was removed in vacuo, and the crude residue was separated by chromatography on silica gel to provide the desired compound.

C. (3R,4S)-(4-(N-((Benzyloxy)carbonyl)amino)-2,3,4,5-tetrahydrofuran-3-yl)-4-nitrophenylcarbonate Using the procedure of Example 42C, but replacing (1S,2S)-2-((3-pyridinyl)methoxy-carbonyl)amino-1-cyclohexanol with the resultant compound of Example 46B provided the desired compound.

D. (4S,5S,3'R,4'S)-2-(N-(4-(N-((Benzyloxy) carbonyl)amino)-2,3,4,5-tetrahydrofuran-3-yl) oxycarbonyl)amino-5-((5-thiazolyl)methoxy) carbonyl)amino-4-hydroxy-1,6-diphenyl-2-azahexane Using the procedure of Example 42D, but replacing (1'S,2'S)-(2-((3-pyridinyl)methoxycarbonyl)amino-1-cyclohexyl)-4-nitrophenylcarbonate with the resultant compound of Example 46C provided the desired compound.

EXAMPLE 47

5S-(((5-Thiazolyl)methoxy)carbonyl)amino-2-(t-butyloxycarbonyl)amino)-4S-hydroxy-1-(3-furanyl)-6-phenyl-2-azahexane Deprotection of the benzyloxycarbonyl group of the resulting compound from Example 21b by hydrogenolysis and coupling of the resulting amine with the resulting compound from Example 7E provided the desired compound in 78% yield. $^1$H NMR (CDCl$_3$): δ 1.40 (s, 9H), 2.45 (m, 1H), 2.70 (m, 1H), 2.96 (m, 2H), 3.55–3.90 (m, 4H), 5.25 (m, 3H), 6.35 (s, 1H), 7.20–7.40 (m, 7H), 7.88 (s, 1H), 8.30 (s, 1H).

EXAMPLE 48

5S-(((5-Thiazolyl)methoxy)carbonyl)amino-2-N-(((N-methyl-N-((2-isopropyl-4-thiazolyl)methyl) amino)carbonyl)-L-valinyl)amino-4S-hydroxy-1-(3-furanyl)-6-phenyl-2-azahexane Deprotection of the t-butyloxycarbonyl group of the resulting compound from Example 47 and coupling of the resulting amine with the resulting compound from Example 6F provided the desired compound in 72% yield. $^1$H NMR (DMSO-d$_6$): δ 0.65 (d, 3H), 0.71 (d, 3H), 1.29 (d, 6H), 1.75 (m, 1H), 2.70 (m, 4H), 2.86 (s, 3H), 3.20 (m, 1H), 3.60 (m, 1H), 3.75 (m, 5H), 4.43 (s, 2H), 4.80 (d, 1H), 5.13 (m, 2H), 6.20 (br d, 1H), 6.39 (m, 1H), 7.17 (m, 7H), 7.47 (s, 1H), 7.50 (t, 1H), 7.83 (d, 1H), 8.96 (s, 1H), 9.04 (d, 1H). Mass spectrum: (M+H)$^+$=712.

EXAMPLE 49

A. Methyl 2-isopropyl-4-oxazole carboxylate

To a solution of 10.0 g of diphenyl sulfoxide in 80 ml of dichloromethane at −78° C. was added 6.0 ml of trifluoromethanesulfonic acid anhydride. After 30 minutes, 50.5 g of potassium phosphate was added, followed by slow addition of a solution of 4.50 g of isobutyryl serine methyl ester via syringe. After 30 minutes at −78° C., 20 minutes at 0° C. and 20 minutes at RT, 200 ml of water was added. Extraction with dichloromethane (4×100 ml), washed with 50 ml of satd. NaCl solution and dried organic layer with anhy. sodium sulfate. Filtering the solution and conc. in vacuo provided 2.70 g of oxazoline which upon oxidation with 8.0 g of nickel peroxide in 100 ml of toluene provided 0.95 g of desired compound (36%). $^1$H NMR (CDCl$_3$): δ 1.48 (d, 6H), 3.15 (m, 1H), 3.90 (s, 3H), 8.15 (s, 1H). Mass spectrum: (M+H)$^+$=187.

B. 4-Hydroxymethyl-2-isopropyloxazole

To a solution of 1.90 g of the resulting compound from Example 49A in 50 ml of dry THF at −25° C. was added 11.2 ml of 1M lithium aluminum hydride solution in THF. After 10 minutes, 0.79 ml of water was added, followed by 0.79 ml of 15% aq. NaOH and 1.69 ml of water. After vigorous stirring for 15 min., the mixture was filtered and the solid washed thoroughly with EtOAc (4×50 ml). The filtrate was concentrated in vacua. Purification by silica gel column chromatography (3% MeOH/97% CH$_2$Cl$_2$) provided 1.25 g of the desired compound (79%). $^1$H NMR (CDCl$_3$): δ 1.35 (d, 6H), 2.48 (t, 1H), 3.08 (m, 1H), 4.57 (d, 2H), 7.48 (s, 1H).

C. 2-Isopropyl-4-oxazolylmethyl-4-nitro-phenyl carbonate

To a solution of 0.66 g of the resulting compound from Example 49B in 40 ml of dichloromethane at 0° C. was added 0.75 ml of triethylamine and 1.04 g of 4-nitrophenyl chloroformate. After 2 h, solvent was removed in vacua and purification by silica gel column chromatography (1% EtOAc/99% CH$_2$Cl$_2$) provided 1.09 g of desired compound (76%). $^1$H NMR (CDCl$_3$): δ 1.38 (d, 6H), 3.10 (m, 1H, 5.20 (s, 2H), 7.40 (d, 2H), 7.67 (s, 1H), 8.28 (d, 2H). Mass spectrum: (M+H)$^+$=307.

D. N-((2-Isopropyl-4-oxazolyl)methoxycarbonny) valine

To a solution of 1.09 g of the resulting carbonate from Example 49C in 14 ml of dry DMF was added 0.6 g of L-valine methyl ester hydrochloride, followed by 0.52 ml of triethylamine. After 2.5 h at RT, the solvent was removed in vacua and the residue was taken up in 250 ml of EtOAc and washed with satd. NaHCO$_3$ (2×25 ml), the satd. NaCl and dried with anhy. sodium sulfate. Filtration, conc. in vacua and purification by silica gel column chromatography (20% EtOAc/80% CH$_2$Cl$_2$) provided 0.55 g of methyl ester which upon basic hydrolysis with lithium hydroxide provided 0.80 g of the desired compound (99%). $^1$H NMR (DMSO-d$_6$): δ 0.58 (t, 6H), 1.27 (d, 6H), 3.05 (m, 1H), 3.85 (m, 1H), 4.86 (s, 1H), 7.49 (br d, 1H), 7.98 (s, 1H). Mass spectrum: (M+H)$^+$=285.

E. 5S-(((5-Thiazolyl)methoxy)carbonyl)amino-2-((N-2-isopropyl-4-oxazolyl)methoxycarbonyl)amino-4S-hydroxy-1-(3-furanyl)-6-phenyl-2-azahexane Deprotection of the t-butyloxycarbonyl group of the resulting compound from Example 47 and coupling of the resulting amine with the resulting compound from Example 49D using the procedure of Example 2E provided the desired compound in 63% yield. $^1$H NMR (DMSO-d$_6$): δ 0.63 (d, 3H), 0.70 (d, 3H), 1.22 (d, 6H), 1.70 (m, 1H), 2.70 (m, 4H), 3.0 (m, 1H), 3.60–3.75 (m, 5H), 4.77 (d, 1H), 4.83 (s, 2H), 5.12 (s, 2H), 6.38 (s, 1H), 7.15–7.20 (m, 7H), 7.47 (s, 1H), 7.50 (t, 1H), 7.72 (s, 1H), 7.90 (s, 1H), 9.0 (s, 1H), 9.03 (s, 1H). Mass spectrum: (M+H)$^+$=683.

EXAMPLE 50

5S-(((5-Thiazolyl)methoxy)carbonyl)amino-2-((N-2-isopropyl-4-oxazolyl)methoxycarbonyl)amino-4S-hydroxy-1,6-diphenyl-2-azahexane Deprotection of the t-butyloxycarbonyl group of the resulting compound from Example 7F with 4N HCl and coupling of the resulting amine with the resulting compound from Example 49D using the procedure of Example 2E provided the desired compound in 75% yield. $^1$H NMR (DMSO-d$_6$): δ 0.47 (d, 3H), 0.56 (d, 3H), 1.22 (d, 6H), 1.58 (m, 1H), 2.70 (m, 4H), 3.0 (m, 1H), 3.55 (m, 2H), 3.80–3.96 (m, 4H), 4.83 (s, 2H), 4.87 (d, 1H), 5.12 (s, 2H), 7.20 (m, 10H), 7.83 (s, 1H), 7.91 (s, 1H), 9.02 (s, 1H), 9.07 (s, 1H). Mass spectrum: (M+H)$^+$=693.

EXAMPLE 51

A. Hydrazone of 4-Fluorobenzaldehyde and t-butylcarbazate

Using the procedure of Example 1D, but replacing benzaldehyde with 4-fluorobenzaldehyde provided the desired compound. $^1$H NMR (CDCl$_3$): δ 1.47 (s, 9H), 7.25 (m, 2H), 7.65 (m, 2H), 7.95 (s, 1H), 10.90 (br s, 1 H).

B. N(1)-t-butyloxycarbonyl-N(2)-4-fluorobenzyl-hydrazine

Using the procedure of Example 1E, the compound from Example 51A was hydrogenated to provide the desired compound. $^1$H NMR (CDCl$_3$): δ 1.47 (s, 9H), 3.97 (s, 2H), 6.0 (br s, 1H), 7.0 (m, 2H), 7.0 (m, 2H).

C. 2-(t-Butyloxycarbonyl)amino-4S-hydroxy-5S-(benzyloxycarbonyl)amino-1-(4-fluorophenyl)-6-phenyl-2-azahexane Using the procedure of Example 1F, but replacing N(1)-t-butyloxycarbonyl-N(2)-benzyl hydrazine with the resulting compound from Example 51B provided the desired compound in 40% yield. $^1$H NMR (CDCl$_3$): δ 1.35 (s, 9H), 2.41 (m, 1H), 2.77 (m, 1H), 2.96 (m, 2H), 3.57–3.94 (m, 4H), 4.48 (s, 1H), 5.12 (s, 1H), 5.34 (m, 1H), 7.0 (m, 2H), 7.30 (m, 12H).

D. 5S-(((2-Isopropyl-4-oxazolyl)methoxycarbonyl-valinyl)amino-2-(t-butyloxycarbonyl)amino-4S-hydroxy-1-(4-fluorophenyl)-6-phenyl-2-azahexane Deprotection of the benzyloxycarbonyl group of the resulting compound from Example 51hC and coupling of the resulting amine with the resulting compound from Example 49D provided the desired compound in 85% yield. $^1$H NMR (DMSO-d$_6$): δ 0.70 (m, 6H), 1.72 (m, 1H), 2.60–3.05 (m, 4H), 3.52 (m, 1H), 3.80 (m, 2H), 4.0 (m, 1H), 4.70 (m, 1H), 4.85 (s, 2H), 7.05–7.30 (m, 8H), 7.52 br d, 1H), 7.92 (s, 1H), 7.95 (m, 1H).

EXAMPLE 52

A. Hydrazone of 4-hydroxybenzaldehyde and t-butylcarbazate

Using the procedure of Example 1D, but replacing benzaldehyde with 4-hydroxybenzaldehyde provided the desired compound. $^1$H NMR (DMSO-d$_6$): δ 1.48 (s, 9H), 6.77

(d, 2H), 7.40 (d, 2H), 7.88 (s, 1H), 9.80 (br s, 1H), 10.66 (br s, 1H). Mass spectrum: (M+H)$^+$=237.

B. N(1)-t-Butyloxycarbonyl-N(2)-4-hydroxybenzyl-hydrazine

Using the procedure of Example 1E, the hydrazone resulting from Example 52A was hydrogenated to provide the desired compound. $^1$H NMR (DMSO-d$_6$): δ 1.40 (s, 9H), 3.71 (d, 2H), 4.47 (m, 1H), 6.68 (d, 2H), 7.10 (d, 2H), 8.10 (br s, 1H), 9.23(s, 1H). Mass spectrum: (M+H)$^+$=239.

C. 5S-(Benzyloxycarbonyl)amino-2-(t-butyloxycarbonyl)amino-4S-hydroxy -1-(4-hydroxyphenyl)-6-phenyl-2-azahexane To a solution of 2.0 g of the resulting epoxide from Example 1C in 60 ml of isopropyl alcohol was added 1.6 g of the hydrazine resulting from Example 52B. The solution was heated to reflux for 20 h. After cooling to RT, the desired compound crystallized out from the solution and was collected by suction filtration to provide 56% yield of product. $^1$H NMR (CDCl$_3$): δ 1.36 (s, 9H), 2.40 (m, 1H), 2.74 (m, 1H), 2.95 (m, 2H), 3.55–3.90 (m, 4H), 4.55 (br s, 1H), 5.07 (s, 2H), 5.20 (m, 1H), 5.36 (m, 1H), 5.48 (s, 1H), 6.75 (d, 2H), 7.10 (d, 2H), 7.15–7.40 (m, 10H). Mass spectrum: (M+H)$^+$=536.

EXAMPLE 53

5S-(((2-Isopropyl-4-oxazolyl)methoxycarbonyl)-valinyl)amino-2-(t-butyloxycarbonyl)amino-4S-hydroxy-1-(4-hydroxyphenyl)-6-phenyl-2-azahexane Deprotection of the benzyloxycarbonyl protecting group of the resulting compound from Example 52C and coupling of the resulting amine with the resulting compound from Example 49D provided the desired compound in 51% yield. $^1$H NMR (DMSO-d$_6$): δ 0.70 (d, 6H), 1.27 (s, 9H), 1.78 (m, 1H), 2.60–2.80 (m, 4H), 3.03 (m, 1H), 3.55 (m, 1H), 3.70 (br s, 1H), 3.82 (m, 1H), 4.03 (m, 1h), 4.62 (br s, 1H), 4.83 (s, 1H), 6.62 (d, 2H), 7.05 (d, 2H), 7.20 (m, 5H), 7.55 (br d, 1H), 7.87 (s, 1H), 7.92 (s, 1H), 9.19 (s, 1H). Mass spectrum: (M+H)$^+$=668.

EXAMPLE 54

A. 5S-(((5-Thiazolyl)methoxy)carbonyl)amino-2-(t-butyloxycarbonyl)amino-4S-hydroxy-1-(4-hydroxyphenyl)-6-phenyl-2-azahexane Deprotection of the benzyloxycarbonyl protecting group by hydrogenolysis of the compound resulting from Example 52C and coupling of the resulting amine with ((5-thiazolyl) methyl)-(4-nitrophenyl)carbonate provided the desired compound. $^1$H NMR (DMSO-d$_6$): δ 1.27 (s, 9H), 2.60 (m, 2H), 2.80 (m, 1H), 3.50–3.80 (m, 3H), 4.50 (br d, 1H), 5.15 (s, 2H), 6.62 (d, 2H), 7.05 (d, 2H), 7.20 (m, 5H), 7.80 (s, 1H), 7.92 (s, 1H), 9.0 (s, 1H), 9.20 (s, 1H). Mass spectrum: (M+H)$^+$=543.

B. 5S-(((5-Thiazolyl)methoxy)carbonyl)amino-2-N-((N-methyl-N-2-isopropyl-4-thiazolyl)methyl)amino)carbonyl)-L-valinyl-amino-4S-hydroxy-1-(4-hydroxyphenyl)-6-phenyl-2-azahexane Deprotection of the t-butyloxycarbonyl protecting group of the resulting compound from Example 54A with 4N HCl and coupling of the resulting amine with the resulting compound from Example 6F using the procedure described in Example 2E provided the desired compound. $^1$H NMR (DMSO-d$_6$): 0.55 (d, 3H), 0.6 2 (d, 3H), 1.25 (d, 6H), 1.05 (m, 1H), 1.70 (m, 1H), 2.70 (m, 2H), 2.85 (s, 3H), 3.20 (m, 1H), 3.72 (m, 2H), 4.42 (s, 2H), 4.82 (m, 1H), 5.12 (s, 2H), 6.15 (br d, 1H), 6.60 (d, 2H), 7.05 (d, 2H), 7.20 (m, 5H), 7.92 (s, 1H), 8.30 (s, 1H), 8.92 (s, 1H), 9.02 (s, 1H), 9.20 (s, 1H). Mass spectrum: (M+H)$^+$=738.

EXAMPLE 55

A. 5Hydrazone of 3-hydroxybenzaldehyde and t-butylcarbazate

Using the procedure of Example 1D, but replacing benzaldehyde with 3-hydroxybenzaldehyde provided the desired compound. $^1$H NMR (DMSO-d$_6$): δ 1.53 (s, 9H), 5.38 (s, 1H), 6.87 (m, 1H), 7.10 (m, 1H), 7.22 (m, 2H), 7.75 (s, 1H), 7.94 (s, 1H).

B. N(1)-t-butyloxycarbonyl-N(2)-3-khydroxybenzyl hydrazine

Using the procedure of Example 1E, the resulting hydrazone from Example 55A was hydrogenated to provide the desired compound. $^1$H NMR (CDCl$_3$), δ 1.48 (s, 9H), 3.93 (s, 2h), 5.55 (s, 1H), 6.09 (s, 1H), 6.80 (m, 3H), 7.20(t, 1H).

C. 5S-(Benzyloxycarbonyl)amino-2-(t-butyloxycarbonyl)amino-4S-hydroxy-1-(3-hydroxyphenyl)-6-phenyl-2-azahexane Using the procedure of Example 52C, but using the resulting hydrazine from Example 55B provided desired compound. $^1$H NMR (CDCl$_3$): δ 1.35 (s, 9H), 2.45 (m, 1H), 2.76 (m, 1H), 2.95 (m, 2H), 3.60–3.90 (m, 4H), 4.50 (s, 1H), 5.07 (s, 2H), 5.23 (br s, 1H), 5.40 (m, 1H), 5.50 (s, 1H), 6.78 (m, 3H), 7.25 (m, 11H). Mass spectrum: (M+H)$^+$=536.

EXAMPLE 56

A. 5S-(((5-Thiazolyl)methoxy)carbonyl)amino-2-(t-butyloxycarbonyl)amino-4S-hydroxy-1-(3-hydroxyphenyl)-6-phenyl-2-azahexane Deprotection of the benzyloxycarbonyl protecting group of the resulting compound from Example 55C by hydrogenolysis and coupling of the resulting amine with the resulting compound from Example 6F using the procedure described in Example 2E provided the desired compound. $^1$H NMR (DMSO-d$_6$): δ 1.28 (s, 9H), 2.60 (m, 2H), 2.80 (m, 1H), 3.55 (m, 1H), 3.73 (m, 2H), 4.55 (m, 1H), 5.16 (s, 2H), 6.60 (br d, 1H), 6.73 (m, 2H), 7.03–7.20 (m, 7H), 7.85 (s, 1H), 9.04 (s, 1H), 9.22 (s, 1H). Mass spectrum: (M+H)$^+$=543.

B. 5S-(((5-Thiazolyl)methoxy)carbonyl)amino-2-N-((((N-methyl-N-2-isopropyl-4-thiazolyl)methyl)amino)carbonyl)-L-valnylamino-4S-hydroxy-1-(3-hydroxyphenyl)-6-phenyl-2-azahexane Deprotection of the t-butyloxycarbonyl protecting group of the resulting compound from Example 56A with 4N HCl and coupling of the resulting amine with the resulting compound from Example 6F using the procedure described in Example 2E provided the desired compound. $^1$H NMR (DMSO-d$_6$): δ 0.55 (d, 3H), 0.60 (d, 3H), 0.85 (m, 1H), 1.28 (d, 6H), 1.70 (m, 1H), 2.67 (m, 2H), 2.85 (s, 3H), 3.60–3.80 (m, 5H), 4.92 (s, 2H), 4.88 (m, 1H), 5.10 (s, 2H), 6.12 (br d, 1H), 6.60 (m, 1H), 6.70 (m, 2H), 7.0 (m, 1H), 7.15 (m, 7H), 7.82 (s, 1H), 8.97 (s, 1H), 9.02 (s, 1H), 9.20 (s, 1H). Mass spectrum: (M+H)$^+$=738.

EXAMPLE 57

A. Hydrazone of 4-((2-morpholinyl)ethoxy) benzaldehyde and t-butycarbazate

Using the procedure of Example 1D, but replacing benzaldehyde with 4-((2-morpholinyl)ethoxy)benzaldehyde provided the desired compound. $^1$H NMR (CDCl$_3$): δ 1.53 (s, 9H), 2.58 (m, 4H), 2.80 (t, 2H), 3.74 (m, 4H), 4.13 (t, 2H), 6.88 (d, 2H), 7.60 (d, 2H), 7.75 (br s, 2H).

B. N(1)-t-Butyloxycarbonyl-N(2)-4-((2-morpholinyl)ethoxy)benzyl hydrazine

Using the procedure of Example 1E, the resulting hydrazone of Example 57A was hydrogenated to provide the desired compound. $^1$H NMR (CDCl$_3$): δ 1.47 (s, 9H), 2.58 (m, 4H), 2.80 (t, 2H), 3.74 (m, 4H), 3.93 (m, 2H), 4.10 (t, 2H), 4.11 (br s, 1H), 6.0 (br s, 1H), 6.88 (d, 2H), 7.26 (d, 2H).

C. 2-(t-Butyloxycarbonyl)amino-5S-(benzyloxycarbonyl)amino-4S-hydroxy-1-(4-((2-morpholinyl)ethoxy)phenyl)-6-phenyl-2-azahexane Using the procedure of Example 1F, but replacing the hydrazine with the resulting hydrazine from Example 57B provided the desired compound. $^1$H NMR (CDCl$_3$): δ 1.27 (s, 9H), 2.45 (m, 4H), 2.65 (t, 2H), 2.75 (m, 1H), 3.55 (m, 4H), 3.72 (m, 1H), 4.03 (t, 2H), 4.55 (m, 1H), 4.92 (m, 2H), 6.82 (d, 2H), 7.20 (m, 12H), 7.90 (s, 1H). Mass spectrum: (M+H)$^+$=649.

EXAMPLE 58

2-(t-Butyloxycarbonyl)amino-5S-(benzyloxycarbonyl)amino-4S-hydroxy-1-(4-biphenyl)-6-phenyl-2-azahexane Using the procedure of Example 1F, but replacing the hydrazine with N(1)-t-butyloxycarbonyl-N(2)-(4-phenyl) benzyl hydrazine provided the desired compound. $^1$H NMR (CDCl$_3$): δ 1.34 (s, 9H), 2.48 (m, 1H), 2.80 (m, 1H), 2.96 (m, 2H), 3.60–4.00 (m, 4H), 5.07 (s, 2H), 5.22 (m, 1H), 5.40 (br d, 1H), 7.20–7.55 (m, 19H).

EXAMPLE 59

A. Hydrazone of 2-thiazolecarboxaldehyde and t-butylcarbazate

Using the procedure of Example 1D, but replacing benzaldehyde with 2-thiazolecarboxaldehyde (Dondoni, et. al., *Synthesis*, 998 (1987)), provided the desired compound.

B. N-(1)-t-Butyloxycarbonyl-N(2)-(2-thiazolyl) methyl-hydrazine

Using the procedure of Example 39B, but replacing the resultant compound of Example 39A with the resultant compound of Example 59A provided the desired compound.

C. 5S-N-(Benzyloxycarbonyl)amino-2-N-(t-butyloxycarbonyl)amino-4S-hydroxy-1-(2-thiazolyl)-6-phenyl-2-azahexane Using the procedure of Example 52C, but replacing the resulting hydrazine from Example 52B with the resulting hydrazine from Example 59B provided the desired compound. $^1$H NMR (CDCl$_3$) δ 1.40 (s, 9H), 2.58–2.66 (m, 1H), 2.72 (t, 1H), 2.96 (d, 2H), 3.55–3.62 (m, 1H), 3.63–3.74 (m, 1H), 4.22 (d, 1H), 4.39 (d, 1H), 4.65–4.72 (m, 1H), 5.07 (s, 2H), 5.35–5.44 (m, 1H), 6.77 (br, 1H), 7.19–7.39 (m, 11H), 7.73 (d, 1H). Mass spectrum: (M+H)$^+$=527.

EXAMPLE 60

A. N(1)-t-Butyloxycarbonyl-N(2)-((α-methylbenzyl)-hydrazine

Using the procedure of Example 14A, but replacing p-anisaldehyde with acetophenone, provided the desired compound.

B. 5S-N-(Benzyloxycarbonyl)amino-2-N-(t-butyloxycarbonyl)amino-4S-hydroxy-1-methyl-1,6-diphenyl-2-azahexane Using the procedure of Example 52C, but replacing the resulting hydrazine from Example 52B with the resulting hydrazine from Example 60A provided the desired compound. $_1$H NMR (CDCl$_3$) δ 1.48 (s, 9H), 1.53 (d, 3H), 2.07–2.17 (m 1H), 2.74 (t, 1H), 2.93 (d, 2H), 3.40–3.47 (m, 1H), 3.57–3.65 (m, 1H), 3.85–3.95 (m, 1H), 4.55 (br, 1H), 4.99 (br, 1H), 5.10 (d, 2H), 5.41 (d, 1H), 7.14–7.38 (m, 15H). Mass spectrum: (M+H)$^+$=534.

EXAMPLE 61

A. N(1)-t-Butyloxycarbonyl-N(2)-(α-ethylbenzyl)-hydrazine Using the procedure of Example 14A, but replacing p-anisaldehyde with propiophenone, provided the desired compound.

B. 5S-N-(Benzyloxycarbonyl)amino-2-N-(t-butyloxycarbonyl)amino-4S-hydroxy-1-ethyl-1,6-diphenyl-2-azahexane Using the procedure of Example 52C, but replacing the resulting hydrazine from Example 52B with the resulting hydrazine from Example 61A provided, after silica gel chromatography using 50% ether in hexane, 1S and 1R isomer (1:1) of the desired compound. $^1$H NMR (CDCl$_3$) δ 0.95 (t, 3H), 1.48 (s, 9H), 1.67–1.76 (m, 1H), 1.91–2.01 (m, 1H), 2.06–2.13 (m, 1H), 2.71 (t, 1H), 2.94 (d, 2H), 3.38–3.45 (m, 1H), 3.51–3.65 (m, 2H), 4.55–4.64 (br, 1H), 4.92 (br, 1H), 5.13 (d, 2H), 5.46 (d, 1H), 7.10–7.40 (m, 15H). Mass spectrum(M+H)$^+$=548.

EXAMPLE 62

A. 2-chloro-2-phenylpropane 4.8 g of a-methylstyrene was cooled to 0° C. and HCl gas was slowly bubbled for 2 min. The resulting mixture was 30% desired product in stating material.

B. N-(1)-t-Butyloxycarbonyl-N(2)-(α,α-dimethyl) benzyl-hydrazine 2.1 g of the resultant compound of Example 62A and 1.08 g of t-butyl carbonate were dissolved in 20 ml of CH$_2$Cl$_2$ and refluxed. After 20 hrs the reaction mixture was diluted with 100 ml of CH$_2$Cl$_2$ and washed with saturated aqueous NaHCO$_3$, water and saturated NaCl, dried over NaSO$_4$ and concentrated in vacuo. The residue was purified by silica gel chromatography using 50% EtOAc in hexane provided the desired compound.

C. 5S-N-(Benzyloxycarbonyl)amino-2-N-(t-butyloxycarbonyl)amino-4S-hydroxy-1,1-dimethyl-1,6-diphenyl-2-azahexane Using the procedure of Example 52C, but replacing the resulting hydrazine from Example 52B with the resulting hydrazine from Example 62B provided the desired compound. $^1$H NMR (CDCl$_3$) δ 1.39 (s, 9H), 1.54 (s, 6H), 1.97–2.08 (m, 1H), 2.57 (t, 1H), 2.90 (d, 2H), 3.47 (d,1H), 3.57 (t, 1H), 4.48 (br, 1H), 497 (d, 2H), 5.15 (d, 1H), 5.29 (br, 1H), 7.14–7.48 (m, 15H). Mass spectrum: (M+H)$^+$=548.

EXAMPLE 63

A. N(1)-t-Butyloxycarbonyl-N(2)-(4-methylbenzyl)-hydrazine

Using the procedure of Example 14A, but replacing p-anisaldehyde with p-tolualdehyde, provided the desired compound.

B. 5S-N- (Benzyloxycarbonyl)amino-2- N-(t-butyloxycarbonyl)amino-4S-hydroxy-1-(4-methylphenyl)-6-phenyl-2-azahexane Using the procedure of Example 52C, but replacing t he resulting hydrazine from Example 52B with the resulting hydrazine from Example 63A provided the desired compound. $^1$H NMR (CDCl$_3$) δ 1.35 (s, 9H), 2.31 (s, 3H), 2.42–2.49 (m, 1H), 2.73–2.87 (m, 1H), 2.95 (d, 2H), 3.55–3.62 (m, 1H), 3.68–3.74 (m, 2H), 3.92–3.99 (m, 1H), 4.25–4.70 (br, 1H), 5.07 (s, 2H), 5.15–5.30 (br, 1H), 5.32–5.39 (br d 1H), 7.09–7.37 (m, 14H). Mass spectrum: (M+H)$^+$=534.

EXAMPLE 64

A. N (1)-t-Butyloxycarbonyl-N (2)-(3-methylbenzyl)-hydraze

Using the procedure of Example 14A, but replacing p-anisaldehyde with m-tolualdehyde, provided the desired compound.

B. 5S-N-(Benzyloxycarbonyl)amino-2-N-(t-butyloxycarbonyl)amino-4S-hydroxy-1-(3-methylphenyl)-6-phenyl-2-azahexane Using the procedure of Example 52C, but replacing the resulting hydrazine from Example 52B with the resulting hydrazine from Example 64A provided the desired compound. $^1$H NMR (CDCl$_3$) δ 1.45 (s, 9H), 2.33 (s, 3H), 2.41–2.48 (m, 1H), 2.78 (t, 1H), 2.96 (d, 2H), 3.54–3.62 (m, 1H), 3.67–3.83 (m, 2H), 3.92–3.98 (m, 1H), 4.45–4.56 (br, 1H), 5.08 (s, 2H), 5.23 (br, 1H), 5.37 (br d, 1H), 7.04–7.35 (m, 14H). Mass spectrum: (M+H)$^+$=534.

EXAMPLE 65

A. N (1)-t-Butyloxycarbonyl-N (2)-(2-methylbenzyl)-hydrazine

Using the procedure of Example 14A, but replacing p-anisaldehyde with o-tolualdehyde, provided the desired compound.

B. 5S-N-(Benzyloxycarbonyl)amino-2-N-(t-butyloxycarbonyl)amino-4S-hydroxy-1-(2-methylphenyl)-6-phenyl-2-azahexane Using the procedure of Example 52C, but replacing the resulting hydrazine from Example 52B with the resulting hydrazine from Example 65A provided the desired compound. $^1$H NMR (CDCl$_3$) δ 1.28 (s, 9H), 2.37 (s 3H), 2.48–2.52 (m, 1H), 2.79 (t, 1H) 2.95 (d, 2H), 3.59–3.63 (m, 1H), 3.72–3.82 (m, 2H), 3.91–3.98 (m, 1H), 4.34–4.52 (br, 1H), 5.07 (s, 2H), 5.21 (br, 1H), 5.77–5.83 (br d, 1H), 7.12–7.34 (m, 14H). Mass spectrum: (M+H)$^+$=534.

EXAMPLE 66

A. N(1)-t-Butyloxycarbonyl-N(2)-(4-chlorobenzyl)-hydrazine

Using the procedure of Example 14A, but replacing p-anisaldehyde with 4-chlorobenzaldehyde, provided the desired compound.

B. 5S-N-(Benzyloxycarbonyl)amino-2-N-(t-butyloxycarbonyl)amino-4S-hydroxy-1-(4-chlorolphenyl)-6-phenyl-2-azahexane Using the procedure of Example 52C, but replacing the resulting hydrazine from Example 52B with the resulting hydrazine from Example 66A provided the desired compound. $^1$H NMR (CDCl$_3$) δ 1.32 (s, 9H), 2.41–2.49 (m, 1H), 2.74–2.83 (m, 1H), 2.96 (d, 2H), 3.55–3.62 (m, 1H), 3.69–3.86 (m, 2H), 3.92–3.98 (m, 1H), 4.35–4.65 (br, 1H), 5.08 (s, 2H), 5.13–5.23 (br, 1H), 5.28–5.38 (br, 1H), 7.23–7.37 (m, 14H). Mass spectrum: (M+H)$^+$=554.

EXAMPLE 67

A. N(1)-t-Butyloxycarbonyl-N(2)-(3-chlorobenzyl)-hydrazine

Using the procedure of Example 14A, but replacing p-anisaldehyde with 3-chlorobenzaldehyde, provided the desired compound.

B. 5S-N-(Benzyloxycarbonyl)amino-2-N-(t-butyloxycarbonyl)amino-4S-hydroxy-1-(3-chlorophenyl)-6-phenyl-2-azahexane Using the procedure of Example 52C, but replacing the hydrazine from Example 52B with the hydrazine from Example 67A provided the desired compound. $^1$H NMR (CDCl$_3$) δ 1.35 (s, 9H), 2.41–2.53 (m, 1H), 2.79 (t, 1H), 2.87 (d, 2H), 3.55–3.63 (m, 1H), 3.68–3.87 (m, 2H), 3.92–4.04 (m, 1H), 4.30–4.60 (br, 1H), 5.08 (s, 2H), 5.16–5.28 (br d, 1H), 5.30–5.40 (br, 1H), 7.19–7.35 (m, 14H). Mass spectrum: (M+H)$^+$=554.

EXAMPLE 68

A. N(1)-t-Butyloxycarbonyl-N(2)-(2-chlorobenzyl)-hydrazine

Using the procedure of Example 14A, but replacing p-anisaldehyde with 2-chlorobenzaldehyde, provided the desired compound.

B. 5S-N-(Benzyloxycarbonyl)amino-2-N-(t-butyloxycarbonyl)amino-4S-hydroxy-1-(2-chlorophenyl)-6-phenyl-2-azahexane Using the procedure of Example 52C, but replacing the resulting hydrazine from Example 52B with the resulting hydrazine from Example 68A provided the desired compound. $^1$H NMR (CDCl$_3$) δ 1.32 (s, 9H), 2.57–2.64 (m, 1H), 2.84 (t, 1H), 2.96 (d, 2H), 3.60–3.67 (m, 1H), 3.71–3.81 (m, 2H), 4.03 (s, 2H), 5.08 (s, 2H), 5.34 (br, 1H), 5.36 (br d, 1H), 7.19–7.37 (m, 13H), 7.47–7.54 (m, 1H). Mass spectrum: (M+H)$^+$=554.

EXAMPLE 69

A. N(1)-t-Butyloxycarbonyl-N(2)-(2-phenylethyl)-hydrazine

Using the procedure of Example 14A, but replacing p-anisaldehyde with phenylacetaldehyde, provided the desired compound.

B. 5S-N-(Benzyloxycarbonyl)amino-2-N-(t-butyloxycarbonyl)amino-4S-hydroxy-1-benzyl-6-phenyl-2-azahexane Using the procedure of Example 52C, but replacing the resulting hydrazine from Example 52B with the resulting hydrazine from Example 69A provided the desired compound. $^1$H NMR (CDCl$_3$) δ 1.43 (s, 9H), 2.44–2.51 (m, 1H), 2.78–2.93 (m, 4H), 2.96 (d, 2H), 3.55–3.62 (m, 1H), 3.65 (d, 1H), 3.69–3.77 (m, 1H), 4.10–4.40 (br, 1H), 5.06 (s, 2H), 5.21–5.28 (br, 1H), 5.30–5.38 (br d, 1H), 7.17–7.32 (m, 15H). Mass spectrum: (M+H)$^+$=534.

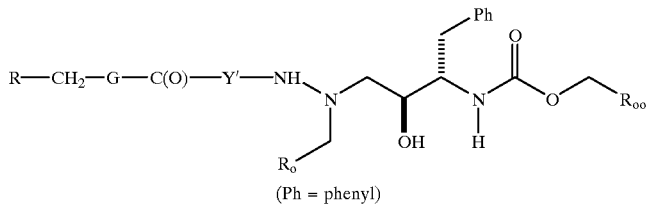

R—CH$_2$—G—C(O)—Y'—NH ... (Ph = phenyl)

| R | G | Y' | R$_o$ | R$_{oo}$ |
|---|---|---|---|---|
| 4-thiazolyl | N(CH$_3$) | Val | phenyl | 5-thiazolyl |
| 2-methyl-4-thiazolyl | N(CH$_3$) | Val | phenyl | 5-thiazolyl |
| 2-(1,1-dimethyl)ethyl-4-thiazolyl | N(CH$_3$) | Val | phenyl | 5-thiazolyl |
| 2-cyclobutyl-4-thiazolyl | N(CH$_3$) | Val | phenyl | 5-thiazolyl |
| 2-cyclopropyl-4-thiazolyl | N(CH$_3$) | Val | phenyl | 5-thiazolyl |
| 2-ethyl-4-thiazolyl | N(CH$_3$) | Val | phenyl | 5-thiazolyl |
| 2-(2-propenyl)-4-thiazolyl | N(CH$_3$) | Val | phenyl | 5-thiazolyl |
| 2-(1-pyrrolidinyl)-4-thiazolyl | N(CH$_3$) | Val | phenyl | 5-thiazolyl |
| 2-(1-propyl)-4-thiazolyl | N(CH$_3$) | Val | phenyl | 5-thiazolyl |
| 2-(2-methyl)propyl-4-thiazolyl | N(CH$_3$) | Val | phenyl | 5-thiazolyl |
| 4-oxazolyl | N(CH$_3$) | Val | phenyl | 5-thiazolyl |
| 2-methyl-4-oxazolyl | N(CH$_3$) | Val | phenyl | 5-thiazolyl |
| 2-(1,1-dimethyl)ethyl-4-oxazolyl | N(CH$_3$) | Val | phenyl | 5-thiazolyl |
| 2-cyclobutyl-4-oxazolyl | N(CH$_3$) | Val | phenyl | 5-thiazolyl |
| 2-cyclopropyl-4-oxazolyl | N(CH$_3$) | Val | phenyl | 5-thiazolyl |
| 2-ethyl-4-oxazolyl | N(CH$_3$) | Val | phenyl | 5-thiazolyl |
| 2-(2-propenyl)-4-oxazolyl | N(CH$_3$) | Val | phenyl | 5-thiazolyl |
| 2-(N,N-dimethylamino)-4-oxazolyl | N(CH$_3$) | yal | phenyl | 5-thiazolyl |
| 2-(1-pyrrolidinyl)-4-oxazolyl | N(CH$_3$) | Val | phenyl | 5-thiazolyl |
| 2-(1-propyl)-4-oxazolyl | N(CH$_3$) | Val | phenyl | 5-thiazolyl |
| 2-(2-methyl)propyl-4-oxazolyl | N(CH$_3$) | Val | phenyl | 5-thiazolyl |
| 2-pyridinyl | N(CH$_3$) | Val | phenyl | 5-thiazolyl |
| 6-isopropyl-2-pyridinyl | N(CH$_3$) | Val | phenyl | 5-thiazolyl |
| 6-methyl-2-pyridinyl | N(CH$_3$) | Val | phenyl | 5-thiazolyl |
| 6-(1,1-dimethyl)ethyl-2-pyridinyl | N(CH$_3$) | Val | phenyl | 5-thiazolyl |
| 6-cyclobutyl-2-pyridinyl | N(CH$_3$) | Val | phenyl | 5-thiazolyl |
| 6-cyclopropyl-2-pyridinyl | N(CH$_3$) | Val | phenyl | 5-thiazolyl |
| 6-ethyl-2-pyridinyl | N(CH$_3$) | Val | phenyl | 5-thiazolyl |
| 6-(2-propenyl)-2-pyridinyl | N(CH$_3$) | Val | phenyl | 5-thiazolyl |
| 6-propyl-2-pyridinyl | N(CH$_3$) | Val | phenyl | 5-thiazolyl |
| 6-(2-methyl)propyl-2-pyridinyl | N(CH$_3$) | Val | phenyl | 5-thiazolyl |
| 4-thiazolyl | O | Val | phenyl | 5-thiazolyl |
| 2-isopropyl-4-thiazolyl | O | Val | phenyl | 5-thiazolyl |
| 2-methyl-4-thiazolyl | O | Val | phenyl | 5-thiazolyl |
| 2-(1,1-dimethyl)ethyl-4-thiazolyl | O | Val | phenyl | 5-thiazolyl |
| 2-cyclobutyl-4-thiazolyl | O | Val | phenyl | 5-thiazolyl |
| 2-cyclopropyl-4-thiazolyl | O | Val | phenyl | 5-thiazolyl |
| 2-ethyl-4-thiazolyl | O | Val | phenyl | 5-thiazolyl |
| 2-(2-propenyl)-4-thiazolyl | O | Val | phenyl | 5-thiazolyl |
| 2-(N,N-dimethylamino)-4-thiazolyl | O | Val | phenyl | 5-thiazolyl |
| 2-(1-pyrrolidinyl)-4-thiazolyl | O | Val | phenyl | 5-thiazolyl |
| 2-(1-propyl)-4-thiazolyl | O | Val | phenyl | 5-thiazolyl |
| 2-(2-methyl)propyl-4-thiazolyl | O | Val | phenyl | 5-thiazolyl |
| 4-oxazolyl | O | Val | phenyl | 5-thiazolyl |
| 2-isopropyl-4-oxazolyl | O | Val | phenyl | 5-thiazolyl |
| 2-methyl-4-oxazolyl | O | Val | phenyl | 5-thiazolyl |
| 2-(1,1-dimethyl)ethyl-4-oxazolyl | O | Val | phenyl | 5-thiazolyl |
| 2-cyclobutyl-4-oxazolyl | O | Val | phenyl | 5-thiazolyl |
| 2-cyclopropyl-4-oxazolyl | O | Val | phenyl | 5-thiazolyl |
| 2-ethyl-4-oxazolyl | O | Val | phenyl | 5-thiazolyl |
| 2-(2-propenyl)-4-oxazolyl | O | Val | phenyl | 5-thiazolyl |
| 2-(N,N-dimethylamino)-4-oxazolyl | O | Val | phenyl | 5-thiazolyl |
| 2-(1-pyrrolidinyl)-4-oxazolyl | O | Val | phenyl | 5-thiazolyl |
| 2-(1-propyl)-4-oxazolyl | O | Val | phenyl | 5-thiazolyl |
| 2-(2-methyl)propyl-4-oxazolyl | O | Val | phenyl | 5-thiazolyl |
| 2-pyridinyl | O | Val | phenyl | 5-thiazolyl |
| 6-isopropyl-2-pyridinyl | O | Val | phenyl | 5-thiazolyl |
| 6-methyl-2-pyridinyl | O | Val | phenyl | 5-thiazolyl |
| 6-(1,1-dimethyl)ethyl-2-pyridinyl | O | Val | phenyl | 5-thiazolyl |

-continued

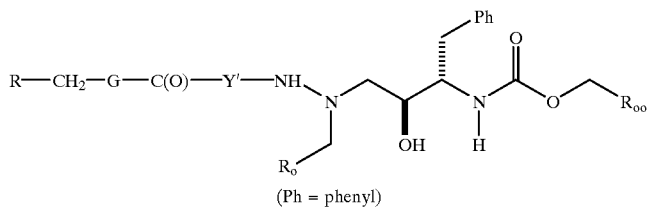

(Ph = phenyl)

| R | G | Y' | $R_o$ | $R_{oo}$ |
|---|---|---|---|---|
| 6-cyclobutyl-2-pyridinyl | O | Val | phenyl | 5-thiazolyl |
| 6-cyclopropyl-2-pyridinyl | O | Val | phenyl | 5-thiazolyl |
| 6-ethyl-2-pyridinyl | O | Val | phenyl | 5-thiazolyl |
| 6-(2-propenyl)-2-pyridinyl | O | Val | phenyl | 5-thiazolyl |
| 6-propyl-2-pyridinyl | O | Val | phenyl | 5-thiazolyl |
| 6-(2-methyl)propyl-2-pyridinyl | O | Val | phenyl | 5-thiazolyl |
| 4-thiazolyl | $N(CH_3)$ | Ala | phenyl | 5-thiazolyl |
| 2-isopropyl-4-thiazolyl | $N(CH_3)$ | Ala | phenyl | 5-thiazolyl |
| 2-methyl-4-thiazolyl | $N(CH_3)$ | Ala | phenyl | 5-thiazolyl |
| 2-(1,1-dimethyl)ethyl-4-thiazolyl | $N(CH_3)$ | Ala | phenyl | 5-thiazolyl |
| 2-cyclobutyl-4-thiazolyl | $N(CH_3)$ | Ala | phenyl | 5-thiazolyl |
| 2-cyclopropyl-4-thiazolyl | $N(CH_3)$ | Ala | phenyl | 5-thiazolyl |
| 2-ethyl-4-thiazolyl | $N(CH_3)$ | Ala | phenyl | 5-thiazolyl |
| 2-(2-propenyl)-4-thiazolyl | $N(CH_3)$ | Ala | phenyl | 5-thiazolyl |
| 2-(N,N-dimethylamino)-4-thiazolyl | $N(CH_3)$ | Ala | phenyl | 5-thiazolyl |
| 2-(1-pyrrolidinyl)-4-thiazolyl | $N(CH_3)$ | Ala | phenyl | 5-thiazolyl |
| 2-(1-propyl)-4-thiazolyl | $N(CH_3)$ | Ala | phenyl | 5-thiazolyl |
| 2-(2-methyl)propyl-4-thiazolyl | $N(CH_3)$ | Ala | phenyl | 5-thiazolyl |
| 4-oxazolyl | $N(CH_3)$ | Ala | phenyl | 5-thiazolyl |
| 2-isopropyl-4-oxazolyl | $N(CH_3)$ | Ala | phenyl | 5-thiazolyl |
| 2-methyl-4-oxazolyl | $N(CH_3)$ | Ala | phenyl | 5-thiazolyl |
| 2-(1,1-dimethyl)ethyl-4-oxazolyl | $N(CH_3)$ | Ala | phenyl | 5-thiazolyl |
| 2-cyclobutyl-4-oxazolyl | $N(CH_3)$ | Ala | phenyl | 5-thiazolyl |
| 2-cyclopropyl-4-oxazolyl | $N(CH_3)$ | Ala | phenyl | 5-thiazolyl |
| 2-ethyl-4-oxazolyl | $N(CH_3)$ | Ala | phenyl | 5-thiazolyl |
| 2-(2-propenyl)-4-oxazolyl | $N(CH_3)$ | Ala | phenyl | 5-thiazolyl |
| 2-(N,N-dimethylamino)-4-oxazolyl | $N(CH_3)$ | Ala | phenyl | 5-thiazolyl |
| 2-(1-pyrrolidinyl)-4-oxazolyl | $N(CH_3)$ | Ala | phenyl | 5-thiazolyl |
| 2-(1-propyl)-4-oxazolyl | $N(CH_3)$ | Ala | phenyl | 5-thiazolyl |
| 2-(2-methyl)propyl-4-oxazolyl | $N(CH_3)$ | Ala | phenyl | 5-thiazolyl |
| 2-pyridinyl | $N(CH_3)$ | Ala | phenyl | 5-thiazolyl |
| 6-isopropyl-2-pyridinyl | $N(CH_3)$ | Ala | phenyl | 5-thiazolyl |
| 6-methyl-2-pyridinyl | $N(CH_3)$ | Ala | phenyl | 5-thiazolyl |
| 6-(1,1-dimethyl)ethyl-2-pyridinyl | $N(CH_3)$ | Ala | phenyl | 5-thiazolyl |
| 6-cyclobutyl-2-pyridinyl | $N(CH_3)$ | Ala | phenyl | 5-thiazolyl |
| 6-cyclopropyl-2-pyridinyl | $N(CH_3)$ | Ala | phenyl | 5-thiazolyl |
| 6-ethyl-2-pyridinyl | $N(CH_3)$ | Ala | phenyl | 5-thiazolyl |
| 6-(2-propenyl)-2-pyridinyl | $N(CH_3)$ | Ala | phenyl | 5-thiazolyl |
| 6-propyl-2-pyridinyl | $N(CH_3)$ | Ala | phenyl | 5-thiazolyl |
| 6-(2-methyl)propyl-2-pyridinyl | $N(CH_3)$ | Ala | phenyl | 5-thiazolyl |
| 4-thiazolyl | O | Ala | phenyl | 5-thiazolyl |
| 2-isopropyl-4-thiazolyl | O | Ala | phenyl | 5-thiazolyl |
| 2-methyl-4-thiazolyl | O | Ala | phenyl | 5-thiazolyl |
| 2-(1,1-dimethyl)ethyl-4-thiazolyl | O | Ala | phenyl | 5-thiazolyl |
| 2-cyclobutyl-4-thiazolyl | O | Ala | phenyl | 5-thiazolyl |
| 2-cyclopropyl-4-thiazolyl | O | Ala | phenyl | 5-thiazolyl |
| 2-ethyl-4-thiazolyl | O | Ala | phenyl | 5-thiazolyl |
| 2-(2-propenyl)-4-thiazolyl | O | Ala | phenyl | 5-thiazolyl |
| 2-(N,N-dimethylamino)-4-thiazolyl | O | Ala | phenyl | 5-thiazolyl |
| 2-(1-pyrrolidinyl)-4-thiazolyl | O | Ala | phenyl | 5-thiazolyl |
| 2-(1-propyl)-4-thiazolyl | O | Ala | phenyl | 5-thiazolyl |
| 2-(2-methyl)propyl-4-thiazolyl | O | Ala | phenyl | 5-thiazolyl |
| 4-oxazolyl | O | Ala | phenyl | 5-thiazolyl |
| 2-isopropyl-4-oxazolyl | O | Ala | phenyl | 5-thiazolyl |
| 2-methyl-4-oxazolyl | O | Ala | phenyl | 5-thiazolyl |
| 2-(1,1-dimethyl)ethyl-4-oxazolyl | O | Ala | phenyl | 5-thiazolyl |
| 2-cyclobutyl-4-oxazolyl | O | Ala | phenyl | 5-thiazolyl |
| 2-cyclopropyl-4-oxazolyl | O | Ala | phenyl | 5-thiazolyl |
| 2-ethyl-4-oxazolyl | O | Ala | phenyl | 5-thiazolyl |
| 2-(2-propenyl)-4-oxazolyl | O | Ala | phenyl | 5-thiazolyl |
| 2-(N,N-dimethylamino)-4-oxazolyl | O | Ala | phenyl | 5-thiazolyl |
| 2-(1-pyrrolidinyl)-4-oxazolyl | O | Ala | phenyl | 5-thiazolyl |
| 2-(1-propyl)-4-oxazolyl | O | Ala | phenyl | 5-thiazolyl |
| 2-(2-methyl)propyl-4-oxazolyl | O | Ala | phenyl | 5-thiazolyl |
| 2-pyridinyl | O | Ala | phenyl | 5-thiazolyl |
| 6-isopropyl-2-pyridinyl | O | Ala | phenyl | 5-thiazolyl |
| 6-methyl-2-pyridinyl | O | Ala | phenyl | 5-thiazolyl |

-continued

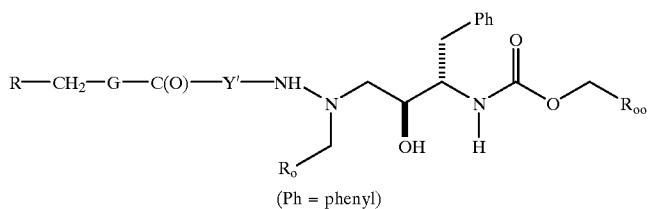

(Ph = phenyl)

| R | G | Y' | $R_o$ | $R_{oo}$ |
|---|---|---|---|---|
| 6-(1,1-dimethyl)ethyl-2-pyridinyl | O | Ala | phenyl | 5-thiazolyl |
| 6-cyclobutyl-2-pyridinyl | O | Ala | phenyl | 5-thiazolyl |
| 6-cyclopropyl-2-pyridinyl | O | Ala | phenyl | 5-thiazolyl |
| 6-ethyl-2-pyridinyl | O | Ala | phenyl | 5-thiazolyl |
| 6-(2-propenyl)-2-pyridinyl | O | Ala | phenyl | 5-thiazolyl |
| 6-propyl-2-pyridinyl | O | Ala | phenyl | 5-thiazolyl |
| 6-(2-methyl)propyl-2-pyridinyl | O | Ala | phenyl | 5-thiazolyl |
| 4-thiazolyl | $N(CH_3)$ | Ile | phenyl | 5-thiazolyl |
| 2-isopropyl-4-thiazolyl | $N(CH_3)$ | Ile | phenyl | 5-thiazolyl |
| 2-methyl-4-thiazolyl | $N(CH_3)$ | Ile | phenyl | 5-thiazolyl |
| 2-(1,1-dimethyl)ethyl-4-thiazolyl | $N(CH_3)$ | Ile | phenyl | 5-thiazolyl |
| 2-cyclobutyl-4-thiazolyl | $N(CH_3)$ | Ile | phenyl | 5-thiazolyl |
| 2-cyclopropyl-4-thiazolyl | $N(CH_3)$ | Ile | phenyl | 5-thiazolyl |
| 2-ethyl-4-thiazolyl | $N(CH_3)$ | Ile | phenyl | 5-thiazolyl |
| 2-(2-propenyl)-4-thiazolyl | $N(CH_3)$ | Ile | phenyl | 5-thiazolyl |
| 2-(N,N-dimethylamino)-4-thiazolyl | $N(CH_3)$ | Ile | phenyl | 5-thiazolyl |
| 2-(1-pyrrolidinyl)-4-thiazolyl | $N(CH_3)$ | Ile | phenyl | 5-thiazolyl |
| 2-(1-propyl)-4-thiazolyl | $N(CH_3)$ | Ile | phenyl | 5-thiazolyl |
| 2-(2-methyl)propyl-4-thiazolyl | $N(CH_3)$ | Ile | phenyl | 5-thiazolyl |
| 4-oxazolyl | $N(CH_3)$ | Ile | phenyl | 5-thiazolyl |
| 2-isopropyl-4-oxazolyl | $N(CH_3)$ | Ile | phenyl | 5-thiazolyl |
| 2-methyl-4-oxazolyl | $N(CH_3)$ | Ile | phenyl | 5-thiazolyl |
| 2-(1,1-dimethyl)ethyl-4-oxazolyl | $N(CH_3)$ | Ile | phenyl | 5-thiazolyl |
| 2-cyclobutyl-4-oxazolyl | $N(CH_3)$ | Ile | phenyl | 5-thiazolyl |
| 2-cyclopropyl-4-oxazolyl | $N(CH_3)$ | Ile | phenyl | 5-thiazolyl |
| 2-ethyl-4-oxazolyl | $N(CH_3)$ | Ile | phenyl | 5-thiazolyl |
| 2-(2-propenyl)-4-oxazolyl | $N(CH_3)$ | Ile | phenyl | 5-thiazolyl |
| 2-(N,N-dimethylamino)-4-oxazolyl | $N(CH_3)$ | Ile | phenyl | 5-thiazolyl |
| 2-(1-pyrrolidinyl)-4-oxazolyl | $N(CH_3)$ | IleIe | phenyl | 5-thiazolyl |
| 2-(1-propyl)-4-oxazolyl | $N(CH_3)$ | Ile | phenyl | 5-thiazolyl |
| 2-(2-methyl)propyl-4-oxazolyl | $N(CH_3)$ | Ile | phenyl | 5-thiazolyl |
| 2-pyridinyl | $N(CH_3)$ | Ile | phenyl | 5-thiazolyl |
| 6-isopropyl-2-pyridinyl | $N(CH_3)$ | Ile | phenyl | 5-thiazolyl |
| 6-methyl-2-pyridinyl | $N(CH_3)$ | Ile | phenyl | 5-thiazolyl |
| 6-(1,1-dimethyl)ethyl-2-pyridinyl | $N(CH_3)$ | Ile | phenyl | 5-thiazolyl |
| 6-cyclobutyl-2-pyridinyl | $N(CH_3)$ | Ile | phenyl | 5-thiazolyl |
| 6-cyclopropyl-2-pyridinyl | $N(CH_3)$ | Ile | phenyl | 5-thiazolyl |
| 6-ethyl-2-pyridinyl | $N(CH_3)$ | Ile | phenyl | 5-thiazolyl |
| 6-(2-propenyl)-2-pyridinyl | $N(CH_3)$ | Ile | phenyl | 5-thiazolyl |
| 6-propyl-2-pyridinyl | $N(CH_3)$ | Ile | phenyl | 5-thiazolyl |
| 6-(2-methyl)propyl-2-pyridinyl | $N(CH_3)$ | Ile | phenyl | 5-thiazolyl |
| 4-thiazolyl | O | Ile | phenyl | 5-thiazolyl |
| 2-isopropyl-4-thiazolyl | O | Ile | phenyl | 5-thiazolyl |
| 2-methyl-4-thiazolyl | O | Ile | phenyl | 5-thiazolyl |
| 2-(1,1-dimethyl)ethyl-4-thiazolyl | O | Ile | phenyl | 5-thiazolyl |
| 2-cyclobutyl-4-thiazolyl | O | Ile | phenyl | 5-thiazolyl |
| 2-cyclopropyl-4-thiazolyl | O | Ile | phenyl | 5-thiazolyl |
| 2-ethyl-4-thiazolyl | O | Ile | phenyl | 5-thiazolyl |
| 2-(2-propenyl)-4-thiazolyl | O | Ile | phenyl | 5-thiazolyl |
| 2-(N,N-dimethylamino)-4-thiazolyl | O | Ile | phenyl | 5-thiazolyl |
| 2-(1-pyrrolidinyl)-4-thiazolyl | O | Ile | phenyl | 5-thiazolyl |
| 2-(1-propyl)-4-thiazolyl | O | Ile | phenyl | 5-thiazolyl |
| 2-(2-methyl)propyl-4-thiazolyl | O | Ile | phenyl | 5-thiazolyl |
| 4-oxazolyl | O | Ile | phenyl | 5-thiazolyl |
| 2-isopropyl-4-oxazolyl | O | Ile | phenyl | 5-thiazolyl |
| 2-methyl-4-oxazolyl | O | Ile | phenyl | 5-thiazolyl |
| 2-(1,1-dimethyl)ethyl-4-oxazolyl | O | Ile | phenyl | 5-thiazolyl |
| 2-cyclobutyl-4-oxazolyl | O | Ile | phenyl | 5-thiazolyl |
| 2-cyclopropyl-4-oxazolyl | O | Ile | phenyl | 5-thiazolyl |
| 2-ethyl-4-oxazolyl | O | Ile | phenyl | 5-thiazolyl |
| 2-(2-propenyl)-4-oxazolyl | O | Ile | phenyl | 5-thiazolyl |
| 2-(N,N-dimethylamino)-4-oxazolyl | O | Ile | phenyl | 5-thiazolyl |
| 2-(1-pyrrolidinyl)-4-oxazolyl | O | Ile | phenyl | 5-thiazolyl |
| 2-(1-propyl)-4-oxazolyl | O | Ile | phenyl | 5-thiazolyl |
| 2-(2-methyl)propyl-4-oxazolyl | O | Ile | phenyl | 5-thiazolyl |
| 2-pyridinyl | O | Ile | phenyl | 5-thiazolyl |
| 6-isopropyl-2-pyridinyl | O | Ile | phenyl | 5-thiazolyl |

-continued

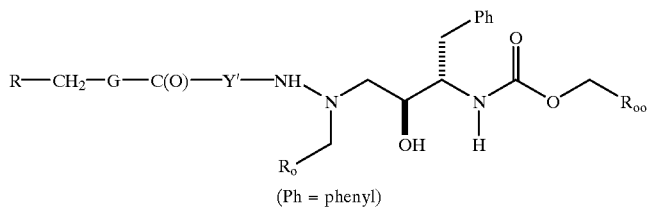

(Ph = phenyl)

| R | G | Y' | $R_o$ | $R_{oo}$ |
|---|---|---|---|---|
| 6-methyl-2-pyridinyl | O | Ile | phenyl | 5-thiazolyl |
| 6-(1,1-dimethyl)ethyl-2-pyridinyl | O | Ile | phenyl | 5-thiazolyl |
| 6-cyclobutyl-2-pyridinyl | O | Ile | phenyl | 5-thiazolyl |
| 6-cyclopropyl-2-pyridinyl | O | Ile | phenyl | 5-thiazolyl |
| 6-ethyl-2-pyridinyl | O | Ile | phenyl | 5-thiazolyl |
| 6-(2-propenyl)-2-pyridinyl | O | Ile | phenyl | 5-thiazolyl |
| 6-propyl-2-pyridinyl | O | Ile | phenyl | 5-thiazolyl |
| 6-(2-methyl)propyl-2-pyridinyl | O | Ile | phenyl | 5-thiazolyl |
| 4-thiazolyl | $N(CH_3)$ | Val | phenyl | 5-oxazolyl |
| 2-isopropyl-4-thiazolyl | $N(CH_3)$ | Val | phenyl | 5-oxazolyl |
| 2-methyl-4-thiazolyl | $N(CH_3)$ | Val | phenyl | 5-oxazolyl |
| 2-(1,1-dimethyl)ethyl-4-thiazolyl | $N(CH_3)$ | Val | phenyl | 5-oxazolyl |
| 2-cyclobutyl-4-thiazolyl | $N(CH_3)$ | Val | phenyl | 5-oxazolyl |
| 2-cyclopropyl-4-thiazolyl | $N(CH_3)$ | Val | phenyl | 5-oxazolyl |
| 2-ethyl-4-thiazolyl | $N(CH_3)$ | Val | phenyl | 5-oxazolyl |
| 2-(2-propenyl)-4-thiazolyl | $N(CH_3)$ | Val | phenyl | 5-oxazolyl |
| 2-(N,N-dimethylamino)-4-thiazolyl | $N(CH_3)$ | Val | phenyl | 5-oxazolyl |
| 2-(1-pyrrolidinyl)-4-thiazolyl | $N(CH_3)$ | Val | phenyl | 5-oxazolyl |
| 2-(1-propyl)-4-thiazolyl | $N(CH_3)$ | Val | phenyl | 5-oxazolyl |
| 2-(2-methyl)propyl-4-thiazolyl | $N(CH_3)$ | Val | phenyl | 5-oxazolyl |
| 4-oxazolyl | $N(CH_3)$ | Val | phenyl | 5-oxazolyl |
| 2-isopropyl-4-oxazolyl | $N(CH_3)$ | Val | phenyl | 5-oxazolyl |
| 2-methyl-4-oxazolyl | $N(CH_3)$ | Val | phenyl | 5-oxazolyl |
| 2-(1,1-dimethyl)ethyl-4-oxazolyl | $N(CH_3)$ | Val | phenyl | 5-oxazolyl |
| 2-cyclobutyl-4-oxazolyl | $N(CH_3)$ | Val | phenyl | 5-oxazolyl |
| 2-cyclopropyl-4-oxazolyl | $N(CH_3)$ | Val | phenyl | 5-oxazolyl |
| 2-ethyl-4-oxazolyl | $N(CH_3)$ | Val | phenyl | 5-oxazolyl |
| 2-(2-propenyl)-4-oxazolyl | $N(CH_3)$ | Val | phenyl | 5-oxazolyl |
| 2-(N,N-dimethylamino)-4-oxazolyl | $N(CH_3)$ | Val | phenyl | 5-oxazolyl |
| 2-(1-pyrrolidinyl)-4-oxazolyl | $N(CH_3)$ | Val | phenyl | 5-oxazolyl |
| 2-(1-propyl)-4-oxazolyl | $N(CH_3)$ | Val | phenyl | 5-oxazolyl |
| 2-(2-methyl)propyl-4-oxazolyl | $N(CH_3)$ | Val | phenyl | 5-oxazolyl |
| 2-pyridinyl | $N(CH_3)$ | Val | phenyl | 5-oxazolyl |
| 6-isopropyl-2-pyridinyl | $N(CH_3)$ | Val | phenyl | 5-oxazolyl |
| 6-methyl-2-pyridinyl | $N(CH_3)$ | Val | phenyl | 5-oxazolyl |
| 6-(1,1-dimethyl)ethyl-2-pyridinyl | $N(CH_3)$ | Val | phenyl | 5-oxazolyl |
| 6-cyclobutyl-2-pyridinyl | $N(CH_3)$ | Val | phenyl | 5-oxazolyl |
| 6-cyclopropyl-2-pyridinyl | $N(CH_3)$ | Val | phenyl | 5-oxazolyl |
| 6-ethyl-2-pyridinyl | $N(CH_3)$ | Val | phenyl | 5-oxazolyl |
| 6-(2-propenyl)-2-pyridinyl | $N(CH_3)$ | Val | phenyl | 5-oxazolyl |
| 6-propyl-2-pyridinyl | $N(CH_3)$ | Val | phenyl | 5-oxazolyl |
| 6-(2-methyl)propyl-2-pyridinyl | $N(CH_3)$ | Val | phenyl | 5-oxazolyl |
| 4-thiazolyl | O | Val | phenyl | 5-oxazolyl |
| 2-isopropyl-4-thiazolyl | O | Val | phenyl | 5-oxazolyl |
| 2-methyl-4-thiazolyl | O | Val | phenyl | 5-oxazolyl |
| 2-(1,1-dimethyl)ethyl-4-thiazolyl | O | Val | phenyl | 5-oxazolyl |
| 2-cyclobutyl-4-thiazolyl | O | Val | phenyl | 5-oxazolyl |
| 2-cyclopropyl-4-thiazolyl | O | Val | phenyl | 5-oxazolyl |
| 2-ethyl-4-thiazolyl | O | Val | phenyl | 5-oxazolyl |
| 2-(2-propenyl)-4-thiazolyl | O | Val | phenyl | 5-oxazolyl |
| 2-(1-propyl)-4-thiazolyl | O | Val | phenyl | 5-oxazolyl |
| 2-(2-methyl)propyl-4-thiazolyl | O | Val | phenyl | 5-oxazolyl |
| 4-oxazolyl | O | Val | phenyl | 5-oxazolyl |
| 2-isopropyl-4-oxazolyl | O | Val | phenyl | 5-oxazolyl |
| 2-methyl-4-oxazolyl | O | Val | phenyl | 5-oxazolyl |
| 2-(1,1-dimethyl)ethyl-4-oxazolyl | O | Val | phenyl | 5-oxazolyl |
| 2-cyclobutyl-4-oxazolyl | O | Val | phenyl | 5-oxazolyl |
| 2-cyclopropyl-4-oxazolyl | O | Val | phenyl | 5-oxazolyl |
| 2-ethyl-4-oxazolyl | O | Val | phenyl | 5-oxazolyl |
| 2-(2-propenyl)-4-oxazolyl | O | Val | phenyl | 5-oxazolyl |
| 2-(N,N-dimethylamino)-4-oxazolyl | O | Val | phenyl | 5-oxazolyl |
| 2-(1-pyrrolidinyl)-4-oxazolyl | O | Val | phenyl | 5-oxazolyl |
| 2-(1-propyl)-4-oxazolyl | O | Val | phenyl | 5-oxazolyl |
| 2-(2-methyl)propyl-4-oxazolyl | O | Val | phenyl | s-oxazolyl |
| 2-pyridinyl | O | Val | phenyl | 5-oxazolyl |
| 6-isopropyl-2-pyridinyl | O | Val | phenyl | 5-oxazolyl |
| 6-methyl-2-pyridinyl | O | Val | phenyl | 5-oxazolyl |

-continued

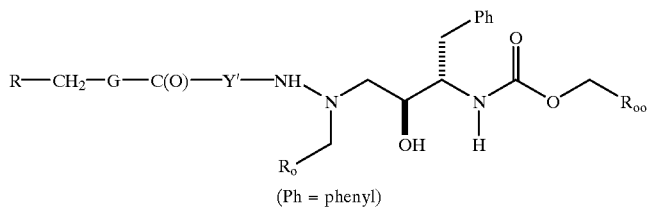

(Ph = phenyl)

| R | G | Y' | $R_o$ | $R_{oo}$ |
|---|---|---|---|---|
| 6-(1,1-dimethyl)ethyl-2-pyridinyl | O | Val | phenyl | 5-oxazolyl |
| 6-cyclobutyl-2-pyridinyl | O | Val | phenyl | 5-oxazolyl |
| 6-cyclopropyl-2-pyridinyl | O | Val | phenyl | 5-oxazolyl |
| 6-ethyl-2-pyridinyl | O | Val | phenyl | 5-oxazolyl |
| 6-(2-propenyl)-2-pyridinyl | O | Val | phenyl | 5-oxazolyl |
| 6-propyl-2-pyridinyl | O | Val | phenyl | 5-oxazolyl |
| 6-(2-methyl)propyl-2-pyridinyl | O | Val | phenyl | 5-oxazolyl |
| 4-thiazolyl | $N(CH_3)$ | Ala | phenyl | 5-oxazolyl |
| 2-isopropyl-4-thiazolyl | $N(CH_3)$ | Ala | phenyl | 5-oxazolyl |
| 2-methyl-4-thiazolyl | $N(CH_3)$ | Ala | phenyl | 5-oxazolyl |
| 2-(1,1-dimethyl)ethyl-4-thiazolyl | $N(CH_3)$ | Ala | phenyl | 5-oxazolyl |
| 2-cyclobutyl-4-thiazolyl | $N(CH_3)$ | Ala | phenyl | 5-oxazolyl |
| 2-cyclopropyl-4-thiazolyl | $N(CH_3)$ | Ala | phenyl | 5-oxazolyl |
| 2-ethyl-4-thiazolyl | $N(CH_3)$ | Ala | phenyl | 5-oxazolyl |
| 2-(2-propenyl)-4-thiazolyl | $N(CH_3)$ | Ala | phenyl | 5-oxazolyl |
| 2-(N,N-dimethylamino)-4-thiazolyl | $N(CH_3)$ | Ala | phenyl | 5-oxazolyl |
| 2-(1-pyrrolidinyl)-4-thiazolyl | $N(CH_3)$ | Ala | phenyl | 5-oxazolyl |
| 2-(1-propyl)-4-thiazolyl | $N(CH_3)$ | Ala | phenyl | 5-oxazolyl |
| 2-(2-methyl)propyl-4-thiazolyl | $N(CH_3)$ | AJa | phenyl | 5-oxazolyl |
| 4-oxazolyl | $N(CH_3)$ | Ala | phenyl | 5-oxazolyl |
| 2-isopropyl-4-oxazolyl | $N(CH_3)$ | Ala | phenyl | 5-oxazolyl |
| 2-methyl-4-oxazolyl | $N(CH_3)$ | Ala | phenyl | 5-oxazolyl |
| 2-(1,1-dimethyl)ethyl-4-oxazolyl | $N(CH_3)$ | Ala | phenyl | 5-oxazolyl |
| 2-cyclobutyl-4-oxazolyl | $N(CH_3)$ | Ala | phenyl | 5-oxazolyl |
| 2-cyclopropyl-4-oxazolyl | $N(CH_3)$ | Ala | phenyl | 5-oxazolyl |
| 2-ethyl-4-oxazolyl | $N(CH_3)$ | Ala | phenyl | 5-oxazolyl |
| 2-(2-propenyl)-4-oxazolyl | $N(CH_3)$ | Ala | phenyl | 5-oxazolyl |
| 2-(N,N-dimethylamino)-4-oxazolyl | $N(CH_3)$ | Ala | phenyl | 5-oxazolyl |
| 2-(1-pyrrolidinyl)-4-oxazolyl | $N(CH_3)$ | Ala | phenyl | 5-oxazolyl |
| 2-(1-propyl)-4-oxazolyl | $N(CH_3)$ | Ala | phenyl | 5-oxazolyl |
| 2-(2-methyl)propyl-4-oxazolyl | $N(CH_3)$ | Ala | phenyl | 5-oxazolyl |
| 2-pyridinyl | $N(CH_3)$ | Ala | phenyl | 5-oxazolyl |
| 6-isopropyl-2-pyridinyl | $N(CH_3)$ | Ala | phenyl | 5-oxazolyl |
| 6-methyl-2-pyridinyl | $N(CH_3)$ | Ala | phenyl | 5-oxazolyl |
| 6-(1,1-dimethyl)ethyl-2-pyridinyl | $N(CH_3)$ | Ala | phenyl | 5-oxazolyl |
| 6-cyclobutyl-2-pyridinyl | $N(CH_3)$ | Ala | phenyl | 5-oxazolyl |
| 6-cyclopropyl-2-pyridinyl | $N(CH_3)$ | Ala | phenyl | 5-oxazolyl |
| 6-ethyl-2-pyridinyl | $N(CH_3)$ | Ala | phenyl | 5-oxazolyl |
| 6-(2-propenyl)-2-pyridinyl | $N(CH_3)$ | Ala | phenyl | 5-oxazolyl |
| 6-propyl-2-pyridinyl | $N(CH_3)$ | Ala | phenyl | 5-oxazolyl |
| 6-(2-methyl)propyl-2-pyridinyl | $N(CH_3)$ | Ala | phenyl | 5-oxazolyl |
| 4-thiazolyl | O | Ala | phenyl | 5-oxazolyl |
| 2-isopropyl-4-thiazolyl | O | Ala | phenyl | 5-oxazolyl |
| 2-methyl-4-thiazolyl | O | Ala | phenyl | 5-oxazolyl |
| 2-(1,1-dimethyl)ethyl-4-thiazolyl | O | Ala | phenyl | 5-oxazolyl |
| 2-cyclobutyl-4-thiazolyl | O | Ala | phenyl | 5-oxazolyl |
| 2-cyclopropyl-4-thiazolyl | O | Ala | phenyl | 5-oxazolyl |
| 2-ethyl-4-thiazolyl | O | Ala | phenyl | 5-oxazolyl |
| 2-(2-propenyl)-4-thiazolyl | O | Ala | phenyl | 5-oxazolyl |
| 2-(N,N-dimethylamino)-4-thiazolyl | O | Ala | phenyl | 5-oxazolyl |
| 2-(1-pyrrolidinyl)-4-thiazolyl | O | Ala | phenyl | 5-oxazolyl |
| 2-(1-propyl)-4-thiazolyl | O | Ala | phenyl | 5-oxazolyl |
| 2-(2-methyl)propyl-4-thiazolyl | O | Ala | phenyl | 5-oxazolyl |
| 4-oxazolyl | O | Ala | phenyl | 5-oxazolyl |
| 2-isopropyl-4-oxazolyl | O | Ala | phenyl | 5-oxazolyl |
| 2-methyl-4-oxazolyl | O | Ala | phenyl | 5-oxazolyl |
| 2-(1,1-dimethyl)ethyl-4-oxazolyl | O | Ala | phenyl | 5-oxazolyl |
| 2-cyclobutyl-4-oxazolyl | O | Ala | phenyl | 5-oxazolyl |
| 2-cyclopropyl-4-oxazolyl | O | Ala | phenyl | 5-oxazolyl |
| 2-ethyl-4-oxazolyl | O | Ala | phenyl | 5-oxazolyl |
| 2-(2-propenyl)-4-oxazolyl | O | Ala | phenyl | 5-oxazolyl |
| 2-(N,N-dimethylamino)-4-oxazolyl | O | Ala | phenyl | 5-oxazolyl |
| 2-(1-pyrrolidinyl)-4-oxazolyl | O | Ala | phenyl | 5-oxazolyl |
| 2-(1-propyl)-4-oxazolyl | O | Ala | phenyl | 5-oxazolyl |
| 2-(2-methyl)propyl-4-oxazolyl | O | Ala | phenyl | 5-oxazolyl |
| 2-pyridinyl | O | Ala | phenyl | 5-oxazolyl |
| 6-isopropyl-2-pyridinyl | O | Ala | phenyl | 5-oxazolyl |

-continued

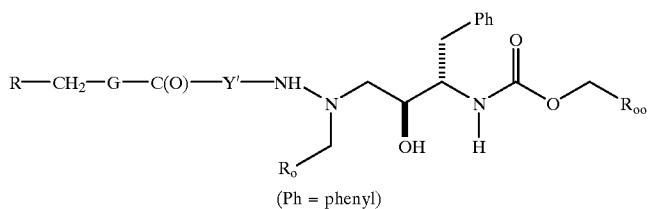

(Ph = phenyl)

| R | G | Y' | $R_o$ | $R_{oo}$ |
|---|---|---|---|---|
| 6-methyl-2-pyridinyl | O | Ala | phenyl | 5-oxazolyl |
| 6-(1,1-dimethyl)ethyl-2-pyridinyl | O | Ala | phenyl | 5-oxazolyl |
| 6-cyclobutyl-2-pyridinyl | O | Ala | phenyl | 5-oxazolyl |
| 6-cyclopropyl-2-pyridinyl | O | Ala | phenyl | 5-oxazolyl |
| 6-ethyl-2-pyridinyl | O | Ala | phenyl | 5-oxazolyl |
| 6-(2-propenyl)-2-pyridinyl | O | Ala | phenyl | 5-oxazolyl |
| 6-propyl-2-pyridinyl | O | Ala | phenyl | 5-oxazolyl |
| 6-(2-methyl)propyl-2-pyridinyl | O | Ala | phenyl | 5-oxazolyl |
| 4-thiazolyl | $N(CH_3)$ | Ile | phenyl | 5-oxazolyl |
| 2-isopropyl-4-thiazolyl | $N(CH_3)$ | Ile | phenyl | 5-oxazolyl |
| 2-methyl-4-thiazolyl | $N(CH_3)$ | Ile | phenyl | 5-oxazolyl |
| 2-(1,1-dimethyl)ethyl-4-thiazolyl | $N(CH_3)$ | Ile | phenyl | 5-oxazolyl |
| 2-cyclobutyl-4-thiazolyl | $N(CH_3)$ | Ile | phenyl | 5-oxazolyl |
| 2-cyclopropyl-4-thiazolyl | $N(CH_3)$ | Ile | phenyl | 5-oxazolyl |
| 2-ethyl-4-thiazolyl | $N(CH_3)$ | Ile | phenyl | 5-oxazolyl |
| 2-(2-propenyl)-4-thiazolyl | $N(CH_3)$ | Ile | phenyl | 5-oxazolyl |
| 2-(N,N-dimethylamino)-4-thiazolyl | $N(CH_3)$ | Ile | phenyl | 5-oxazolyl |
| 2-(1-pyrrolidinyl)-4-thiazolyl | $N(CH_3)$ | Ile | phenyl | 5-oxazolyl |
| 2-(1-propyl)-4-thiazolyl | $N(CH_3)$ | Ile | phenyl | 5-oxazolyl |
| 2-(2-methyl)propyl-4-thiazolyl | $N(CH_3)$ | Ile | phenyl | 5-oxazolyl |
| 4-oxazolyl | $N(CH_3)$ | Ile | phenyl | 5-oxazolyl |
| 2-isopropyl-4-oxazolyl | $N(CH_3)$ | Ile | phenyl | 5-oxazolyl |
| 2-methyl-4-oxazolyl | $N(CH_3)$ | Ile | phenyl | 5-oxazolyl |
| 2-(1,1-dimethyl)ethyl-4-oxazolyl | $N(CH_3)$ | Ile | phenyl | 5-oxazolyl |
| 2-cyclobutyl-4-oxazolyl | $N(CH_3)$ | Ile | phenyl | 5-oxazolyl |
| 2-cyclopropyl-4-oxazolyl | $N(CH_3)$ | Ile | phenyl | 5-oxazolyl |
| 2-ethyl-4-oxazolyl | $N(CH_3)$ | Ile | phenyl | 5-oxazolyl |
| 2-(2-propenyl)-4-oxazolyl | $N(CH_3)$ | Ile | phenyl | 5-oxazolyl |
| 2-(N,N-dimethylamino)-4-oxazolyl | $N(CH_3)$ | Ile | phenyl | 5-oxazolyl |
| 2-(1-pyrrolidinyl)-4-oxazolyl | $N(CH_3)$ | Ile | phenyl | 5-oxazolyl |
| 2-(1-propyl)-4-oxazolyl | $N(CH_3)$ | Ile | phenyl | 5-oxazolyl |
| 2-(2-methyl)propyl-4-oxazolyl | $N(CH_3)$ | Ile | phenyl | 5-oxazolyl |
| 2-pyridinyl | $N(CH_3)$ | Ile | phenyl | 5-oxazolyl |
| 6-isopropyl-2-pyridinyl | $N(CH_3)$ | Ile | phenyl | 5-oxazolyl |
| 6-methyl-2-pyridinyl | $N(CH_3)$ | Ile | phenyl | 5-oxazolyl |
| 6-(1,1-dimethyl)ethyl-2-pyridinyl | $N(CH_3)$ | Ile | phenyl | 5-oxazolyl |
| 6-cyclobutyl-2-pyridinyl | $N(CH_3)$ | Ile | phenyl | 5-oxazolyl |
| 6-cyclopropyl-2-pyridinyl | $N(CH_3)$ | Ile | phenyl | 5-oxazolyl |
| 6-ethyl-2-pyridinyl | $N(CH_3)$ | Ile | phenyl | 5-oxazolyl |
| 6-(2-propenyl)-2-pyridinyl | $N(CH_3)$ | Ile | phenyl | 5-oxazolyl |
| 6-propyl-2-pyridinyl | $N(CH_3)$ | Ile | phenyl | 5-oxazolyl |
| 6-(2-methyl)propyl-2-pyridinyl | $N(CH_3)$ | Ile | phenyl | 5-oxazolyl |
| 4-thiazolyl | O | Ile | phenyl | 5-oxazolyl |
| 2-isopropyl-4-thiazolyl | O | Ile | phenyl | 5-oxazolyl |
| 2-methyl-4-thiazolyl | O | Ile | phenyl | 5-oxazolyl |
| 2-(1,1-dimethyl)ethyl-4-thiazolyl | O | Ile | phenyl | 5-oxazolyl |
| 2-cyclobutyl-4-thiazolyl | O | Ile | phenyl | 5-oxazolyl |
| 2-cyclopropyl-4-thiazolyl | O | Ile | phenyl | 5-oxazolyl |
| 2-ethyl-4-thiazolyl | O | Ile | phenyl | 5-oxazolyl |
| 2-(2-propenyl)-4-thiazolyl | O | Ile | phenyl | 5-oxazolyl |
| 2-(N,N-dimethylamino)-4-thiazolyl | O | Ile | phenyl | 5-oxazolyl |
| 2-(1-pyrrolidinyl)-4-thiazolyl | O | Ile | phenyl | 5-oxazolyl |
| 2-(1-propyl)-4-thiazolyl | O | Ile | phenyl | 5-oxazolyl |
| 2-(2-methyl)propyl-4-thiazolyl | O | Ile | phenyl | 5-oxazolyl |
| 4-oxazolyl | O | Ile | phenyl | 5-oxazolyl |
| 2-isopropyl-4-oxazolyl | O | Ile | phenyl | 5-oxazolyl |
| 2-methyl-4-oxazolyl | O | Ile | phenyl | 5-oxazolyl |
| 2-(1,1-dimethyl)ethyl-4-oxazolyl | O | Ile | phenyl | 5-oxazolyl |
| 2-cyclobutyl-4-oxazolyl | O | Ile | phenyl | 5-oxazolyl |
| 2-cyclopropyl-4-oxazolyl | O | Ile | phenyl | 5-oxazolyl |
| 2-ethyl-4-oxazolyl | O | Ile | phenyl | 5-oxazolyl |
| 2-(2-propenyl)-4-oxazolyl | O | Ile | phenyl | 5-oxazolyl |
| 2-(N,N-dimethylamino)-4-oxazolyl | O | Ile | phenyl | 5-oxazolyl |
| 2-(1-pyrrolidinyl)-4-oxazolyl | O | Ile | phenyl | 5-oxazolyl |
| 2-(1-propyl)-4-oxazolyl | O | Ile | phenyl | 5-oxazolyl |
| 2-(2-methyl)propyl-4-oxazolyl | O | Ile | phenyl | 5-oxazolyl |
| 2-pyridinyl | O | Ile | phenyl | 5-oxazolyl |

-continued

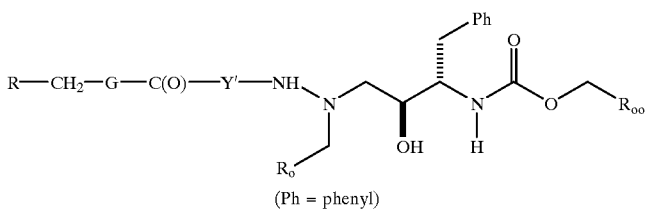

(Ph = phenyl)

| R | G | Y' | $R_o$ | $R_{oo}$ |
|---|---|---|---|---|
| 6-isopropyl-2-pyridinyl | O | Ile | phenyl | 5-oxazolyl |
| 6-methyl-2-pyridinyl | O | Ile | phenyl | 5-oxazolyl |
| 6-(1,1-dimethyl)ethyl-2-pyridinyl | O | Ile | phenyl | 5-oxazolyl |
| 6-cyclobutyl-2-pyridinyl | O | Ile | phenyl | 5-oxazolyl |
| 6-cyclopropyl-2-pyridinyl | O | Ile | phenyl | 5-oxazolyl |
| 6-ethyl-2-pyridinyl | O | Ile | phenyl | 5-oxazolyl |
| 6-(2-propenyl)-2-pyridinyl | O | Ile | phenyl | 5-oxazolyl |
| 6-propyl-2-pyridinyl | O | Ile | phenyl | 5-oxazolyl |
| 6-(2-methyl)propyl-2-pyridinyl | O | Ile | phenyl | 5-oxazolyl |
| 4-thiazolyl | N(CH$_3$) | Val | phenyl | 5-isoxazolyl |
| 2-isopropyl-4-thiazolyl | N(CH$_3$) | Val | phenyl | 5-isoxazolyl |
| 2-methyl-4-thiazolyl | N(CH$_3$) | Val | p henyl | 5-isoxazolyl |
| 2-(1,1-dimethyl)ethyl-4-thiazolyl | N(CH$_3$) | Val | phenyl | 5-isoxazolyl |
| 2-cyclobutyl-4-thiazolyl | N(CH$_3$) | Val | phenyl | 5-isoxazolyl |
| 2-cyclopropyl-4-thiazolyl | N(CH$_3$) | Val | phenyl | 5-isoxazolyl |
| 2-ethyl-4-thiazolyl | N(CH$_3$) | Val | phenyl | 5-isoxazolyl |
| 2-(2-propenyl)-4-thiazolyl | N(CH$_3$) | Val | phenyl | 5-isoxazolyl |
| 2-(N,N-dimethylamino)-4-thiazolyl | N(CH$_3$) | Val | phenyl | 5-isoxazolyl |
| 2-(1-pyrrolidinyl)-4-thiazolyl | N(CH$_3$) | Val | phenyl | 5-isoxazolyl |
| 2-(1-propyl)-4-thiazolyl | N(CH$_3$) | Val | phenyl | 5-isoxazolyl |
| 2-(2-methyl)propyl-4-thiazolyl | N(CH$_3$) | Val | phenyl | 5-isoxazolyl |
| 4-oxazolyl | N(CH$_3$) | Val | phenyl | 5-isoxazolyl |
| 2-methyl-4-oxazolyl | N(CH$_3$) | Val | phenyl | 5-isoxazolyl |
| 2-(1,1-dimethyl)ethyl-4-oxazolyl | N(CH$_3$) | Val | phenyl | 5-isoxazolyl |
| 2-cyclobutyl-4-oxazolyl | N(CH$_3$) | Val | phenyl | 5-isoxazolyl |
| 2-cyclopropyl-4-oxazolyl | N(CH$_3$) | Val | phenyl | 5-isoxazolyl |
| 2-ethyl-4-oxazolyl | N(CH$_3$) | Val | phenyl | 5-isoxazolyl |
| 2-(2-propenyl)-4-oxazolyl | N(CH$_3$) | Val | phenyl | 5-isoxazolyl |
| 2-(N,N-dimethylamino)-4-oxazolyl | N(CH$_3$) | Val | phenyl | 5-isoxazolyl |
| 2-(1-pyrrolidinyl)-4-oxazolyl | N(CH$_3$) | Val | phenyl | 5-isoxazolyl |
| 2-(1-propyl)-4-oxazolyl | N(CH$_3$) | Val | phenyl | 5-isoxazolyl |
| 2-(2-methyl)propyl-4-oxazolyl | N(CH$_3$) | Val | phenyl | 5-isoxazolyl |
| 2-pyridinyl | N(CH$_3$) | Val | phenyl | 5-isoxazolyl |
| 6-isopropyl-2-pyridinyl | N(CH$_3$) | Val | phenyl | 5-isoxazolyl |
| 6-methyl-2-pyridinyl | N(CH$_3$) | Val | phenyl | 5-isoxazolyl |
| 6-(1,1-dimethyl)ethyl-2-pyridinyl | N(CH$_3$) | Val | phenyl | 5-isoxazolyl |
| 6-cyclobutyl-2-pyridinyl | N(CH$_3$) | Val | phenyl | 5-isoxazolyl |
| 6-cyclopropyl-2-pyridinyl | N(CH$_3$) | Val | phenyl | 5-isoxazolyl |
| 6-ethyl-2-pyridinyl | N(CH$_3$) | Val | phenyl | 5-isoxazolyl |
| 6-(2-propenyl)-2-pyridinyl | N(CH$_3$) | Val | phenyl | 5-isoxazolyl |
| 6-propyl-2-pyridinyl | N(CH$_3$) | Val | phenyl | 5-isoxazolyl |
| 6-(2-methyl)propyl-2-pyridinyl | N(CH$_3$) | Val | phenyl | 5-isoxazolyl |
| 4-thiazolyl | O | Val | phenyl | 5-isoxazolyl |
| 2-isopropyl-4-thiazolyl | O | Val | phenyl | 5-isoxazolyl |
| 2-methyl-4-thiazolyl | O | Val | phenyl | 5-isoxaiolyl |
| 2-(1,1-dimethyl)ethyl-4-thiazolyl | O | Val | phenyl | 5-isoxazolyl |
| 2-cyclobutyl-4-thiazolyl | O | Val | phenyl | 5-isoxazolyl |
| 2-cyclopropyl-4-thiazolyl | O | Val | phenyl | 5-isoxazolyl |
| 2-ethyl-4-thiazolyl | O | Val | phenyl | 5-isoxazolyl |
| 2-(2-propenyl)-4-thiazolyl | O | Val | phenyl | 5-isoxazolyl |
| 2-(N,N-dimethylamino)-4-thiazolyl | O | Val | phenyl | 5-isoxazolyl |
| 2-(1-pyrrolidinyl)-4-thiazolyl | O | Val | phenyl | 5-isoxazolyl |
| 2-(1-propyl)-4-thiazolyl | O | Val | phenyl | 5-isoxazolyl |
| 2-(2-methyl)propyl-4-thiazolyl | O | Val | phenyl | 5-isoxazolyl |
| 4-oxazolyl | O | Val | phenyl | 5-isoxazolyl |
| 2-isopropyl-4-oxazolyl | O | Val | phenyl | 5-isoxazolyl |
| 2-methyl-4-oxazolyl | O | Val | phenyl | 5-isoxazolyl |
| 2-(1,1-dimethyl)ethyl-4-oxazolyl | O | Val | phenyl | 5-isoxazolyl |
| 2-cyclobutyl-4-oxazolyl | O | Val | phenyl | 5-isoxazolyl |
| 2-cyclopropyl-4-oxazolyl | O | Val | phenyl | 5-isoxazolyl |
| 2-ethyl-4-oxazolyl | O | Val | phenyl | 5-isoxazolyl |
| 2-(2-propenyl)-4-oxazolyl | O | Val | phenyl | 5-isoxazolyl |
| 2-(N,N-dimethylamino)-4-oxazolyl | O | Val | phenyl | 5-isoxazolyl |
| 2-(1-pyrrolidinyl)-4-oxazolyl | O | Val | phenyl | 5-isoxazolyl |
| 2-(1-propyl)-4-oxazolyl | O | Val | phenyl | 5-isoxazolyl |
| 2-(2-methyl)propyl-4-oxazolyl | O | Val | phenyl | 5-isoxazolyl |
| 2-pyridinyl | O | Val | phenyl | 5-isoxazolyl |

-continued

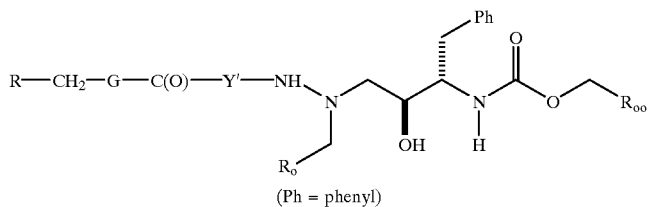

(Ph = phenyl)

| R | G | Y' | $R_o$ | $R_{oo}$ |
|---|---|---|---|---|
| 6-isopropyl-2-pyridinyl | O | Val | phenyl | 5-isoxazolyl |
| 6-methyl-2-pyridinyl | O | Val | phenyl | 5-isoxazolyl |
| 6-(1,1-dimethyl)ethyl-2-pyridinyl | O | Val | phenyl | 5-isoxazolyl |
| 6-cyclobutyl-2-pyridinyl | O | Val | phenyl | 5-isoxazolyl |
| 6-cyclopropyl-2-pyridinyl | O | Val | phenyl | 5-isoxazolyl |
| 6-ethyl-2-pyridinyl | O | Val | phenyl | 5-isoxazolyl |
| 6-(2-propenyl)-2-pyridinyl | O | Val | phenyl | 5-isoxazolyl |
| 6-propyl-2-pyridinyl | O | Val | phenyl | 5-isoxazolyl |
| 6-(2-methyl)propyl-2-pyridinyl | O | Val | phenyl | 5-isoxazolyl |
| 4-thiazolyl | $N(CH_3)$ | Ala | phenyl | 5-isoxazolyl |
| 2-isopropyl-4-thiazolyl | $N(CH_3)$ | Ala | phenyl | 5-isoxazolyl |
| 2-methyl-4-thiazolyl | $N(CH_3)$ | Ala | phenyl | 5-isoxazolyl |
| 2-(1,1-dimethyl)ethyl-4-thiazolyl | $N(CH_3)$ | Ala | phenyl | 5-isoxazolyl |
| 2-cyclobutyl-4-thiazolyl | $N(CH_3)$ | Ala | phenyl | 5-isoxazolyl |
| 2-cyclopropyl-4-thiazolyl | $N(CH_3)$ | Ala | phenyl | 5-isoxazolyl |
| 2-ethyl-4-thiazolyl | $N(CH_3)$ | Ala | phenyl | 5-isoxazolyl |
| 2-(2-propenyl)-4-thiazolyl | $N(CH_3)$ | Ala | phenyl | 5-isoxazolyl |
| 2-(N,N-dimethylamino)-4-thiazolyl | $N(CH_3)$ | Ala | phenyl | 5-isoxazolyl |
| 2-(1-pyrrolidinyl)-4-thiazolyl | $N(CH_3)$ | Ala | phenyl | 5-isoxazolyl |
| 2-(1-propyl)-4-thiazolyl | $N(CH_3)$ | Ala | phenyl | 5-isoxazolyl |
| 2-(2-methyl)propyl-4-thiazolyl | $N(CH_3)$ | Ala | phenyl | 5-isoxazolyl |
| 4-oxazolyl | $NCH_3$ | Ala | phenyl | 5-isoxazolyl |
| 2-isopropyl-4-oxazolyl | $N(CH_3)$ | Ala | phenyl | 5-isoxazolyl |
| 2-methyl-4-oxazolyl | $N(CH_3)$ | Ala | phenyl | 5-isoxazolyl |
| 2-(1,1-dimethyl)ethyl-4-oxazolyl | $N(CH_3)$ | Ala | phenyl | 5-isoxazolyl |
| 2-cyclobutyl-4-oxazolyl | $N(CH_3)$ | Ala | phenyl | 5-isoxazolyl |
| 2-cyclopropyl-4-oxazolyl | $N(CH_3)$ | Ala | phenyl | 5-isoxazolyl |
| 2-ethyl-4-oxazolyl | $N(CH_3)$ | Ala | phenyl | 5-isoxazolyl |
| 2-(2-propenyl)-4-oxazolyl | $N(CH_3)$ | Ala | phenyl | 5-isoxazolyl |
| 2-(N,N-dimethylamino)-4-oxazolyl | $N(CH_3)$ | Ala | phenyl | 5-isoxazolyl |
| 2-(1-pyrrolidinyl)-4-oxazolyl | $N(CH_3)$ | Ala | phenyl | 5-isoxazolyl |
| 2-(1-propyl)-4-oxazolyl | $N(CH_3)$ | Ala | phenyl | 5-isoxazolyl |
| 2-(2-methyl)propyl-4-oxazolyl | $N(CH_3)$ | Ala | phenyl | 5-isoxazolyl |
| 2-pyridinyl | $N(CH_3)$ | Ala | phenyl | 5-isoxazolyl |
| 6-isopropyl-2-pyridinyl | $N(CH_3)$ | Ala | phenyl | 5-isoxazolyl |
| 6-methyl-2-pyridinyl | $N(CH_3)$ | Ala | phenyl | 5-isoxazolyl |
| 6-(1,1-dimethyl)ethyl-2-pyridinyl | $N(CH_3)$ | Ala | phenyl | 5-isoxazolyl |
| 6-cyclobutyl-2-pyridinyl | $N(CH_3)$ | Ala | phenyl | 5-isoxazolyl |
| 6-cyclopropyl-2-pyridinyl | $N(CH_3)$ | Ala | phenyl | 5-isoxazolyl |
| 6-ethyl-2-pyridinyl | $N(CH_3)$ | Ala | phenyl | 5-isoxazolyl |
| 6-(2-propenyl)-2-pyridinyl | $N(CH_3)$ | Ala | phenyl | 5-isoxazolyl |
| 6-propyl-2-pyridinyl | $N(CH_3)$ | Ala | phenyl | 5-isoxazolyl |
| 6-(2-methyl)propyl-2-pyridinyl | $N(CH_3)$ | Ala | phenyl | 5-isoxazolyl |
| 4-thiazolyl | O | Ala | phenyl | 5-isoxazolyl |
| 2-isopropyl-4-thiazolyl | O | Ala | phenyl | 5-isoxazolyl |
| 2-methyl-4-thiazolyl | O | Ala | phenyl | 5-isoxazolyl |
| 2-(1,1-dimethyl)ethyl-4-thiazolyl | O | Ala | phenyl | 5-isoxazolyl |
| 2-cyclobutyl-4-thiazolyl | O | Ala | phenyl | 5-isoxazolyl |
| 2-cyclopropyl-4-thiazolyl | O | Ala | phenyl | 5-isoxazolyl |
| 2-ethyl-4-thiazolyl | O | Ala | phenyl | 5-isoxazolyl |
| 2-(2-propenyl)-4-thiazolyl | O | Ala | phenyl | 5-isoxazolyl |
| 2-(N,N-dimethylamino)-4-thiazolyl | O | Ala | phenyl | 5-isoxazolyl |
| 2-(1-pyrrolidinyl)-4-thiazolyl | O | Ala | phenyl | 5-isoxazolyl |
| 2-(1-propyl)-4-thiazolyl | O | Ala | phenyl | 5-isoxazolyl |
| 2-(2-methyl)propyl-4-thiazolyl | O | Ala | phenyl | 5-isoxazolyl |
| 4-oxazolyl | O | Ala | phenyl | 5-isoxazolyl |
| 2-isopropyl-4-oxazolyl | O | Ala | phenyl | 5-isoxazolyl |
| 2-methyl-4-oxazolyl | O | Ala | phenyl | 5-isoxazolyl |
| 2-(1,1-dimethyl)ethyl-4-oxazolyl | O | Ala | phenyl | 5-isoxazolyl |
| 2-cyclobutyl-4-oxazolyl | O | Ala | phenyl | 5-isoxazolyl |
| 2-cyclopropyl-4-oxazolyl | O | Ala | phenyl | 5-isoxazolyl |
| 2-ethyl-4-oxazolyl | O | Ala | phenyl | 5-isoxazolyl |
| 2-(2-propenyl)-4-oxazolyl | O | Ala | phenyl | 5-isoxazolyl |
| 2-(N,N-dimethylamino)-4-oxazolyl | O | Ala | phenyl | 5-isoxazolyl |
| 2-(1-pyrrolidinyl)-4-oxazolyl | O | Ala | phenyl | 5-isoxazolyl |
| 2-(1-propyl)-4-oxazolyl | O | Ala | phenyl | 5-isoxazolyl |
| 2-(2-methyl)propyl-4-oxazolyl | O | Ala | phenyl | 5-isoxazolyl |

-continued

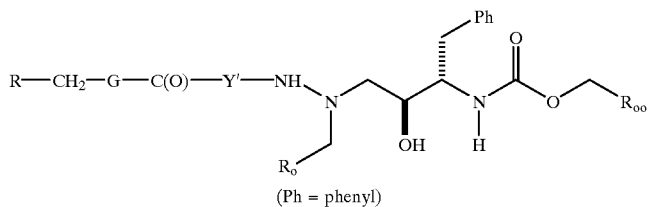

(Ph = phenyl)

| R | G | Y' | R₀ | R₀₀ |
|---|---|---|---|---|
| 2-pyridinyl | O | Ala | phenyl | 5-isoxazolyl |
| 6-isopropyl-2-pyridinyl | O | Ala | phenyl | 5-isoxazolyl |
| 6-methyl-2-pyridinyl | O | Ala | phenyl | 5-isoxazolyl |
| 6-(1,1-dimethyl)ethyl-2-pyridinyl | O | Ala | phenyl | 5-isoxazolyl |
| 6-cyclobutyl-2-pyridinyl | O | Ala | phenyl | 5-isoxazolyl |
| 6-cyclopropyl-2-pyridinyl | O | Ala | phenyl | 5-isoxazolyl |
| 6-ethyl-2-pyridinyl | O | Ala | phenyl | 5-isoxazolyl |
| 6-(2-propenyl)-2-pyridinyl | O | Ala | phenyl | 5-isoxazolyl |
| 6-propyl-2-pyridinyl | O | Ala | phenyl | 5-isdxazolyl |
| 6-(2-methyl)propyl-2-pyridinyl | O | Ala | phenyl | 5-isoxazolyl |
| 4-thiazolyl | N(CH₃) | Ile | phenyl | 5-isoxazolyl |
| 2-isopropyl-4-thiazolyl | N(CH₃) | Ile | phenyl | 5-isoxazolyl |
| 2-methyl-4-thiazolyl | N(CH₃) | Ile | phenyl | 5-isoxazolyl |
| 2-(1,1-dimethyl)ethyl-4-thiazolyl | N(CH₃) | Ile | phenyl | 5-isoxazolyl |
| 2-cyclobutyl-4-thiazolyl | N(CH₃) | Ile | phenyl | 5-isoxazolyl |
| 2-cyclopropyl-4-thiazolyl | N(CH₃) | Ile | phenyl | 5-isoxazolyl |
| 2-ethyl-4-thiazolyl | N(CH₃) | Ile | phenyl | 5-isoxazolyl |
| 2-(2-propenyl)-4-thiazolyl | N(CH₃) | Ile | phenyl | 5-isoxazolyl |
| 2-(N,N-dimethylamino)-4-thiazolyl | N(CH₃) | Ile | phenyl | 5-isoxazolyl |
| 2-(1-pyrrolidinyl)-4-thiazolyl | N(CH₃) | Ile | phenyl | 5-isoxazolyl |
| 2-(1-propyl)-4-thiazolyl | N(CH₃) | Ile | phenyl | 5-isoxazolyl |
| 2-(2-methyl)propyl-4-thiazolyl | N(CH₃) | Ile | phenyl | 5-isoxazolyl |
| 4-oxazolyl | N(CH₃) | Ile | phenyl | 5-isoxazolyl |
| 2-isopropyl-4-oxazolyl | N(CH₃) | Ile | phenyl | 5-isoxazolyl |
| 2-methyl-4-oxazolyl | N(CH₃) | Ile | phenyl | 5-isoxazolyl |
| 2-(1,1-dimethyl)ethyl-4-oxazolyl | N(CH₃) | Ile | phenyl | 5-isoxazolyl |
| 2-cyclobutyl-4-oxazolyl | N(CH₃) | Ile | phenyl | 5-isoxazolyl |
| 2-cyclopropyl-4-oxazolyl | N(CH₃) | Ile | phenyl | 5-isoxazolyl |
| 2-ethyl-4-oxazolyl | N(CH₃) | Ile | phenyl | 5-isoxazolyl |
| 2-(2-propenyl)-4-oxazolyl | N(CH₃) | Ile | phenyl | 5-isoxazolyl |
| 2-(N,N-dimethylamino)-4-oxazolyl | N(CH₃) | Ile | phenyl | 5-isoxazolyl |
| 2-(1-pyrrolidinyl)-4-oxazolyl | N(CH₃) | Ile | phenyl | 5-isoxazolyl |
| 2-(1-propyl)-4-oxazolyl | N(CH₃) | Ile | phenyl | 5-isoxazolyl |
| 2-(2-methyl)propyl-4-oxazolyl | N(CH₃) | Ile | phenyl | 5-isoxazolyl |
| 2-pyridinyl | N(CH₃) | Ile | phenyl | 5-isoxazolyl |
| 6-isopropyl-2-pyridinyl | N(CH₃) | Ile | phenyl | 5-isoxazolyl |
| 6-methyl-2-pyridinyl | N(CH₃) | Ile | phenyl | 5-isoxazolyl |
| 6-(1,1-dimethyl)ethyl-2-pyridinyl | N(CH₃) | Ile | phenyl | 5-isoxazolyl |
| 6-cyclobutyl-2-pyridinyl | N(CH₃) | Ile | phenyl | 5-isoxazolyl |
| 6-cyclopropyl-2-pyridinyl | N(CH₃) | Ile | phenyl | 5-isoxazolyl |
| 6-ethyl-2-pyridinyl | N(CH₃) | Ile | phenyl | 5-isoxazolyl |
| 6-(2-propenyl)-2-pyridinyl | N(CH₃) | Ile | phenyl | 5-isoxazolyl |
| 6-propyl-2-pyridinyl | N(CH₃) | Ile | phenyl | 5-isoxazolyl |
| 6-(2-methyl)propyl-2-pyridinyl | N(CH₃) | Ile | phenyl | 5-isoxazolyl |
| 4-thiazolyl | O | Ile | phenyl | 5-isoxazolyl |
| 2-isopropyl-4-thiazolyl | O | Ile | phenyl | 5-ispxazolyl |
| 2-methyl-4-thiazolyl | O | Ile | phenyl | 5-isoxazolyl |
| 2-(1,1-dimethyl)ethyl-4-thiazolyl | O | Ile | phenyl | 5-isoxazolyl |
| 2-cyclobutyl-4-thiazolyl | O | Ile | phenyl | 5-isoxazolyl |
| 2-cyclopropyl-4-thiazolyl | O | Ile | phenyl | 5-isoxazolyl |
| 2-ethyl-4-thiazolyl | O | Ile | phenyl | 5-isoxazolyl |
| 2-(2-propenyl)-4-thiazolyl | O | Ile | phenyl | 5-isoxazolyl |
| 2-(N,N-dimethylamino)-4-thiazolyl | O | Ile | phenyl | 5-isoxazolyl |
| 2-(1-pyrrolidinyl)-4-thiazolyl | O | Ile | phenyl | 5-isoxazolyl |
| 2-(1-propyl)-4-thiazolyl | O | Ile | phenyl | 5-isoxazolyl |
| 2-(2-methyl)propyl-4-thiazolyl | O | Ile | phenyl | 5-isoxazolyl |
| 4-oxazolyl | O | Ile | phenyl | 5-isoxazolyl |
| 2-isopropyl-4-oxazolyl | O | Ile | phenyl | 5-isoxazolyl |
| 2-methyl-4-oxazolyl | O | Ile | phenyl | 5-isoxazolyl |
| 2-(1,1-dimethyl)ethyl-4-oxazolyl | O | Ile | phenyl | 5-isoxazolyl |
| 2-cyclobutyl-4-oxazolyl | O | Ile | phenyl | 5-isoxazolyl |
| 2-cyclopropyl-4-oxazolyl | O | Ile | phenyl | 5-isoxazolyl |
| 2-ethyl-4-oxazolyl | O | Ile | phenyl | 5-isoxazolyl |
| 2-(2-propenyl)-4-oxazolyl | O | Ile | phenyl | 5-isoxazolyl |
| 2-(N,N-dimethylamino)-4-oxazolyl | O | Ile | phenyl | 5-isoxazolyl |
| 2-(1-pyrrolidinyl)-4-oxazolyl | O | Ile | phenyl | 5-isoxazolyl |
| 2-(1-propyl)-4-oxazolyl | O | Ile | phenyl | 5-isoxazolyl |

-continued

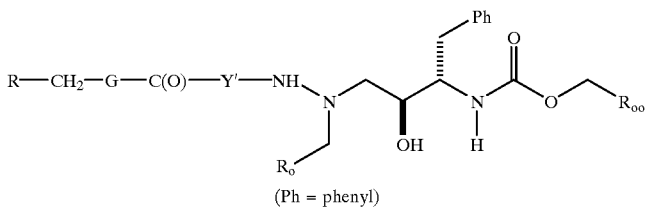

(Ph = phenyl)

| R | G | Y' | $R_o$ | $R_{oo}$ |
|---|---|---|---|---|
| 2-(2-methyl)propyl-4-oxazolyl | O | Ile | phenyl | 5-isoxazolyl |
| 2-pyridinyl | O | Ile | phenyl | 5-isoxazolyl |
| 6-isopropyl-2-pyridinyl | O | Ile | phenyl | 5-isoxazolyl |
| 6-methyl-2-pyridinyl | O | Ile | phenyl | 5-isoxazolyl |
| 6-(1,1-dimethyl)ethyl-2-pyridinyl | O | Ile | phenyl | 5-isoxazolyl |
| 6-cyclobutyl-2-pyridinyl | O | Ile | phenyl | 5-isoxazolyl |
| 6-cyclopropyl-2-pyridinyl | O | Ile | phenyl | 5-isoxazolyl |
| 6-ethyl-2-pyridinyl | O | Ile | phenyl | 5-isoxazolyl |
| 6-(2-propenyl)-2-pyridinyl | O | Ile | phehyl | 5-isoxazolyl |
| 6-propyl-2-pyridinyl | O | Ile | phenyl | 5-isoxazolyl |
| 6-(2-methyl)propyl-2-pyridinyl | O | Ile | phenyl | 5-isoxazolyl |
| 4-thiazolyl | $N(CH_3)$ | Val | 4-fluorophenyl | 5-thiazolyl |
| 2-isopropyl-4-thiazolyl | $N(CH_3)$ | Val | 4-fluorophenyl | 5-thiazolyl |
| 2-methyl-4-thiazolyl | $N(CH_3)$ | Val | 4-fluorophenyl | 5-thiazolyl |
| 2-(1,1-dimethyl)ethyl-4-thiazolyl | $N(CH_3)$ | Val | 4-fluorophenyl | 5-thiazolyl |
| 2-cyclobutyl-4-thiazolyl | $N(CH_3)$ | Val | 4-fluorophenyl | 5-thiazolyl |
| 2-cyclopropyl-4-thiazolyl | $N(CH_3)$ | Val | 4-fluorophenyl | 5-thiazolyl |
| 2-ethyl-4-thiazolyl | $N(CH_3)$ | Val | 4-fluorophenyl | 5-thiazolyl |
| 2-(2-propenyl)-4-thiazolyl | $N(CH_3)$ | Val | 4-fluorophenyl | 5-thiazolyl |
| 2-(N,N-dimethylamino)-4-thiazolyl | $N(CH_3)$ | Val | 4-fluorophenyl | 5-thiazolyl |
| 2-(1-pyrrolidinyl)-4-thiazolyl | $N(CH_3)$ | Val | 4-fluorophenyl | 5-thiazolyl |
| 2-(1-propyl)-4-thiazolyl | $N(CH_3)$ | Val | 4-fluorophenyl | 5-thiazolyl |
| 2-(2-methyl)propyl-4-thiazolyl | $N(CH_3)$ | Val | 4-fluorophenyl | 5-thiazolyl |
| 4-oxazolyl | $N(CH_3)$ | Val | 4-fluorophenyl | 5-thiazolyl |
| 2-isopropyl-4-oxazolyl | $N(CH_3)$ | Val | 4-fluorophenyl | 5-thiazolyl |
| 2-methyl-4-oxazolyl | $N(CH_3)$ | Val | 4-fluorophenyl | 5-thiayolyl |
| 2-(1,1-dimethyl)ethyl-4-oxazolyl | $N(CH_3)$ | Val | 4-fluorophenyl | 5-thiazolyl |
| 2-cyclobutyl-4-oxazolyl | $N(CH_3)$ | Val | 4-fluorophenyl | 5-thiazolyl |
| 2-cyclopropyl-4-oxazolyl | $N(CH_3)$ | Val | 4-fluorophenyl | 5-thiazolyl |
| 2-ethyl-4-oxazolyl | $N(CH_3)$ | Val | 4-fluorophenyl | 5-thiazolyl |
| 2-(2-propenyl)-4-oxazolyl | $N(CH_3)$ | Val | 4-fluorophenyl | 5-thiazolyl |
| 2-(N,N-dimethylamino)-4-oxazolyl | $N(CH_3)$ | Val | 4-fluorophenyl | 5-thiazolyl |
| 2-(1-pyrrolidinyl)-4-oxazolyl | $N(CH_3)$ | Val | 4-fluorophenyl | 5-thiazolyl |
| 2-(1-propyl)-4-oxazolyl | $N(CH_3)$ | Val | 4-fluorophenyl | 5-thiazolyl |
| 2-(2-methyl)propyl-4-oxazolyl | $N(CH_3)$ | Val | 4-fluorophenyl | 5-thiazolyl |
| 2-pyridinyl | $N(CH_3)$ | Val | 4-fluorophenyl | 5-thiazolyl |
| 6-isopropyl-2-pyridinyl | $N(CH_3)$ | Val | 4-fluorophenyl | 5-thiazolyl |
| 6-methyl-2-pyridinyl | $N(CH_3)$ | Val | 4-fluorophenyl | 5-thiazolyl |
| 6-(1,1-dimethyl)ethyl-2-pyridinyl | $N(CH_3)$ | Val | 4-fluorophenyl | 5-thiazolyl |
| 6-cyclobutyl-2-pyridinyl | $N(CH_3)$ | Val | 4-fluorophenyl | 5-thiazolyl |
| 6-cyclopropyl-2-pyridinyl | $N(CH_3)$ | Val | 4-fluorophenyl | 5-thiazolyl |
| 6-ethyl-2-pyridinyl | $N(CH_3)$ | Val | 4-tluorophenyl | 5-thiazolyl |
| 6-(2-propenyl)-2-pyridinyl | $N(CH_3)$ | Val | 4-fluorophenyl | 5-thiazolyl |
| 6-propyl-2-pyridinyl | $N(CH_3)$ | Val | 4-fluorophenyl | 5-thiazolyl |
| 6-(2-methyl)propyl-2-pyridinyl | $N(CH_3)$ | Val | 4-fluorophenyl | 5-thiazolyl |
| 4-thiazolyl | $N(CH_3)$ | Val | 5-oxazolyl | 5-thiazolyl |
| 2-isopropyl-4-thiazolyl | $N(CH_3)$ | Val | 5-oxazolyl | 5-thiazolyl |
| 2-methyl-4-thiazolyl | $N(CH_3)$ | Val | 5-oxazolyl | 5-thiazolyl |
| 2-(1,1-dimethyl)ethyl-4-thiazolyl | $N(CH_3)$ | Val | 5-oxazolyl | 5-thiazolyl |
| 2-cyclobutyl-4-thiazolyl | $N(CH_3)$ | Val | 5-oxazolyl | 5-thiazolyl |
| 2-cyclopropyl-4-thiazolyl | $N(CH_3)$ | Val | 5-oxazolyl | 5-thiazolyl |
| 2-ethyl-4-thiazolyl | $N(CH_3)$ | Val | 5-oxazolyl | 5-thiazolyl |
| 2-(2-propenyl)-4-thiazolyl | $N(CH_3)$ | Val | 5-oxazolyl | 5-thiazolyl |
| 2-(N,N-dimethylamino)-4-thiazolyl | $N(CH_3)$ | Val | 5-oxazolyl | 5-thiazolyl |
| 2-(1-pyrrolidinyl)-4-thiazolyl | $N(CH_3)$ | Val | 5-oxazolyl | 5-thiazolyl |
| 2-(1-propyl)-4-thiazolyl | $N(CH_3)$ | Val | 5-oxazolyl | 5-thiazolyl |
| 2-(2-methyl)propyl-4-thiazolyl | $N(CH_3)$ | Val | 5-oxazolyl | 5-thiazolyl |
| 4-oxazolyl | $N(CH_3)$ | Val | 5-oxazolyl | 5-thiazolyl |
| 2-isopropyl-4-oxazolyl | $N(CH_3)$ | Val | 5-oxazolyl | 5-thiazolyl |
| 2-methyl-4-oxazolyl | $N(CH_3)$ | Val | 5-oxazolyl | 5-thiazolyl |
| 2-(1,1-dimethyl)ethyl-4-oxazolyl | $N(CH_3)$ | Val | 5-oxazolyl | 5-thiazolyl |
| 2-cyclobutyl-4-oxazolyl | $N(CH_3)$ | Val | 5-oxazolyl | 5-thiazolyl |
| 2-cyclopropyl-4-oxazolyl | $N(CH_3)$ | Val | 5-oxazolyl | 5-thiazolyl |
| 2-ethyl-4-oxazolyl | $N(CH_3)$ | Val | 5-oxazolyl | 5-thiazolyl |
| 2-(2-propenyl)-4-oxazolyl | $N(CH_3)$ | Val | 5-oxazolyl | 5-thiazolyl |
| 2-(N,N-dimethylamino)-4-oxazolyl | $N(CH_3)$ | Val | 5-oxazolyl | 5-thiazolyl |
| 2-(1-pyrrolidinyl)-4-oxazolyl | $N(CH_3)$ | Val | 5-oxazolyl | 5-thiazolyl |

-continued

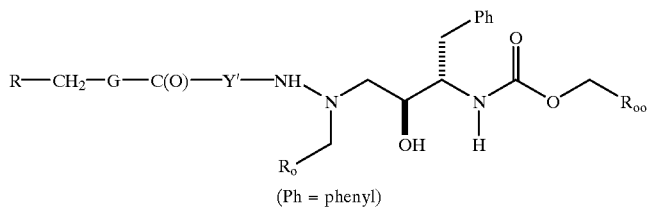

(Ph = phenyl)

| R | G | Y' | $R_o$ | $R_{oo}$ |
|---|---|---|---|---|
| 2-(1-propyl)-4-oxazolyl | N(CH$_3$) | Val | 5-oxazolyl | 5-thiazolyl |
| 2-(2-methyl)propyl-4-oxazolyl | N(CH$_3$) | Val | 5-oxazolyl | 5-thiazolyl |
| 2-pyridinyl | N(CH$_3$) | Val | 5-oxazolyl | 5-thiazolyl |
| 6-isopropyl-2-pyridinyl | N(CH$_3$) | Val | 5-oxazolyl | 5-thiazolyl |
| 6-methyl-2-pyridinyl | N(CH$_3$) | Val | 5-oxazolyl | 5-thiazolyl |
| 6-(1,1-dimethyl)ethyl-2-pyridinyl | N(CH$_3$) | Val | 5-oxazolyl | 5-thiazolyl |
| 6-cyclobutyl-2-pyridinyl | N(CH$_3$) | Val | 5-oxazolyl | 5-thiazolyl |
| 6-cyclopropyl-2-pyridinyl | N(CH$_3$) | Val | 5-oxazolyl | 5-thiazolyl |
| 6-ethyl-2-pyridinyl | N(CH$_3$) | Val | 5-oxazolyl | 5-thiazolyl |
| 6-(2-propenyl)-2-pyridinyl | N(CH$_3$) | Val | 5-oxazolyl | 5-thiazolyl |
| 6-propyl-2-pyridinyl | N(CH$_3$) | Val | 5-oxazolyl | 5-thiazolyl |
| 6-(2-methyl)propyl-2-pyridinyl | N(CH$_3$) | Val | 5-oxazolyl | 5-thiazolyl |
| 4-thiazolyl | N(CH$_3$) | Val | 5-isoxazolyl | 5-thiazolyl |
| 2-isopropyl-4-thiazolyl | N(CH$_3$) | Val | 5-isoxazolyl | 5-thiazolyl |
| 2-methyl-4-thiazolyl | N(CH$_3$) | Val | 5-isoxazolyl | 5-thiazolyl |
| 2-(1,1-dimethyl)ethyl-4-thiazolyl | N(CH$_3$) | Val | 5-isoxazolyl | 5-thiazolyl |
| 2-cyclobutyl-4-thiazolyl | N(CH$_3$) | Val | 5-isoxazolyl | 5-thiazolyl |
| 2-cyclopropyl-4-thiazolyl | N(CH$_3$) | Val | 5-isoxazolyl | 5-thiazolyl |
| 2-ethyl-4-thiazolyl | N(CH$_3$) | Val | 5-isoxazolyl | 5-thiazolyl |
| 2-(2-propenyl)-4-thiazolyl | N(CH$_3$) | Val | 5-isoxazolyl | 5-thiazolyl |
| 2-(N,N-dimethylamino)-4-thiazolyl | N(CH$_3$) | Val | 5-isoxazolyl | 5-thiazolyl |
| 2-(1-pyrrolidinyl)-4-thiazolyl | N(CH$_3$) | Val | 5-isoxazolyl | 5-thiazolyl |
| 2-(1-propyl)-4-thiazolyl | N(CH$_3$) | Val | 5-isoxazolyl | 5-thiazolyl |
| 2-(2-methyl)propyl-4-thiazolyl | N(CH$_3$) | Val | 5-isoxazolyl | 5-thiazolyl |
| 4-oxazolyl | N(CH$_3$) | Val | 5-isoxazolyl | 5-thiazolyl |
| 2-isopropyl-4-oxazolyl | N(CH$_3$) | Val | 5-isoxazolyl | 5-thiazolyl |
| 2-methyl-4-oxazolyl | N(CH$_3$) | Val | 5-isoxazolyl | 5-thiazolyl |
| 2-(1,1-dimethyl)ethyl-4-oxazolyl | N(CH$_3$) | Val | 5-isoxazolyl | 5-thiazolyl |
| 2-cyclobutyl-4-oxazolyl | N(CH$_3$) | Val | 5-isoxazolyl | 5-thiazolyl |
| 2-cyclopropyl-4-oxazolyl | N(CH$_3$) | Val | 5-isoxazolyl | 5-thiazolyl |
| 2-ethyl-4-oxazolyl | N(CH$_3$) | Val | 5-isoxazolyl | 5-thiazolyl |
| 2-(2-propenyl)-4-oxazolyl | N(CH$_3$) | Val | 5-isoxazolyl | 5-thiazolyl |
| 2-(N,N-dimethylamino)-4-oxazolyl | N(CH$_3$) | Val | 5-isoxazolyl | 5-thiazolyl |
| 2-(1-pyrrolidinyl)-4-oxazolyl | N(CH$_3$) | Val | 5-isoxazolyl | 5-thiazolyl |
| 2-(1-propyl)-4-oxazolyl | N(CH$_3$) | Val | 5-isoxazolyl | 5-thiazolyl |
| 2-(2-methyl)propyl-4-oxazolyl | N(CH$_3$) | Val | 5-isoxazolyl | 5-thiazolyl |
| 2-pyridinyl | N(CH$_3$) | Val | 5-isoxazolyl | 5-thiazolyl |
| 6-isopropyl-2-pyridinyl | N(CH$_3$) | Val | 5-isoxazolyl | 5-thiazolyl |
| 6-methyl-2-pyridinyl | N(CH$_3$) | Val | 5-isoxazolyl | 5-thiazolyl |
| 6-(1,1-dimethyl)ethyl-2-pyridinyl | N(CH$_3$) | Val | 5-isoxazolyl | 5-thiazolyl |
| 6-cyclobutyl-2-pyridinyl | N(CH$_3$) | Val | 5-isoxazolyl | 5-thiazolyl |
| 6-cyclopropyl-2-pyridinyl | N(CH$_3$) | Val | 5-isoxazolyl | 5-thiazolyl |
| 6-ethyl-2-pyridinyl | N(CH$_3$) | Val | 5-isoxazolyl | 5-thiazolyl |
| 6-(2-propenyl)-2-pyridinyl | N(CH$_3$) | Val | 5-isoxazolyl | 5-thiazolyl |
| 6-propyl-2-pyridinyl | N(CH$_3$) | Val | 5-isoxazolyl | 5-thiazolyl |
| 6-(2-methyl)propyl-2-pyridinyl | N(CH$_3$) | Val | 5-isoxazolyl | 5-thiazolyl |
| 4-thiazolyl | N(CH$_3$) | Val | 5-thiazolyl | 5-thiazolyl |
| 2-isopropyl-4-thiazolyl | N(CH$_3$) | Val | 5-thiazolyl | 5-thiazolyl |
| 2-methyl-4-thiazolyl | N(CH$_3$) | Val | 5-thiazolyl | 5-thiazolyl |
| 2-(1,1-dimethyl)ethyl-4-thiazolyl | N(CH$_3$) | Val | 5-thiazolyl | 5-thiazolyl |
| 2-cyclobutyl-4-thiazolyl | N(CH$_3$) | Val | 5-thiazolyl | 5-thiazolyl |
| 2-cyclopropyl-4-thiazolyl | N(CH$_3$) | Val | 5-thiazolyl | 5-thiazolyl |
| 2-ethyl-4-thiazolyl | N(CH$_3$) | Val | 5-thiazolyl | 5-thiazolyl |
| 2-(2-propenyl)-4-thiazolyl | N(CH$_3$) | Val | 5-thiazolyl | 5-thiazolyl |
| 2-(N,N-dimethylamino)-4-thiazolyl | N(CH$_3$) | Val | 5-thiazolyl | 5-thiazolyl |
| 2-(1-pyrrolidinyl)-4-thiazolyl | N(CH$_3$) | Val | 5-thiazolyl | 5-thiazolyl |
| 2-(1-propyl)-4-thiazolyl | N(CH$_3$) | Val | 5-thiazolyl | 5-thiazolyl |
| 2-(2-methyl)propyl-4-thiazolyl | N(CH$_3$) | Val | 5-thiazolyl | 5-thiazolyl |
| 4-oxazolyl | N(CH$_3$) | Val | 5-thiazolyl | 5-thiazolyl |
| 2-isopropyl-4-oxazolyl | N(CH$_3$) | Val | 5-thiazolyl | 5-thiazolyl |
| 2-methyl-4-oxazolyl | N(CH$_3$) | Val | 5-thiazolyl | 5-thiazolyl |
| 2-(1,1-dimethyl)ethyl-4-oxazolyl | N(CH$_3$) | Val | 5-thiazolyl | 5-thiazolyl |
| 2-cyclobutyl-4-oxazolyl | N(CH$_3$) | Val | 5-thiazolyl | 5-thiazolyl |
| 2-cyclopropyl-4-oxazolyl | N(CH$_3$) | Val | 5-thiazolyl | 5-thiazolyl |
| 2-ethyl-4-oxazolyl | N(CH$_3$) | Val | 5-thiazolyl | 5-thiazolyl |
| 2-(2-propenyl)-4-oxazolyl | N(CH$_3$) | Val | 5-thiazolyl | 5-thiazolyl |
| 2-(N,N-dimethylamino)-4-oxazolyl | N(CH$_3$) | Val | 5-thiazolyl | 5-thiazolyl |

-continued

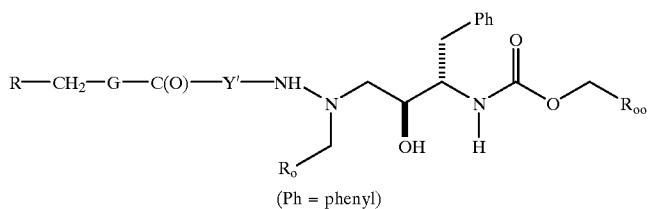

(Ph = phenyl)

| R | G | Y' | $R_o$ | $R_{oo}$ |
|---|---|---|---|---|
| 2-(1-pyrrolidinyl)-4-oxazolyl | N(CH$_3$) | Val | 5-thiazolyl | 5-thiazolyl |
| 2-(1-propyl)-4-oxazolyl | N(CH$_3$) | Val | 5-thiazolyl | 5-thiazolyl |
| 2-(2-methyl)propyl-4-oxazolyl | N(CH$_3$) | Val | 5-thiazolyl | 5-thiazolyl |
| 2-pyridinyl | N(CH$_3$) | Val | 5-thiazolyl | 5-thiazolyl |
| 6-isopropyl-2-pyridinyl | N(CH$_3$) | Val | 5-thiazolyl | 5-thiazolyl |
| 6-methyl-2-pyridinyl | N(CH$_3$) | Val | 5-thiazolyl | 5-thiazolyl |
| 6-(1,1-dimethyl)ethyl-2-pyridinyl | N(CH$_3$) | Val | 5-thiazolyl | 5-thiazolyl |
| 6-cyclobutyl-2-pyridinyl | N(CH$_3$) | Val | 5-thiazolyl | 5-thiazolyl |
| 6-cyclopropyl-2-pyridinyl | N(CH$_3$) | Val | 5-thiazolyl | 5-thiazolyl |
| 6-ethyl-2-pyridinyl | N(CH$_3$) | Val | 5-thiazolyl | 5-thiazolyl |
| 6-(2-propenyl)-2-pyridinyl | N(CH$_3$) | Val | 5-thiazolyl | 5-thiazolyl |
| 6-propyl-2-pyridinyl | N(CH$_3$) | Val | 5-thiazolyl | 5-thiazolyl |
| 6-(2-methyl)propyl-2-pyridinyl | N(CH$_3$) | Val | 5-thiazolyl | 5-thiazolyl |
| 4-thiazolyl | N(CH$_3$) | Val | 5-oxazolyl | phenyl |
| 2-isopropyl-4-thiazolyl | N(CH$_3$) | Val | 5-oxazolyl | phenyl |
| 2-methyl-4-thiazolyl | N(CH$_3$) | Val | 5-oxazolyl | phenyl |
| 2-(1,1-dimethyl)ethyl-4-thiazolyl | N(CH$_3$) | Val | 5-oxazolyl | phenyl |
| 2-cyclobutyl-4-thiazolyl | N(CH$_3$) | Val | 5-oxazolyl | phenyl |
| 2-cyclopropyl-4-thiazolyl | N(CH$_3$) | Val | 5-oxazolyl | phenyl |
| 2-ethyl-4-thiazolyl | N(CH$_3$) | Val | 5-oxazolyl | phenyl |
| 2-(2-propenyl)-4-thiazolyl | N(CH$_3$) | Val | 5-oxazolyl | phenyl |
| 2-(N,N-dimethylamino)-4-thiazolyl | N(CH$_3$) | Val | 5-oxazolyl | phenyl |
| 2-(1-pyrrolidinyl)-4-thiazolyl | N(CH$_3$) | Val | 5-oxazolyl | phenyl |
| 2-(1-propyl)-4-thialolyl | N(CH$_3$) | Val | 5-oxazolyl | phenyl |
| 2-(2-methyl)propyl-4-thiazolyl | N(CH$_3$) | Val | 5-oxazolyl | phenyl |
| 4-oxazolyl | N(CH$_3$) | Val | 5-oxazolyl | phenyl |
| 2-isopropyl-4-oxazolyl | N(CH$_3$) | Val | 5-oxazolyl | phenyl |
| 2-methyl-4-oxazolyl | N(CH$_3$) | Val | 5-oxazolyl | phenyl |
| 2-(1,1-dimethyl)ethyl-4-oxazolyl | N(CH$_3$) | Val | 5-oxazolyl | phenyl |
| 2-cyclobutyl-4-oxazolyl | N(CH$_3$) | Val | 5-oxazolyl | phenyl |
| 2-cyclopropyl-4-oxazolyl | N(CH$_3$) | Val | 5-oxazolyl | phenyl |
| 2-ethyl-4-oxazolyl | N(CH$_3$) | Val | 5-oxazolyl | phenyl |
| 2-(2-propenyl)-4-oxazolyl | N(CH$_3$) | Val | 5-oxazolyl | phenyl |
| 2-(N,N-dimethylamino)-4-oxazolyl | N(CH$_3$) | Val | 5-oxazolyl | phenyl |
| 2-(1-pyrrolidinyl)-4-oxazolyl | N(CH$_3$) | Val | 5-oxazolyl | phenyl |
| 2-(1-propyl)-4-oxazolyl | N(CH$_3$) | Val | 5-oxazolyl | phenyl |
| 2-(2-methyl)propyl-4-oxazolyl | N(CH$_3$) | Val | 5-oxazolyl | phenyl |
| 2-pyridinyl | N(CH$_3$) | Val | 5-oxazolyl | phenyl |
| 6-isopropyl-2-pyridinyl | N(CH$_3$) | Val | 5-oxazolyl | phenyl |
| 6-methyl-2-pyridinyl | N(CH$_3$) | Val | 5-oxazolyl | phenyl |
| 6-(1,1-dimethyl)ethyl-2-pyridinyl | N(CH$_3$) | Val | 5-oxazolyl | phenyl |
| 6-cyclobutyl-2-pyridinyl | N(CH$_3$) | Val | 5-oxazolyl | phenyl |
| 6-cyclopropyl-2-pyridinyl | N(CH$_3$) | Val | 5-oxazolyl | phenyl |
| 6-ethyl-2-pyridinyl | N(CH$_3$) | Val | 5-oxazolyl | phenyl |
| 6-(2-propenyl)-2-pyridinyl | N(CH$_3$) | Val | 5-oxazolyl | phenyl |
| 6-propyl-2-pyridinyl | N(CH$_3$) | Val | 5-oxazolyl | phenyl |
| 6-(2-methyl)propyl-2-pyridinyl | N(CH$_3$) | Val | 5-oxazolyl | phenyl |
| 4-thiazolyl | N(CH$_3$) | Val | 5-isoxazolyl | phenyl |
| 2-isopropyl-4-thiazolyl | N(CH$_3$) | Val | 5-isoxazolyl | phenyl |
| 2-methyl-4-thiazolyl | N(CH$_3$) | Val | 5-isoxazolyl | phenyl |
| 2-(1,1-dimethyl)ethyl-4-thiazolyl | N(CH$_3$) | Val | 5-isoxazolyl | phenyl |
| 2-cyclobutyl-4-thiazolyl | N(CH$_3$) | Val | 5-isoxazolyl | phenyl |
| 2-cyclopropyl-4-thiazolyl | N(CH$_3$) | Val | 5-isoxazolyl | phenyl |
| 2-ethyl-4-thiazolyl | N(CH$_3$) | Val | 5-isoxazolyl | phenyl |
| 2-(2-propenyl)-4-thiazolyl | N(CH$_3$) | Val | 5-isoxazolyl | phenyl |
| 2-(N,N-dimethylamino)-4-thiazolyl | N(CH$_3$) | Val | 5-isoxazolyl | phenyl |
| 2-(1-pyrrolidinyl)-4-thiazolyl | N(CH$_3$) | Val | 5-isoxazolyl | phenyl |
| 2-(1-propyl)-4-thiazolyl | N(CH$_3$) | Val | 5-isoxazolyl | phenyl |
| 2-(2-methyl)propyl-4-thiazolyl | N(CH$_3$) | Val | 5-isoxazolyl | phenyl |
| 4-oxazolyl | N(CH$_3$) | Val | 5-isoxazolyl | phenyl |
| 2-isopropyl-4-oxazolyl | N(CH$_3$) | Val | 5-isoxazolyl | phenyl |
| 2-methyl-4-oxazolyl | N(CH$_3$) | Val | 5-isoxazolyl | phenyl |
| 2-(1,1-dimethyl)ethyl-4-oxazolyl | N(CH$_3$) | Val | 5-isoxazolyl | phenyl |
| 2-cyclobutyl-4-oxazolyl | N(CH$_3$) | Val | 5-isoxazolyl | phenyl |
| 2-cyclopropyl-4-oxazolyl | N(CH$_3$) | Val | 5-isoxazolyl | phenyl |
| 2-ethyl-4-oxazolyl | N(CH$_3$) | Val | 5-isoxazolyl | phenyl |
| 2-(2-propenyl)-4-oxazolyl | N(CH$_3$) | Val | 5-isoxazolyl | phenyl |

-continued

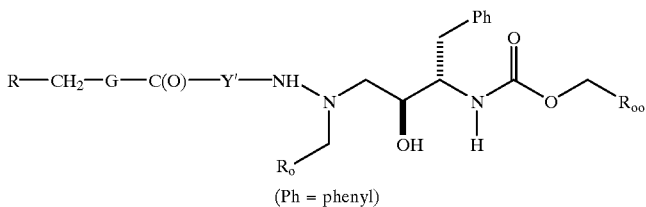

(Ph = phenyl)

| R | G | Y' | $R_o$ | $R_{oo}$ |
|---|---|---|---|---|
| 2-(N,N-dimethylamino)-4-oxazolyl | $N(CH_3)$ | Val | 5-isoxazolyl | phenyl |
| 2-(1-pyrrolidinyl)-4-oxazolyl | $N(CH_3)$ | Val | 5-isoxazolyl | phenyl |
| 2-(1-propyl)-4-oxazolyl | $N(CH_3)$ | Val | 5-isoxazolyl | phenyl |
| 2-(2-methyl)propyl-4-oxazolyl | $N(CH_3)$ | Val | 5-isoxazolyl | phenyl |
| 2-pyridinyl | $N(CH_3)$ | Val | 5-isoxazolyl | phenyl |
| 6-isopropyl-2-pyridinyl | $N(CH_3)$ | Val | 5-isoxazolyl | phenyl |
| 6-methyl-2-pyridinyl | $N(CH_3)$ | Val | 5-isoxazolyl | phenyl |
| 6-(1,1-dimethyl)ethyl-2-pyridinyl | $N(CH_3)$ | Val | 5-isoxazolyl | phenyl |
| 6-cyclobutyl-2-pyridinyl | $N(CH_3)$ | Val | 5-isoxazolyl | phenyl |
| 6-cyclopropyl-2-pyridinyl | $N(CH_3)$ | Val | 5-isoxazolyl | phenyl |
| 6-ethyl-2-pyridinyl | $N(CH_3)$ | Val | 5-isoxazolyl | phenyl |
| 6-(2-propenyl)-2-pyridinyl | $N(CH_3)$ | Val | 5-isoxazolyl | phenyl |
| 6-propyl-2-pyridinyl | $N(CH_3)$ | Val | 5-isoxazolyl | phenyl |
| 6-(2-methyl)propyl-2-pyridinyl | $N(CH_3)$ | Val | 5-isoxazolyl | phenyl |
| 4-thiazolyl | $N(CH_3)$ | Val | 5-thiazolyl | phenyl |
| 2-isopropyl-4-thiazolyl | $N(CH_3)$ | Val | 5-thiazolyl | phenyl |
| 2-methyl-4-thiazolyl | $N(CH_3)$ | Val | 5-thiazolyl | phenyl |
| 2-(1,1-dimethyl)ethyl-4-thiazolyl | $N(CH_3)$ | Val | 5-thiazolyl | phenyl |
| 2-cyclobutyl-4-thiazolyl | $N(CH_3)$ | Val | 5-thiazolyl | phenyl |
| 2-cyclopropyl-4-thiazolyl | $N(CH_3)$ | Val | 5-thiazolyl | phenyl |
| 2-ethyl-4-thiazolyl | $N(CH_3)$ | Val | 5-thiazolyl | phenyl |
| 2-(2-propenyl)-4-thiazolyl | $N(CH_3)$ | Val | 5-thiazolyl | phenyl |
| 2-(N,N-dimethylamino)-4-thiazolyl | $N(CH_3)$ | Val | 5-thiazolyl | phenyl |
| 2-(1-pyrrolidinyl)-4-thiazolyl | $N(CH_3)$ | Val | 5-thiazolyl | phenyl |
| 2-(1-propyl)-4-thazolyl | $N(CH_3)$ | Val | 5-thiazolyl | phenyl |
| 2-(2-methyl)propyl-4-thiazolyl | $N(CH_3)$ | Val | 5-thiazolyl | phenyl |
| 4-oxazolyl | $N(CH_3)$ | Val | 5-thiazolyl | phenyl |
| 2-isopropyl-4-oxazolyl | $N(CH_3)$ | Val | 5-thiazolyl | phenyl |
| 2-methyl-4-oxazolyl | $N(CH_3)$ | Val | 5-thiazolyl | phenyl |
| 2-(1,1-dimethyl)ethyl-4-oxazolyl | $N(CH_3)$ | Val | 5-thiazolyl | phenyl |
| 2-cyclobutyl-4-oxazolyl | $N(CH_3)$ | Val | 5-thiazolyl | phenyl |
| 2-cyclopropyl-4-oxazolyl | $N(CH_3)$ | Val | 5-thiazolyl | phenyl |
| 2-ethyl-4-oxazolyl | $N(CH_3)$ | Val | 5-thiazolyl | phenyl |
| 2-(2-propenyl)-4-oxazolyl | $N(CH_3)$ | Val | 5-thiazolyl | phenyl |
| 2-(N,N-dimethylamino)-4-oxazolyl | $N(CH_3)$ | Val | 5-thiazolyl | phenyl |
| 2-(1-pyrrolidinyl)-4-oxazolyl | $N(CH_3)$ | Val | 5-thiazolyl | phenyl |
| 2-(1-propyl)-4-oxazolyl | $N(CH_3)$ | Val | 5-thiazolyl | phenyl |
| 2-(2-methyl)propyl-4-oxazolyl | $N(CH_3)$ | Val | 5-thiazolyl | phenyl |
| 2-pyridinyl | $N(CH_3)$ | Val | 5-thiazolyl | phenyl |
| 6-isopropyl-2-pyridinyl | $N(CH_3)$ | Val | 5-thiazolyl | phenyl |
| 6-methyl-2-pyridinyl | $N(CH_3)$ | Val | 5-thiazolyl | phenyl |
| 6-(1,1-dimethyl)ethyl-2-pyridinyl | $N(CH_3)$ | Val | 5-thiazolyl | phenyl |
| 6-cyclobutyl-2-pyridinyl | $N(CH_3)$ | Val | 5-thiazolyl | phenyl |
| 6-cyclopropyl-2-pyridinyl | $N(CH_3)$ | Val | 5-thiazolyl | phenyl |
| 6-ethyl-2-pyridinyl | $N(CH_3)$ | Val | 5-thiazolyl | phenyl |
| 6-(2-propenyl)-2-pyridinyl | $N(CH_3)$ | Val | 5-thiazolyl | phenyl |
| 6-propyl-2-pyridinyl | $N(CH_3)$ | Val | 5-thiazolyl | phenyl |
| 6-(2-methyl)propyl-2-pyridinyl | $N(CH_3)$ | Val | 5-thiazolyl | phenyl |
| 2-(1-butyl)-4-thiazolyl | $N(CH_3)$ | Val | phenyl | 5-thiazolyl |
| 2-(1-butyl)-4-oxazolyl | $N(CH_3)$ | Val | phenyl | 5-thiazolyl |
| 6-(1-butyl)-2-pyridinyl | $N(CH_3)$ | Val | phenyl | 5-thiazolyl |
| 2-(1-butyl)-4-thiazolyl | O | Val | phenyl | 5-thiazolyl |
| 2-(1-butyl)-4-oxazolyl | O | Val | phenyl | 5-thiazolyl |
| 6-(1-butyl)-2-pyridinyl | O | Val | phenyl | 5-thiazolyl |
| 2-(1-butyl)-4-thiazolyl | $N(CH_3)$ | Ala | phenyl | 5-thiazolyl |
| 2-(1-butyl)-4-oxazolyl | $N(CH_3)$ | Ala | phenyl | 5-thiazolyl |
| 6-(1-butyl)-2-pyridinyl | $N(CH_3)$ | Ala | phenyl | 5-thiazolyl |
| 2-(1-butyl)-4-thiazolyl | O | Ala | phenyl | 5-thiazolyl |
| 2-(1-butyl)-4-oxazolyl | O | Ala | phenyl | 5-thiazolyl |
| 6-(1-butyl)-2-pyridinyl | O | Ala | phenyl | 5-thiazolyl |
| 2-(1-butyl)-4-thiazolyl | $N(CH_3)$ | Ile | phenyl | 5-thiazolyl |
| 2-(1-butyl)-4-oxazolyl | $N(CH_3)$ | Ile | phenyl | 5-thiazolyl |
| 6-(1-butyl)-2-pyridinyl | $N(CH_3)$ | Ile | phenyl | 5-thiazolyl |
| 2-(1-butyl)-4-thiazolyl | O | Ile | phenyl | 5-thiazolyl |
| 2-(1-butyl)-4-oxazolyl | O | Ile | phenyl | 5-thiazolyl |
| 6-(1-butyl)-2-pyridinyl | O | Ile | phenyl | 5-thiazolyl |
| 2-(1-butyl)-4-thiazolyl | $N(CH_3)$ | Val | phenyl | 5-oxazolyl |

-continued

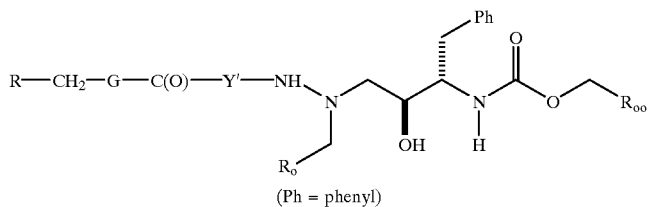

(Ph = phenyl)

| R | G | Y' | $R_o$ | $R_{oo}$ |
|---|---|---|---|---|
| 2-(1-butyl)-4-oxazolyl | N(CH₃) | Val | phenyl | 5-oxazolyl |
| 6-(1-butyl)-2-pyridinyl | N(CH₃) | Val | phenyl | 5-oxazolyl |
| 2-(1-butyl)-4-thiazolyl | O | Val | phenyl | 5-oxazolyl |
| 2-(1-butyl)-4-oxazolyl | O | Val | phenyl | 5-oxazolyl |
| 6-(1-butyl)-2-pyridinyl | O | Val | phenyl | 5-oxazolyl |
| 2-(1-butyl)-4-thiazolyl | N(CH₃) | Ala | phenyl | 5-oxazolyl |
| 2-(1-butyl)-4-oxazolyl | N(CH₃) | Ala | phenyl | 5-oxazolyl |
| 6-(1-butyl)-2-pyridinyl | N(CH₃) | Ala | phenyl | 5-oxazolyl |
| 2-(1-butyl)-4-thiazolyl | O | Ala | phenyl | 5-oxazolyl |
| 2-(1-butyl)-4-oxazolyl | O | Ala | phenyl | 5-oxazolyl |
| 6-(1-butyl)-2-pyridinyl | O | Ala | phenyl | 5-oxazolyl |
| 2-(1-butyl)-4-thiazolyl | N(CH₃) | Ile | phenyl | 5-oxazolyl |
| 2-(1-butyl)-4-oxazolyl | N(CH₃) | Ile | phenyl | 5-oxazolyl |
| 6-(1-butyl)-2-pyridinyl | N(CH₃) | Ile | phenyl | 5-oxazolyl |
| 2-(1-butyl)-4-thiazolyl | O | Ile | phenyl | 5-oxazolyl |
| 2-(1-butyl)-4-oxazolyl | O | Ile | phenyl | 5-oxazolyl |
| 6-(1-butyl)-2-pyridinyl | O | Ile | phenyl | 5-oxazolyl |
| 2-(1-butyl)-4-thiazolyl | N(CH₃) | Val | phenyl | 5-isoxazolyl |
| 2-(1-butyl)-4-oxazolyl | N(CH₃) | Val | phenyl | 5-isoxazolyl |
| 6-(1-butyl)-2-pyridinyl | N(CH₃) | Val | phenyl | 5-isoxazolyl |
| 2-(1-butyl)-4-thiazolyl | O | Val | phenyl | 5-isoxazolyl |
| 2-(1-butyl)-4-oxazolyl | O | Val | phenyl | 5-isoxazolyl |
| 6-(1-butyl)-2-pyridinyl | O | Val | phenyl | 5-isoxazolyl |
| 2-(1-butyl)-4-thiazolyl | N(CH₃) | Ala | phenyl | 5-isoxazolyl |
| 2-(1-butyl)-4-oxazolyl | N(CH₃) | Ala | phenyl | 5-isoxazolyl |
| 6-(1-butyl)-2-pyridinyl | N(CH₃) | Ala | phenyl | 5-isoxazolyl |
| 2-(1-butyl)-4-thiazolyl | O | Ala | phenyl | 5-isoxazolyl |
| 2-(1-butyl)-4-oxazolyl | O | Ala | phenyl | 5-isoxazolyl |
| 6-(1-butyl)-2-pyridinyl | O | Ala | phenyl | 5-isoxazolyl |
| 2-(1-butyl)-4-thiazolyl | N(CH₃) | Ile | phenyl | 5-isoxazolyl |
| 2-(1-butyl)-4-oxazolyl | N(CH₃) | Ile | phenyl | 5-isoxazolyl |
| 6-(1-butyl)-2-pyridinyl | N(CH₃) | Ile | phenyl | 5-isoxazolyl |
| 2-(1-butyl)-4-thiazolyl | O | Ile | phenyl | 5-isoxazolyl |
| 2-(1-butyl)-4-oxazolyl | O | Ile | phenyl | 5-isoxazolyl |
| 6-(1-butyl)-2-pyridinyl | O | Ile | phenyl | 5-isoxazolyl |
| 2-(1-butyl)-4-thiazolyl | O | Ile | 4-fluorophenyl | 5-thiazolyl |
| 2-(1-butyl)-4-oxazolyl | O | Ile | 4-fluorophenyl | 5-thiazolyl |
| 6-(1-buiyl)-2-pyridinyl | O | Ile | 4-fluorophenyl | 5-thiazolyl |
| 2-(1-butyl)-4-thiazolyl | O | Ile | 5-oxazolyl | 5-thiazolyl |
| 2-(1-butyl)-4-oxazolyl | O | Ile | 5-oxazolyl | 5-thiazolyl |
| 6-(1-butyl)-2-pyridinyl | O | Ile | 5-oxazolyl | 5-thiazolyl |
| 2-(1-butyl)-4-thiazolyl | O | Ile | 5-isoxazolyl | 5-thiazolyl |
| 2-(1-butyl)-4-oxazolyl | O | Ile | 5-isoxazolyl | 5-thiazolyl |
| 6-(1-butyl)-2-pyridinyl | O | Ile | 5-isoxazolyl | 5-thiazolyl |
| 2-(1-butyl)-4-thiazolyl | O | Ile | 5-thiazolyl | 5-thiazolyl |
| 2-(1-butyl)-4-oxazolyl | O | Ile | 5-thiazolyl | 5-thiazolyl |
| 6-(1-butyl)-2-pyridinyl | O | Ile | 5-thiazolyl | 5-thiazolyl |
| 2-(1-butyl)-4-thiazolyl | O | Ile | 5-oxazolyl | phenyl |
| 2-(1-butyl)-4-oxazolyl | O | Ile | 5-oxazolyl | phenyl |
| 6-(1-butyl)-2-pyridinyl | O | Ile | 5-oxazolyl | phenyl |
| 2-(1-butyl)-4-thiazolyl | O | Ile | 5-isoxazolyl | phenyl |
| 2-(1-butyl)-4-oxazolyl | O | Ile | 5-isoxazolyl | phenyl |
| 6-(1-butyl)-2-pyridinyl | O | Ile | 5-isoxazolyl | phenyl |
| 2-(1-butyl)-4-thiazolyl | O | Ile | 5-thiazolyl | phenyl |
| 2-(1-butyl)-4-oxazolyl | O | Ile | 5-thiazolyl | phenyl |
| 6-(1-butyl)-2-pyridinyl | O | Ile | 5-thiazolyl | phenyl |
| 2-(2-butyl)-4-thiazolyl | N(CH₃) | Val | phenyl | 5-thiazolyl |
| 2-(2-butyl)-4-oxazolyl | N(CH₃) | Val | phenyl | 5-thiazolyl |
| 6-(2-butyl)-2-pyridinyl | N(CH₃) | Val | phenyl | 5-thiazolyl |
| 2-(2-butyl)-4-thiazolyl | O | Val | phenyl | 5-thiazolyl |
| 2-(2-butyl)-4-oxazolyl | O | Val | phenyl | 5-thiazolyl |
| 6-(2-butyl)-2-pyridinyl | O | Val | phenyl | 5-thiazolyl |
| 2-(2-butyl)-4-thiazolyl | N(CH₃) | Ala | phenyl | 5-thiazolyl |
| 2-(2-butyl)-4-oxazolyl | N(CH₃) | Ala | phenyl | 5-thiazolyl |
| 6-(2-butyl)-2-pyridinyl | N(CH₃) | Ala | phenyl | 5-thiazolyl |
| 2-(2-butyl)-4-thiazolyl | O | Ala | phenyl | 5-thiazolyl |
| 2-(2-butyl)-4-oxazolyl | O | Ala | phenyl | 5-thiazolyl |

-continued

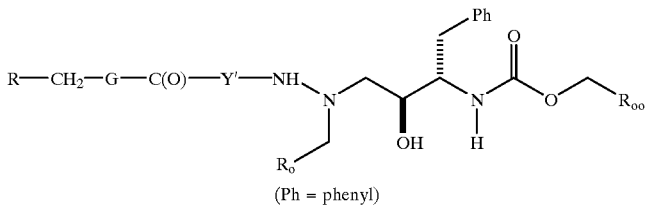

(Ph = phenyl)

| R | G | Y' | $R_o$ | $R_{oo}$ |
|---|---|---|---|---|
| 6-(2-butyl)-2-pyridinyl | O | Ala | phenyl | 5-thiazolyl |
| 2-(2-butyl)-4-thiazolyl | N(CH$_3$) | Ile | phenyl | 5-thiazolyl |
| 2-(2-butyl)-4-oxazolyl | N(CH$_3$) | Ile | phenyl | 5-thiazolyl |
| 6-(2-butyl)-2-pyridinyl | N(CH$_3$) | Ile | phenyl | 5-thiazolyl |
| 2-(2-butyl)-4-thiazolyl | O | Ile | phenyl | 5-thiazolyl |
| 2-(2-butyl)-4-oxazolyl | O | Ile | phenyl | 5-thiazolyl |
| 6-(2-butyl)-2-pyridinyl | O | Ile | phenyl | 5-thiazolyl |
| 2-(2-butyl)-4-thiazolyl | N(CH$_3$) | Val | phenyl | 5-oxazolyl |
| 2-(2-butyl)-4-oxazolyl | N(CH$_3$) | Val | phenyl | 5-oxazolyl |
| 6-(2-butyl)-2-pyridinyl | N(CH$_3$) | Val | phenyl | 5-oxazolyl |
| 2-(2-butyl)-4-thiazolyl | O | Val | phenyl | 5-oxazolyl |
| 2-(2-butyl)-4-oxazolyl | O | Val | phenyl | 5-oxazolyl |
| 6-(2-butyl)-2-pyildinyl | O | Val | phenyl | 5-oxazolyl |
| 2-(2-butyl)-4-thiazolyl | N(CH$_3$) | Ala | phenyl | 5-oxazolyl |
| 2-(2-butyl)-4-oxazolyl | N(CH$_3$) | Ala | phenyl | 5-oxazolyl |
| 6-(2-butyl)-2-pyridinyl | N(CH$_3$) | Ala | phenyl | 5-oxazolyl |
| 2-(2-butyl)-4-thiazolyl | O | Ala | phenyl | 5-oxazolyl |
| 2-(2-butyl)-4-oxazolyl | O | Ala | phenyl | 5-oxazolyl |
| 6-(2-butyl)-2-pyridinyl | O | Ala | phenyl | 5-oxazolyl |
| 2-(2-butyl)-4-thiazolyl | N(CH$_3$) | Ile | phenyl | 5-oxazolyl |
| 2-(2-butyl)-4-oxazolyl | N(CH$_3$) | Ile | phenyl | 5-oxazolyl |
| 6-(2-butyl)-2-pyridinyl | N(CH$_3$) | Ile | phenyl | 5-oxazolyl |
| 2-(2-butyl)-4-thiazolyl | O | Ile | phenyl | 5-oxazolyl |
| 2-(2-butyl)-4-oxazolyl | O | Ile | phenyl | 5-oxazolyl |
| 6-(2-butyl)-2-pyridinyl | O | Ile | phenyl | 5-oxazolyl |
| 2-(2-butyl)-4-thiazolyl | N(CH$_3$) | Val | phenyl | 5-isoxazolyl |
| 2-(2-butyl)-4-oxazolyl | N(CH$_3$) | Val | phenyl | 5-isoxazolyl |
| 6-(2-butyl)-2-pyridinyl | N(CH$_3$) | Val | phenyl | 5-isoxazolyl |
| 2-(2-butyl)-4-thiazolyl | O | Val | phenyl | 5-isoxazolyl |
| 2-(2-butyl)-4-oxazolyl | O | Val | phenyl | 5-isoxazolyl |
| 6-(2-butyl)-2-pyridinyl | O | Val | phenyl | 5-isoxazolyl |
| 2-(2-butyl)-4-thiazolyl | N(CH$_3$) | Ala | phenyl | 5-isoxazolyl |
| 2-(2-butyl)-4-oxazolyl | N(CH$_3$) | Ala | phenyl | 5-isoxazolyl |
| 6-(2-butyl)-2-pyridinyl | N(CH$_3$) | Ala | phenyl | 5-isoxazolyl |
| 2-(2-butyl)-4-thiazolyl | O | Ala | phenyl | 5-isoxazolyl |
| 2-(2-butyl)-4-oxazolyl | O | Ala | phenyl | 5-isoxazolyl |
| 6-(2-butyl)-2-pyridinyl | O | Ala | phenyl | 5-isoxazolyl |
| 2-(2-butyl)-4-thiazolyl | N(CH$_3$) | Ile | phenyl | 5-isoxazolyl |
| 2-(2-butyl)-4-oxazolyl | N(CH$_3$) | Ile | phenyl | 5-isoxazolyl |
| 6-(2-butyl)-2-pyridinyl | N(CH$_3$) | Ile | phenyl | 5-isoxazolyl |
| 2-(2-butyl)-4-thiazolyl | O | Ile | phenyl | 5-isoxazolyl |
| 2-(2-butyl)-4-oxazolyl | O | Ile | phenyl | 5-isoxazolyl |
| 6-(2-butyl)-2-pyridinyl | O | Ile | phenyl | 5-isoxazolyl |
| 2-(2-butyl)-4-thiazolyl | O | Ile | 4-fluorophenyl | 5-thiazolyl |
| 2-(2-butyl)-4-oxazolyl | O | Ile | 4-fluorophenyl | 5-thiazolyl |
| 6-(2-butyl)-2-pyridinyl | O | Ile | 4-fluorophenyl | 5-thiazolyl |
| 2-(2-butyl)-4-thiazolyl | O | Ile | 5-oxazolyl | 5-thiazolyl |
| 2-(2-butyl)-4-oxazolyl | O | Ile | 5-oxazolyl | 5-thiazolyl |
| 6-(2-butyl)-2-pyridinyl | O | Ile | 5-oxazolyl | 5-thiazolyl |
| 2-(2-butyl)-4-thiazolyl | O | Ile | 5-isoxazolyl | 5-thiazolyl |
| 2-(2-butyl)-4-oxazolyl | O | Ile | 5-isoxazolyl | 5-thiazolyl |
| 6-(2-butyl)-2-pyridinyl | O | Ile | 5-isoxazolyl | 5-thiazolyl |
| 2-(2-butyl)-4-thiazolyl | O | Ile | 5-thiazolyl | 5-thiazolyl |
| 2-(2-butyl)-4-oxazolyl | O | Ile | 5-thiazolyl | 5-thiazolyl |
| 6-(2-butyl)-2-pyridinyl | O | Ile | 5-thiazolyl | 5-thiazolyl |
| 2-(2-butyl)-4-thiazolyl | O | Ile | 5-oxazolyl | phenyl |
| 2-(2-butyl)-4-oxazolyl | O | Ile | 5-oxazolyl | phenyl |
| 6-(2-butyl)-2-pyridinyl | O | Ile | 5-oxazolyl | phenyl |
| 2-(2-butyl)-4-thiazolyl | O | Ile | 5-isoxazolyl | phenyl |
| 2-(2-butyl)-4-oxazolyl | O | Ile | 5-isoxazolyl | phenyl |
| 6-(2-butyl)-2-pyridinyl | O | Ile | 5-isoxazolyl | phenyl |
| 2-(2-butyl)-4-thiazolyl | O | Ile | 5-thiazolyl | phenyl |
| 2-(2-butyl)-4-oxazolyl | O | Ile | 5-thiazolyl | phenyl |
| 6-(2-butyl)-2-pyridinyl | O | Ile | 5-thiazolyl | phenyl |
| 4-thiazolyl | N(CH$_3$) | Val | 3-furanyl | 5-thiazolyl |
| 2-isopropyl-4-thiazolyl | N(CH$_3$) | Val | 3-furanyl | 5-thiazolyl |
| 2-methyl-4-thiazolyl | N(CH$_3$) | Val | 3-furanyl | 5-thiazolyl |

-continued

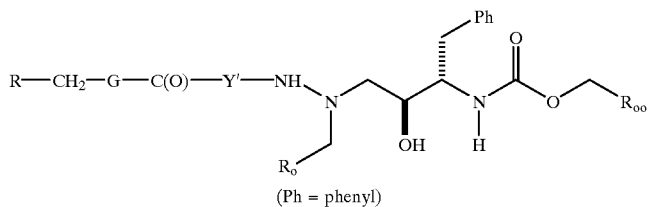

(Ph = phenyl)

| R | G | Y' | $R_o$ | $R_{oo}$ |
|---|---|---|---|---|
| 2-(1,1-dimethyl)ethyl-4-thiazolyl | N(CH$_3$) | Val | 3-furanyl | 5-thiazolyl |
| 2-cyclobutyl-4-thiazolyl | N(CH$_3$) | Val | 3-furanyl | 5-thiazolyl |
| 2-cyclopropyl-4-thiazolyl | N(CH$_3$) | Val | 3-furanyl | 5-thiazolyl |
| 2-ethyl-4-thiazolyl | N(CH$_3$) | Val | 3-furanyl | 5-thiazolyl |
| 2-(2-propenyl)-4-thiazolyl | N(CH$_3$) | Val | 3-furanyl | 5-thiazolyl |
| 2-(N,N-dimethylamino)-4-thiazolyl | N(CH$_3$) | Val | 3-furanyl | 5-thiazolyl |
| 2-(1-pyrrolidinyl)-4-thiazolyl | N(CH$_3$) | Val | 3-furanyl | 5-thiazolyl |
| 2-(1-propyl)-4-thiazolyl | N(CH$_3$) | Val | 3-furanyl | 5-thiazolyl |
| 2-(2-methyl)propyl-4-thiazolyl | N(CH$_3$) | Val | 3-furanyl | 5-thiazolyl |
| 4-oxazolyl | N(CH$_3$) | Val | 3-furanyl | 5-thiazolyl |
| 2-isopropyl-4-oxazolyl | N(CH$_3$) | Val | 3-furanyl | 5-thiazolyl |
| 2-methyl-4-oxazolyl | N(CH$_3$) | Val | 3-furanyl | 5-thiazolyl |
| 2-(1,1-dimethyl)ethyl-4-oxazolyl | N(CH$_3$) | Val | 3-furanyl | 5-thiazolyl |
| 2-cyclobutyl-4-oxazolyl | N(CH$_3$) | Val | 3-furanyl | 5-thiazolyl |
| 2-cyclopropyl-4-oxazolyl | N(CH$_3$) | Val | 3-furanyl | 5-thiazolyl |
| 2-ethyl-4-oxazolyl | N(CH$_3$) | Val | 3-furanyl | 5-thiazolyl |
| 2-(2-propenyl)-4-oxazolyl | N(CH$_3$) | Val | 3-furanyl | 5-thiazolyl |
| 2-(N,N-dimethylamino)-4-oxazolyl | N(CH$_3$) | Val | 3-furanyl | 5-thiazolyl |
| 2-(1-pyrrolidinyl)-4-oxazolyl | N(CH$_3$) | Val | 3-furanyl | 5-thiazolyl |
| 2-(1-propyl)-4-oxazolyl | N(CH$_3$) | Val | 3-furanyl | 5-thiazolyl |
| 2-(2-methyl)propyl-4-oxazolyl | N(CH$_3$) | Val | 3-furanyl | 5-thiazolyl |
| 2-pyridinyl | N(CH$_3$) | Val | 3-furanyl | 5-thiazolyl |
| 6-isopropyl-2-pyridinyl | N(CH$_3$) | Val | 3-furanyl | 5-thiazolyl |
| 6-methyl-2-pyridinyl | N(CH$_3$) | Val | 3-furanyl | 5-thiazolyl |
| 6-(1,1-dimethyl)ethyl-2-pyridinyl | N(CH$_3$) | Val | 3-furanyl | 5-thiazolyl |
| 6-cyclobutyl-2-pyridinyl | N(CH$_3$) | Val | 3-furanyl | 5-thiazolyl |
| 6-cyclopropyl-2-pyridinyl | N(CH$_3$) | Val | 3-furanyl | 5-thiazolyl |
| 6-ethyl-2-pyridinyl | N(CH$_3$) | Val | 3-furanyl | 5-thiazolyl |
| 6-(2-propenyl)-2-pyridinyl | N(CH$_3$) | Val | 3-furanyl | 5-thiazolyl |
| 6-propyl-2-pyridinyl | N(CH$_3$) | Val | 3-furanyl | 5-thiazolyl |
| 6-(2-methyl)propyl-2-pyridinyl | N(CH$_3$) | Val | 3-furanyl | 5-thiazolyl |
| 2-(1-butyl)-4-thiazolyl | O | Ile | 3-furanyl | 5-thiazolyl |
| 2-(1-butyl)-4-oxazolyl | O | Ile | 3-furanyl | 5-thiazolyl |
| 6-(1-butyl)-2-pyridinyl | O | Ile | 3-furanyl | 5-thiazolyl |
| 2-(2-butyl)-4-thiazolyl | O | Ile | 3-furanyl | 5-thiazolyl |
| 2-(2-butyl)-4-oxazolyl | O | Ile | 3-furanyl | 5-thiazolyl |
| 6-(2-butyl)-2-pyridinyl | O | Ile | 3-furanyl | 5-thiazolyl |
| 4-thiazolyl | N(CH$_3$) | Val | 2-furanyl | 5-thiazolyl |
| 2-isopropyl-4-thiazolyl | N(CH$_3$) | Val | 2-furanyl | 5-thiazolyl |
| 2-methyl-4-thiazolyl | N(CH$_3$) | Val | 2-furanyl | 5-thiazolyl |
| 2-(1,1-dimethyl)ethyl-4-thiazolyl | N(CH$_3$) | Val | 2-furanyl | 5-thiazolyl |
| 2-cyclobutyl-4-thiazolyl | N(CH$_3$) | Val | 2-furanyl | 5-thiazolyl |
| 2-cyclopropyl-4-thiazolyl | N(CH$_3$) | Val | 2-furanyl | 5-thiazolyl |
| 2-ethyl-4-thiazolyl | N(CH$_3$) | Val | 2-furanyl | 5-thiazolyl |
| 2-(2-propenyl)-4-thiazolyl | N(CH$_3$) | Val | 2-furanyl | 5-thiazolyl |
| 2-(N,N-dimethylamino)-4-thiazolyl | N(CH$_3$) | Val | 2-furanyl | 5-thiazolyl |
| 2-(1-pyrrolidinyl)-4-thiazolyl | N(CH$_3$) | Val | 2-furanyl | 5-thiazolyl |
| 2-(1-propyl)-4-thiazolyl | N(CH$_3$) | Val | 2-furanyl | 5-thiazolyl |
| 2-(2-methyl)propyl-4-thiazolyl | N(CH$_3$) | Val | 2-furanyl | 5-thiazolyl |
| 4-oxazolyl | N(CH$_3$) | Val | 2-furanyl | 5-thiazolyl |
| 2-isopropyl-4-oxazolyl | N(CH$_3$) | Val | 2-furanyl | 5-thiazolyl |
| 2-methyl-4-oxazolyl | N(CH$_3$) | Val | 2-furanyl | 5-thiazolyl |
| 2-(1,1-dimethyl)ethyl-4-oxazolyl | N(CH$_3$) | Val | 2-furanyl | 5-thiazolyl |
| 2-cyclobutyl-4-oxazolyl | N(CH$_3$) | Val | 2-furanyl | 5-thiazolyl |
| 2-cyclopropyl-4-oxazolyl | N(CH$_3$) | Val | 2-furanyl | 5-thiazolyl |
| 2-ethyl-4-oxazolyl | N(CH$_3$) | Val | 2-furanyl | 5-thiazolyl |
| 2-(2-propenyl)-4-oxazolyl | N(CH$_3$) | Val | 2-furanyl | 5-thiazolyl |
| 2-(N,N-dimethylamino)-4-oxazolyl | N(CH$_3$) | Val | 2-furanyl | 5-thiazolyl |
| 2-(1-pyrrolidinyl)-4-oxazolyl | N(CH$_3$) | Val | 2-furanyl | 5-thiazolyl |
| 2-(1-propyl)-4-oxazolyl | N(CH$_3$) | Val | 2-turanyl | 5-thiazolyl |
| 2-(2-methyl)propyl-4-oxazolyl | N(CH$_3$) | Val | 2-furanyl | 5-thiazolyl |
| 2-pyridinyl | N(CH$_3$) | Val | 2-furanyl | 5-thiazolyl |
| 6-isopropyl-2-pyridinyl | N(CH$_3$) | Val | 2-furanyl | 5-thiazolyl |
| 6-methyl-2-pyridinyl | N(CH$_3$) | Val | 2-furanyl | 5-thiazolyl |
| 6-(1,1-dimethyl)ethyl-2-pyridinyl | N(CH$_3$) | Val | 2-furanyl | 5-thiazolyl |
| 6-cyclobutyl-2-pyridinyl | N(CH$_3$) | Val | 2-furanyl | 5-thiazolyl |
| 6-cyclopropyl-2-pyridinyl | N(CH$_3$) | Val | 2-furanyl | 5-thiazolyl |

-continued

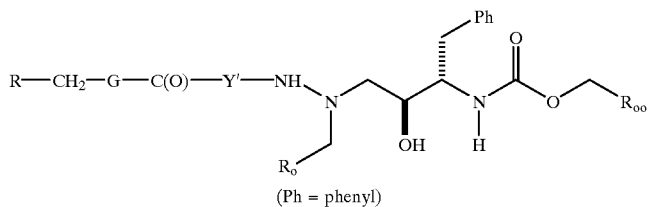

(Ph = phenyl)

| R | G | Y' | $R_o$ | $R_{oo}$ |
|---|---|---|---|---|
| 6-ethyl-2-pyridinyl | N(CH$_3$) | Val | 2-furanyl | 5-thiazolyl |
| 6-(2-propenyl)-2-pyridinyl | N(CH$_3$) | Val | 2-furanyl | 5-thiazolyl |
| 6-propyl-2-pyridinyl | N(CH$_3$) | Val | 2-furanyl | 5-thiazolyl |
| 6-(2-methyl)propyl-2-pyridinyl | N(CH$_3$) | Val | 2-furanyl | 5-thiazolyl |
| 2-(1-butyl)-4-thiazolyl | O | Ile | 2-furanyl | 5-thiazolyl |
| 2-(1-butyl)-4-oxazolyl | O | Ile | 2-furanyl | 5-thiazolyl |
| 6-(1-butyl)-2-pyridinyl | O | Ile | 2-furanyl | 5-thiazolyl |
| 2-(2-butyl)-4-thiazolyl | O | Ile | 2-furanyl | 5-thiazolyl |
| 2-(2-butyl)-4-oxazolyl | O | Ile | 2-furanyl | 5-thiazolyl |
| 6-(2-butyl)-2-pyridinyl | O | Ile | 2-furanyl | 5-thiazolyl |
| 4-thiazolyl | N(CH$_3$) | Val | 4-pyridinyl | 5-thiazolyl |
| 2-isopropyl-4-thiazolyl | N(CH$_3$) | Val | 4-pyridinyl | 5-thiazolyl |
| 2-methyl-4-thiazolyl | N(CH$_3$) | Val | 4-pyridinyl | 5-thiazolyl |
| 2-(1,1-dimethyl)ethyl-4-thiazolyl | N(CH$_3$) | Val | 4-pyridinyl | 5-thiazolyl |
| 2-cyclobutyl-4-thiazolyl | N(CH$_3$) | Val | 4-pyridinyl | 5-thiazolyl |
| 2-cyclopropyl-4-thiazolyl | N(CH$_3$) | Val | 4-pyridinyl | 5-thiazolyl |
| 2-ethyl-4-thiazolyl | N(CH$_3$) | Val | 4-pyridinyl | 5-thiazolyl |
| 2-(2-propenyl)-4-thiazolyl | N(CH$_3$) | Val | 4-pyridinyl | 5-thiazolyl |
| 2-(N,N-dimethylamino)-4-thiazolyl | N(CH$_3$) | Val | 4-pyridinyl | 5-thiazolyl |
| 2-(1-pyrrolidinyl)-4-thiazolyl | N(CH$_3$) | Val | 4-pyridinyl | 5-thiazolyl |
| 2-(1-propyl)-4-thiazolyl | N(CH$_3$) | Val | 4-pyridinyl | 5-thiazolyl |
| 2-(2-methyl)propyl-4-thiazolyl | N(CH$_3$) | Val | 4-pyridinyl | 5-thiazolyl |
| 4-oxazolyl | N(CH$_3$) | Val | 4-pyridinyl | 5-thiazolyl |
| 2-isopropyl-4-oxazolyl | N(CH$_3$) | Val | 4-pyridinyl | 5-thiazolyl |
| 2-methyl-4-oxazolyl | N(CH$_3$) | Val | 4-pyridinyl | 5-thiazolyl |
| 2-(1,1-dimethyl)ethyl-4-oxazolyl | N(CH$_3$) | Val | 4-pyridinyl | 5-thiazolyl |
| 2-cyclobutyl-4-oxazolyl | N(CH$_3$) | Val | 4-pyridinyl | 5-thiazolyl |
| 2-cyclopropyl-4-oxazolyl | N(CH$_3$) | Val | 4-pyridinyl | 5-thiazolyl |
| 2-ethyl-4-oxazolyl | N(CH$_3$) | Val | 4-pyridinyl | 5-thiazolyl |
| 2-(2-propenyl)-4-oxazolyl | N(CH$_3$) | Val | 4-pyridinyl | 5-thiazolyl |
| 2-(N,N-dimethylamino)-4-oxazolyl | N(CH$_3$) | Val | 4-pyridinyl | 5-thiazolyl |
| 2-(1-pyrrolidinyl)-4-oxazolyl | N(CH$_3$) | Val | 4-pyridinyl | 5-thiazolyl |
| 2-(1-propyl)-4-oxazolyl | N(CH$_3$) | Val | 4-pyridinyl | 5-thiazolyl |
| 2-(2-methyl)propyl-4-oxazolyl | N(CH$_3$) | Val | 4-pyridinyl | 5-thiazolyl |
| 2-pyridinyl | N(CH$_3$) | Val | 4-pyridinyl | 5-thiazolyl |
| 6-isopropyl-2-pyridinyl | N(CH$_3$) | Val | 4-pyridinyl | 5-thiazolyl |
| 6-methyl-2-pyridinyl | N(CH$_3$) | Val | 4-pyridinyl | 5-thiazolyl |
| 6-(1,1-dimethyl)ethyl-2-pyridinyl | N(CH$_3$) | Val | 4-pyridinyl | 5-thiazolyl |
| 6-cyclobutyl-2-pyridinyl | N(CH$_3$) | Val | 4-pyridinyl | 5-thiazolyl |
| 6-cyclopropyl-2-pyridinyl | N(CH$_3$) | Val | 4-pyridinyl | 5-thiazolyl |
| 6-ethyl-2-pyridinyl | N(CH$_3$) | Val | 4-pyridinyl | 5-thiazolyl |
| 6-(2-propenyl)-2-pyridinyl | N(CH$_3$) | Val | 4-pyridinyl | 5-thiazolyl |
| 6-propyl-2-pyridinyl | N(CH$_3$) | Val | 4-pyridinyl | 5-thiazolyl |
| 6-(2-methyl)propyl-2-pyridinyl | N(CH$_3$) | Val | 4-pyridinyl | 5-thiazolyl |
| 2-(1-butyl)-4-thiazolyl | O | Ile | 4-pyridinyl | 5-thiazolyl |
| 2-(1-butyl)-4-oxazolyl | O | Ile | 4-pyridinyl | 5-thiazolyl |
| 6-(1-butyl)-2-pyridinyl | O | Ile | 4-pyridinyl | 5-thiazolyl |
| 2-(2-butyl)-4-thiazolyl | O | Ile | 4-pyridinyl | 5-thiazolyl |
| 2-(2-butyl)-4-oxazolyl | O | Ile | 4-pyridinyl | 5-thiazolyl |
| 6-(2-butyl)-2-pyridinyl | O | Ile | 4-pyridinyl | 5-thiazolyl |
| 4-thiazolyl | N(CH$_3$) | Val | 4-methoxyphenyl | 5-thiazolyl |
| 2-isopropyl-4-thiazolyl | N(CH$_3$) | Val | 4-methoxyphenyl | 5-thiazolyl |
| 2-methyl-4-thiazolyl | N(CH$_3$) | Val | 4-methoxyphenyl | 5-thiazolyl |
| 2-(1,1-dimethyl)ethyl-4-thiazolyl | N(CH$_3$) | Val | 4-methoxyphenyl | 5-thiazolyl |
| 2-cyclobutyl-4-thiazolyl | N(CH$_3$) | Val | 4-methoxyphenyl | 5-thiazolyl |
| 2-cyclopropyl-4-thiazolyl | N(CH$_3$) | Val | 4-methoxyphenyl | 5-thiazolyl |
| 2-ethyl-4-thiazolyl | N(CH$_3$) | Val | 4-methoxyphenyl | 5-thiazolyl |
| 2-(2-propenyl)-4-thiazolyl | N(CH$_3$) | Val | 4-methoxyphenyl | 5-thiazolyl |
| 2-(N,N-dimethylamino)-4-thiazolyl | N(CH$_3$) | Val | 4-methoxyphenyl | 5-thiazolyl |
| 2-(1-pyrrolidinyl)-4-ihiazolyl | N(CH$_3$) | Val | 4-methoxyphenyl | 5-thiazolyl |
| 2-(1-propyl)-4-thiazolyl | N(CH$_3$) | Val | 4-methoxyphenyl | 5-thiazolyl |
| 2-(2-methyl)propyl-4-thiazolyl | N(CH$_3$) | Val | 4-methoxyphenyl | 5-thiazolyl |
| 4-oxazolyl | N(CH$_3$) | Val | 4-methoxyphenyl | 5-thiazolyl |
| 2-isopropyl-4-oxazolyl | N(CH$_3$) | Val | 4-methoxyphenyl | 5-thiazolyl |
| 2-methyl-4-oxazolyl | N(CH$_3$) | Val | 4-methoxyphenyl | 5-thiazolyl |
| 2-(1,1-dimethyl)ethyl-4-oxazolyl | N(CH$_3$) | Val | 4-methoxyphenyl | 5-thiazolyl |
| 2-cyclobutyl-4-oxazolyl | N(CH$_3$) | Val | 4-methoxyphenyl | 5-thiazolyl |

-continued

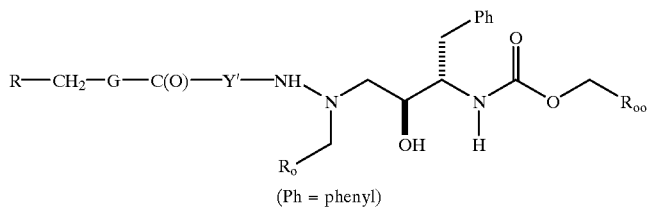

(Ph = phenyl)

| R | G | Y' | $R_o$ | $R_{oo}$ |
|---|---|---|---|---|
| 2-cyclopropyl-4-oxazolyl | $N(CH_3)$ | Val | 4-methoxyphenyl | 5-thiazolyl |
| 2-ethyl-4-oxazolyl | $N(CH_3)$ | Val | 4-methoxyphenyl | 5-thiazolyl |
| 2-(2-propenyl)-4-oxazolyl | $N(CH_3)$ | Val | 4-methoxyphenyl | 5-thiazolyl |
| 2-(N,N-dimethylamino)-4-oxazolyl | $N(CH_3)$ | Val | 4-methoxyphenyl | 5-thiazolyl |
| 2-(1-pyrrolidinyl)-4-oxazolyl | $N(CH_3)$ | Val | 4-methoxyphenyl | 5-thiazolyl |
| 2-(1-propyl)-4-oxazolyl | $N(CH_3)$ | Val | 4-methoxyphenyl | 5-thiazolyl |
| 2-(2-methyl)propyl-4-oxazolyl | $N(CH_3)$ | Val | 4-methoxyphenyl | 5-thiazolyl |
| 2-pyridinyl | $N(CH_3)$ | Val | 4-methoxyphenyl | 5-thiazolyl |
| 6-isopropyl-2-pyridinyl | $N(CH_3)$ | Val | 4-methoxyphenyl | 5-thiazolyl |
| 6-methyl-2-pyridinyl | $N(CH_3)$ | Val | 4-methoxyphenyl | 5-thiazolyl |
| 6-(1,1-dimethyl)ethyl-2-pyridinyl | $N(CH_3)$ | Val | 4-methoxyphenyl | 5-thiazolyl |
| 6-cyclobutyl-2-pyridinyl | $N(CH_3)$ | Val | 4-methoxyphenyl | 5-thiazolyl |
| 6-cyclopropyl-2-pyridinyl | $N(CH_3)$ | Val | 4-methoxyphenyl | 5-thiazolyl |
| 6-ethyl-2-pyridinyl | $N(CH_3)$ | Val | 4-methoxyphenyl | 5-thiazolyl |
| 6-(2-propenyl)-2-pyridinyl | $N(CH_3)$ | Val | 4-methoxyphenyl | 5-thiazolyl |
| 6-propyl-2-pyridinyl | $N(CH_3)$ | Val | 4-methoxyphenyl | 5-thiazolyl |
| 6-(2-methyl)propyl-2-pyridinyl | $N(CH_3)$ | Val | 4-methpxphenyl | 5-thiazolyl |
| 2-(1-butyl)-4-thiazolyl | O | Ile | 4-methoxyphenyl | 5-thiazolyl |
| 2-(1-butyl)-4-oxazolyl | O | Ile | 4-methoxyphenyl | 5-thiazolyl |
| 6-(1-butyl)-2-pyridinyl | O | Ile | 4-methoxyphenyl | 5-thiazolyl |
| 2-(2-butyl)-4-thiazolyl | O | Ile | 4-methoxyphenyl | 5-thiazolyl |
| 2-(2-butyl)-4-oxazolyl | O | Ile | 4-methoxyphenyl | 5-thiazolyl |
| 6-(2-butyl)-2-pyridinyl | O | Ile | 4-methoxyphenyl | 5-thiazolyl |
| 4-thiazolyl | $N(CH_3)$ | Val | 4-tetrahydropyranyl | 5-thiazolyl |
| 2-isopropyl-4-thiazolyl | $N(CH_3)$ | Val | 4-tetrahydropyranyl | 5-thiazolyl |
| 2-methyl-4-thiazolyl | $N(CH_3)$ | Val | 4-tetrahydropyranyl | 5-thiazolyl |
| 2-(1,1-dimethyl)ethyl-4-thiazolyl | $N(CH_3)$ | Val | 4-tetrahydropyranyl | 5-thiazolyl |
| 2-cyclobutyl-4-thiazolyl | $N(CH_3)$ | Val | 4-tetrahydropyranyl | 5-thiazolyl |
| 2-cyclopropyl-4-thiazolyl | $N(CH_3)$ | Val | 4-tetrahydropyranyl | 5-thiazolyl |
| 2-ethyl-4-thiazolyl | $N(CH_3)$ | Val | 4-tetrahydropyranyl | 5-thiazolyl |
| 2-(2-propenyl)-4-thiazolyl | $N(CH_3)$ | Val | 4-tetrahydropyranyl | 5-thiazolyl |
| 2-(N,N-dimethylamino)-4-thiazolyl | $N(CH_3)$ | Val | 4-tetrahydropyranyl | 5-thiazolyl |
| 2-(1-pyrrolidinyl)-4-thiazolyl | $N(CH_3)$ | Val | 4-tetrahydropyranyl | 5-thiazolyl |
| 2-(1-propyl)-4-thiazolyl | $N(CH_3)$ | Val | 4-tetrahydropyranyl | 5-thiazolyl |
| 2-(2-methyl)propyl-4-thiazolyl | $N(CH_3)$ | Val | 4-tetrahydropyranyl | 5-thiazolyl |
| 4-oxazolyl | $N(CH_3)$ | Val | 4-tetrahydropyranyl | 5-thiazolyl |
| 2-isopropyl-4-oxazolyl | $N(CH_3)$ | Val | 4-tetrahydropyranyl | 5-thiazolyl |
| 2-methyl-4-oxazolyl | $N(CH_3)$ | Val | 4-tetrahydropyranyl | 5-thiazolyl |
| 2-(1,1-dimethyl)ethyl-4-oxazolyl | $N(CH_3)$ | Val | 4-tetrahydropyranyl | 5-thiazolyl |
| 2-cyclobutyl-4-oxazolyl | $N(CH_3)$ | Val | 4-tetrahydropyranyl | 5-thiazolyl |
| 2-cyclopropyl-4-oxazolyl | $N(CH_3)$ | Val | 4-tetrahydropyranyl | 5-thiazolyl |
| 2-ethyl-4-oxazolyl | $N(CH_3)$ | Val | 4-tetrahydropyranyl | 5-thiazolyl |
| 2-(2-propenyl)-4-oxazolyl | $N(CH_3)$ | Val | 4-tetrahydropyranyl | 5-thiazolyl |
| 2-(N,N-dimethylamino)-4-oxazolyl | $N(CH_3)$ | Val | 4-tetrahydropyranyl | 5-thiazolyl |
| 2-(1-pyrrolidinyl)-4-oxazolyl | $N(CH_3)$ | Val | 4-tetrahydropyranyl | 5-thiazolyl |
| 2-(1-propyl)-4-oxazolyl | $N(CH_3)$ | Val | 4-tetrahydropyranyl | 5-thiazolyl |
| 2-(2-methyl)propyl-4-oxazolyl | $N(CH_3)$ | Val | 4-tetrahydropyranyl | 5-thiazolyl |
| 2-pyridinyl | $N(CH_3)$ | Val | 4-tetrahydropyranyl | 5-thiazolyl |
| 6-isopropyl-2-pyridinyl | $N(CH_3)$ | Val | 4-tetrahydropyranyl | 5-thiazolyl |
| 6-methyl-2-pyridinyl | $N(CH_3)$ | Val | 4-tetrahydropyranyl | 5-thiazolyl |
| 6-(1,1-dimethyl)ethyl-2-pyridinyl | $N(CH_3)$ | Val | 4-tetrahydropyranyl | 5-thiazolyl |
| 6-cyclobutyl-2-pyridinyl | $N(CH_3)$ | Val | 4-tetrahydropyranyl | 5-thiazolyl |
| 6-cyclopropyl-2-pyridinyl | $N(CH_3)$ | Val | 4-tetrahydropyranyl | 5-thiazolyl |
| 6-ethyl-2-pyridinyl | $N(CH_3)$ | Val | 4-tetrahydropyranyl | 5-thiazolyl |
| 6-(2-propenyl)-2-pyridinyl | $N(CH_3)$ | Val | 4-tetrahydropyranyl | 5-thiazolyl |
| 6-propyl-2-pyridinyl | $N(CH_3)$ | Val | 4-tetrahydropyranyl | 5-thiazolyl |
| 6-(2-methyl)propyl-2-pyridinyl | $N(CH_3)$ | Val | 4-tetrahydropyranyl | 5-thiazolyl |
| 2-(1-butyl)-4-thiazolyl | O | Ile | 4-tetrahydropyranyl | 5-thiazolyl |
| 2-(1-butyl)-4-oxazolyl | O | Ile | 4-tetrahydropyranyl | 5-thiazolyl |
| 6-(1-butyl)-2-pyridinyl | O | Ile | 4-tetrahydropyranyl | 5-thiazolyl |
| 2-(2-butyl)-4-thiazolyl | O | Ile | 4-tetrahydropyranyl | 5-thiazolyl |
| 2-(2-butyl)-4-oxazolyl | O | Ile | 4-tetrahydropyranyl | 5-thiazolyl |
| 6-(2-butyl)-2-pyridinyl | O | Ile | 4-tetrahydropyranyl | 5-thiazolyl |

Fluorogenic Assay for Screening Inhibitors of HIV Protease

The inhibitory potency of the compounds of the invention can be determined by the following method.

A compound of the invention is dissolved in DMSO and a small aliquot further diluted with DMSO to 100 times the final concentration desired for testing. The reaction is carried out in a 6×50 mm tube in a total volume of 300 microliters. The final concentrations of the components in the reaction buffer are: 125 mM sodium acetate, 1 M sodium chloride, 5 mM dithiothreitol, 0.5 mg/ml bovine serum albumin, 1.3 μM fluorogenic substrate, 2% (v/v) dimethylsulfoxide, pH 4.5. After addition of inhibitor, the reaction mixture is placed in the fluorometer cell holder and incubated at 30° C. for several minutes. The reaction is initiated by the addition of a small aliquot of cold HIV protease. The fluorescence intensity (excitation 340 nM, emmision 490 nM) is recorded as a function of time. The reaction rate is determined for the first six to eight minutes. The observed rate is directly proportional to the moles of substrate cleaved per unit time. The percent inhibition is 100×(1−(rate in presence of inhibitor)/(rate in absence of inhibitor)).

Fluorogenic substrate: Dabcyl-Ser-Gln-Asn-Tyr-Pro-Ile-Val-Gln-EDANS wherein DABCYL=4-(4-dimethylamino-phenyl)azobenzoic acid and EDANS=5-((2-aminoethyl)amino)-naphthalene-1-sulfonic acid.

Table 1 shows the inhibitory potencies of compounds of the invention against HIV-1 protease.

TABLE 1

| Compound of Example | Percent Inhibition | Inhibitor Concentration (nanomolar) |
| --- | --- | --- |
| 1F | 50 | 5.1 |
| 2E | 50 | 0.5 |
| 4B | 50 | 3.9 |
| 5B | 60 | 0.5 |
| 6H | 73 | 0.5 |
| 7F | 50 | 4.4 |
| 8 | 77 | 0.5 |
| 9F | 61 | 0.5 |
| 10 | 50 | 0.5 |
| 11 | 69 | 0.5 |
| 12 | 78 | 0.5 |
| 13D | 71 | 0.5 |
| 14B | 50 | 10 |
| 15 | 44 | 0.5 |
| 16 | 50 | 0.5 |
| 17B | 50 | 12 |
| 47 | 50 | 2.1 |
| 48 | 66 | 0.5 |
| 49E | 75 | 0.5 |
| 50 | 73 | 0.5 |
| 51 | 50 | 0.5 |
| 52 | 50 | 7.5 |
| 53 | 57 | 0.5 |
| 54B | 56 | 0.5 |
| 55C | 50 | 7.4 |
| 56B | 49 | 0.5 |
| 57C | 50 | 9.9 |
| 58 | 50 | 18 |

Antiviral Activity

The anti-HIV activity of the compounds of the invention can be determined in MT4 cells according to the procedure of Kempf, et. al. (*Antimicrob. Agents Chemother*. 1991, 35, 2209). The $IC_{50}$ is the concentration of compound that gives 50% inhibition of the cytopathic effect of HIV. The $LC_{50}$ is the concentration of compound at which 50% of the cells remain viable.

Table 2 shows the inhibitory potencies of compounds of the invention against $HIV-1_{3B}$ in MT4 cells.

TABLE 2

| Compound of Example | $IC_{50}$ (micromolar) | $LC_{50}$ (micromolar) |
| --- | --- | --- |
| 1F | 36 | >100 |
| 2E | 0.78–1.231 | 56 |
| 5B | 0.15–0.26 | >100 |
| 7F | 6.5–18.2 | 44 |
| 8 | 0.10–0.11 | 17 |
| 9F | 0.46–1.0 | 19 |
| 10 | 0.83–1.1 | 19 |
| 11 | 0.23 | 18 |
| 12 | 0.10–0.105 | 53 |
| 13D | 0.102–0.15 | 58 |
| 15 | 0.44–0.6 | >100 |
| 16 | 0.20–0.27 | 57 |
| 48 | 0.088–0.114 | |
| 49 | 0.029–0.032 | |
| 50 | 0.016–0.031 | |
| 51D | 0.209–0.274 | |
| 53 | 0.055 | |
| 54B | 0.037–0.067 | |

The compounds of the present invention can be used in the form of salts derived from inorganic or organic acids. These salts include but are not limited to the following: acetate, adipate, alginate, citrate, aspartate, benzoate, benzenesulfonate bisulfate, butyrate, camphorate, camphorsulfonate, digluconate, cyclopentanepropionate, dodecylsulfate, ethanesulfonate, glucoheptanonate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

Preferred salts of the compounds of the invention include hydrochloride, methanesulfonate, sulfonate, phosphonate and isethionate.

The compounds of the present invention can also be used in the form of esters. Examples of such esters include a hydroxyl-substituted compound of formula A, B or C which has been acylated with a blocked or unblocked amino acid residue, a phosphate function, a hemisuccinate residue, an acyl residue of the formula R*C(O)— or R*C(S)— wherein R* is hydrogen, loweralkyl, haloalkyl, alkoxy, thioalkoxy, alkoxyalkyl, thioalkoxyalkyl or haloalkoxy, or an acyl residue of the formula $R_a$—C($R_b$)($R_d$)—C(O)— or $R_a$—C($R_b$)($R_d$)—C(S)— wherein $R_b$ and $R_d$ are independently selected from hydrogen or loweralkyl and $R_a$ is —N($R_e$)($R_f$), $OR_e$ or —$SR_e$ wherein $R_e$ and $R_f$ are independently selected from hydrogen, loweralkyl and haloalkyl, or an amino-acyl residue of the formula $R_{180}NH(CH_2)_2NHCH_2C(O)$— or $R_{180}NH(CH_2)_2OCH_2C(O)$— wherein $R_{180}$ is hydrogen, loweralkyl, arylalkyl, cycloalkylalkyl, alkanoyl, benzoyl or an a-amino acyl group. The amino acid esters of particular interest are glycine and lysine; however, other amino acid residues can also be used, including those wherein the amino acyl group is —$C(O)CH_2NR_{200}R_{201}$ wherein $R_{200}$ and $R_{201}$ are independently selected from hydrogen and loweralkyl or the group —$NR_{200}R_{201}$ forms a nitrogen containing heterocyclic ring. These esters serve as pro-drugs of the compounds of the present invention and serve to increase the solubility of these substances in the gastrointestinal tract. These esters also serve to increase solubility for intravenous administration of the compounds. Other prodrugs include a hydroxyl-substituted compound of formula A, B or C wherein the hydroxyl group is functionalized with a substituent of the formula —$CH(R_g)OC(O)R_{181}$ or —$CH(R_g)OC(S)R_{181}$ wherein $R_{181}$ is loweralkyl, haloalkyl, alkoxy, thioalkoxy or haloalkoxy and $R_g$ is hydrogen, loweralkyl, haloalkyl, alkoxycarbonyl, aminocarbonyl, alkylaminocarbonyl or dialkylaminocarbonyl. Such prodrugs can be prepared according to the procedure of Schreiber (Tetrahedron Lett. 1983, 24, 2363) by ozonolysis of the corresponding methallyl ether in methanol followed by treatment with acetic anhydride.

The prodrugs of this invention are metabolized in vivo to provide the hydroxyl-substituted compound of formula A, B or C. The preparation of the prodrug esters is carried out by reacting a hydroxyl-substituted compound of formula A, B or C with an activated amino acyl, phosphoryl, hemisuccinyl or acyl derivative as defined above. The resulting product is then deprotected to provide the desired pro-drug ester. Prodrugs of the invention can also be prepared by alkylation of the hydroxyl group with (haloalkyl)esters, transacetalization with bis-(alkanoyl)acetals or condensation of the hydroxyl group with an activated aldehyde followed by acylation of the intermediate hemiacetal.

The compounds of the invention are useful for inhibiting retroviral protease, in particular HIV protease, in vitro or in vivo (especially in mammals and in particular in humans). The compounds of the present invention are also useful for the inhibition of retroviruses in vivo, especially human immunodeficiency virus (HIV). The compounds of the present invention are also useful for the treatment or prophylaxis of diseases caused by retroviruses, especially acquired immune deficiency syndrome or an HIV infection in a human or other mammal.

Total daily dose administered to a human or other mammal host in single or divided doses may be in amounts, for example, from 0.001 to 300 mg/kg body weight daily and more usually 0.1 to 50 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capabale of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natureal and synthetic.

Methods to form liposomes are known in the art. See, for example, Prescott, Ed., *Methods in Cell Biology*, Volume XIV, Academic Press, New York, N.Y. (1976), p. 33 et seq.

While the compounds of the invention can be administered as the sole active pharmaceutical agent, they can also be used in combination with one or more immunomodulators, antiviral agents, other antiinfective agents or vaccines. Other antiviral agents to be administered in combination with a compound of the present invention include AL-721, beta interferon, polymannoacetate, reverse transcriptase inhibitors (for example, dideoxycytidine (DDC), dideoxyinosine (DDI), BCH-189, AzdU, carbovir, DDA, D4C, D4T, DP-AZT, FLT (fluorothymidine), BCH-189, 5-halo-3'-thia-dideoxycytidine, PMEA, zidovudine (AZT) and the like), non-nucleoside reverse transcriptase inhibitors (for example, R82193, L-697,661, BI-RG-587 (nevirapine), retroviral protease inhibitors (for example, HIV protease inhibitors such as Ro 31-8959, SC-52151, KNI-227, KNI-272 and the like), HEPT compounds, L,697, 639, R82150, U-87201 E and the like), TAT inhibitors (for example, RO-24-7429 and the like), trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, BW882C87, foscarnet, BW256U87, BW348U87, L-693,989, BV ara-U, CMV triclonal antibodies, FIAC, HOE-602, HPMPC, MSL-109, TI-23, trifluridine, vidarabine, famciclovir, penciclovir, acyclovir, ganciclovir, castanospermine, rCD4/CD4-IgG, CD4-PE40, butyl-DNJ, hypericin, oxamyristic acid, dextran sulfate and pentosan polysulfate. Immunomodulators that can be administered in combination with a compound of the present invention include bropirimine, Ampligen, anti-human alpha interferon antibody, colony stimulting factor, CL246,738, Imreg-1, Imreg-2, diethydithiocarbamate, interleukin-2, alpha-interferon, inosine pranobex, methionine enkephalin, muramyl-tripeptide, TP-5, erythropoietin, naltrexone, tumor necrosis facator, beta interferon, gamma interferon, interleukin-3, interleukin-4, autologous CD8+ infusion, alpha interferon immunoglobulin, IGF-1, anti-Leu-3A, autovaccination, biostimulation, extracorporeal photophoresis, FK-565, FK-506, G-CSF, GM-CSF, hyperthermia, isopinosine, IVIG, HIVIG, passive immunotherapy and polio vaccine hyperimmunization. Other anti-infective agents that can be administered in combination with a compound of the present invention include pentamidine isethionate. Any of a variety of HIV or AIDS vaccines (for example, gp120 (recombinant), Env 2–3 (gp120), HIVAC-1e (gp120), gp160 (recombinant), VaxSyn HIV-1 (gp160), Immuno-Ag (gp160), HGP-30, HIV-Immunogen, p24 (recombinant), VaxSyn HIV-1 (p24) can be used in combination with a compound of the present invention.

Other agents that can be used in combination with the compounds of this invention are ansamycin LM 427, apurinic acid, ABPP, AI-721, carrisyn, AS-101, avarol, azimexon, colchicine, compound Q, CS-85, N-acetyl cysteine, (2-oxothiazolidine-4-carboxylate), D-penicillamine, diphenylhydantoin, EL-10, erythropoieten, fusidic acid, glucan, HPA-23, human growth hormone, hydroxchloroquine, iscador, L-ofloxacin or other quinolone antibiotics, lentinan, lithium carbonate, MM-1, monolaurin, MTP-PE, naltrexone, neurotropin, ozone, PAI, panax ginseng, pentofylline, pentoxifylline, Peptide T, pine cone extract, polymannoacetate, reticulose, retrogen, ribavirin, ribozymes, RS-47, Sdc-28, silicotungstate, THA, thymic humoral factor, thymopentin, thymosin fraction 5, thymosin alpha one, thymostimulin, UA001, uridine, vitamin B12 and wobemugos.

Other agents that can be used in combination with the compounds of this invention are antifungals such as amphotericin B, clotrimazole, flucytosine, fluconazole, itraconazole, ketoconazole and nystatin and the like.

Other agents that can be used in combination with the compounds of this invention are antibacterials such as amikacin sulfate, azithromycin, ciprofloxacin, tosufloxacin, clarithromycin, clofazimine, ethambutol, isoniazid, pyrazinamide, rifabutin, rifampin, streptomycin and TLC G-65 and the like.

Other agents that can be used in combination with the compounds of this invention are anti-neoplastics such as alpha interferon, COMP (cyclophosphamide, vincristine, methotrexate and prednisone), etoposide, mBACOD (methotrexate, bleomycin, doxorubicin, cyclophosphamide, vincristine and dexamethasone), PRO-MACE/MOPP (prednisone, methotrexate (w/leucovi n rescue), doxorubicin, cyclophosphamide, etoposide/ mechlorethamine, vincristine, prednisone and procarbazine), vincristine, vinblastine, angioinhibins, pentosan polysulfate, platelet factor 4 and SP-PG and the like.

Other agents that can be used in combination with the compounds of this invention are drugs for treating neurological disease such as peptide T, ritalin, lithium, elavil, phenytoin, carbamazipine, mexitetine, heparin and cytosine arabinoside and the like.

Other agents that can be used in combination with the compounds of this invention are anti-protozoals such as albendazole, azithromycin, clarithromycin, clindamycin, corticosteroids, dapsone, DIMP, eflornithine, 566C80, fansidar, furazolidone, L,671,329, letrazuril, metronidazole, paromycin, pefloxacin, pentamidine, piritrexim, primaquine, pyrimethamine, somatostatin, spiramycin, sulfadiazine, trimethoprim, TMP/SMX, trimetrexate and WR 6026 and the like.

Among the preferred agents for treatment of HIV or AIDS in combination with the compounds of this invention are reverse transcriptase inhibitors.

It will be understood that agents which can be combined with the compounds of the present invention for the treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

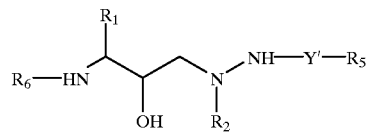

wherein $R_1$ and $R_2$ are independently selected from:
(i) hydrogen,
(ii) loweralkyl,
(iii) aryl,
(iv) thioalkoxyalkyl,
(v) (aryl)alkyl,
(vi) cycloalkyl,
(vii) cycloalkylalkyl,
(viii) hydroxyalkyl,
(ix) alkoxyalkyl,
(x) aryloxyalkyl,
(xi) haloalkyl,
(xii) carboxyalkyl,
(xiii) alkoxycarbonylalkyl, (xiv) aminoalkyl,
(xv) (N-protected)aminoalkyl,
(xvi) alkylaminoalkyl,
(xvii) ((N-protected)(alkyl)amino)alkyl,
(xviii) dialkylaminoalkyl,
(xix) guanidinoalkyl,
(xx) loweralkenyl,
(xxi) heterocyclic,
(xxii) (heterocyclic)alkyl),
(xxiii) arylthioalkyl,
(xxiv) arylsulfonylalkyl,
(xxv) (heterocyclic)thioalkyl,
(xxvi) (heterocyclic)sulfonylalkyl,
(xxvii) (heterocyclic)oxyalkyl,
(xxviii) arylalkoxyalkyl,
(xxix) arylthioalkoxyalkyl,
(xxx) arylalkylsulfonylalkyl,
(xxxi) (heterocyclic)alkoxyalkyl,
(xxxii) (heterocyclic)thioalkoxyalkyl,
(xxxiii) (heterocyclic)alkylsulfonylalkyl,
(xxxiv) cycloalkyloxyalkyl,
(xxxv) cycloalkylthioalkyl,
(xxxvi) cycloalkylsulfonylalkyl,
(xxxvii) cycloalkylalkoxyalkyl,
(xxxviii) cycloalkylthioalkoxyalkyl,
(xxxix) cycloalkylalkylsulfonylalkyl,
(xl) aminocarbonyl,
(xli) alkylaminocarbonyl,
(xlii) dialkylaminocarbonyl,
(xliii) aroylalkyl,
(xliv) (heterocyclic)carbonylalkyl,
(xlv) polyhydroxyalkyl,
(xlvi) aminocarbonylalkyl,
(xlvii) alkylaminocarbonylalkyl,
(xlviii) dialkylaminocarbonylalkyl,
(xlix) aryloxyalkyl and
(l) alkylsulfonylalkyl,
wherein heterocyclic is selected from pyridyl, thiazolyl, isothiazolyl, oxazolyl, isoxazolyl, furanyl, thienyl, tetrahydrofuranyl, tetrahydrothienyl and tetrahydro[2H] pyranyl and wherein the heterocyclic is unsubstituted or monosubstituted or disubstituted with substituents independently selected from hydroxy, halo, amino, alkylamino, dialkylamino, alkoxy, polyalkoxy, haloalkyl, cycloalkyl, cycloalkylalkyl, aryl, arylalkyl, —COOH, —SO$_3$H, loweralkenyl and loweralkyl;

Y' is

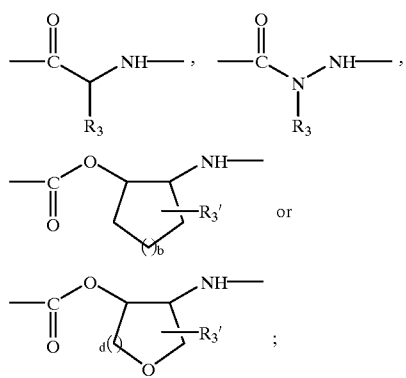

b is 0–3;
d is 1–2
R$_3$' is hydrogen or loweralkyl;

R$_3$ is selected from:
(i) hydrogen,
(ii) loweralkyl,
(iii) aryl,
(iv) thioalkoxyalkyl,
(v) (aryl)alkyl,
(vi) cycloalkyl,
(vii) cycloalkylalkyl,
(viii) hydroxyalkyl,
(ix) alkoxyalkyl,
(x) aryloxyalkyl,
(xi) haloalkyl,
(xii) carboxyalkyl,
(xiii) alkoxycarbonylalkyl,
(xiv) aminoalkyl,
(xv) (N-protected)arninoalkyl,
(xvi) alkylaminoalkyl,
(xvii) ((N-protected)(alkyl)arnino)alkyl,
(xviii) dialkylaninoalkyl,
(xix) guanidinoalkyl,
(xx) loweralkenyl,
(xxi) heterocyclic,
(xxii) (heterocyclic)alkyl,
(xxiii) aiylthioalkyl,
(xxiv) arylsulfonylalkyl,
(xxv) (heterocyclic)thioalkyl,
(xxvi) (heterocyclic)sulfonylalkyl,
(xxvii) (heterocyclic)oxyalkyl,
(xxviii) arylalkoxyalkyl,
(xxix) arylthioalkoxyalkyl,
(xxx) arylalkylsulfonylalkyl,
(xxxi) (heterocyclic)alkoxyalkyl,
(xxxii) (heterocyclic)thioalkoxyalkyl,
(xxxiii) (heterocyclic)alkylsulfonylalkyl,
(xxxiv) cycloalkyloxyalkyl,
(xxxv) cycloalkylthioalkyl,
(xxxvi) cycloalkylsulfonylalkyl,
(xxxvii) cycloalkylalkoxyalkyl,
(xxxviii) cycloalkylthioalkoxyalkyl,
(xxxix) cycloalkylalkylsulfonylalkyl,
(xl) amninocarbonyl,
(xli) alkylaminocarbonyl,
(xlii) dialkylaminocarbonyl,
(xliii) aroylalkyl,
(xliv) (heterocyclic)carbonylalkyl,
(xlv) polyhydroxyalkyl,
(xlvi) aminocarbonylalkyl,
(xlvii) alkylaminocarbonylalkyl,
(xlviii) dialkylaminocarbonylalkyl,
(xlix) aryloxyalkyl and
(l) alkylsulfonylalkyl,
wherein heterocyclic is selected from pyridyl, thiazolyl, isothiazolyl, oxazolyl, isoxazolyl, furanyl, thienyl, tetrahydrofuranyl, tetrahydrothienyl and tetrahydro[2H] pyranyl and wherein the heterocyclic is unsubstituted or monosubstituted or disubstituted with substituents independently selected from hydroxy, halo, amino, alkylamino, dialkylamino, alkoxy, polyalkoxy, haloalkyl, cycloalkyl, cycloalkylalkyl, aryl, arylalkyl, —COOH, —SO$_3$H, loweralkenyl and loweralkyl;
R$_5$ and R$_6$ are —C(T)—G—R$_7$ wherein at each occurrence T is independently selected from O and S; at each occurrence G is independently selected from —CH$_2$—, —O—, —S— and —N(R$_8$)— wherein at each occurrence R$_8$ is independently selected from hydrogen, loweralkyl and cycloalkyl; and at each occurrence R$_7$ is independently selected:

(i) heterocyclic and (ii) (heterocyclic)alkyl, wherein at each occurrence the heterocyclic is unsubstituted or monosubstituted or disubstituted with substituents independently selected from hydroxy, halo, amino, alkylamino, dialkylamino, alkoxy, polyalkoxy, haloalkyl, cycloalkyl, cycloalkylalkyl, aryl, arylalkyl, —COOH, —SO₃H, loweralkenyl and loweralkyl, with the proviso that at least one of R₇ is not oxazole or thiazole; or a pharmaceutically acceptable salt, ester or prodrug thereof.

2. The compound of claim 1 wherein $R_1$ and $R_2$ are independently selected from loweralkyl, cycloalkylalkyl, aryl, arylalkyl, heterocyclic and (heterocyclic)alkyl wherein heterocyclic is selected from pyridyl, thiazolyl, isothiazolyl, oxazolyl, isoxazolyl, furanyl, thienyl, tetrahydrofuranyl, tetrahydrothienyl and tetrahydro[2H]pyranyl and wherein the heterocyclic is unsubstituted or monosubstituted or disubstituted with substituents independently selected from hydroxy, halo, amino, alkylamino, dialkylamino, alkoxy, polyalkoxy, haloalkyl, cycloalkyl, cycbalkylalkyl, aryl, arylalkyl, —COOH, —SO₃H, loweralkenyl and loweralkyl; $R_3$ is loweralkyl; and $R_5$ and $R_6$ are —C(O)—G—R₇ wherein at each occurrence G is independently selected from —O—, —S— and —N(R₈)— wherein at each occurrence $R_8$ is independently selected from hydrogen, loweralkyl and cycloalkyl; and at each occurrence $R_7$ is independently selected from (heterocyclic)alkyl wherein at each occurrence the heterocyclic is unsubstituted or monosubstituted or disubstituted with substituents independently selected from hydroxy, halo, amino, alkylamino, dialkylamino, alkoxy, polyalkoxy, haloalkyl, cycloalkyl, cycloalkylalkyl, aryl, arylalkyl, —COOH, —SO₃H, loweralkenyl and loweralkyl.

3. A compound of the formula:

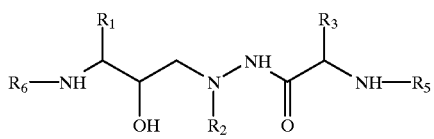

C wherein $R_1$ and $R_2$ are independently selected from:
(i) hydrogen,
(ii) loweralkyl,
(iii) aryl,
(iv) thioalkoxyalkyl,
(v) (aryl)alkyl,
(vi) cycloalkyl,
(vii) cycloalkylakyl,
(viii) hydroxyalkyl,
(ix) alkoxyalkyl,
(x) aryloxyalkyl,
(xi) haloalkyl,
(xii) carboxyalkyl,
(xiii) alkoxycarbonylalkyl,
(xiv) aminoalkyl,
(xv) (N-protected)aminoalkyl,
(xvi) akylaminoalkyl,
(xvii) ((N-protected)(alkyl)amino)alkyl,
(xviii) dialkylarninoakyl,
(xix) guanidinoalkyl,
(xx) loweralkenyl,
(xxi) heterocyclic,
(xxii) (heterocyclic)alkyl),
(xxiii) arylthioakyl,
(xxiv) arylsulfonylalkyl,
(xxv) (heterocyclic)thioalkyl,
(xxvi) (heterocyclic)sulfonylalkyl,
(xxvii) (heterocyclkc)oxyalkyl,
(xxviii) arylalkoxyalkyl,
(xxix) arylthioalkoxyalkyl,
(xxx) arylalkylsulonylalky,
(xxxi) (heterocyclic))alkoxyalkyl,
(xxxii) (heterocyclic)thioalkoxyalkyl,
(xxxiii) (heterocyclic)alkylsulfonylalkyl,
(xxxiv) cycloalkyloxyalkyl,
(xxxv) cycloalkyflthioalkyl,
(xxxvi) cycloalkylsufornylalkyl,
(xxxvii) cycloalkylalkoxyalkyl,
(xxxviii) cycloalkylthoalkoxyalkyl,
(xxxix) cycloalkylakylsugonyalakyl,
(Xl) aminocarbonyl,
(xli) alkylaminocarbonyl,
(xlii) dialkylarnnocarbonyl,
(xliii) aroylakyl,
(xliv) (heterocyclic)carbonylalkyl,
(xlv) polyhydroxyalkyl,
(xlvi) aminocarbonylalkyl,
(xlvii) alkylaminocarbonytalkyl,
(xlviii) dialkylaminocarbonylalkyl,
(xlix) aryloxyakyl and
(l) alkylsulfonylalkyl, wherein heterocyclic is selected from pyridyl, thiazolyl, isothiazolyl, oxazolyl, isoxazolyl, furanyl, thienyl, tetrahydrofuranyl, tetrahydrothienyl and tetrahydro[2H] pyranyl and wherein the heterocyclic is unsubstituted or monosubstituted or disubstituted with substituents independently selected from hydroxy, halo, amino, alkylamino, dialkylamino, alkoxy, polyalkoxy, haloalkyl, cycloalkyl, cycloalkylalkyl, aryl, arylalkyl, —COOH, —SO₃H, loweralkenyl and loweralkyl;

$R_3$ is selected from:
(i) hydrogen,
(ii) loweralkyl,
(iii) aryl,
(iv) thioalkoxyalkyl,
(v) (aryl)alkyl,
(vi) cycloalkyl,
(vii) cydoalkylalkyl,
(viii) hydroxyalkyl,
(ix) alkoxyalkyl,
(x) aryloxyalkyl,
(xi) haloalkyl,
(xii) carboxyalkyl,
(xiii) alkoxycarbonylalkyl,
(xiv) aminoalkyl,
(xv) (N-protected)aminoalkyl,
(xvi) alkylaminoakyl,
(xvii) ((N-protected)(alkyl)amino)alkyl,
(xviii) dialkylaminoalkyl,
(xix) guanidinoalkyl,
(xx) loweralkenyl,
(xxi) heterocyclic,
(xxii) (heterocyclic)alkyl),
(xxiii) arylthioalkyl,
(xxiv) arylsuffonylalky,
(xxv) (heterocyclic)thioalkyl,
(xxvi) (heterocyclic)sulfonylalkyl,
(xxvii) (heterocyclic)oxyalkyl,
(xxviii) arylalkoxyalkyl,
(xxix) arylthioalkoxyalkyl,
(xxx) arylakylsulfonylalkyl,
(xxxi) (heterocyclic))alkoxyalkyl, (xxxii) (heterocyclic)thioalkoxyalkyl,
(xxxiii) (heterocyclic)alkylsulfonylalkyl,
(xxxiv) cycloalkyboxyalkyi,
(xxxv) cycloalkylthioalkyl,
(xxxvi) cycloalkylsulfonylalkyl,
(xxxvii) cycloalkylalkoxyalkyl,
(xxxviii) cycloalkylthioalkoxyalkyl,
(xxxix) cycloalkylalkylsulfonylakyl,
(xl) aminocarbonyl,
(xli) alkylaminocarbonyl,
(xlii) dialkylaminocarbonyl,
(xliii) aroylalkyl,
(xliv) (heterocyclic)carbonylalkyl,
(xlv) polyhydroxyalkyl,
(xlvi) aminocarbonylalkyl,
(xlvii) alkylaminocarbonylalkyl,
(xlviii) dialkylaminocarbonylalkyl,
(xlix) aryloxyalkyl and
(l) alkylsulfonylalkyl,
wherein heterocyclic is selected from pyridyl, thiazolyl, isothiazolyl, oxazolyl, isoxazolyl, furanyl, thienyl, tetrahydrofuranyl, tetrahydrothienyl and tetrahydro[2]Hpyranyl and wherein the heterocyclic is unsubstituted or monosubsiftuted or disubstituted with substiuents independently selected from hydroxy, halo, amino, alkylamino, dialkylamino, alkoxy, polyalkoxy, haloalkyl, cycloalkyl, cycloalkylalkyl, aryl, arylalkyl, —COOH, —SO$_3$H, loweralkenyl and loweralkyl;

R$_5$ and R$_6$ are —C(T)—G—R$_7$ wherein at each occurrence T is independently selected from O and S; at each occurrence G is independently selected from —CH$_2$—, —O—, —S— and —N(R$_8$)— wherein at each occurrence R$_8$ is independently selected tram hydrogen, loweralkyl and cycloalkyl; and at each occurrence R$_7$ is independently selected from:
(i) heterocyclic and (ii) (heterocycyclic)alkyl;
and wherein at each occurrence the heterocyclic is unsubstiuted or monosubstituted or disubstituted with substituents independently selected from hydroxy, halo, amino, alkylamino, dialkylamino, alkoxy, polyalkoxy, haloalkyl, cycloalkyl, cycloalkylalkyl, aryl, arylaikyl, —COOH, —SO$_3$H, loweralkenyl and loweralkyl; or
a pharmaceutically acceptable salt, ester or prodrug thereof.

4. The compound of claim 3 wherein R$_1$ and R$_2$ are independently selected from loweralkyl, cycloalkylalayl, aryl, aryealkyl, heterocyclic and (hetermcyclic)alkyl wherein heterocyclic is selected from pyridyl, thiazolyl, isothiazolyl, oxazolyl, isoxazolyl, furanyl, thienyl, tetrahydrofuranyl, tetrahydrothienyl and tetrahydro[2H]pyranyl and wherein the heterocyclic is unsubstituted or monosubstituted or disubsttuted with substituents independently selected from hydroxy, halo, amino, alkylamino, dialkylamino, alkoxy, polyalkoxy, haloalkyl, cycloalkyl, cycloalkylalkyl, aryl, arylalkyl, —COOH, —SO$_3$H, loweralkenyl and loweralkyl; R$_3$ is selected from loweralkyl; and R$_5$ and R$_6$ are —C(O)—G—R$_7$ wherein at each occurrence G is independently selected from —O—, —S— and —N(R$_8$)— wherein at each occurrence R$_8$ is independently selected from hydrogen, loweralkyl and cycloalkyl; and at each occurrence R$_7$ is independently selected from (heterocyclic)alkyl wherein at each occurrence the heterocyclic is unsubstituted or monosubstituted or disubstituted with substituents independently selected from hydroxy, halo, amino, alkylamino, dialkylamino alkoxy, polyalkoxy, haloalkyl, cycloalkyl, cycloalkylalkyl, aryl, arylkyl, —COOH, —SO$_3$H, loweralkenyl and loweralkyl.

5. The compound of claim 4 wherein R$_1$ and R$_2$ are independently selected from arylalkyl and (heterocyclic)alkyl wherein heterocyclic is selected from pyridyl, thiazolyl, isothiazolyl, oxazolyl, isoxazolyl, furanyl, thienyl, tetrahydrofuranyl, tetrahydrothienyl and tetrahydro[2H]pyranyl and wherein the heterocyclic is unsubstituted or monosubstituted or disubstituted with substituents independently selected from hydroxy, halo, amino, alkylamino, dialkylamino, alkoxy, polyalkoxy, haloalkyl, cycloalkyl, cycloalkylalkyl, aryl, arylalkyl, —COOH, —SO$_3$H, loweralkenyl and lowerakyl; R$_5$ is —C(O)—G—R$_7$ wherein G is selected from —O— and —N(CH$_3$)— and R$_7$ is selected from pyridylmethyl, substituted pyrldylmethyl wherein the pyridine ring is substituted with loweralkyl, oxazolylmethyl, substituted oxazolylmethyl wherein the oxazole ring is substituted with loweralkyl, isoxazolylmethyl, substituted isoxazolylmethyl wherein the isoxazole ring is substituted with loweralkyl, thiazolylmethyl, substituted thiazolylmethyl wherein the thiazole ring is substituted with loweralkyl, isothiazolylmethyl and substituted isothiazolylmethyl wherein the isothiazole ring is substituted with loweralkyl;

and R$_6$ is —C(O)—G—R$_7$ wherein G is —O— and R$_7$ is selected from pyridylmethyl, oxazolylmethyl, isoxazolylmethyl, thiazolylmethyl and isothiazolylmethyl.

6. A compound selected from the group consisting of:

5S-N-((5-Isoxazolyl)methoxy)carbonylamino-2-N-((N-methyl-N-((2-isopropyl-4-oxazolyl)methyl)amino)carbonyl)-L-valinylamino-4S-hydroxy-1,6-diphenyl-2-azahexane;

5S-(((5-Thiazolyl)methoxy)carbanyl)amino-2-N-((3-Isopropyl-5-isoxazolyl)methoxycarbonyl)valinylamino-4S-hydroxy-1,6-diphenyl-2-azahexane;

5S-(((5-Thiazolyl)methoxy)carbonyl)amino-2-N-((3-Isopropyl-5-isothiazolyl)methoxycarbonyl)valinylamino-4S-hydroxy-1,6-diphenyl-2-azahexane; and 5S-(((S-Isothiazolyl)methoxy)carbonyl)amino-2-N-((N-Methyl-N-((2-isopropyl-4-thiazolyl)methyl)amino)carbonyl)-L-valinylamino4S-hydroxy-1,6-diphenyl-2-azahexane;

or a pharnaceutically acceptable salt, ester or prodrug thereof.

7. A compound of the formula:

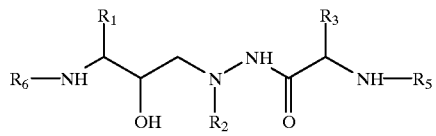

wherein R$_1$ and R$_2$ are independently selected from:
(i) loweralkyl,
(i) aryl,
(ii) (aryl)alkyl,
(iv) cycloalkylakyl,
(v) heterocyclic and
(vi) (heterocyclic)alkyl,
wherein heterocyclic is selected from pyridyl, thiazolyl, isothiazolyl, oxazolyl, isoxazolyl, furanyl, thienyl, tetrahydrofuranyl, tetrahydrothienyl and tetrahydro[2H]pyranyl and wherein the heterocyclic is unsubstituted or monosubstituted or disubstituted with substituents independently selected from hydroxy, halo, amino, alkylamino, dialkylamino, alkoxy, polyalkoxy, haloalkyl, cycloalkyl, cycloalkylalkyl, aryl, arylalkyl, —COOH, —SO₃H, loweralkenyl and lowerakyl;

R₃ is loweralkyl; and

R₅ and R₆ are —C(O)—G—R₇ wherein at each occurrence G is independently selected from —O—, —S— and —N(R₈)— wherein at each occurrence R₈ is independently selected from hydrogen, loweralkyl and cycloalkyl; and at each occurrence R₇ is independently selected from (heterocyclic)alkyl wherein at each occurrence the heterocyclic is independently unsubstituted or monosubstltuted or disubstituted with substituents independently selected from hydroxy, halo, amino, alkylamino, dialkylamino, alkoxy, polyalkoxy, haloalkyl, cycloalkyl, cycloalkylalkyl, aryl, arylaikyl, —COOH, —SO₃H, loweralkenyl and loweraikyl; or a pharmaceutically acceptable salt, ester or prodrug thereof.

8. A compound of the formula:

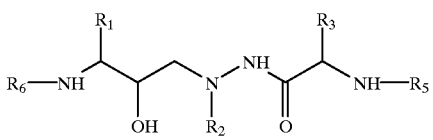

wherein R₁ and R₂ are independently selected from:
(i) cyclohexylmethyl,
(ii) benzyl,
(iii) substituted benzyl wherein the phenyl ring of the benzyl group is substituted with loweralkyl, halo, alkoxy, amino, alkylamino or dialkylamino, and
(vi) (heterocyclic)alkyl, wherein heterocyclic is selected from pyridyl, thiazolyl, isothiazolyl, oxazolyl, isoxazolyl, furanyl, thlenyl, tetrahydrofuranyl, tetrahydrothienyl and tetrahydro[2H]pyranyl and wherein the heterocyclic is unsubstituted or monosubstituted or disubstituted with substituents independently selected from hydroxy, halo, amino, alkylamino, dialkylamino, alkoxy, polyalkoxy, haloalkyl, cycloalkyl, cycloalkylalkyl, aryl, arylalkyl, —COOH, —SO₃H, loweralkenyl and loweralkyl;

R₃ is loweralkyl; and

R₅ is —C(O)—G—R₇ wherein G is —O— or —N(CH₃)— and R₇ is (heterocyclic)methyl or (loweralkyl-substituted heterocyclic)methyl; and R₆ is —C(O)—O—CH₂-heterocyclic;

or a pharmaceutically acceptable salt, ester or prodrug thereof.

9. The compound of claim 8 wherein R₁ is benzyl and R₂ is benzyl or (heterocyclic)methyl, wherein heterocyclic is selected from pyridyl, thiazolyl, isothiazolyl, oxazolyl, isoxazolyl, furanyl, thienyl, tetrahydrofuranyl, tetrahydrothienyl and tetrahydro[2H]pyranyl and wherein the heterocyclic is unsubstituted or monosubstituted or disubstituted with substituents independently selected from hydroxy, halo, amino, alkylamino, dialkylamino, alkoxy, polyalkoxy, haloalkyl, cycloalkyl, cycloalkylalkyl, aryl, arylalkyl, —COOH, —SO₃H, loweralkenyl and loweralkyl; and R₃ is methyl, isopropyl or sec-butyl.

10. A compound of the formula:

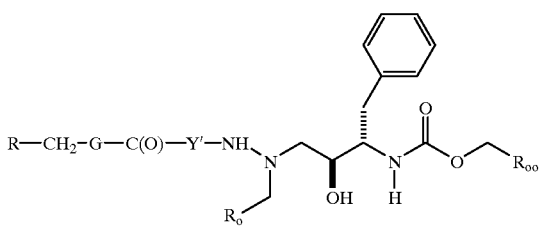

wherein

G is —N(CH₃)—, Y' is valinyl, R₀ is phenyl, R₀₀ is 5-thiazolyl and R is 2-pyridinyl;

G is —N(CH₃)—, Y' is valinyl, R₀ is phenyl, R₀₀ is 5-thiazolyl and R is 6-isopropyl-2-pyridinyl;

G is —N(CH₃)—, Y' is valinyl, R₀ is phenyl, R₀₀ is 5-thiazolyl and R is 6-methyl-2-pyridinyl;

G is —N(CH₃)—, Y' is valinyl, R₀ is phenyl, R₀₀ is 5-thiazolyl and R is 6-(1,1-dimcthyl)ediyl-2-pyridinyl;

G is —N(CH₃)—, Y' is valinyl, Rois phenyl, R₀₀ is 5-thiazolyl and R is 6-cyclobutyl-2-pyridinyl;

G is —N(CH₃)—, Y' is valinyl, R₀ is phenyl, R₀₀ is 5-thiazolyl and R is 6-cyclopropyl-2-pyridinyl;

G is —N(CH₃)—, Y' is valinyl, R₀ is phenyl, R₀₀ is 5-thiazolyl and R is 6-ethyl-2-pyridinyl;

G is —N(CH₃)—, Y' is valinyl, R₀ is phenyl, R₀₀ is 5-thiazolyl and R is 6-(2-propenyl)-2-pyridinyl;

G is —N(CH₃)—, Y' is valinyl, R₀ is phenyl, R₀₀ is 5-thiazolyl and R is 6-propyl-2-pyridinyl;

G is —N(CH₃)—, Y' is valinyl, R₀ is phenyl, R₀₀ is 5-thiazolyl and R is 6-(2-methyl)propyl-2-pyridinyl;

G is —O—, Y' is valinyl, R₀ is phenyl, R₀₀ is 5-thiazolyl and R is 2-pyridinyl;

G is —O—, Y' is valinyl, R₀ is phenyl, R₀₀ is 5-thiazolyl and R is 6-isopropyl-2-pyridinyl;

G is —O—, Y' is valinyl, R₀ is phenyl, R₀₀ is 5-thiazolyl and R is 6-methyl-2-pyrdinyl;

G is —O—, Y' is valinyl, R₀ is phenyl, R₀₀ is 5-thiazolyl and R is 6-(1,1-dimethyi)ethyl-2-pyridinyl;

G is —O—, Y' is valinyl, R₀ is phenyl, R₀₀ is 5-thiazolyl and R is 6-cyclobutyl-2-pyridinyl;

G is —O—, Y' is valinyl, R₀ is phenyl, R₀₀ is 5-thiazolyl and R is 6-cyclopropyl-2-pyridinyl;

G is —O—, Y is valinyl, R₀ is phenyl, R₀₀ is 5-thiazolyl and R is 6-ethyl-2-pyridinyl;

G is —O—, Y' is valinyl, R₀ is phenyl, R₀₀ is 5-thiazolyl and R is 6(2-propenyl)-2-pyridinyl;

G is —O—, Y' is valinyl, R₀ is phenyl, R₀₀ is 5-thiazolyl and R is 6-propyl-2-pyridinyl;

G is —O—, Y' is valinyl, R₀ is phenyl, R₀₀ is 5-thiazolyl and R is 6-(2-methyl)propyl-2-pyridinyl;

G is —N(CH₃)—, Y' is alaninyl, R₀ is phenyl, R₀₀ is 5-thiazolyl and R is 2-pyridinyl;

G is —N(CH₃)—, Y' is alaninyl, R₀ is phenyl, R₀₀ is 5-thiazolyl and R is 6-isopropyl-2-pyridinyl;

G is —N(CH₃)—, Y' is alaninyl, R₀ is phenyl, R₀₀ is 5-thiazolyl and R is 6methyl-2-pyridinyl;

G is —N(CH₃)—, Y' is alaninyl, R₀ is phenyl, R₀₀ is 5-thiazolyl and R is 6-(1,1-dimethyl)ethyl-2-pyridinyl;

G is —N(CH₃)—, Y' is alaninyl, R₀ is phenyl, R₀₀ is 5-thiazolyl and R is 6cyclobutyl-2-pyridinyl;

G is —N(CH$_3$)—, Y' is alaninyl, R$_o$ is phenyl, R$_{oo}$ is 5-thiazolyl and R is 6-cyclopropyl-2-pyridinyl;

G is —N(CH$_3$)—, Y' is alaninyl, R$_o$ is phenyl, R$_{oo}$ is 5-thiazolyl and R is 6ethyl-2-pyridinyl;

G is —N(CH$_3$)—, Y' is alaninyl, R$_o$ is phenyl, R$_{oo}$ is 5-thiazolyl and R is 6-(2-propenyl)-2-pyridinyl;

G is —N(CH$_3$)—, Y' is alaninyl, R$_o$ is phenyl, R$_{oo}$ is 5-thiazolyl and R is 6propyl-2-pyridinyl;

G is —N(CH$_3$)—, Y' is alaninyl, R$_o$ is phenyl, R$_{oo}$ is 5-thiazolyl and R is 6-(2-methyl)propyl-2-pyridinyl;

G is —O—, Y' is alaninyl, R$_o$ is phenyl, R$_{oo}$ is 5-thiazolyl and R is 2-pyridinyl;

G is —O—, Y' is alaninyl, R$_o$ is phenyl, R$_{oo}$ is 5-thiazolyl and R is 6-isopropyl-2-pyridinyl;

G is —O—, Y' is alaninyl, R$_o$ is phenyl, R$_{oo}$ is 5-thiazolyl and R is 6-methyl-2-pyridinyl;

G is —O—, Y' is alaninyl, R$_o$ is phenyl, R$_{oo}$ is 5-thiazolyl and R is 6-(1,1-dimethyl)ethyl-2-pyridinyl;

G is —O—, Y' is alaninyl, R$_o$ is phenyl, R$_{oo}$ is 5-thiazolyl and R is 6-cyclobutyl-2-pyridinyl;

G is —O—, Y' is alaninyl, R$_o$ is phenyl, R$_{oo}$ is 5-thiazolyl and R is 6-cyclopropyl-2-pyridinyl;

G is —O—, Y' is alaninyl, R$_o$ is phenyl, R$_{oo}$ is 5-thiazolyl and R is 6-ethyl-2-pyridinyl;

G is —O—, Y' is alaninyl, R$_o$ is phenyl, R$_{oo}$ is 5-thiazolyl and R is 6-(2-propenyl)-2-pyridinyl:

G is —O—, Y' is alaninyl, R$_o$ is phenyl, R$_{oo}$ is 5-thiazolyl and R is 6propyl-2-pyridinyl;

G is —O—, Y' is alaninyl, R$_o$ is phenyl, R$_{oo}$ is 5-thiazolyl and R is 6(2-methyl)propyl-2-pyridinyl;

G is —N(CH$_3$)—, Y' is isoleucinyl, R$_o$ is phenyl, R$_{oo}$ is 5-thiazolyl and R is 2-pyridinyl;

G is —N(CH$_3$)—, Y' is isoleucinyl, R$_o$ is phenyl, R$_{oo}$ is 5-thiazolyl and R is 6-isopropyl-2-pyridinyl;

G is —N(CH$_3$)—, Y' is isoleucinyl, R$_o$ is phenyl, R$_{oo}$ is 5-thiazolyl and R is 6-methyl-2-pyridinyl;

G is —N(CH$_3$)—, Y' is isoleucinyl, R$_o$ is phenyl, R$_{oo}$ is 5-thiazolyl and R is 6-(1,1-dimethyl)ethyl-2-pyridinyl;

G is —N(CH$_3$)—, Y' is isolcucinyl, R$_o$ is phenyl, R$_{oo}$ is 5-thiazolyl and R is 6-cyclobutyl-2-pyridinyl;

G is —N(CH$_3$)—, Y' is isoleucinyl, R$_o$ is phenyl, R$_{oo}$ is 5-thiazolyl and R is 6-cyclopropyl-2-pyridinyl;

G is —N(CH$_3$)—, Y' is isoleucinyl, R$_o$ is phenyl, R$_{oo}$ is 5-thiazolyl and R is 6-ethyl-2-pyridinyl;

G is —N(CH$_3$)—, Y' is isoleucinyl, R$_o$ is phenyl, R$_{oo}$ is 5-thiazolyl and R is 6-(2-propenyl)-2-pyridinyl;

G is —N(CH$_3$)—, Y' is isoleucinyl, R$_o$ is phenyl, R$_{oo}$ is 5-thiazolyl and R is 6-propyl-2-pyridinyl;

G is —N(CH$_3$)—, Y' is isoleucinyl, R$_o$ is phenyl, R$_{oo}$ is 5-thiazolyl and R is 6-(2-methyl)propyl-2-pyridinyl;

G is —O—, Y' is isoleucinyl, R$_o$ is phenyl, R$_{oo}$ is 5-thiazolyl and R is 2-pyridinyl;

G is —O—, Y' is isoleucinyl, R$_o$ is phenyl, R$_{oo}$ is 5-thiazolyl and R is 6isopropyl-2-pyridinyl;

G is —O—, Y' is isoleucinyl, R$_o$ is phenyl, R$_{oo}$ is 5-thiazolyl and R is 6methyl-2-pyridinyl;

G is —O—, Y' is isoleucinyl, R$_o$ is phenyl, R$_{oo}$ is 5-thiazolyl and R is 6(1,1-dimethyl)ethyl-2-pyridinyl;

G is —O—, Y' is isoleucinyl, R$_o$ is phenyl, R$_{oo}$ is 5-thiazolyl and R is 6-cyclobutyl-2-pyridinyl;

G is —O—, Y' is isoleucinyl, R$_o$ is phenyl, R$_{oo}$ is 5-thiazolyl and R is 6-cyclopropyl-2-pyridinyl;

G is —O—, Y is isoleucinyl, R$_o$ is phenyl, R$_{oo}$ is 5-thiazolyl and R is 6-ethyl-2-pyridinyl;

G is —O—, Y' is isoleucinyl, R$_o$ is phenyl, R$_{oo}$ is 5-thiazolyl and R is 6(2-propenyl)-2-pyridinyl;

G is —O—, Y' is isoleucinyl, R$_o$ is phenyl, R$_{oo}$ is 5-thiazolyl and R is 6-propyl-2-pyridinyl;

G is —O—, Y' is isoleucinyl, R$_o$ is phenyl, R$_{oo}$ is 5-thiazolyl and R is 6-($^2$-methyl)propyl-2-pyridinyl;

G is —N(CH$_3$)—, Y' is valinyl, R$_o$ is phenyl, R$_{oo}$ is 5-oxazolyl and R is 2-pyridinyl;

G is —N(CH$_3$)—, Y' is valinyl, R$_o$ is phenyl, R$_{oo}$ is 5-oxazolyl and R is 6-isopropyl-2-pyridinyl;

G is —N(CH$_3$)—, Y' is valinyl, R$_o$ is phenyl, R$_{oo}$ is 5-oxazolyl and R is 6-methyl-2-pyridinyl;

G is —N(CH$_3$)—, Y' is valinyl, R$_o$ is phenyl, R$_{oo}$ is 5-oxazolyl and R is 6-(1,1-dirnethylethyl-2-pyridinyl;

G is —N(CH$_3$)—, Y' is valinyl, R$_o$ is phenyl, R$_{oo}$ is 5-oxazolyl and R is 6-cyclobutyl-2-pyridinyl;

G is —N(CH$_3$)—, Y' is valinyl, R$_o$ is phenyl, R$_{oo}$ is 5-oxazolyl and R is 6-cyclopropyl-2-pyridinyl;

G is —N(CH$_3$)—, Y' is valinyl, R$_o$ is phenyl, R$_{oo}$ is 5-oxazolyl and R is 6-ethyl-2-pyridinyl;

G is —N(CH$_3$)—, Y' is valinyl, R$_o$ is phenyl, R$_{oo}$ is 5-oxazolyl and R is 6-(2-propenyl)-2-pyrdinyl;

G is —N(CH$_3$)—, Y' is valinyl, R$_o$ is phenyl, R$_{oo}$ is 5-oxazolyl and R is 6-propyl-2-pyridinyl;

G is —N(CH$_3$)—, Y' is valinyl, R$_o$ is phenyl, R$_{oo}$ is 5-oxazolyl and R is 6-(2-methyl)propyl-2-pyridinyl;

G is —O—, Y' is valinyl, R$_o$ is phenyl, R$_{oo}$ is 5-oxazodyl and R is 2-pyridinyl;

G is —O—, Y' is valinyl, R$_o$ is phenyl, R$_{oo}$ is 5-oxazolyl and R is 6-isopropyl-2-pyridinyl;

G is —O—, Y' is valinyl, R$_o$ is phenyl, R$_{oo}$ is 5-oxazolyl and R is 6-methyl-2-pyridinyl;

G is —O—, Y' is valinyl, R$_o$ is phenyl, R$_{oo}$ is 5-oxazolyl and R is 6-(1,1-dimethyl)ethyl-2-pyridinyl;

G is —O—, Y' is valinyl, R$_o$ is phenyl, R$_{oo}$ is 5-oxazolyl and R is 6cyclobutyl-2-pyridinyl;

G is —O—, Y' is valinyl, R$_o$ is phenyl, R$_{oo}$ is 5-oxazolyl and R is 6-cyclopropyl-2-pyridinyl;

G is —O—, Y' is valinyl, R$_o$ is phenyl, R$_{oo}$ is 5-oxazolyl and R is 6ethyl-2-pyridinyl;

G is —O—, Y' is valinyl, R$_o$ is phenyl, R$_{oo}$ is 5-oxazolyl and R is 6-(2-propenyl)-2-pyridinyl;

G is —O—, Y' is valinyl, R$_o$ is phenyl, R$_{oo}$ is 5-oxazolyl and R is 6-propyl-2-pyridinyl;

G is —O—, Y' is valinyl, R$_o$ is phenyl, R$_{oo}$ is 5-oxazolyl and R is 6-(2-methyl)propyl-2-pyridinyl;

G is —N(CH$_3$)—, Y' is alaninyl, R$_o$ is phenyl, R$_{oo}$ is 5-oxazolyl and R is 2-pyridinyl;

G is —N(CH$_3$)—, Y' is alaninyl, R$_o$ is phenyl, R$_{oo}$ is 5-oxazolyl and R is 6-isopropyl-2-pyridinyl;

G is —N(CH$_3$)—, Y' is alaninyl, R$_o$ is phenyl, R$_{oo}$ is 5-oxazolyl and R is 6-methyl-2-pyridinyl;

G is —N(CH$_3$)—, Y' is alaninyl, R$_o$ is phenyl, R$_{oo}$ is 5-oxazolyl and R is 6-(1,1-dimethyl)ethyl-2-pyridinyl;

G is —N(CH$_3$)—, Y' is alaninyl, R$_o$ is phenyl, R$_{oo}$ is 5-oxazolyl and R is 6-cyclobutyl-2-pyridinyl;

G is —N(CH$_3$)—, Y' is alaninyl, R$_o$ is phenyl, R$_{oo}$ is 5-oxazolyl and R is 6-cyclopropyl-2-pyridinyl;

G is —N(CH$_3$)—, Y' is alaninyl, R$_o$ is phenyl, R$_{oo}$ is 5-oxazolyl and and R is 6-ethyl-2-pyridinyl;

G is —N(CH$_3$)—, Y' is alaninyl, R$_o$ is phenyl, R$_{oo}$ is 5-oxazolyl and R is 6-(2-propenyl)-2-pyridinyl;

G is —N(CH$_3$)—, Y' is alaninyl, R$_o$ is phenyl, R$_{oo}$ is 5-oxazolyl and R is 6-propyl-2-pyridinyl;

G is —N(CH$_3$)—, Y' is alaninyl, R$_o$ is phenyl, R$_{oo}$ is 5-oxazolyl and R is 6-(2-methyl)propyl-2-pyridinyl;

G is —O—, Y' is alaninyl, R$_o$ is phenyl, R$_{oo}$ is 5-oxazolyl and R is 2-pyridinyl;

G is —O—, Y' is alaninyl, R$_o$ is phenyl, R$_{oo}$ is 5-oxazolyl and R is 6-isopropyl-2-pyridinyl;

G is —O—, Y' is alaninyl, R$_o$ is phenyl, R$_{oo}$ is 5-oxazolyl and R is 6-methyl-2-pyridinyl;

G is —O—, Y' is alaninyl, R$_o$ is phenyl, R$_{oo}$ is 5-oxazolyl and R is 6-(1,1-dimethyl)ethyl-2-pyridinyl;

G is —O—, Y' is alaninyl, R$_o$ is phenyl, R$_{oo}$ is 5-oxazolyl and R is 6-cyclobutyl-2-pyridinyl;

G is —O—, Y' is alaninyl, R$_o$ is phenyl, R$_{oo}$ is 5-oxazolyl and R is 6-cyclopropyl-2-pyridinyl;

G is —O—, Y' is alaninyl, R$_o$ is phenyl, R$_{oo}$ is 5-oxazolyl and R is 6-ethyl-2-pyridinyl;

G is —O—, Y' is alaninyl, R$_o$ is phenyl, R$_{oo}$ is 5-oxazolyl and R is 6-(2-propenyl)-2-pyridinyl;

G is —O—, Y' is alaninyl, R$_o$ is phenyl, R$_{oo}$ is 5-oxazolyl and R is 6-propyl-2-pyridinyl;

G is —O—, Y' is alaninyl, R$_o$ is phenyl, R$_{oo}$ is 5-oxazolyl and R is 6-(2-methyl)propyl-2-pyridinyl;

G is —N(CH$_3$)—, Y' is isoleucinyl, R$_o$ is phenyl, R$_{oo}$ is 5-oxazolyl and R is 2-pyridinyl, G is —N(CH$_3$)—, Y' is isoleucinyl, R$_o$ is phenyl, R$_{oo}$ is 5-oxazolyl and R is 6-isopropyl-2-pyridinyl;

G is —N(CH$_3$)—, Y' is isoleucinyl, R$_o$ is phenyl, R$_{oo}$ is 5-oxazolyl and R is 6methyl-2-pyridinyl;

G is —N(CH$_3$)—, Y' is isoleucinyl, R$_o$ is phenyl, R$_{oo}$ is 5-oxazolyl and R is 6(1,1-dimethyl)ethyl-2-pyridinyl;

G is —N(CH$_3$)—, Y' is isoleucinyl, R$_o$ is phenyl, R$_{oo}$ is 5-oxazolyl and R is 6-cyclobutyl-2-pyridinyl;

G is —N(CH$_3$)—, Y' is isoleucinyl, R$_o$ is phenyl, R$_{oo}$ is 5-oxazoly and R is 6-cyclopropyl-2-pyridinyl;

G is —N(CH$_3$)—, Y' is isoleucinyl, R$_o$ is phenyl, R$_{oo}$ is 5-oxazolyl and R is 6-ethyl-2-pyridinyl;

G is —N(CH$_3$)—, Y' is isoleucinyl, R$_o$ is phenyl, R$_{oo}$ is 5-oxazolyl and R is 6-(2-propenyl)-2-pyridinyl;

G is —N(CH$_3$)—, Y' is isoleucinyl, R$_o$ is phenyl, R$_{oo}$ is 5-oxazolyl and R is 6-propyl-2-pyridinyl;

G is —N(CH$_3$)—, Y' is isoleucinyl, R$_o$ is phenyl, R$_{oo}$ is 5-oxazolyl and R is 6-(2-methyl)propyl-2-pyridinyl;

G is —O—, Y' is isoleucinyl, R$_o$ is phenyl, R$_{oo}$ is 5-oxazolyl and R is 2-pyridinyl;

G is —O—, Y' is isoleucinyl, R$_o$ is phenyl, R$_{oo}$ is 5-oxazolyl and R is 6-isopropyl-2-pyridinyl;

G is —O—, Y' is isoleucinyl, R$_o$ is phenyl, R$_{oo}$ is 5-oxazolyl and R is 6methyl-2-pyridinyl;

G is —O—, Y' is isoleucinyl, R$_o$ is phenyl, R$_{oo}$ is 5-oxazolyl and R is 6-(1,1-dimothylethyl-2-pyridinyl;

G is —O—, Y' is isoleucinyl, R$_o$ is phenyl, R$_{oo}$ is 5-oxazolyl and R is 6-cyclobutyl-2-pyridinyl;

G is —O—, Y' is isoleucinyl, R$_o$ is phenyl, R$_{oo}$ is 5-oxazolyl and R is 6-cyclopropyl-2-pyridinyl;

G is —O—, Y' is isolcucinyl, R$_o$ is phenyl, R$_{oo}$ is 5-oxazolyl and R is 6-ethyl-2-pyridinyl;

G is —O—, Y' is isoleucinyl, R$_o$ is phenyl, R$_{oo}$ is 5-oxazolyl and R is 6-(2-propenyl)-2-pyridinyl;

G is —O—, Y' is isoleucinyl, R$_o$ is phenyl, R$_{oo}$ is 5-oxazolyl and R is 6-propyl-2-pyridinyl;

G is —O—, Y' is isoleucinyl, R$_o$ is phenyl, R$_{oo}$ is 5-oxazolyl and R is 6(2-methyl)propyl-2-pyridinyl;

G is —N(CH$_3$)—, Y' is valinyl, R$_o$ is phenyl, R$_{oo}$ is 5-isoxazolyl and R is 4-oxazolyl;

G is —N(CH$_3$)—, Y' is valinyl, R$_o$ is phenyl, R$_{oo}$ is 5-isoxazolyl and R is 2-isopropyl-4-oxazolyl;

G is —N(CH$_3$)—, Y' is valinyl, R$_o$ is phenyl, R$_{oo}$ is 5-isoxazolyl and R is 2-methyl4-oxazolyl;

G is —N(CH$_3$)—, Y' is valinyl, R$_o$ is phenyl, R$_{oo}$ is 5-isoxazolyl and R is 2-(1,1-dimethy)ethyl-4-oxazolyl;

G is —N(CH$_3$)—, Y' is valinyl, R$_o$ is phenyl, R$_{oo}$ is 5-isoxazolyl and R is 2-cyclobutyl4-oxazolyl;

G is —N(CH$_3$)—, Y' is valinyl, R$_o$ is phenyl, R$_{oo}$ is 5-isoxazolyl and R is 2-cyclopropyl-4-oxazolyl;

G is —N(CH$_3$)—, Y' is valinyl, R$_o$ is phenyl, R$_{oo}$ is 5-isoxazolyl and R is 2-ethyl-4-oxazolyl;

G is —N(CH$_3$)—, Y' is valinyl, R$_o$ is phenyl, R$_{oo}$ is 5-isoxazolyl and R is 2-($^2$-propenyl)-4-oxazolyl;

G is —N(CH$_3$)—, Y' is valinyl, R$_o$ is phenyl, R$_{oo}$ is 5-isoxazolyl and R is 2-(N,N-dimethylamino)-4-oxazolyl;

G is —N(CH$_3$)—, Y' is valinyl, R$_o$ is phenyl, R$_{oo}$ is 5-isoxazolyl and R is 2-(1-pyrrolidinyl)-4-oxazolyl;

G is —N(CH$_3$)—, Y' is valinyl, R$_o$ is phenyl, R$_{oo}$ is 5-isoxazolyl and R is 2-(2-methyl)propyl-4-oxazolyl;

G is —N(CH$_3$)—, Y' is valinyl, R$_o$ is phenyl, R$_{oo}$ is 5-isoxazolyl and R is 2-pyridinyl;

G is —N(CH$_3$)—, Y' is valinyl, R$_o$ is phenyl, R$_{oo}$ is 5-isoxazolyl and R is 6-isopropyl-2-pyridinyl;

G is —N(CH$_3$)—, Y' is valinyl, R$_o$ is phenyl, R$_{oo}$ is 5-isoxazolyl and R is 6-methyl-2-pyridinyl;

G is —N(CH$_3$)—, Y' is valinyl, R$_o$ is phenyl, R$_{oo}$ is 5-oxazolyl and R is 6-(1,1-dimethyl)ethyl-2-pyridinyl;

G is —N(CH$_3$)—, Y' is valinyl, R$_o$ is phenyl, R$_{oo}$ is 5-isoxazolyl and R is 6cyclobutiy-2-pyridinyl;

G is —N(CH$_3$)—, Y' is valinyl, R$_o$ is phenyl, R$_{oo}$ is 5-isoxazolyl and R is 6-cyclopropyl-2-pyridinyl;

G is —N(CH$_3$)—, Y' is valinyl, R$_o$ is phenyl, R$_{oo}$ is 5-isoxazolyl and R is 6-ethyl-2-pyridinyl;

G is —N(CH$_3$)—, Y' is valinyl, R$_o$ is phenyl, R$_{oo}$ is 5-isoxazolyl and R is 6-(2-propenyl)-2-pyridinyl;

G is —N(CH$_3$)—, Y' is valinyl, R$_o$ is phenyl, R$_{oo}$ is 5-isoxazolyl and R is 6-propyl-2-pyridinyl;

G is —N(CH$_3$)—, Y' is valinyl, R$_o$ is phenyl, R$_{oo}$ is 5-isoxazolyl and R is 6-(2-methyl)propyl-2-pyridinyl;

G is —O—, Y' is valinyl, R$_o$ is phenyl, R$_{oo}$ is 5-isoxazolyl and R is 4-thiazolyl;

G is —O—, Y' is valinyl, R$_o$ is phenyl, R$_{oo}$ is 5-isoxazolyl and R is 2-isopropyl-4-thiazolyl;

G is —O—, Y' is valinyl, R$_o$ is phenyl, R$_{oo}$ is 5-isoxazolyl and R is 2-methyl-4-thiazolyl;

G is —O—, Y' is valinyl, R$_o$ is phenyl, R$_{oo}$ is 5-isoxazolyl and R is 2-(1,1-dimethyl)ethyl-4-thiazolyl;

G is —O—, Y' is valinyl, R$_o$ is phenyl, R$_{oo}$ is 5-isoxazolyl and R is 2-cyclobutyl-4-thiazolyl;

G is —O—, Y' is valinyl, R$_o$ is phenyl, R$_{oo}$ is 5-isoxazolyl and R is 2-cyclopropyl-4-thiazolyl;

G is —O—, Y' is valinyl, R$_o$ is phenyl, R$_{oo}$ is 5-isoxazolyl and R is 2-ethyl-4-thiazolyl;

G is —O—, Y' is valinyl, R$_o$ is phenyl, R$_{oo}$ is 5-isoxazolyl and R is 2-(2-propenyl)-4-thiazolyl;

G is —O—, Y' is valinyl, $R_o$ is phenyl, $R_{oo}$ is 5-isoxazolyl and R is 2-(N,N-dimethylamino)-4-thiazolyl;

G is —O—, Y' is valinyl, $R_o$ is phenyl, $R_{oo}$ is 5-isoxazolyl and R is 2-(1-propyl)-4-thiazolyl;

G is —O—, Y' is valinyl, $R_o$ is phenyl, $R_{oo}$ is 5-isoxazolyl and R is 2-(2-methyl)propyl-4-thiazolyl;

G is —O—, Y' is valinyl, $R_o$ is phenyl, $R_{oo}$ is 5-isoxazolyl and R is 4-oxazolyl;

G is —O—, Y' is valinyl, $R_o$ is phenyl, $R_{oo}$ is 5-isoxazolyl and R is 2-isopropyl-4-oxazolyl;

G is —O—, Y' is valinyl, $R_o$ is phenyl, $R_{oo}$ is 5-isoxazolyl and R is 2-methyl-4-oxazolyl;

G is —O—, Y' is valinyl, $R_o$ is phenyl, $R_{oo}$ is 5-isoxazolyl and R is 2-(1,1-dimethy)ethyl-4-oxazolyl;

G is —O—, Y' is valinyl, $R_o$ is phenyl, $R_{oo}$ is 5-isoxazolyl and R is 2-cyclobutyl-4-oxazolyl;

G is —O—, Y' is valinyl, $R_o$ is phenyl, $R_{oo}$ is 5-isoxazolyl and R is 2-cyclopropyl-4-oxazolyl;

G is —O—, Y' is valinyl, $R_o$ is phenyl, $R_{oo}$ is 5-isoxazolyl and R is 2-ethyl-4-oxazolyl;

G is —O—, Y' is valinyl, $R_o$ is phenyl, $R_{oo}$ is 5-isoxazolyl and R is 2-(2-propenyl)-4-oxazolyl;

G is —O—, Y' is valinyl, $R_o$ is phenyl, $R_{oo}$ is 5-isoxazolyl and R is 2-(N,N-dimethylamino)-4-oxazolyl;

G is —O—, Y' is valinyl, $R_o$ is phenyl, $R_{oo}$ is 5-isoxazolyl and R is 2-(1-propyl)-4-oxazolyl;

G is —O—, Y' is valinyl, $R_o$ is phenyl, $R_{oo}$ is 5-isoxazolyl and R is 2-(2-methyl)propyl-4-oxazolyl;

G is —O—, Y' is valinyl, $R_o$ is phenyl, $R_{oo}$ is 5-isoxazolyl and R is 2-pyridinyl;

G is —O—, Y' is vablnyl, $R_o$ is phenyl, $R_{oo}$ is 5-voxazolyl and R is 6-isopropyl-2-pyridinyl;

G is —O—, Y' is valinyl, $R_o$ is phenyl, $R_{oo}$ is 5-isoxazolyl and R is 6-methyl-2-pyridinyl;

G is —O—, Y' is valinyl, $R_o$ is phenyl, $R_{oo}$ is 5-isoxazolyl and R is 6-(1,1-dimethyl)ethyl-2-pyridinyl;

G is —O—, Y' is valinyl, $R_o$ is phenyl, $R_{oo}$ is 5-isoxazolyl and R is 6-cyclobutyl-2-pyridinyl;

G is —O—, Y' is valinyl, $R_o$ is phenyl, $R_{oo}$ is 5-isoxazolyl and R is 6-cyclopropyl-2-pyridinyl;

G is —O—, Y' is valinyl, $R_o$ is phenyl, $R_{oo}$ is 5-isoxazolyl and R is 6ethyl-2-pyridinyl;

G is —O—, Y' is valinyl, $R_o$ is phenyl, $R_{oo}$ is 5-isoxazolyl and R is 6-(2-propenyl)-2-pyridinyl;

G is —O—, Y' is valinyl, $R_o$ is phenyl, $R_{oo}$ is 5-isoxazolyl and R is 6-propyl-2-pyridinyl;

G is —O—, Y' is valinyl, $R_o$ is phenyl, $R_{oo}$ is 5-isoxazolyl and R is 6-(2-methyl)propyl-2-pyridinyl;

G is —N(CH$_3$)—, Y' is alaninyl, $R_o$ is phenyl, $R_{oo}$ is 5-isoxazolyl and R is 4-thiazolyl;

G is —N(CH$_3$)—, Y' is alaninyl, $R_o$ is phenyl, $R_{oo}$ is 5-isoxazolyl and R is 2-isopropyl-4-thiazolyl;

G is —N(CH$_3$)—, Y' is alaninyl, $R_o$ is phenyl, $R_{oo}$ is 5-isoxazolyl and R is 2-methyl-4-thiazolyl;

G is —N(CH$_3$)—, Y' is alaninyl, $R_o$ is phenyl, $R_{oo}$ is 5-isoxazolyl and R is 2-(1,1-dimethyl)ethyl-4-thiazolyl;

G is —N(CH$_3$)—, Y' is alaninyl, $R_o$ is phenyl, $R_{oo}$ is 5-isoxazolyl and R is 2-cyclobutyl-4-thiazolyl;

G is —N(CH$_3$)—, Y' is alaninyl, $R_o$ is phenyl, $R_{oo}$ is 5-isoxazolyl and R is 2-cyclopropyl-4-thiazolyl;

G is —N(CH$_3$)—, Y' is alaninyl, $R_o$ is phenyl, $R_{oo}$ is 5-isoxazolyl and R is 2-ethyl-4-thiazolyl;

G is —N(CH$_3$)—, Y' is alaninyl, $R_o$ is phenyl, $R_{oo}$ is 5-isoxazolyl and R is 2-(2-propenyl)-4-thiazolyl;

G is —N(CH$_3$)—, Y' is alaninyl, $R_o$ is phenyl, $R_{oo}$ is 5-isoxazolyl and R is 2-(N,N-dimediylamino)-4-thiazolyl;

G is —N(CH$_3$)—, Y' is alaninyl, $R_o$ is phenyl, $R_{oo}$ is 5-isoxazolyl and R is 2-(1-propyl)-4-thiazolyl;

G is —N(CH$_3$)—, Y' is alaninyl, $R_o$ is phenyl, $R_{oo}$ is 5-isoxazolyl and R is 2-(2-methyl)propyl-4-thiazolyl;

G is —N(CH$_3$)—, Y' is alaninyl, $R_o$ is phenyl, $R_{oo}$ is 5-isoxazolyl and R is 2-(1-pyrrolidinyl)-4-thiazolyl;

G is —N(CH$_3$)—, Y' is alanyl, $R_o$ is phenyl, $R_{oo}$ is 5-isoxazolyl and R is 4-oxazolyl;

G is —N(CH$_3$)—, Y' is alanyl, $R_o$ is phenyl, $R_{oo}$ is 5-isoxazolyl and R is 2-isopropyl-4-oxazolyl;

G is —N(CH$_3$)—, Y' is alanyl, $R_o$ is phenyl, $R_{oo}$ is 5-isoxazolyl and R is 2-methyl-4-oxazolyl;

G is —N(CH$_3$)—, Y' is alanyl, $R_o$ is phenyl, $R_{oo}$ is 5-isoxazolyl and R is 2-(1,1-dimethyethyl-4-oxazolyl;

G is —N(CH$_3$)—, Y' is alanyl, $R_o$ is phenyl, $R_{oo}$ is 5-isoxazolyl and R is 2-cyclobutyl-4-oxazolyl;

G is —N(CH$_3$)—, Y' is alanyl, $R_o$ is phenyl, $R_{oo}$ is 5-isoxazolyl and R is 2-cyclopropyl-4-oxazolyl;

G is —N(CH$_3$)—, Y' is alanyl, $R_o$ is phenyl, $R_{oo}$ is 5-isoxazolyl and R is 2-ethyl-4-oxazolyl;

G is —N(CH$_3$)—, Y' is alanyl, $R_o$ is phenyl, $R_{oo}$ is 5-isoxazolyl and R is 2-(2-propenyl)-4-oxazolyl;

G is —N(CH$_3$)—, Y' is alanyl, $R_o$ is phenyl, $R_{oo}$ is 5-isoxazolyl and R is 2-(N,N-dimethylamino)-4-oxazolyl;

G is —N(CH$_3$)—, Y' is alanyl, $R_o$ is phenyl, $R_{oo}$ is 5-isoxazolyl and R is 2-(1-propyl)-4-oxazolyl;

G is —N(CH$_3$)—, Y' is alanyl, $R_o$ is phenyl, $R_{oo}$ is 5-isoxazolyl and R is 2-(2-methyl)propyl-4-oxazolyl;

G is —N(CH$_3$)—, Y' is alanyl, $R_o$ is phenyl, $R_{oo}$ is 5-isoxazolyl and R is 2-pyridinyl;

G is —N(CH$_3$)—, Y' is alanyl, $R_o$ is phenyl, $R_{oo}$ is 5-isoxazolyl and R is 6-isopropyl-2-pyridinyl;

G is —N(CH$_3$)—, Y' is alanyl, $R_o$ is phenyl, $R_{oo}$ is 5-isoxazolyl and R is 6-methyl-2-pyridinyl;

G is —N(CH$_3$)—, Y' is alanyl, $R_o$ is phenyl, $R_{oo}$ is 5-isoxazolyl and R is 6-(1,1-dimethyl)ethyl-2-pyridinyl;

G is —N(CH$_3$)—, Y' is alanyl, $R_o$ is phenyl, $R_{oo}$ is 5-isoxazolyl and R is 6-cyclobutyl-2-pyridinyl;

G is —N(CH$_3$)—, Y' is alanyl, $R_o$ is phenyl, $R_{oo}$ is 5-isoxazolyl and R is 6-cyclopropyl-2-pyridinyl;

G is —N(CH$_3$)—, Y' is alanyl, $R_o$ is phenyl, $R_{oo}$ is 5-isoxazolyl and R is 6-ethyl-2-pyridinyl;

G is —N(CH$_3$)—, Y' is alanyl, $R_o$ is phenyl, $R_{oo}$ is 5-isoxazolyl and R is 6-(2-propenyl)-2-pyridinyl;

G is —N(CH$_3$)—, Y' is alanyl, $R_o$ is phenyl, $R_{oo}$ is 5-isoxazolyl and R is 6-propyl-2-pyridinyl;

G is —N(CH$_3$)—, Y' is alanyl, $R_o$ is phenyl, $R_{oo}$ is 5-isoxazolyl and R is 6-(2-methyl)propyl-2-pyridinyl;

G is —O—, Y' is alanyl, $R_o$ is phonyl, $R_{oo}$ is 5-isoxazolyl and R is 4-thiazolyl;

G is —O—, Y' is alanyl, $R_o$ is phenyl, $R_{oo}$ is 5-isoxazolyl and R is 2-isopropyl-4-thiazolyl;

G is —O—, Y' is alanyl, $R_o$ is phenyl, $R_{oo}$ is 5-isoxazolyl and R is 2-methyl-4-thiazolyl;

G is —O—, Y' is alanyl, $R_o$ is phenyl, $R_{oo}$ is 5-isoxazolyl and R is 2-(1,1-dimethyl)ethyl-4-thiazolyl;

G is —O—, Y' is alanyl, R$_o$ is phenyl, R$_{oo}$ is 5-isoxazolyl and R is 2-cyclobutyl-4-tiiazolyl;

G is —O—, Y' is alanyl, R$_o$ is phenyl, R$_{oo}$ is 5-isoxazolyl and R is 2-cyclopropyl-4-thiazolyl;

G is —O—, Y is alanyl, R$_o$ is phenyl, R$_{oo}$ is 5-isoxazolyl and R is 2-ethyl-4-thiazolyl;

G is —O—, Y' is alanyl, R$_o$ is phenyl, R$_{oo}$ is 5-isoxazolyl and R is 2-(2-propenyl)-4-thiazolyl;

G is —O—, Y' is alanyl, R$_o$ is phenyl, R$_{oo}$ is 5-isoxazolyl and R is 2-(N,N-dimethylamino)-4-thiazolyl;

G is —O—, Y' is alanyl, R$_o$ is phenyl, R$_{oo}$ is 5-isoxazolyl and R is 2-(1-propyl)-4-thiazolyl;

G is —O—, Y' is alanyl, R$_o$ is phenyl, R$_{oo}$ is 5-isoxazolyl and R is 2-(2-methyl)propyl-4-thiazolyl;

G is —O—, Y' is alanyl, R$_o$ is phenyl, R$_{oo}$ is 5-isoxazolyl and R is 4-oxazolyl;

G is —O—, Y' is alanyl, R$_o$ is phenyl, R$_{oo}$ is 5-isoxazolyl and R is 2-isopropyl-4-oxazolyl;

G is —O—, Y' is alanyl, R$_o$ is phenyl, R$_{oo}$ is 5-isoxazolyl and R is 2-methyl-4-oxazolyi;

G is —O—, Y' is alanyl, R$_o$ is phenyl, R$_{oo}$ is 5-isoxazolyl and R is 2-(1,1-dimethy)ethyl-4-oxazolyl;

G is —O—, Y' is alanyl, R$_o$ is phenyl, R$_{oo}$ is 5-isoxazolyl and R is 2-cyclobutyl-4-oxazolyl;

G is —O—, Y' is alanyl, R$_o$ is phenyl, R$_{oo}$ is 5-isoxazolyl and R is 2-cyclopropyl-4-oxazolyl;

G is —O—, Y' is alanyl, R$_o$ is phenyl, R$_{oo}$ is 5-isoxazolyl and R is 2-ethyl-4-oxazolyl;

G is —O—, Y' is alanyl, R$_o$ is phenyl, R$_{oo}$ is 5-isoxazolyl and R is 2-(2-propenyl)-4-oxazolyl;

G is —O—, Y' is alanyl, R$_o$ is phenyl, R$_{oo}$ is 5-isoxazolyl and R is 2-(N,N-dimethylamino)-4-oxazolyl;

G is —O—, Y' is alanyl, R$_o$ is phenyl, R$_{oo}$ is 5-isoxazolyl and R is 2-(1-propyl)-4-oxazolyl;

G is —O—, Y' is alanyl, R$_o$ is phenyl, R$_{oo}$ is 5-isoxazolyl and R is 2-(2-methyl)propyl-4-oxazolyl;

G is —O—, Y' is alanyl, R$_o$ is phenyl, R$_{oo}$ is 5-isoxazolyl and R is 2-pyridinyl;

G is —O—, Y' is alanyl, R$_o$ is phenyl, R$_{oo}$ is 5-voxazolyl and R is 6-isopropyl-2-pyridinyl;

G is —O—, Y' is alanyl, R$_o$ is phenyl, R$_{oo}$ is 5-isoxazolyl and R is 6-methyl-2-pyridinyl;

G is —O—, Y' is alanyl, R$_o$ is phenyl, R$_{oo}$ is 5-isoxazolyl and R is 6-(1,1-dimethyl)ethyl-2-pyridinyl;

G is —O—, Y' is alanyl, R$_o$ is phenyl, R$_{oo}$ is 5-isoxazolyl and R is 6cyclobutyl-2-pyridinyl;

G is —O—, Y' is alanyl, R$_o$ is phenyl, R$_{oo}$ is 5-isoxazolyl and R is 6-cyclopropyl-2-pyridinyl;

G is —O—, Y' is alanyl, R$_o$ is phenyl, R$_{oo}$ is 5-isoxazolyl and R is 6-ethyl-2-pyridinyl;

G is —O—, Y' is alanyl, R$_o$ is phenyl, R$_{oo}$ is 5-isoxazolyl and R is 6-(2-propenyl)-2-pyridinyl;

G is —O—, Y' is alanyl, R$_o$ is phenyl, R$_{oo}$ is 5-isoxazolyl and R is 6-propyl-2-pyridinyl;

G is —O—, Y' is alanyl, R$_o$ is phenyl, R$_{oo}$ is 5-isoxazolyl and R is 6-(2-methyl)propyl-2-pyridinyl;

G is —N(CH$_3$)—, Y' is isoleucyl, R$_o$ is phenyl, R$_{oo}$ is 5-isoxazolyl and R is 4-thiazolyl;

G is —N(CH$_3$)—, Y' is isoleucyl, R$_o$ is phenyl, R$_{oo}$ is 5-isoxazolyl and R is 2-isopropyl-4-thiazolyl;

G is —N(CH$_3$)—, Y' is isoleucyl, R$_o$ is phenyl, R$_{oo}$ is 5-isoxazolyl and R is 2-methyl-4-thiazolyl;

G is —N(CH$_3$)—, Y' is isoleucyl, R$_o$ is phenyl, R$_{oo}$ is 5-isoxazolyl and R is 2-(1,1-dimethyl)ethyl-4-thiazolyl;

G is —N(CH$_3$)—, Y' is isoleucyl, R$_o$ is phenyl, R$_{oo}$ is 5-isoxazolyl and R is 2-cyclobutyl-4-thiazolyl;

G is —N(CH$_3$)—, Y' is isoleucyl, R$_o$ is phenyl, R$_{oo}$ is 5-isoxazolyl and R is 2-cyclopropyl-4-thiazolyl;

G is —N(CH$_3$)—, Y' is isoleucyl$_1$, R$_o$ is phenyl, R$_{oo}$ is 5-isoxazolyl and R is 2-ethyl-4-thiazolyl;

G is —N(CH$_3$)—, Y' is isoleucyl, R$_o$ is phenyl, R$_{oo}$ is 5-isoxazolyl and R is 2-(2-propenyl)-4-thiazolyi;

G is —N(CH$_3$)—, Y' is isoleucyl, R$_o$ is phenyl, R$_{oo}$ is 5-isoxazolyl and R is 2-(N,N-dimethylanino)-4thazolyl;

G is —N(CH$_3$)—, Y' is isoleucyl, R$_o$ is phenyl, R$_{oo}$ is 5-isoxazolyl and R is 2-(1-propyl)-4-thiazolyl;

G is —N(CH$_3$)—, Y' is isoleucyl, R$_o$ is phenyl, R$_{oo}$ is 5-isoxazolyl and R is 2-(2-methyl)propyl-4-thiazolyl;

G is —N(CH$_3$)—, Y' is isoleucyl, R$_o$ is phenyl, R$_{oo}$ is 5-isoxazolyl and R is 2-(1-pyrrolidinyl)-4-thiazolyl;

G is —N(CH$_3$)—, Y' is isoleucyl, R$_o$ is phenyl, R$_{oo}$ is 5-isoxazolyl and R is 4-oxazolyl;

G is —N(CH$_3$)—, Y' is isoleucyl, R$_o$ is phenyl, R$_{oo}$ is 5-isoxazolyl and R is 2-isopropyl-4-oxazolyl;

G is —N(CH$_3$)—, Y' is isoleucyl, R$_o$ is phenyl, R$_{oo}$ is 5-isoxazolyl and R is 2-methyl-4-oxazolyl;

G is —N(CH$_3$)—, Y' is isoleucyl, R$_o$ is phenyl, R$_{oo}$ is 5-isoxazolyl and R is 2-(1,1-dimethy)ethyl-4-oxazolyl;

G is —N(CH$_3$)—, Y' is isoleucyl, R$_o$ is phenyl, R$_{oo}$ is 5-isoxazolyl and R is 2-cyclobutyl-4-oxazolyl;

G is —N(CH$_3$)—, Y' is isoleucyl, R$_o$ is phenyl, R$_{oo}$ is 5-isoxazolyl and R is 2-cyclopropyl-4-oxazolyl;

G is —N(CH$_3$)—, Y' is isoleucyl, R$_o$ is phenyl, R$_{oo}$ is 5-isoxazolyl and R is 2-ethyl-4-oxazolyl;

G is —N(CH$_3$)—, Y' is isoleucyl, R$_o$ is phenyl, R$_{oo}$ is 5-isoxazolyl and R is 2-(2-propenyl)-4-oxazolyl;

G is —N(CH$_3$)—, Y' is isoleucyl, R$_o$ is phenyl, R$_{oo}$ is 5-isoxazolyl and R is 2-(N,N-dimethylamino)-4-oxazolyl;

G is —N(CH$_3$)—, Y' is isoleucyl, R$_o$ is phenyl, R$_{oo}$ is 5-isoxazolyl and R is 2-(1-propyl)-4-oxazolyl;

G is —N(CH$_3$)—, Y' is isoleucyl, R$_o$ is phenyl, R$_{oo}$ is 5-isoxazolyl and R is 2-(2-methyl)propyl-4-oxazolyl;

G is —N(CH$_3$)—, Y' is isoleucyl, R$_o$ is phenyl, R$_{oo}$ is 5-isoxazolyl and R is 2-pyridinyl;

G is —N(CH$_3$)—, Y' is isoleucyl, R$_o$ is phenyl, R$_{oo}$ is 5-isoxazolyl and R is 6-isopropyl-2-pyridinyl;

G is —N(CH$_3$)—, Y' is isoleucyl, R$_o$ is phenyl, R$_{oo}$ is 5-isoxazolyl and R is 6-methyl-2-pyridinyl;

G is —N(CH$_3$)—, Y' is isoleucyl, R$_o$ is phenyl, R$_{oo}$ is 5-isoxazolyl and R is 6(1, -dimethyl)ethyl-2-pyridinyl;

G is —N(CH$_3$)—, Y' is isoleucyl, R$_o$ is phenyl, R$_{oo}$ is 5-isoxazol and R is 6cyclobutyl-2-pyridinyl;

G is —N(CH$_3$)—, Y' is isoleucyl, R$_o$ is phenyl, R$_{oo}$ is 5-isoxazolyl and R is 6cyclopropyl-2-pyridinyl;

G is —N(CH$_3$)—, Y' is isoleucyl, R$_o$ is phenyl, R$_{oo}$ is 5-isoxazolyl and R is 6-ethyl-2-pyridinyl;

G is —N(CH$_3$)—, Y' is isoleucyl, R$_o$ is phenyl, R$_{oo}$ is 5-isoxazolyl and R is 6-(2-propenyl)-2-pyridinyl;

G is —N(CH$_3$)—, Y' is isoleucyl, R$_o$ is phenyl, R$_{oo}$ is 5-isoxazolyl and R is 6propyl-2-pyridinyl;

G is —N(CH$_3$)—, Y' is isoleucyl, R$_o$ is phenyl, R$_{oo}$ is 5-isoxazolyl and R is 6-(2-methyl)propyl-2-pyridinyl;

G is —O—, Y' is isoleucyl, $R_o$ is phenyl, $R_{oo}$ is 5-isoxazolyl and R is 4-thiazolyl;

G is —O—, Y' is isoleucyl, $R_o$ is phenyl, $R_{oo}$ is 5-isoxazolyl and R is 2-isopropyl-4-thiazolyl;

G is —O—, Y' is isoleucyl, $R_o$ is phenyl, $R_{oo}$ is 5-isoxazolyl and R is 2-methyl-4-thiazolyl;

G is —O—, Y' is isoleucyl, $R_o$ is phenyl, $R_{oo}$ is 5-isoxazolyl and R is 2-(1,1-dimethyl)ethyl-4-thiazolyl;

G is —O—, Y' is isoleucyl, $R_o$ is phenyl, $R_{oo}$ is 5-isoxazolyl and R is 2-cyclobutyl4-thiazolyl;

G is —O—, Y' is isoleucyl, $R_o$ is phenyl, $R_{oo}$ is 5-isoxazolyl and R is 2-cyclopropyl-4-thiazolyl;

G is —O—, Y' is isoleucyl, $R_o$ is phenyl, $R_{oo}$ is 5-isoxazolyl and R is 2-ethyl-4-thiazolyl;

G is —O—, Y' is isoleucyl, $R_o$ is phenyl, $R_{oo}$ is 5-isoxazolyl and R is 2-(2-propenyl)-4-thiazolyl;

G is —O—, Y' is isoleucyl, $R_o$ is phenyl, $R_{oo}$ is 5-isoxazolyl and R is 2-(N,N-dimethylamino)-4-thiazolyl;

G is —O—, Y' is isoleucyl, $R_o$ is phenyl, $R_{oo}$ is 5-isoxazolyl and R is 2-(1-propyl)-4-thiazolyl;

G is —O—, Y' is isoleucyl, $R_o$ is phenyl, $R_{oo}$ is 5-isoxazolyl and R is 2-(2-methyl)propyl-4-thiazolyJ;

G is —O—, Y is isoleucyl, $R_o$ is phenyl, $R_{oo}$ is 5-isoxazolyl and R is 2-(1-pyrrolidinyl)-4-thiazolyl;

G is —O—, Y' is isoleucyl, $R_o$ is phenyl, $R_{oo}$ is 5-isoxazolyl and R is 4-oxazolyl;

G is —O—, Y' is isoleucyl, $R_o$ is phenyl, $R_{oo}$ is 5-isoxazolyl and R is 2-isopropyl-4-oxazolyl;

G is —O—, Y' is isoleucyl, $R_o$ is phenyl, $R_{oo}$ is 5-isoxazolyl and R is 2-methyl-4-oxazolyl;

G is —O—, Y' is isoleucyl, $R_o$ is phenyl, $R_{oo}$ is 5-isoxazolyl and R is 2-(1,1-dimethy)etiyl-4-oxazolyl;

G is —O—, Y' is isoleucyl, $R_o$ is phenyl, $R_{oo}$ is 5-isoxazolyl and R is 2-cyclobutyl-4-oxazolyl;

G is —O—, Y' is isoleucyl, $R_o$ is phenyl, $R_{oo}$ is 5-isoxazolyl and R is 2-cyclopropyl-4-oxazolyl;

G is —O—, Y' is isoleucyl, $R_o$ is phenyl, $R_{oo}$ is 5-isoxazolyl and R is 2-ethyl-4-oxazolyl;

G is —O—, Y' is isoleucyl, $R_o$ is phenyl, $R_{oo}$ is 5-isoxazolyl and R is 2-(2-propenyl)-4-oxazolyl;

G is —O—, Y' is isoleucyl, $R_o$ is phenyl, $R_{oo}$ is 5-isoxazolyl and R is 2-(N,N-dirnethylarnino)-4oxazolyl;

G is —O—, Y is isoleucyl, $R_o$ is phenyl, $R_{oo}$ is 5-isoxazolyl and R is 2-(1-propyl)-4-oxazolyl;

G is —O—, Y' is isoleucyl, $R_o$ is phenyl, $R_{oo}$ is 5-isoxazolyl and R is 2-(2-methyl)propyl-4-oxazolyl;

G is —O—, Y' is isoleucyl, $R_o$ is phenyl, $R_{oo}$ is 5-isoxazolyl and R is 2-pyridinyl;

G is —O—, Y' is isoleucyl, $R_o$ is phenyl, $R_{oo}$ is 5-isoxazolyl and R is 6-isopropyl-2-pyridinyl;

G is —O—, Y' is isoleucyl, $R_o$ is phenyl, $R_{oo}$ is 5-isoxazolyl and R is 6-methyl-2-pyridinyl;

G is —O—, Y' is isoleucyl, $R_o$ is phenyl, $R_{oo}$ is 5-isoxazolyl and R is 6-(1,1-dimethyl)ethyl-2-pyridinyl;

G is —O—, Y' is isoleucyl, $R_o$ is phenyl, $R_{oo}$ is 5-isoxazolyl and R is 6-cyclobutyl-2-pyridinyl;

G is —O—, Y' is isoleucyl, $R_o$ is phenyl, $R_{oo}$ is 5-isoxazolyl and R is 6-cyclopropyl-2-pyridinyl;

G is —O—, Y' is isoleucyl, $R_o$ is phenyl, $R_{oo}$ is 5-isoxazolyl and R is 6-ethyl-2-pyridinyl;

G is —O—, Y' is isoleucyl, $R_o$ is phenyl, $R_{oo}$ is 5-isoxazolyl and R is 6-(2-propenyl)-2-pyridinyl;

G is —O—, Y' is isoleucyl, $R_o$ is phenyl, $R_{oo}$ is 5-isoxazolyl and R is 6-propyl-2-pyridinyl;

G is —O—, Y' is isoleucyl, $R_o$ is phenyl, $R_{oo}$ is 5-isoxazolyl and R is 6-(2-methyl)propyl-2-pyridinyl;

G is —N(CH$_3$)—, Y' is valinyl, $R_o$ is 4-fluorophenyl, $R_{oo}$ is 5-thiazolyl and R is 2-pyridinyl;

G is —N(CH$_3$)—, Y' is valinyl, $R_o$ is 4-fluorophenyl, $R_{oo}$ is 5-thiazolyl and R is 6-isopropyl-2-pyridinyl;

G is —N(CH$_3$)—, Y' is valinyl, $R_o$ is 4-fluorophenyl, $R_{oo}$ is 5-thiazolyl and R is 6-methyl-2-pyridinyl;

G is —N(CH$_3$)—, Y' is valinyl, $R_o$ is 4-fluorophenyl, $R_{oo}$ is 5-thiazolyl and R is 6-(1,1-diimethyl)ethyl-2-pyridinyl;

G is —N(CH$_3$)—, Y' is valinyl, $R_o$ is 4-fluorophenyl, $R_{oo}$ is 5-thiazolyl and R is 6-cyclobutyl-2-pyridinyl;

G is —N(CH$_3$)—, Y' is valinyl, $R_o$ is 4-fluorophenyl, $R_{oo}$ is 5-thiazolyl and R is 6-cyclopropyl-2-pyridinyl;

G is —N(CH$_3$)—, Y' is valinyl, $R_o$ is 4-fluorophenyl, $R_{oo}$ is 5-thiazolyl and R is 6-ethyl-2-pyridinyl;

G is —N(CH$_3$)—, Y' is valinyl, $R_o$ is 4-fluorophenyl, $R_{oo}$ is 5-thiazolyl and R is 6-(2-propenyl)-2-pyridinyl;

G is —N(CH$_3$)—, Y' is valinyl, $R_o$ is 4-fluorophenyl, $R_{oo}$ is 5-thiazolyl and R is 6-propyl-2-pyridinyl; G is —N(CH$_3$)—, Y' is valinyl, $R_o$ is 4-fluorophenyl, $R_{oo}$ is 5-thiazolyl and R is 6-(2-methyl)propyl-2-pyridinyl;

G is —N(CH$_3$)—, Y' is valinyl, $R_o$ is 5-oxazolyI, $R_{oo}$ is 5-thiazolyl and R is 2-pyridinyl;

G is —N(CH$_3$)—, Y' is valinyl, $R_o$ is 5-oxazolyl, $R_{oo}$ is 5-thiazolyl and R is 6-isopropyl-2-pyridinyl;

G is —N(CH$_3$)—, Y' is valinyl, $R_o$ is 5-oxazolyl, $R_{oo}$ is 5-thiazolyl and R is 6-methyl-2-pyridinyl;

G is —N(CH$_3$)—, Y' is valinyl, $R_o$ is 5-oxazolyl, $R_{oo}$ is 5-thiazolyl and R is 6-(1,1-dimethyl)ethyl-2-pyridinyl;

G is —N(CH$_3$)—, Y' is valinyl, $R_o$ is 5-oxazolyl, $R_{oo}$ is 5-thiazolyl and R is 6-cyclobutyl-2-pyridinyl;

G is —N(CH$_3$)—, Y' is valinyl, $R_o$ is 5-oxazolyl, $R_{oo}$ is 5-thiazolyl and R is 6-cyclopropyl-2-pyridinyl;

G is —N(CH$_3$)—, Y' is valinyl, $R_o$ is 5-oxazolyl, $R_{oo}$ is 5-thiazolyl and R is 6-ethyl-2-pyridinyl;

G is —N(CH$_3$)—, Y' is valinyl, $R_o$ is 5-oxazolyl, $R_{oo}$ is 5-thiazolyl and R is 6-(2-propenyl)-2-pyridinyl;

G is —N(CH$_3$)—, Y' is valinyl, $R_o$ is 5-oxazolyl, $R_{oo}$ is 5-thiazolyl and R is 6-propyl-2-pyridinyl:

G is —N(CH$_3$)—, Y' is valinyl, $R_o$ is 5-oxazolyl, $R_{oo}$ is 5-thiazolyl and R is 6-(2-methyl)propyl-2-pyridinyl;

G is —N(CH$_3$)—, Y' is valinyl, $R_o$ is 5-isoxazolyl, $R_{oo}$ is 5-thiazolyl and R is 2-pyridinyl;

G is —N(CH$_3$)—, Y' is valinyl, $R_o$ is 5-isoxazolyl, $R_{oo}$ is 5-thiazolyl and R is 6-isopropyl-2-pyridinyl;

G is —N(CH$_3$)—, Y' is valinyl, $R_o$ is 5-isoxazolyl, $R_{oo}$ is 5-thiazolyl and R is 6-methyl-2-pyridinyl;

G is —N(CH$_3$)—, Y' is valinyl, $R_o$ is 5-isoxazolyl, $R_{oo}$ is 5-thiazolyl and R is 6-(1,1-dimethyl)ethyl-2-pyridinyl;

G is —N(CH$_3$)—, Y' is valinyl, $R_o$ is 5-isoxazolyl, $R_{oo}$ is 5-thiazolyl and R is 6-cyclobutyl-2-pyridinyl;

G is —N(CH$_3$)—, Y' is valinyl, $R_o$ is 5-isoxazolyl, $R_{oo}$ is 5-thiazolyl and R is 6-cyclopropyl-2-pyridinyl;

G is —N(CH$_3$)—, Y' is valinyl, $R_o$ is 5-isoxazolyl, $R_{oo}$ is 5-thiazolyl and R is 6-ethyl-2-pyridinyl;

G is —N(CH₃)—, Y' is valinyl, R₀ is 5-isoxazolyl, R₀₀ is 5-thiazolyl and R is 6-(2-propenyl)-2-pyridinyl;

G is —N(CH₃)—, Y' is valinyl, R₀ is 5-isoxazolyl, R₀₀ is 5-thiazolyl and R is 6-propyl-2-pyridinyl;

G is —N(CH₃)—, Y' is valinyl, R₀ is 5-isoxazolyl, R₀₀ is 5-thiazolyl and R is 6-(2-methyl)propyl-2-pyridinyl;

G is —N(CH₃)—, Y' is valinyl, R₀ is 5-thiazolyl, R₀₀ is 5-thiazolyl and R is 2-pyridinyl;

G is —N(CH₃)—, Y' is valinyl, R₀ is 5-thiazolyl, R₀₀ is 5-thiazolyl and R is 6-isopropyl-2-pyridinyl;

G is —N(CH₃)—, Y' is valinyl, R₀ is 5-thiazolyl, R₀₀ is 5-thiazolyl and R is 6-methyl-2-pyridinyl;

G is —N(CH₃)—, Y' is valinyl, R₀ is 5-thiazolyl, R₀₀ is 5-thiazolyl and R is 6-(1,1-dimethyl)ethyl-2-pyridinyl;

G is —N(CH₃)—, Y' is valinyl, R₀ is 5-tiazolyl, R₀₀ is 5-thiazolyl and R is 6-cyclobutyl-2-pyridinyl;

G is —N(CH₃)—, Y' is valinyl, R₀ is 5-thiazolyl, R₀₀ is 5-thiazolyl and R is 6-cyclopropyl-2-pyridinyl;

G is —N(CH₃)—, Y' is valinyl, R₀ is 5-thiazolyl, R₀₀ is 5-thiazolyl and R is 6-ethyl-2-pyridinyl;

G is —N(CH₃)—, Y' is valinyl, R₀ is 5-thiazolyl, R₀₀ is 5-thiazolyl and R is 6-(2-propenyl)-2-pyridinyl;

G is —N(CH₃)—, Y' is valinyl, R₀ is 5-thiazolyl, R₀₀ is 5-thiazolyl and R is 6-propyl-2-pyridinyl;

G is —N(CH₃)—, Y' is valinyl, R₀ is 5-thiazolyl, R₀₀ is 5-thiazolyl and R is 6-(2-methyl)propyl-2-pyridinyl;

G is —N(CH₃)—, Y' is valinyl, R₀ is phenyl, R₀₀ is 5-thiazolyi and R is 6-(1-butyl)1-2-pyridinyl;

G is —O—, Y' is valinyl, R₀ is phenyl, R₀₀ is 5-thiazolyl and R is 6-(1-butyl)1-2-pyridinyl;

G is —N(CH₃)—, Y' is alanyl, R₀ is phenyl, R₀₀ is 5-thiazolyl and R is 6-(1-butyl)1-2-pyridinyl;

G is —O—, Y' is alanyl, R₀ is phenyl, R₀₀ is 5-thiazolyl and R is 6-(1-butyl)1-2-pyridinyl;

G is —N(CH₃)—, Y' is isolcucyl, R₀ is phenyl, R₀₀ is 5-thiazolyl and R is 6-(1-butyl)1-2-pyridinyl;

G is —O—, Y' is isoleucyl, R₀ is phenyl, R₀₀ is 5-thiazolyl and R is 6-(1-butyl)1-2-pyridinyl;

G is —N(CH₃)—, Y' is valinyl, R₀ is phenyl, R₀₀ is 5-oxazolyl and R is 6-(1-butyl)1-2-pyridinyl;

G is —O—, Y' is valinyl, R₀ is phenyl, R₀₀ is 5-oxazolyl and R is 6-(1-butyl)1-2-pyridinyl;

G is —N(CH₃)—, Y' is alanyJ, R₀ is phenyl, R₀₀ is 5-oxazolyl and R is 6-(1-butyl)1-2-pyridinyl;

G is —O—, Y' is alanyl, R₀ is phenyl, R₀₀ is 5-oxazolyl and R is 6-(1-butyl)1-2-pyridinyl;

G is —N(CH₃)—, Y' is isoleucyl, R₀ is phenyl, R₀₀ is 5-oxazolyl and R is 6-(1-butyl)1-2-pyridinyl;

G is —O—, Y' is isoleucyl, R₀ is phenyl, R₀₀ is 5-oxazolyl and R is 6(1-butyl)1-2-pyridinyl;

G is —N(CH₃)—, Y' is valinyl, R₀ is phenyl, R₀₀ is 5-isoxazolyl and R is 6-(1-butyl)1-2-pyridinyl;

G is —O—, Y' is valinyl, R₀ is phenyl, R₀₀ is 5-isoxazolyl and R is 6-(1-butyl)1-2-pyridinyl;

G is —N(CH₃)—, Y' is alanyl, R₀ is phenyl, R₀₀ is 5-isoxazolyl and R is 6-(1-butyl)1-2-pyridinyl;

G is —O—, Y' is alanyl, R₀ is phenyl, R₀₀ is 5-isoxazolyl and R is 6-(1-butyl)1-2-pyridinyl;

G is —N(CH₃)—, Y' is isoleucyl, R₀ is phenyl, R₀₀ is 5-isoxazolyl and R is 6-(1-butyl)1-2-pyridinyl;

G is —O—, Y' is isoleucyl, R₀ is phenyl, R₀₀ is 5-isoxazolyl and R is 6-(1-butyl)1-2-pyridinyl;

G is —N(CH₃)—, Y' is valinyl, R₀ is phenyl, R₀₀ is 5-thiazolyl and R is 6-(2-butyl)1-2-pyridinyl;

G is —O—, Y' is valinyl, R₀ is phenyl, R₀₀ is 5-thiazolyl and R is 6-(2-butyl)1-2-pyridinyl;

G is —N(CH₃)—, Y' is alanyl, R₀ is phenyl, R₀₀ is 5-thiazolyl and R is 6-(2-butyl)1-2-pyridinyl;

G is —O—, Y' is alanyl, R₀ is phenyl, R₀₀ is 5-thiazolyl and R is 6(2-butyl)1-2-pyridinyl;

G is —N(CH₃)—, Y' is isoleucyl, R₀ is phenyl, R₀₀ is 5-thiazolyl and R is 6-(2-butyl)1-2-pyridinyl;

G is —O—, Y' is isoleucyl, R₀ is phenyl, R₀₀ is 5-thiazolyl and R is 6-(2-butyl)1-2-pyridinyl;

G is —N(CH₃)—, Y' is valinyl, R₀ is phenyl, R₀₀ is 5-oxazolyl and R is 6-(2-butyl)1-2-pyridinyl;

G is —O—, Y' is valinyl, R₀ is phenyl, R₀₀ is 5-oxazolyl and R is 6-(2-butyl)1-2-pyridinyl;

G is —N(CH₃)—, Y' is alanyl, R₀ is phenyl, R₀₀ is 5-oxazolyl and R is 6-(2-butyl)1-2-pyridinyl;

G is —O—, Y' is alanyl, R₀ is phenyl, R₀₀ is 5-oxazolyl and R is 6-(2-butyl)1-2-pyridinyl;

G is —N(CH₃)—, Y' is isoleucyl, R₀ is phenyl, R₀₀ is 5-oxazolyl and R is 6-(2-butyl)1-2-pyridinyl;

G is —O—, Y' is isoleucyl, R₀ is phenyl, R₀₀ is 5-oxazolyl and R is 6-(2-butyl)1-2-pyridinyl;

G is —N(CH₃)—, Y' is valinyl, R₀ is phenyl, R₀₀ is 5-isoxazolyl and R is 6-(2-butyl)1-2-pyridinyl;

G is —O—, Y' is valinyl, R₀ is phenyl, R₀₀ is 5-isoxazolyl and R is 6-(2-butyl)l-2-pyridinyl;

G is —N(CH₃)—, Y' is alanyl, R₀ is phenyl, R₀₀ is 5-isoxazolyl and R is 6-(2-butyl)1-2-pyridinyl;

G is —O—, Y is alanyl, R₀ is phenyl, R₀₀ is 5-isoxazolyl and R is 6-(2-butyl)1-2-pyridinyl;

G is —N(CH₃)—, Y' is isoleucyl, R₀ is phenyl, R₀₀ is 5-isoxazolyl and R is 6-(2-butyl)1-2-pyridinyl;

G is —O—, Y' is isoleucyl, R₀ is phenyl, R₀₀ is 5-isoxazolyl and R is 6-(2-butyl)1-2-pyridinyl;

G is —N(CH₃)—, Y' is valinyl, R₀ is 3-furanyl, R₀₀ is 5-thiazolyl and R is 2-pyridinyl;

G is —N(CH₃)—, Y' is valinyl, R₀ is 3-furanyl, R₀₀ is 5-thiazolyl and R is 6-isopropyl-2-pyridinyl;

G is —N(CH₃)—, Y' is valinyl, R₀ is 3-furanyl, R₀₀ is 5-thiazolyl and R is 6-methyl-2-pyridinyl;

G is —N(CH₃)—, Y' is valinyl, R₀ is 3-furanyl, R₀₀ is 5-thiazolyl and R is 6-(1,1-direthyl)ethyl-2-pyridinyl;

G is —N(CH₃)—, Y' is valinyl, R₀ is 3-furanyl, R₀₀ is 5-thiazolyl and R is 6-cyclobutyl-2-pyridinyl;

G is —N(CH₃)—, Y' is valinyl, R₀ is 3-furanyl, R₀₀ is 5-thiazolyl and R is 6-cyclopropyl-2-pyridinyl;

G is —N(CH₃)—, Y' is valinyl, R₀ is 3-furanyl, R₀₀ is 5-thiazolyl and R is 6ethyl-2-pyridinyl;

G is —N(CH₃)—, Y' is valinyl, R₀ is 3-furanyl, R₀₀ is 5-thiazolyl and R is 6-(2-propenyl)-2-pyridinyl;

G is —N(CH₃)—, Y' is valinyl, R₀ is 3-furanyl, R₀₀ is 5-thiazolyl and R is 6-propyl-2-pyridinyl;

G is —N(CH₃)—, Y' is valinyl, R₀ is 3-furanyl, R₀₀ is 5-thiazolyl and R is 6-(2-methyl)propyl-2-pyridinyl;

G is —N(CH₃)—, Y' is valinyl, R₀ is 2-furanyl, R₀₀ is 5-thiazolyl and R is 2-pyridinyl;

G is —N(CH₃)—, Y' is valinyl, R₀ is 2-furanyl, R₀₀ is 5-thiazolyl and R is 6-isopropyl-2-pyridinyl;

G is —N(CH₃)—, Y' is valinyl, R₀ is 2-furanyl, R₀₀ is 5-thiazolyl and R is 6-methyl-2-pyridinyl;

G is —N(CH₃)—, Y' is valinyl, R_o is 2-furanyl, R_oo is 5-thiazolyl and R is 6-(1,1-dimethyl)ethyl-2-pyridinyl;

G is —N(CH₃)—, Y' is valinyl, R_o is 2-furanyl, R_oo is 5-thiazolyl and R is 6-cyclobutyl-2-pyridinyl;

G is —N(CH₃)—, Y' is valinyl, R_o is 2-furanyl, R_oo is 5-thiazolyl and R is 6-cyclopropyl-2-pyridinyl;

G is —N(CH₃)—, Y' is valinyl, R_o is 2-furanyl, R_oo is 5-thiazolyl and R is 6-ethyl-2-pyridinyl;

G is —N(CH₃)—, Y' is valinyl, R_o is 2-furanyl, R_oo is 5-thiazolyl and R is 6-(2-propenyl)-2-pyridinyl;

G is —N(CH₃)—, Y' is valinyl, R_o is 2-furanyl, R_oo is 5-thiazolyl and R is 6-propyl-2-pyridinyl;

G is —N(CH₃)—, Y' is valinyl, R_o is 2-furanyl, R_oo is 5-thiazolyl and R is 6-(2-methyl)propyl-2-pyridinyl;

G is —N(CH₃)—, Y' is valinyl, R_o is 4-pyridinyl, R_oo is 5-thiazolyl and R is 2-pyridinyl;

G is —N(CH₃)—, Y' is valinyl, R_o is 4-pyridinyl, R_oo is 5-thiazolyl and R is 6-isopropyl-2-pyridinyl;

G is —N(CH₃)—, Y' is valinyl, R_o is 4-pyridinyl, R_oo is 5-thiazolyl and R is 6methyl-2-pyridinyl;

G is —N(CH₃)—, Y' is valinyl, R_o is 4-pyridinyl, R_oo is 5-thiazolyl and R is 6-(1,1-dimethyl)ethyl-2-pyridinyl;

G is —N(CH₃)—, Y' is valinyl, R_o is 4-pyridinyl, R_oo is 5-thiazolyl and R is 6-cyclobutyl-2-pyridinyl;

G is —N(CH₃)—, Y' is valinyl, R_o is 4-pyridinyl, R_oo is 5-thiazolyl and R is 6-cyclopropyl-2-pyridinyl;

G is —N(CH₃)—, Y' is valinyl, R_o is 4-pyridinyl, R_oo is 5-thiazolyl and R is 6ethyl-2-pyridinyl;

G is —N(CH₃)—, Y is valinyl, R_o is 4-pyridinyl, R_oo is 5-thiazolyl and R is 6-(2-propenyl)-2-pyridinyl;

G is —N(CH₃)—, Y' is valinyl, R_o is 4-pyridinyl, R_oo is 5-thiazolyl and R is 6-propyl-2-pyridinyl;

G is —N(CH₃)—, Y' is valinyl, R_o is 4-pyridinyl, R_oo is 5-thiazolyl and R is 6-(2-methyl)propyl-2-pyridinyl;

G is —N(CH₃)—, Y' is valinyl, R_o is 4-methoxyphenyl, R_oo is 5-thiazolyl and R is 2-pyridinyl;

G is —N(CH₃)—, Y' is valinyl, R_o is 4-methoxyphenyl, R_oo is 5-thiazolyl and R is 6-isopropyl-2-pyridinyl;

G is —N(CH₃)—, Y' is valinyl, R_o is 4-metboxyphenyl, R_oo is 5-thiazolyl and R is 6-methyl-2-pyridinyl;

G is —N(CH₃)—, Y' is valinyl, R_o is 4-methoxyphenyl, R_oo is 5-thiazolyl and R is 6-(1,1-dimethyl)ethyl-2-pyridinyl;

G is —N(CH₃)—, Y' is valinyl, R_o is 4-methoxyphenyl, R_oo is 5-thiazolyl and R is 6-cyclobutyl-2-pyridinyl;

G is —N(CH₃)—, Y' is valinyl, R_o is 4-methoxyphenyl, R_oo is 5-thiazolyl and R is 6-cyclopropyl-2-pyridinyl;

G is —N(CH₃)—, Y' is valinyl, R_o is 4-methoxyphenyl, R_oo is 5-thiazolyl and R is 6-ethyl-2-pyridinyl;

G is —N(CH₃)—, Y' is valinyl, R_o is 4-methoxyphenyl, R_oo is 5-thiazolyl and R is 6-(2-propenyl)-2-pyridinyl;

G is —N(CH₃)—, Y' is valinyl, R_o is 4-methoxyphenyl, R_oo is 5-thiazolyl and R is 6-propyl-2-pyridinyl;

G is —N(CH₃)—, Y' is valinyl, R_o is 4-methoxyphenyl, R_oo is 5-thiazolyl and R is 6-(2-methyl)propyl-2-pyridinyl;

G is —N(CH₃)—, Y' is valinyl, R_o is 4-tetrahydropyranyl, R_oo is 5-thiazolyl and R is 2-pyridinyl;

G is —N(CH₃)—, Y is valinyl, R_o is 4-tetrahydropyranyl, R_oo is 5-thiazolyl and R is 6-isopropyl-2-pyridinyl;

G is —N(CH₃)—, Y' is valinyl, R_o is 4-tetrahydropyranyl, R_oo is 5-thiazolyl and R is 6-methyl-2-pyridinyl;

G is —N(CH₃)—, Y' is valinyl, R_o is 4-tetrahydropyranyl, R_oo is 5-thiazolyl and R is 6-(1,1-dimethyl)ethyl-2-pyridinyl;

G is —N(CH₃)—, Y' is valinyl, R_o is 4-tetrahydropyranyl, R_oo is 5-thiazolyl and R is 6-cyclobutyl-2-pyridinyl;

G is —N(CH₃)—, Y' is valinyl, R_o is 4-tetrahydropyranyl, R_oo is 5-thiazolyl and R is 6-cyclopropyl-2-pyndinyl;

G is —N(CH₃)—, Y' is valinyl, R_o is 4-tetrahydropyranyl, R_oo is 5-thiazolyl and R is 6-ethyl-2-pyridinyl;

G is —N(CH₃)—, Y' is valinyl, R_o is 4-tetrahydropyranyl, R_oo is 5-thiazolyl and R is 6-(2-propenyl)-2-pyridinyl;

G is —N(CH₃)—, Y' is valinyl, R_o is 4-tetrahydropyranyl, R_oo is 5-thiazolyl and R is 6-propyl-2-pyridinyl;

G is —N(CH₃)—, Y' is valinyl, R_o is 4-tetrahydropyranyl, R_oo is 5-thiazolyl and R is 6-(2-methyl)propyl-2-pyridinyl;

G is —O—, Y' is isoleucyl, R_o is 4-tetrahydropyranyl, R_oo is 5-thiazolyl and R is 2-(1-butyl)-4-thiazolyl;

G is —O—, Y' is isoleucyl, R_o is 4tetrahydropyranyl, R_oo is 5-thiazolyl and R is 2-(1-butyl)-4-oxazolyl;

G is —O—, Y' is isoleucyl, R_o is 4-tetrahydropyranyl, R_oo is 5-thiazolyl and R is 6-(1-butyl)-2-pyridinyl;

G is —O—, Y' is isoleucyl, R_o is 4-tetrahydropyranyl, R_oo is 5-thiazolyl and R is 2-(2-butyl)-4-thiazolyl;

G is —O—, Y' is isoleucyl, R_o is 4-tetrabydropyranyl, R_oo is 5-thiazolyl and R is 2-(2-butyl)-4-oxazolyl; and G is —O—, Y' is isoleucyl, R_o is 4-tetrahydropyranyl, R_oo is 5-thiazolyl and R is 6-(2-butyl)-2-pyridinyl;

or a pharmaceutically acceptable salt, ester of prodrug thereof.

11. A method for inhibiting HIV protease comprising adminstering to a human in need of such treatment a therapeutically effective amount of a compound of claim 1.

12. A pharmaceutical composition comprising a pharmceutical carrier and a therapeutically effective amount of a compound of claim 1.

* * * * *